(12) United States Patent
Shibuya et al.

(10) Patent No.: US 9,454,079 B2
(45) Date of Patent: Sep. 27, 2016

(54) ACTINIC RAY- OR RADIATION-SENSITIVE RESIN COMPOSITION, ACTINIC RAY- OR RADIATION-SENSITIVE FILM AND METHOD OF FORMING PATTERN

(71) Applicant: FUJIFILM CORPORATION, Minato-ku, Tokyo (JP)

(72) Inventors: Akinori Shibuya, Shizuoka (JP); Yoko Tokugawa, Shizuoka (JP); Tomoki Matsuda, Shizuoka (JP); Junichi Ito, Shizuoka (JP); Shohei Kataoka, Shizuoka (JP); Toshiaki Fukuhara, Shizuoka (JP); Naohiro Tango, Shizuoka (JP); Kaoru Iwato, Shizuoka (JP); Masahiro Yoshidome, Shizuoka (JP); Shinichi Sugiyama, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/271,606

(22) Filed: May 7, 2014

(65) Prior Publication Data
US 2014/0248562 A1    Sep. 4, 2014

Related U.S. Application Data

(63) Continuation of application No. PCT/JP2012/079055, filed on Nov. 2, 2012.

(30) Foreign Application Priority Data

| Nov. 7, 2011 | (JP) | ................................. | 2011-243948 |
| Dec. 27, 2011 | (JP) | ................................. | 2011-286896 |
| May 30, 2012 | (JP) | ................................. | 2012-123757 |
| Oct. 19, 2012 | (JP) | ................................. | 2012-232271 |

(51) Int. Cl.

| G03F 7/004 | (2006.01) |
| C07C 303/32 | (2006.01) |
| C07C 309/04 | (2006.01) |
| C07C 309/06 | (2006.01) |
| C07C 309/12 | (2006.01) |
| C07D 295/16 | (2006.01) |
| C07D 327/06 | (2006.01) |
| C07D 339/08 | (2006.01) |
| G03F 7/038 | (2006.01) |
| G03F 7/039 | (2006.01) |
| G03F 7/11 | (2006.01) |
| G03F 7/20 | (2006.01) |
| G03F 7/32 | (2006.01) |

(52) U.S. Cl.
CPC .............. *G03F 7/038* (2013.01); *C07C 303/32* (2013.01); *C07C 309/04* (2013.01); *C07C 309/12* (2013.01); *C07D 295/16* (2013.01); *C07D 327/06* (2013.01); *C07D 339/08* (2013.01); *G03F 7/0045* (2013.01); *G03F 7/0046* (2013.01); *G03F 7/0397* (2013.01); *G03F 7/11* (2013.01); *G03F 7/2041* (2013.01); *G03F 7/325* (2013.01)

(58) Field of Classification Search
CPC .. G03F 7/0397; G03F 7/0045; G03F 7/0046; C07C 303/32; C07C 309/04; C07C 309/06; C07C 309/12; C07D 295/16; C07D 295/36; C07D 317/28; C07D 327/06; C07D 339/08
USPC ............... 430/270.1, 910, 920, 922; 544/59; 549/14, 20, 28; 562/109, 113; 568/77
See application file for complete search history.

(56) References Cited

U.S. PATENT DOCUMENTS

| 7,033,727 | B2 * | 4/2006 | Kodama | ............... | G03F 7/0045 430/270.1 |
| 7,851,130 | B2 * | 12/2010 | Kawanishi | ........... | C07D 333/76 430/270.1 |
| 7,951,523 | B2 * | 5/2011 | Ishizuka | ............... | G03F 7/0046 430/270.1 |
| 8,852,846 | B2 * | 10/2014 | Anryu | ................... | C07D 279/12 430/270.1 |
| 2003/0077540 | A1 | 4/2003 | Kodama et al. | | |
| 2003/0224288 | A1 * | 12/2003 | Kodama | ............... | C07C 381/12 430/270.1 |
| 2008/0081288 | A1 | 4/2008 | Kawanishi et al. | | |
| 2009/0023095 | A1 | 1/2009 | Hada et al. | | |

(Continued)

FOREIGN PATENT DOCUMENTS

| JP | 2002-351077 A | 12/2002 |
| JP | 2003-302754 A | 10/2003 |

(Continued)

OTHER PUBLICATIONS

English Translation of International Preliminary Report on Patentability issued in PCT/JP2012/079055 dated May 22, 2014.

(Continued)

*Primary Examiner* — John S Chu
(74) *Attorney, Agent, or Firm* — Sughrue Mion, PLLC

(57) ABSTRACT

According to one embodiment, there is provided an actinic ray- or radiation-sensitive resin composition including
(A) a compound represented by a general formula (1) below that generates an acid when exposed to actinic rays or radiation, and
(B) a resin.

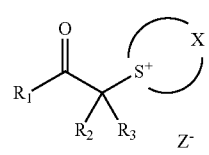

(1)

11 Claims, No Drawings

(56) References Cited

U.S. PATENT DOCUMENTS

| | | | |
|---|---|---|---|
| 2010/0316951 A1* | 12/2010 | Ichikawa | C07C 309/17 430/270.1 |
| 2011/0027716 A1 | 2/2011 | Yamaguchi et al. | |
| 2011/0223536 A1 | 9/2011 | Shibuya et al. | |

FOREIGN PATENT DOCUMENTS

| | | |
|---|---|---|
| JP | 2005-309408 A | 11/2005 |
| JP | 2009-40761 A | 2/2009 |
| JP | 2010-61018 A | 3/2010 |
| JP | 2011-186247 A | 9/2011 |
| KR | 10-0981314 B1 | 9/2010 |
| TW | I313791 B | 8/2009 |
| WO | 2013/047911 A1 | 4/2013 |

OTHER PUBLICATIONS

European Search Report dated May 19, 2015 issued in application No. 12847779.1-1560.
International Search Report of PCT/JP2012/079055, dated Dec. 4, 2012.
Communication dated Feb. 1, 2016 from the Korean Intellectual Property Office in counterpart application No. 10-2014-7013870.
Communication dated Feb. 18, 2016 from the Taiwanese Intellectual Property Office in counterpart application No. 101141189.

* cited by examiner

ACTINIC RAY- OR RADIATION-SENSITIVE RESIN COMPOSITION, ACTINIC RAY- OR RADIATION-SENSITIVE FILM AND METHOD OF FORMING PATTERN

CROSS-REFERENCE TO RELATED APPLICATIONS

This application is a Continuation Application of PCT Application No. PCT/JP2012/079055), filed Nov. 2, 2012) and based upon and claims the benefit of priority from prior Japanese Patent Applications No. 2011-243948, filed Nov. 7, 2011; No. 2011-286896, filed Dec. 27, 2011; No. 2012-123757, filed May 30, 2012; and No. 2012-232271, filed Oct. 19, 2012, the entire contents of all of which are incorporated herein by reference.

BACKGROUND OF THE INVENTION

1. Field of the Invention

The present invention relates to an actinic ray- or radiation-sensitive resin composition, an actinic ray- or radiation-sensitive film and a method of forming a pattern using the same. More specifically, the present invention relates to an actinic ray- or radiation-sensitive resin composition that is suitable for use in a process for producing a semiconductor for an IC or the like, a process for producing a circuit board for a liquid crystal, a thermal head or the like, other photofabrication processes, a process for producing a planographic printing plate and as a composition that is hardened by acid, and also relates to an actinic ray- or radiation-sensitive film and a method of forming a pattern using the same. Furthermore, the present invention relates to a process for manufacturing an electronic device including the method of forming a pattern and an electronic device manufactured by the process.

2. Description of the Related Art

A chemical amplification resist composition is a pattern forming material that is capable of, upon exposure to far ultraviolet or other radiation, generating an acid at the exposed area and, by a reaction catalyzed by the acid, changing the solubility in a developer between the area having been exposed to actinic radiation and the nonexposed area to thereby attain pattern formation on a substrate.

In the use of a KrF excimer laser as an exposure light source, a resin whose fundamental skeleton consists of a poly(hydroxystyrene) exhibiting a low absorption mainly in the region of 248 nm is employed as a major component. Accordingly, there can be attained a high sensitivity, high resolving power and favorable pattern formation. Thus, a system superior to the conventional naphthoquinone diazide/novolak resin system is realized.

On the other hand, in the use of a light source of a further shorter wavelength, for example, an ArF excimer laser (193 nm) as an exposure light source, as the compounds having an aromatic group inherently exhibit a sharp absorption in the region of 193 nm, the above-mentioned chemical amplification system has not been satisfactory. Therefore, resists for an ArF excimer laser containing a resin with an alicyclic hydrocarbon structure have been developed.

A variety of compounds have been developed as a photoacid generator being a main constituent of the chemically amplified resist composition (see, for example, patent references 1 and 2). For example, patent reference 1 describes photoacid generators comprised of sulfonium salts each having an ether structure in its sulfonium cation.

However, discovering an appropriate combination of used resin, photoacid generator, basic compound, additive, solvent, etc., from the viewpoint of comprehensive performance as a resist is extremely difficult, and the current situation is that any combination is still unsatisfactory. For example, there is a demand for the development of a resist excelling in exposure latitude and pattern roughness characteristic, such as line width roughness (LWR), and ensuring less occurrence of particles over time. Moreover, when a liquid-immersion exposure is performed, the acid generated upon exposure to light may be eluted into the immersion liquid to thereby cause the problems of pattern shape deterioration and exposure machine contamination. Therefore, a resist composition ensuring less elution of generated acids into the immersion liquid is desired.

PRIOR ART REFERENCE

Patent Reference

Patent reference 1: Jpn. Pat. Appln. KOKAI Publication No. (hereinafter referred to as JP-A-) 2003-321466, and
Patent reference 2: JP-A-2004-145298.

BRIEF SUMMARY OF THE INVENTION

In view of the above background art, it is an object of the present invention to provide an actinic ray- or radiation-sensitive resin composition excelling in exposure latitude and pattern roughness characteristic, such as LWR, ensuring less occurrence of particles over time and further ensuring, when a liquid-immersion exposure is performed, less elution of generated acids into the immersion liquid. It is other objects of the present invention to provide an actinic ray- or radiation-sensitive film containing the composition and to provide a method of forming a pattern.

The present invention below is completed by the inventors as a result of their hard effort to resolve the problem above.

[1] An actinic ray- or radiation-sensitive resin composition comprising:

(A) a compound represented by a general formula (1) below that generates an acid when exposed to actinic rays or radiation, and (B) a resin,

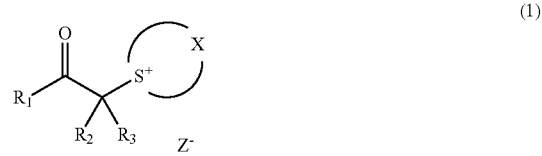

wherein

X represents a bivalent group containing an oxygen atom, a sulfur atom or a nitrogen atom, which bivalent group is connected to $S^+$ to thereby form a cyclic structure;

$R_1$ represents an alkyl group, an alkoxy group, a cycloalkyl group, a cycloalkoxy group, an aryl group or an alkenyl group;

each of $R_2$ and $R_3$ independently represents a hydrogen atom, an alkyl group, a cycloalkyl group or an aryl group, provided that $R_2$ and $R_3$ may be connected to each other to thereby form a ring, and that at least one of $R_2$ and $R_3$ is an alkyl group, a cycloalkyl group or an aryl group;

provided that $R_1$ and $R_2$ may be connected to each other to thereby form a ring; and $Z^-$ represents a sulfonate anion represented by a general formula (2) below or a disulfonylimidate anion represented by a general formula (2') below,

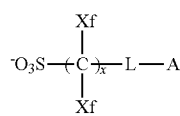
(2)

wherein
each Xfs independently represents a fluorine atom or an alkyl group substituted with at least one fluorine atom;
L represents a single bond or a bivalent connecting group;
A represents an organic group with a cyclic structure; and
x is an integer of 1 to 20,

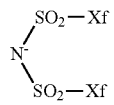
(2')

wherein
Xf is as defined above in the general formula (2), provided that two Xfs may be connected to each other to thereby form a cyclic structure.

[2] The actinic ray- or radiation-sensitive resin composition according to [1], wherein in the general formula (1), X contains an oxygen atom or a group represented by >N—SO$_2$—R$_4$ in which R$_4$ represents an alkyl group, a cycloalkyl group or an aryl group.

[3] The actinic ray- or radiation-sensitive resin composition according to [1], wherein the compound represented by the general formula (1) is represented by general formulae (1a) or (1b) below,

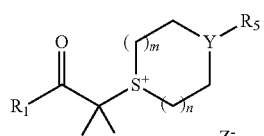
(1a)

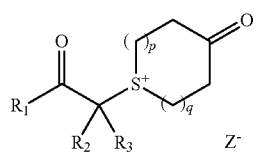
(1b)

wherein
$R_1$, $R_2$ and $R_3$ are as defined above in [1];
Y represents an oxygen atom, a sulfur atom or a nitrogen atom;
$R_5$ represents an electron withdrawing group when Y is a nitrogen atom and is not in existence when Y is an oxygen atom or a sulfur atom; and
each of m, n, p and q is an integer of 0 to 3.

[4] The actinic ray- or radiation-sensitive resin composition according to [3], wherein in the general formula (1a), Y is an oxygen atom or a nitrogen atom, provided that when Y is a nitrogen atom, $R_5$ is a group represented by —SO$_2$—R$_4$, in which R$_4$ represents an alkyl group, a cycloalkyl group or an aryl group.

[5] The actinic ray- or radiation-sensitive resin composition according to any one of [1] to [4], wherein the resin (B) is a resin that is decomposed by an action of the acid to thereby increase its solubility in an alkali developer.

[6] The actinic ray- or radiation-sensitive resin composition according to any one of [1] to [5], wherein the resin (B) contains at least one of repeating units represented by a general formula (3) below and a lactone structure,

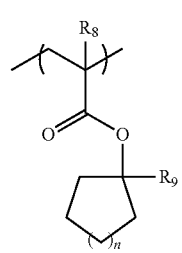
(3)

wherein
$R_8$ represents a hydrogen atom or a substituted or unsubstituted alkyl group having 1 to 10 carbon atoms;
$R_9$ represents a substituted or unsubstituted alkyl group having 1 to 10 carbon atoms; and
n is an integer of 1 to 6.

[7] An actinic ray- or radiation-sensitive film comprising the actinic ray- or radiation-sensitive resin composition according to any one of [1] to [6].

[8] A method of forming a pattern, comprising:
forming the actinic ray- or radiation-sensitive film containing the actinic ray- or radiation-sensitive resin composition according to any one of [1] to [6];
exposing the film to the actinic rays or radiation, and
developing the exposed film.

[9] The method according to [8], wherein the exposure is an ArF liquid-immersion exposure.

[10] A process for manufacturing an electronic device, comprising the method according to [8] or [9].

[11] An electronic device manufactured by the process according to [10].

The present invention has made it feasible to provide an actinic ray- or radiation-sensitive resin composition excelling in exposure latitude and pattern roughness characteristic, such as LWR, ensuring less occurrence of particles over time and further ensuring, when a liquid-immersion exposure is performed, less elution of generated acids into the immersion liquid. The present invention has also made it feasible to provide an actinic ray- or radiation-sensitive film containing the composition and a method of forming a pattern.

DETAILED DESCRIPTION OF THE INVENTION

Embodiments of the present invention will be described below in detail.

With respect to the expression of a group and atomic group used in this specification, the expression even when there is no mention of "substituted and unsubstituted" encompasses groups not only having no substituent but also having substituents. For example, the expression "alkyl groups" which is not shown to be substituted or unsubstituted encompasses not only alkyls having no substituent (unsubstituted alkyls) but also alkyls having substituents (substituted alkyls).

In the present invention, the terms "actinic rays" and "radiation" mean, for example, brightline spectra from a mercury lamp, far ultraviolet represented by excimer laser, extreme ultraviolet (EUV light), X-rays, electron beams (EB) and the like. In the present invention, the term "light" means actinic rays or radiation.

In the present invention, the term "exposure", unless otherwise noted, means not only light irradiation using a mercury lamp, far ultraviolet represented by excimer laser, X-rays, EUV light, etc. but also lithography using particle beams, such as an electron beam and an ion beam. The actinic ray- or radiation-sensitive resin composition according to the present invention is especially suitable for an ArF liquid-immersion exposure.

The actinic ray- or radiation-sensitive resin composition according to the present invention includes (A) a compound represented by a general formula (1) to be described below that generates an acid when exposed to actinic rays or radiation (hereinafter also referred to as a compound (A) or a photoacid generator (A)), and (B) a resin.

Exposure latitude and pattern roughness (LWR) can be improved, and the occurrence of particles over time can be suppressed, by the incorporation of the compound (A) in the actinic ray- or radiation-sensitive resin composition of the present invention. The reason therefor has not been elucidated. However, in the compound (A), after the excitation by light absorption, the C—S⁺ bond is cleaved at high efficiency, so that the amount of acid generated upon exposure is large to thereby realize the uniform distribution of an acid in the light-sensitive resist film. It is presumed that this contributes to the improvement of LWR, and that the volume of generated acid is large to thereby suppress the diffusion of the acid, thereby contributing to the improvement of exposure latitude.

Moreover, at liquid-immersion exposure, especially when an ArF liquid-immersion exposure is performed, the elution of generated acid into the immersion liquid can be inhibited by the incorporation of the compound (A) in the actinic ray- or radiation-sensitive resin composition of the present invention.

The compound (A) necessarily contains a steric hindrance group around the sulfur atom of its sulfonium cation, so that the hydrophilic cation is shielded to thereby inhibit its affinity to water. Accordingly, it is presumed that at an ArF liquid-immersion exposure, the elution of acid generated upon exposure into the immersion liquid can be inhibited. Further, the anion in the compound (A) is an anion of low diffusion in which a cyclic substituent is necessarily introduced, so that the anion at its end assumes a bulky structure with a cyclic structure. It is presumed that this is especially effective in the inhibition of acid diffusion.

The actinic ray- or radiation-sensitive resin composition of the present invention is, for example, a resin composition including a resin containing a group decomposed under the action of an acid, or a resin composition including a resin containing a crosslinkable group. A resin composition including a resin containing a group decomposed under the action of an acid is preferred. The individual components of this resin composition will be described below.

[1] Compound (A)

As mentioned above, the actinic ray- or radiation-sensitive resin composition of the present invention comprises (A) a compound represented by a general formula (1) below that generates an acid when exposed to actinic rays or radiation.

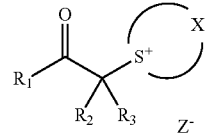

(1)

In the general formula (1), $R_1$ represents an alkyl group, a cycloalkyl group, an alkoxy group, a cycloalkoxy group, an aryl group or an alkenyl group. $R_1$ preferably represents an alkyl group, a cycloalkyl group or an aryl group, and more preferably an aryl group.

The alkyl group represented by $R_1$ is preferably a linear or branched alkyl group having 1 to 20 carbon atoms. The alkyl group in its chain may contain an oxygen atom, a sulfur atom or a nitrogen atom. For example, there can be mentioned a linear alkyl group, such as a methyl group, an ethyl group, an n-propyl group, an n-butyl group, an n-pentyl group, an n-hexyl group, an n-octyl group, an n-dodecyl group, an n-tetradecyl group or an n-octadecyl group, and a branched alkyl group, such as an isopropyl group, an isobutyl group, a t-butyl group, a neopentyl group or a 2-ethylhexyl group. A substituent may be introduced in the alkyl group represented by $R_1$. As substituted alkyl groups, there can be mentioned a cyanomethyl group, a 2,2,2-trifluoroethyl group, a methoxycarbonylmethyl group, an ethoxycarbonylmethyl group and the like.

The cycloalkyl group represented by $R_1$ is preferably one having 3 to 20 carbon atoms. The cycloalkyl group in its ring may contain an oxygen atom or a sulfur atom. As examples thereof, there can be mentioned a cyclopropyl group, a cyclopentyl group, a cyclohexyl group, a norbornyl group, an adamantyl group and the like. A substituent may be introduced in the cycloalkyl group represented by $R_1$. As the substituent, there can be mentioned, for example, an alkyl group or an alkoxy group.

The alkoxy group represented by $R_1$ is preferably one having 1 to 20 carbon atoms. As examples thereof, there can be mentioned a methoxy group, an ethoxy group, an isopropoxy group, a t-butoxy group, a t-amyloxy group and an n-butoxy group. A substituent may be introduced in the alkoxy group represented by $R_1$. As the substituent, there can be mentioned, for example, an alkyl group or a cycloalkyl group.

The cycloalkoxy group represented by $R_1$ is preferably one having 3 to 20 carbon atoms. As examples thereof, there can be mentioned a cyclohexyloxy group, a norbornyloxy group, an adamantyloxy group and the like. A substituent may be introduced in the cycloalkoxy group represented by $R_1$. As the substituent, there can be mentioned, for example, an alkyl group or a cycloalkyl group.

The aryl group represented by $R_1$ is preferably one having 6 to 14 carbon atoms. As examples thereof, there can be mentioned a phenyl group, a naphthyl group, a biphenyl group and the like. As the aryl group represented by $R_1$ is preferably a phenyl group or a naphthyl group, more preferably a phenyl group. A substituent may be introduced in the aryl group represented by $R_1$. As preferred substituents, there can be mentioned an alkyl group, a cycloalkyl group, an alkoxy group, a cycloalkoxy group, an aryloxy group, an alkylthio group, an arylthio group, a hydroxyl group and a halogen atom. The alkyl group, cycloalkyl group, alkoxy group and cycloalkoxy group as the substituents can be the same as set forth above in connection with $R_1$. The aryloxy group as the substituent is preferably a phenyloxy group and a substituent may be introduced in a benzene ring in the phenyloxy group. The arylthio group as the substituent is preferably a phenylthio group and a substituent may be introduced in a benzene ring in the phenylthio group. The substituent on the benzene ring can be the same as set forth above in connection with the substituent on the aryl group represented by $R_1$. Substituents on the aryl group represented by $R_1$ may be connected to each other to thereby form a ring.

As the alkenyl group represented by $R_1$, there can be mentioned a vinyl group or an allyl group.

Each of $R_2$ and $R_3$ represents a hydrogen atom, an alkyl group, a cycloalkyl group or an aryl group, provided that $R_2$ and $R_3$ may be connected to each other to thereby form a ring, and that at least one of $R_2$ and $R_3$ is an alkyl group, a cycloalkyl group or an aryl group. Particular examples and preferred examples of the alkyl groups, cycloalkyl groups and aryl groups represented by $R_2$ and $R_3$ can be the same as set forth above in connection with $R_1$. When $R_2$ and $R_3$ are connected to each other to thereby form a ring, the sum of carbon atoms contributing to ring formation contained in $R_2$ and $R_3$ is preferably in the range of 4 to 7, most preferably 4 or 5.

$R_1$ and $R_2$ may be connected to each other to thereby form a ring. When $R_1$ and $R_2$ are connected to each other to thereby form a ring, preferably, $R_1$ is an aryl group while $R_2$ is an alkylene group having 1 to 4 carbon atoms. Also preferably, $R_1$ is a vinyl group while $R_2$ is an alkylene group having 1 to 4 carbon atoms. Most preferably, $R_1$ is an optionally substituted phenyl group while $R_2$ is a methylene group or an ethylene group.

X represents a bivalent group containing an oxygen atom, a sulfur atom or a nitrogen atom, which bivalent group is connected to a sulfonium cation ($S^+$ in general formula (1)) to thereby form a cyclic structure. When X contains a nitrogen atom, it is preferred for X to be a group wherein the nitrogen atom exhibits a low basicity or no basicity at all. X is preferably a group containing a nitrogen atom substituted with an electron withdrawing group, such as an amide structure, a carbamate structure or a sulfonamide structure. The electron withdrawing group for nitrogen atom substitution may be an ester group.

As a preferred example of X, there can be mentioned a bivalent group containing an oxygen atom or a nitrogen atom, which bivalent group is connected to $S^+$ to thereby form a cyclic structure. Most preferably, there can be mentioned an alkylene group containing an oxygen atom, or an alkylene group with a structure expressed by general formula (IV) below. In formula (IV), it is preferred for the nitrogen atom N to be a constituent atom of the ring formed by connection to $S^+$.

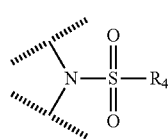

(IV)

In formula (IV), $R_4$ represents an alkyl group, a cycloalkyl group or an aryl group, preferably an alkyl group. Particular examples and preferred examples of the alkyl group, cycloalkyl group and aryl group represented by $R_4$ can be the same as set forth above in connection with $R_1$.

The oxygen atom, sulfur atom or nitrogen atom contained in X may be connected to $S^+$ in general formula (1) through a bivalent connecting group. The bivalent connecting group can be an alkylene group, an alkylene group containing an oxygen atom or the like. The alkylene group preferably has 1 to 4 carbon atoms, more preferably 2 or 3 carbon atoms and most preferably 2 carbon atoms.

The compound represented by the general formula (1) is preferably represented by general formulae (1a) or (1b) below.

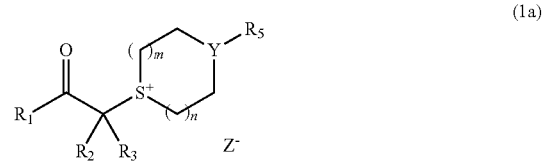

(1a)

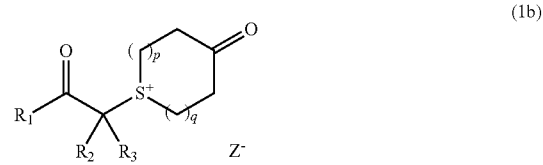

(1b)

In general formulae (1a) and (1b), $R_1$, $R_2$ and $R_3$ are as defined above in connection with general formula (1).

Y represents an oxygen atom, a sulfur atom or a nitrogen atom, preferably an oxygen atom or a nitrogen atom. Each of m, n, p and q is an integer of, preferably 0 to 3, more preferably 1 or 2 and most preferably 1. A substituent may be introduced in the alkylene group for the mutual connection of $S^+$ and Y. As a preferred substituent, there can be mentioned an alkyl group.

$R_5$ represents a group containing an electron withdrawing group when Y is a nitrogen atom and is not in existence when Y is an oxygen atom or a sulfur atom. Preferred examples of the electron withdrawing groups contained in $R_5$ are the same as set forth above in connection with the electron withdrawing groups contained in X.

When Y is a nitrogen atom, it is most preferred for $R_5$ to be a group represented by a formula —$SO_2$—$R_4$. $R_4$ represents an alkyl group, a cycloalkyl group or an aryl group, preferably an alkyl group. Particular examples and preferred examples of the alkyl group, cycloalkyl group and aryl group represented by $R_4$ can be the same as set forth above in connection with $R_1$.

The compound represented by the general formula (1) is most preferably represented by general formulae (1a') or (1b') below.

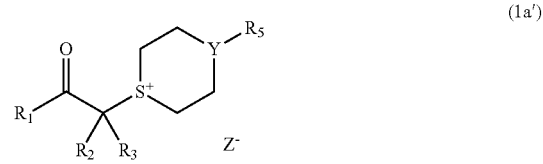

(1a')

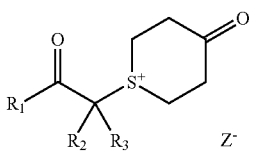

(1b')

In general formulae (1a') and (1b'), $R_1$, $R_2$, $R_3$, Y and $R_5$ are as defined above in connection with general formulae (1a) and (1b).

$Z^-$ represents any of sulfonate anions of general formula (2) below or any of disulfonylimidate anion of general formula (2') below.

A sulfonate anion represented by the general formula (2) will be described below in detail.

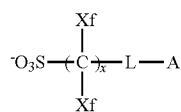

(2)

In formula (2), each Xfs independently represents a fluorine atom or an alkyl group substituted with at least one fluorine atom.

L represents a single bond or a bivalent connecting group.

A represents an organic group containing a cyclic structure.

x is an integer of 1 to 20.

An anion represented by the general formula (2) will be described below in more detail.

Each Xfs independently represents a fluorine atom or an alkyl group substituted with at least one fluorine atom. The alkyl group of the alkyl group substituted with a fluorine atom preferably has 1 to 10 carbon atoms, more preferably 1 to 4 carbon atoms. The alkyl group substituted with a fluorine atom, represented by Xf is preferably a perfluoroalkyl group.

Xf is preferably a fluorine atom or a perfluoroalkyl group having 1 to 4 carbon atoms. In particular, there can be mentioned a fluorine atom, $CF_3$, $CHF_2$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ or $CH_2CH_2C_4F_9$. Of these, a fluorine atom, $CF_3$, $CHF_2$, and $C_2F_5$ are preferable. It is especially preferable for each Xf to be a fluorine atom.

L represents a single bond or a bivalent connecting group. As the bivalent connecting group, there can be mentioned —COO—, —OCO—, —CO—, —O—, —S—, —SO—, —SO₂—, —N(Ri)- (in which Ri represents a hydrogen atom or an alkyl), an alkylene group (preferably 1 to 6 carbon atoms, more preferably 1 to 3 carbon atoms, even more preferably 1 or 2 carbon atoms, and most preferably one carbon atom), a cycloalkylene group (preferably 3 to 10 carbon atoms), an alkenylene group (preferably 2 to 6 carbon atoms), a bivalent connecting group comprised of a combination of two or more of these, or the like. L is preferably —COO—, —OCO—, —CO—, —SO₂—, —CON(Ri)-, —SO₂N(Ri)-, —CON(Ri)-alkylene-, —N(Ri)CO-alkylene-, —COO-alkylene- or —OCO-alkylene-, more preferably —COO—, —OCO—, —COO-alkylene- or —OCO-alkylene-.

When L represents —COO-alkylene- or —OCO-alkylene-, a preferable embodiment for connection of L and A is —COO-alkylene-A or -alkylene-OCO-A.

Specific examples and preferred examples of the alkyl groups represented by Ri can be the same as set forth above in connection with $R_1$ to $R_5$.

The organic group containing a cyclic structure represented by A is not particularly limited as long as a cyclic structure is contained. As the cyclic organic group, there can be mentioned an alicyclic group, an aryl group, a heterocyclic group (including not only any of those exhibiting aromaticity but also those exhibiting no aromaticity, for example, including structures such as a tetrahydropyran ring, a lactone ring, a sultone ring, and a cyclic ketone) or the like.

The alicyclic group may be monocyclic or polycyclic. Preferably, the alicyclic group is a monocycloalkyl group, such as a cyclopentyl group, a cyclohexyl group or a cyclooctyl group, or a polycycloalkyl group, such as a norbornyl group, a norbornene-yl group, a tricyclodecanyl group (for example, a tricyclo[5.2.1.0(2,6)]decanyl group), a tetracyclodecanyl group, a tetracyclododecanyl group or an adamantyl group. An alicyclic group containing a nitrogen atom such as a piperidine group, a decahydroquinoline group and a decahydroisoquinoline group is also preferred. Of the mentioned groups, alicyclic groups with a bulky structure having 7 or more carbon atoms, namely, a norbornyl group, a tricyclodecanyl group, a tetracyclodecanyl group, a tetracyclododecanyl group, an adamantyl group, a decahydroquinoline group and a decahydroisoquinoline group are preferable from the viewpoint of inhibiting any in-film diffusion in the operation of post-exposure bake (PEB), thereby enhancing the exposure latitude.

As the aryl group, there can be mentioned a benzene ring, a naphthalene ring, a phenanthrene ring or an anthracene ring. In particular, the naphthalene of low absorbance is preferable from the viewpoint of the absorbance at 193 nm.

As the heterocyclic group, there can be mentioned a furan ring, a thiophene ring, a benzofuran ring, a benzothiophene ring, a dibenzofuran ring, a dibenzothiophene ring or a pyridine ring. In particular, a furan ring, a thiophene ring and a pyridine ring are preferable.

A substituent may be introduced in the above cyclic organic group. As the substituent, there can be mentioned an alkyl group (may be linear or branched, preferably having 1 to 12 carbon atoms), an aryl group (preferably having 6 to 14 carbon atoms), a hydroxyl group, an alkoxy group, an ester group, an amido group, a urethane group, a ureido group, a thioether group, a sulfonamido group, a sulfonic ester group or the like.

The carbon as a constituent of the cyclic organic group (carbon contributing to ring formation) may be a carbonyl carbon.

x is preferably 1 to 8, more preferably 1 to 4, especially preferably 1 to 3, and most preferably 1.

In the sulfonate anion represented by the general formula (2), it is preferred the content ratio of a fluorine atom is low to realize the uniform distribution of an acid generator in the resist film. More specifically, the content ratio of a fluorine atom represented by (the sum of atomic weight for all of the fluorine atoms contained in the anion)/(the sum of atomic weight for all of the atoms contained in the anion) is preferably 0.30 or less, more preferably 0.25 or less, even more preferably 0.20 or less, and especially preferably 0.15 or less.

Disulfonylimidate anions of general formula (2') as another form of $Z^-$ will be described below.

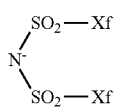
(2')

In general formula (2'), Xfs are as defined above in connection with general formula (2), and preferred examples thereof are also the same as mentioned above. In general formula (2'), two Xfs may be connected to each other to thereby form a ring structure.

It is preferred for the disulfonylimidate anion represented by $Z^-$ to be a bis(alkylsulfonyl)imide anion.

Each of the alkyl groups in the bis(alkylsulfonyl)imide anion is preferably an alkyl group having 1 to 5 carbon atoms.

In the bis(alkylsulfonyl)imide anion, two alkyl groups may be connected to each other to thereby form an alkylene group (preferably 2 to 4 carbon atoms), which may form a ring in cooperation with the imide group and two sulfonyl groups. The ring structure that may be formed in the bis(alkylsulfonyl)imide anion is preferably a 5- to 7-membered ring, more preferably a 6-membered ring.

As substituents that can be introduced in the above alkyl groups and alkylene group formed by the mutual connection of two alkyl groups, there can be mentioned a halogen atom, an alkyl group substituted with a halogen atom, an alkoxy group, an alkylthio group, an alkyloxysulfonyl group, an aryloxysulfonyl group, a cycloalkylaryloxysulfonyl group and the like. A fluorine atom and an alkyl group substituted with a fluorine atom are preferred.

From the viewpoint of acid strength, it is preferred for the pKa value of generated acid to be −1 or below. This would contribute to an enhancement of sensitivity.

Specific examples of the preferred compounds (A) represented by the general formula (1), which however in no way limit the scope of the present invention.

A-1

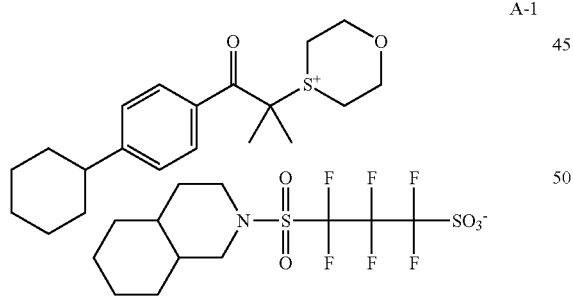

A-2

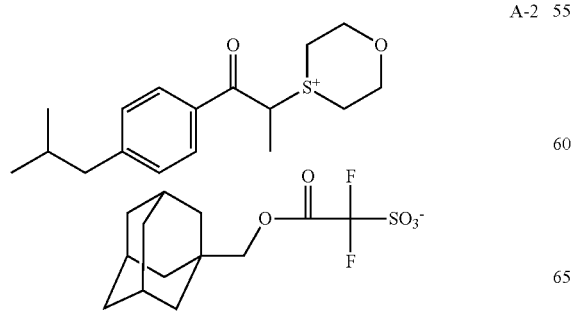

A-3

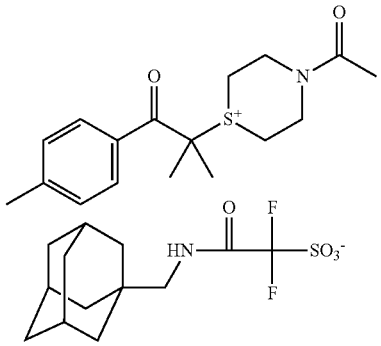

A-4

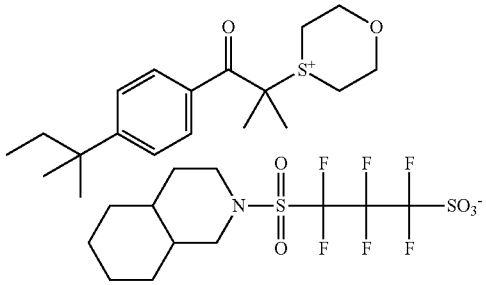

A-5

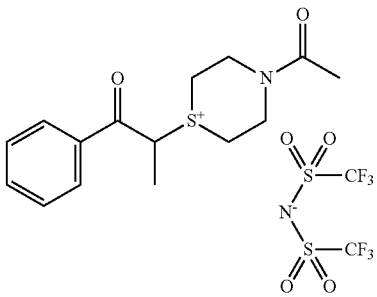

A-6

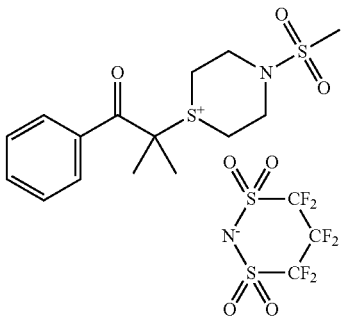

A-7

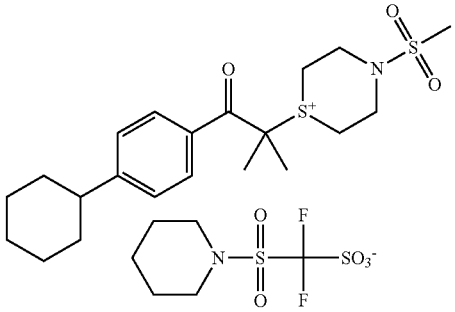

A-8
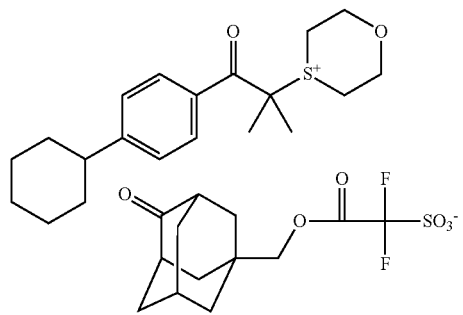
A-9
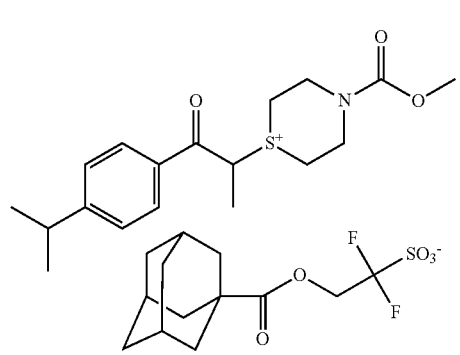
A-10
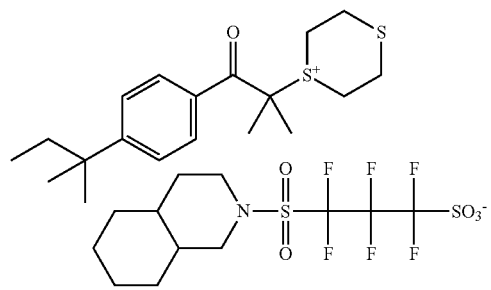
A-11
A-12
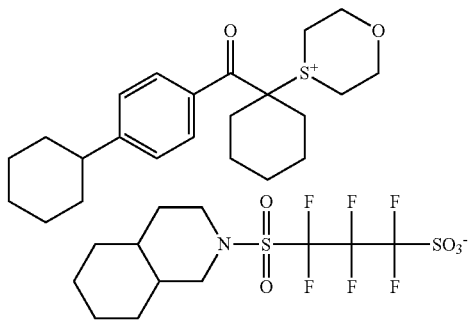
A-13
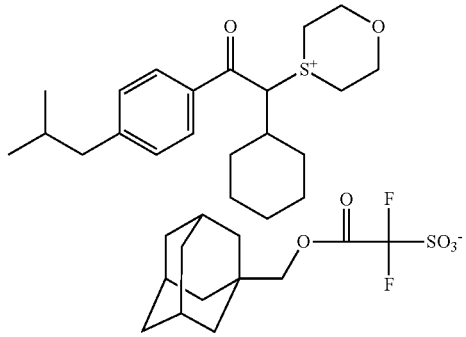
A-14
A-15
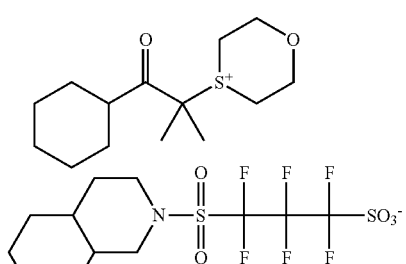
A-16
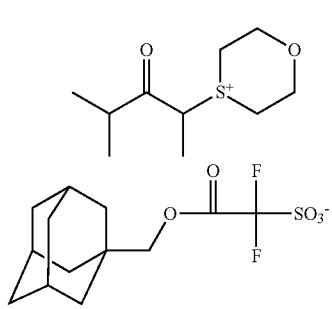

A-17
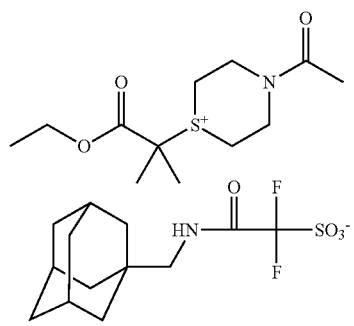
A-18
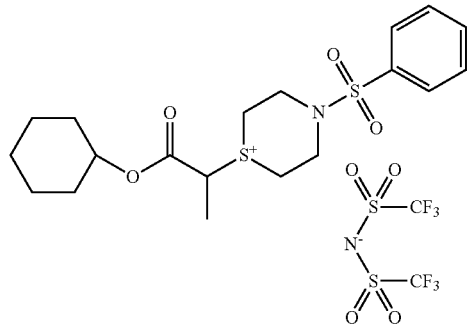
A-19
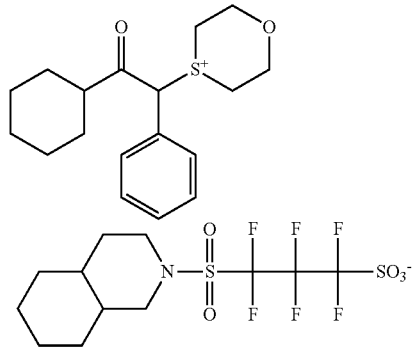
A-20
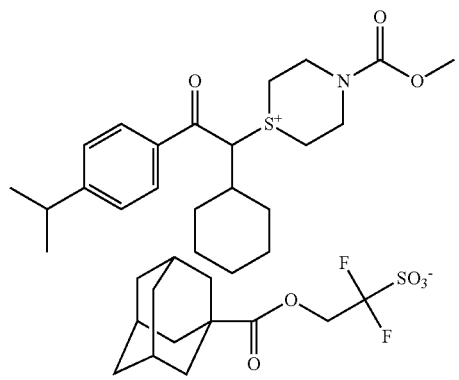
A-21
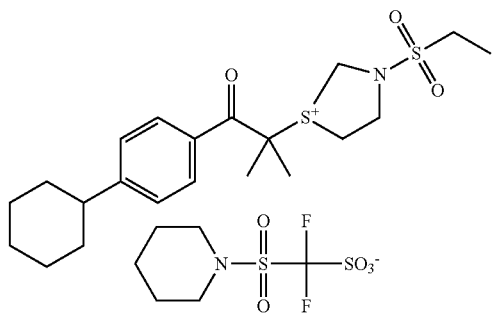
A-22
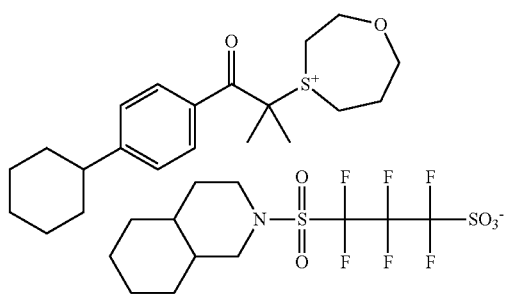
A-23
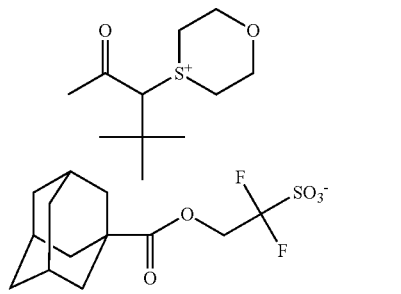
A-24
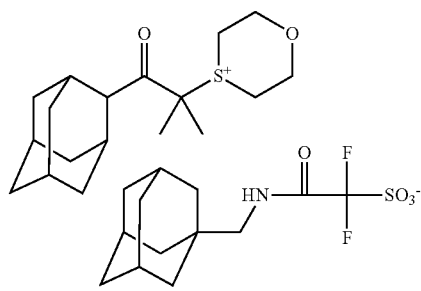
A-25
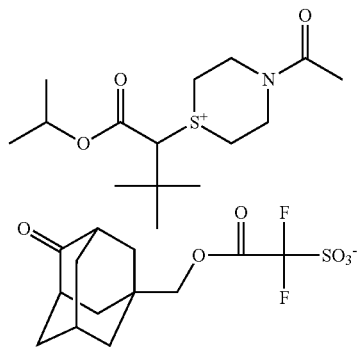

A-26
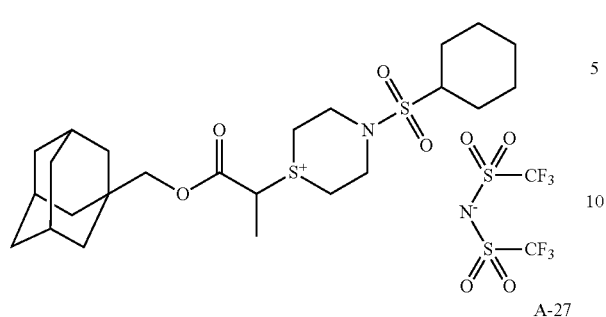
A-27
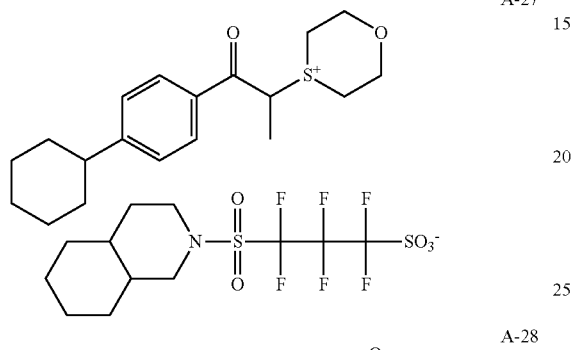
A-28
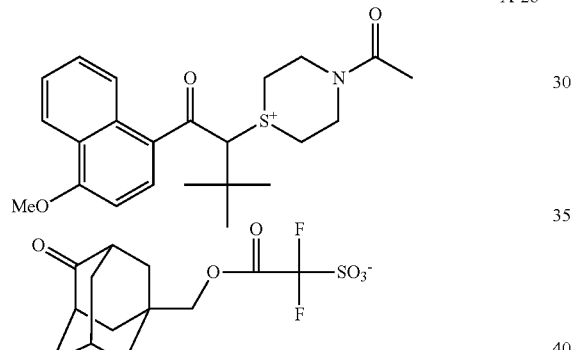
A-29
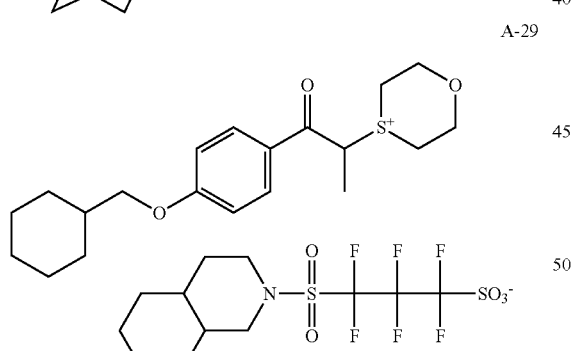
A-30
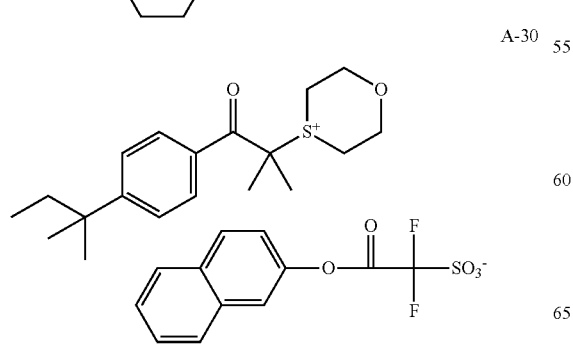
A-31
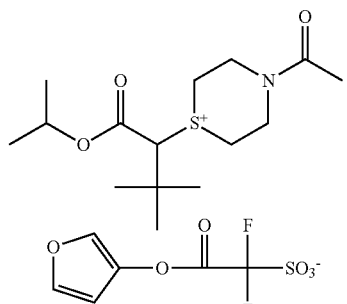
A-32
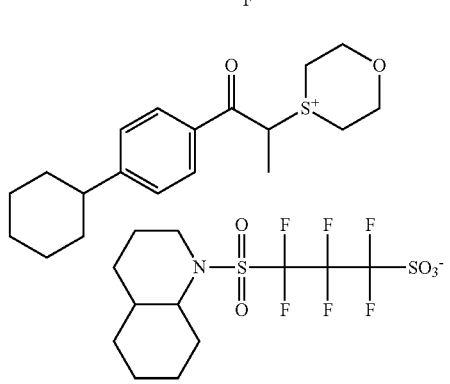
A-33
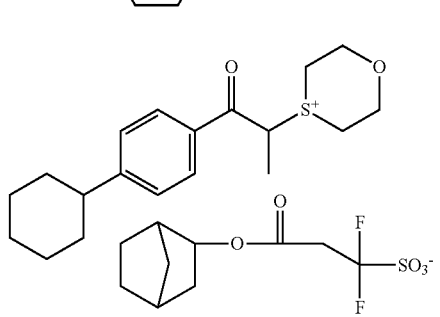
A-34
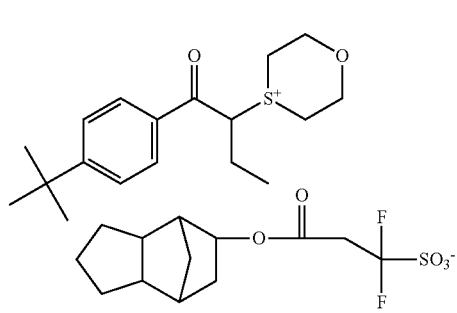
A-35

A-36
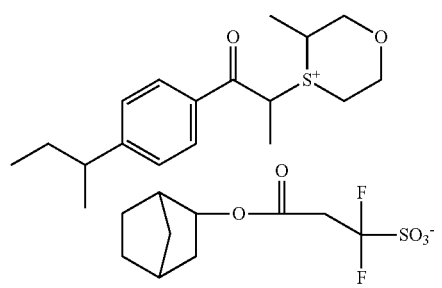
A-37
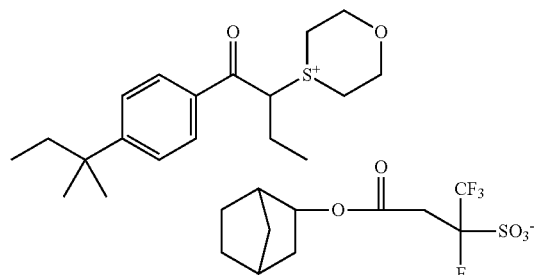
A-38
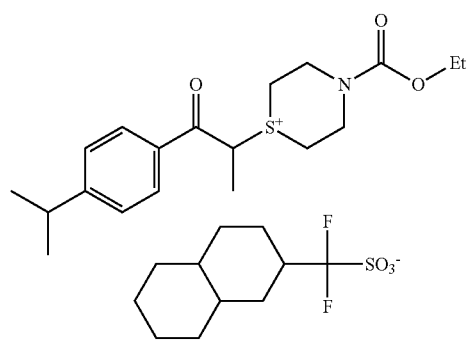
A-39
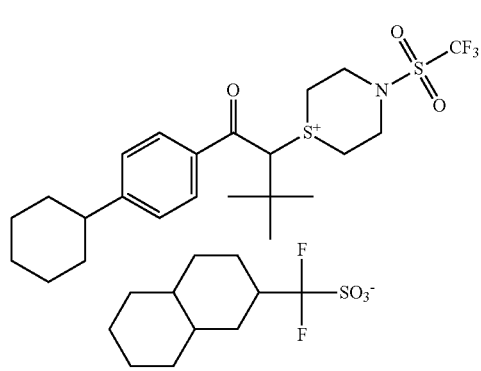
A-40
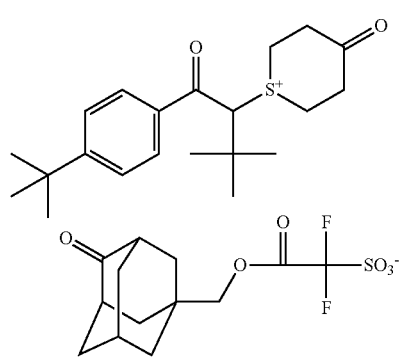
A-41
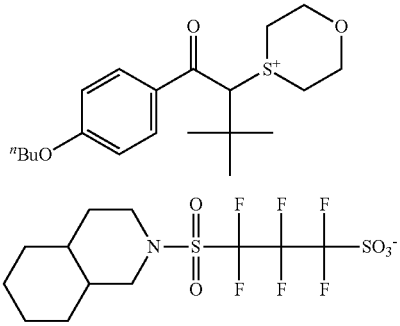
A-42
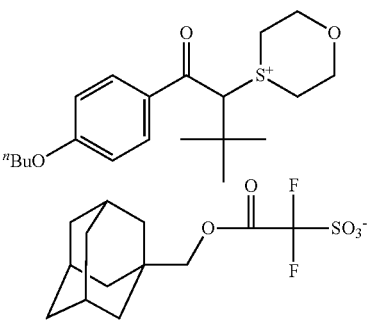
A-43
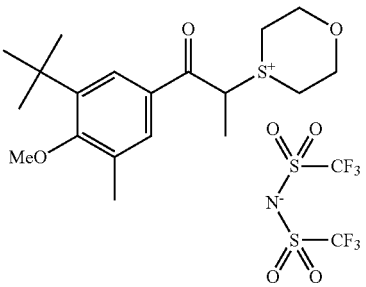
A-44
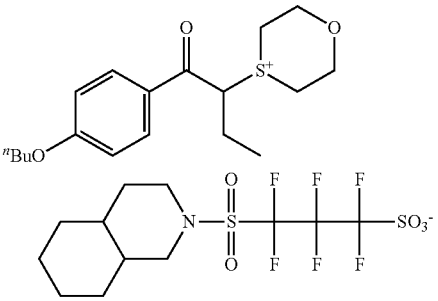
A-45
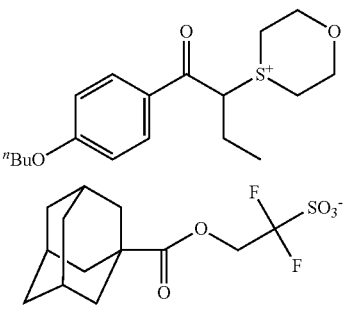

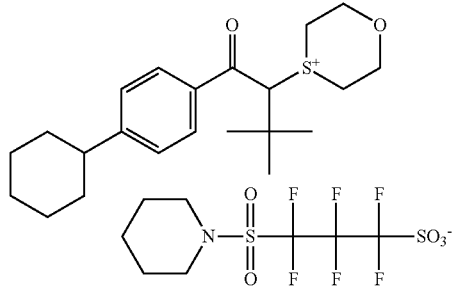
A-46
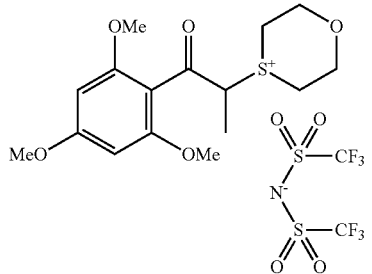
A-51
A-47
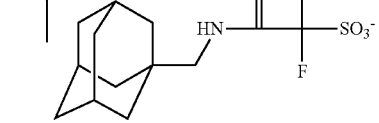
A-52
A-48
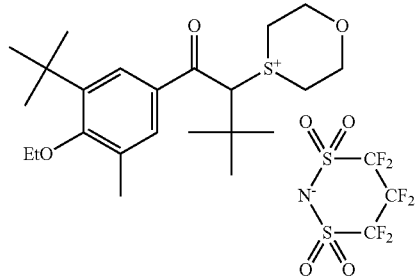
A-53
A-49
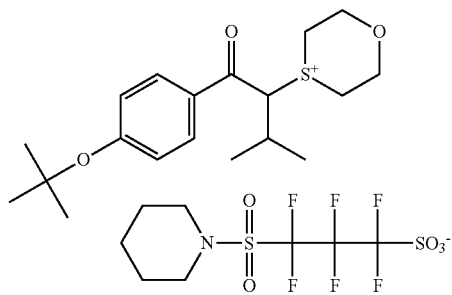
A-54
A-50
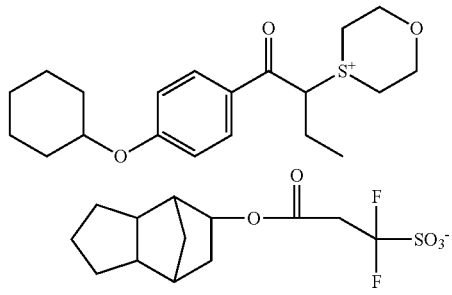
A-55

-continued
A-56
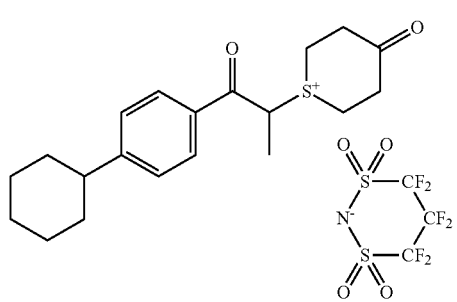
A-57
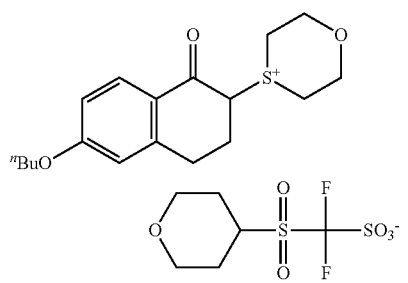
A-58
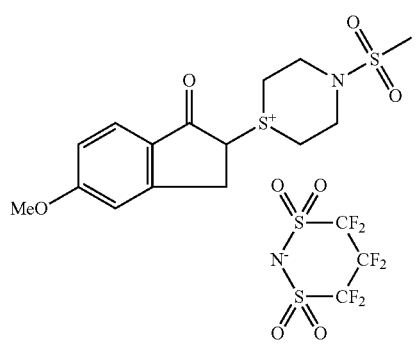
A-59
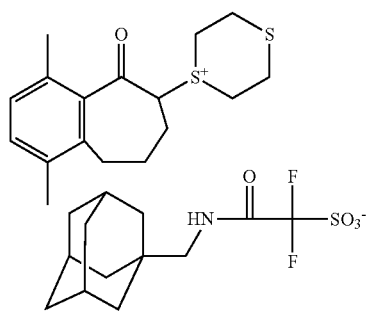
A-60
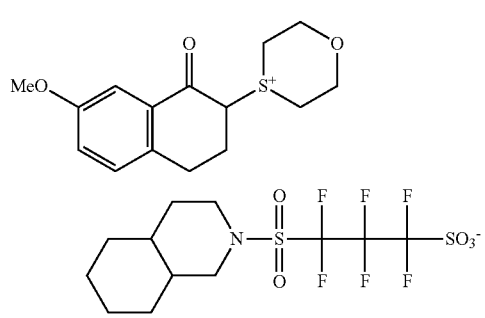
-continued
A-61
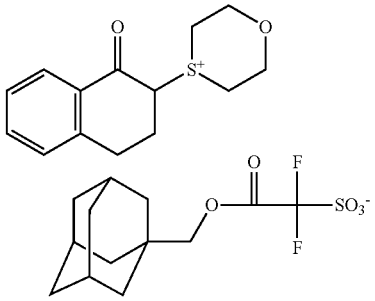
A-62
A-63
A-64
A-66

A-67
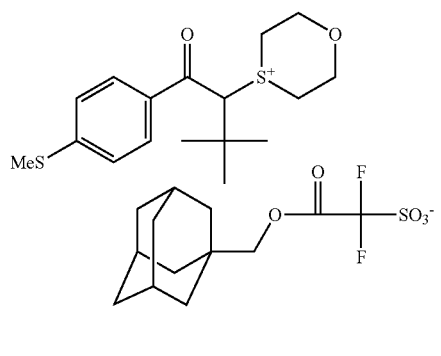
A-68
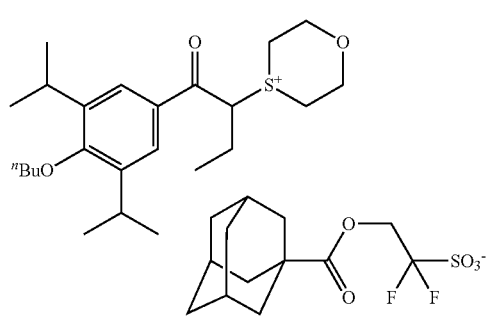
A-69
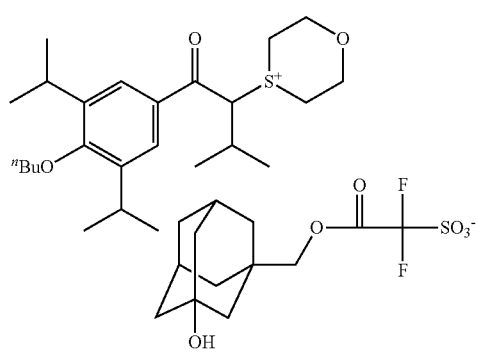
A-70
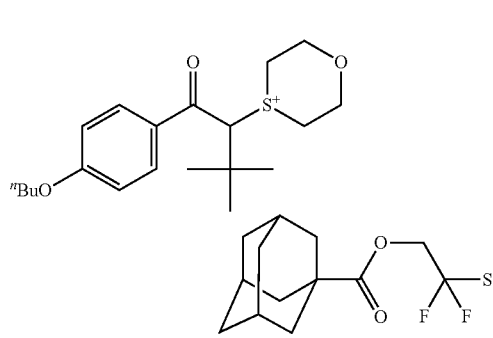
A-71
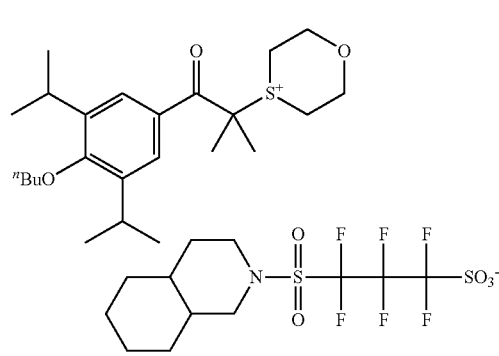
A-72
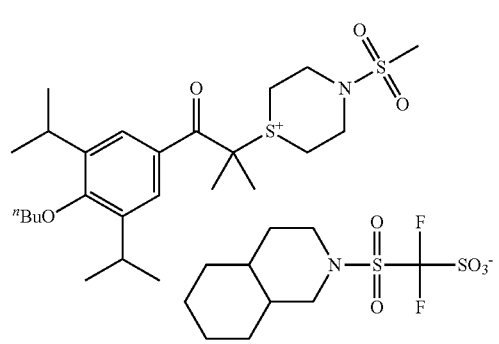
A-73
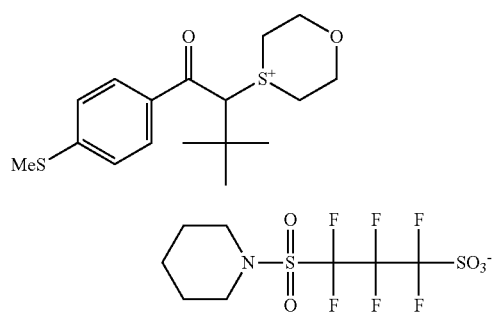
A-74
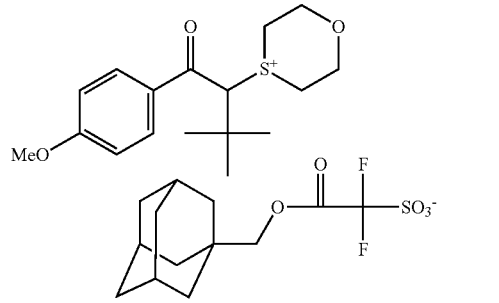

A-75
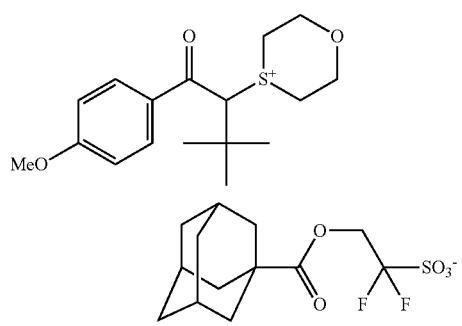
A-76
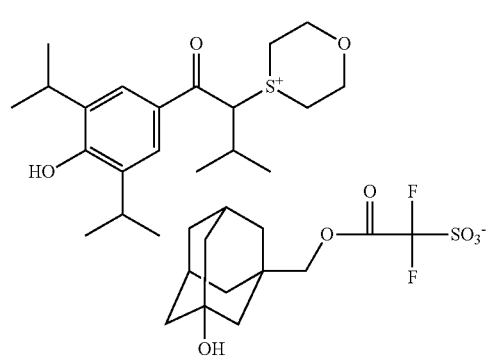
A-77
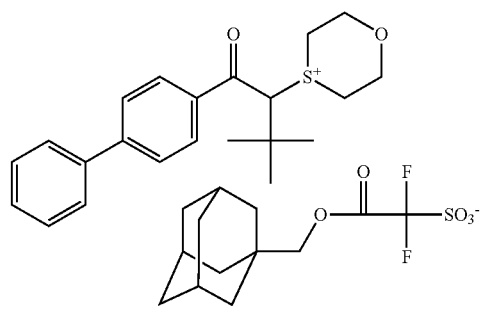
A-78
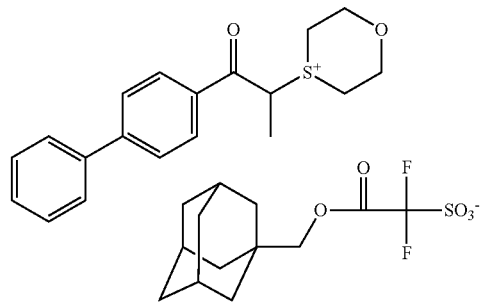
A-79
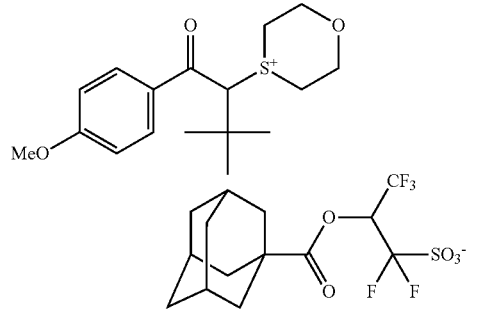
A-80
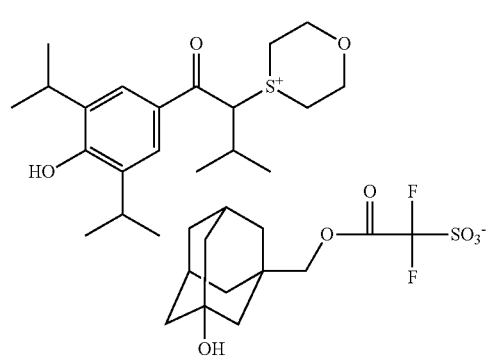
A-81
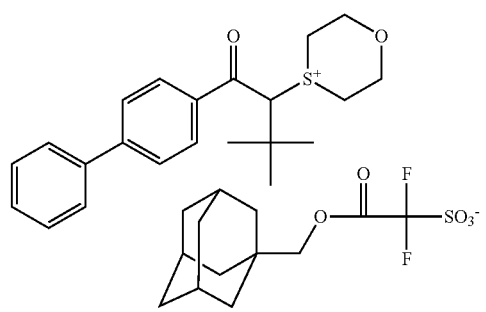
A-82
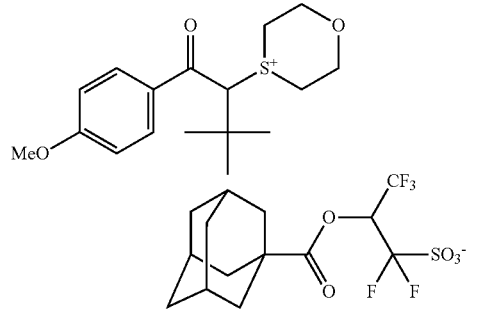
A-83
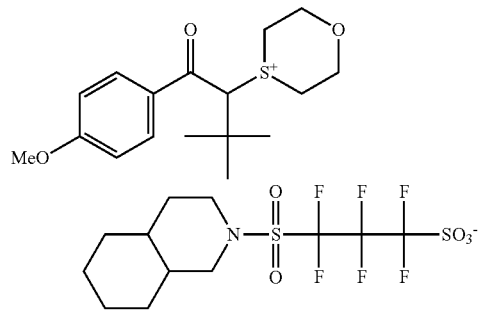
A-84
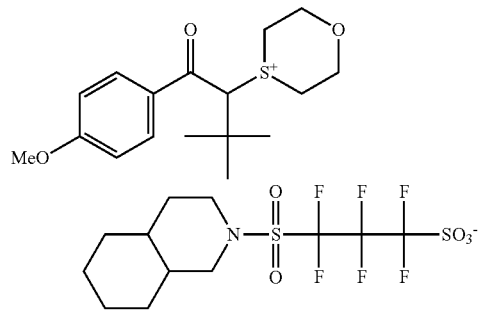

A-85
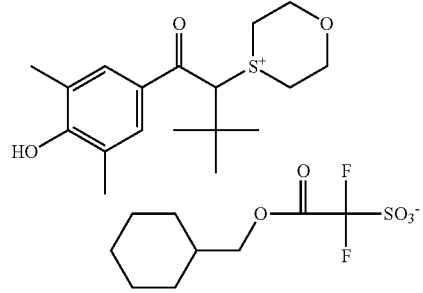
A-86
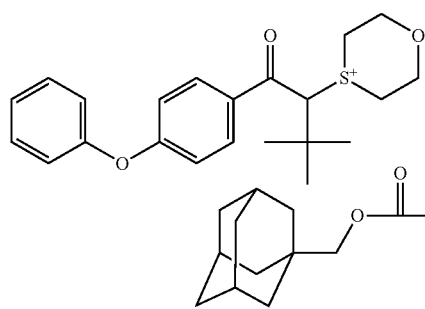
A-87
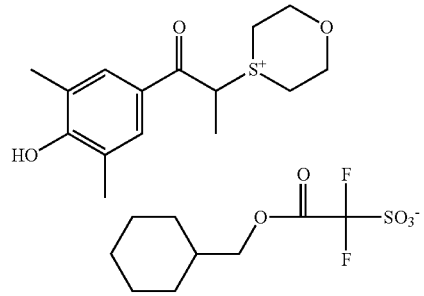
A-88
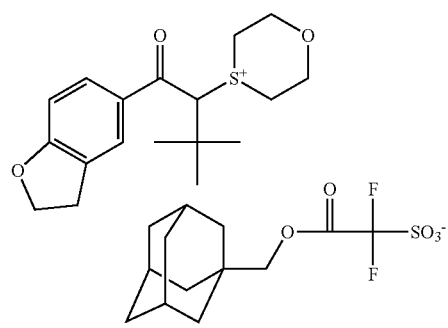
A-89
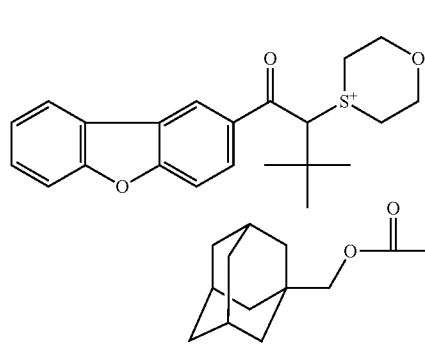
A-90
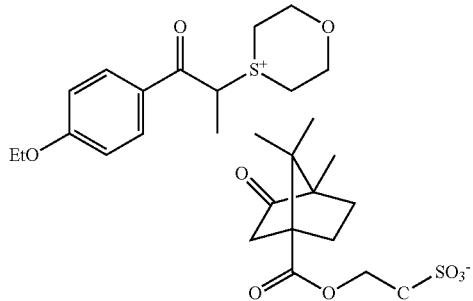
A-91
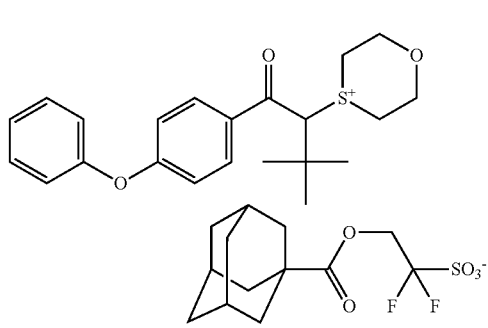
A-92
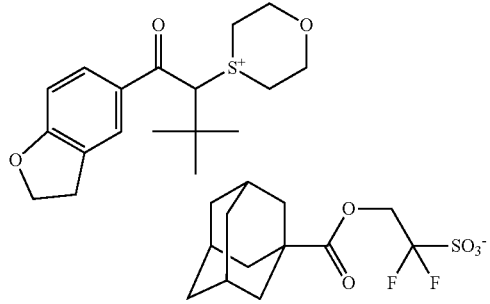
A-93
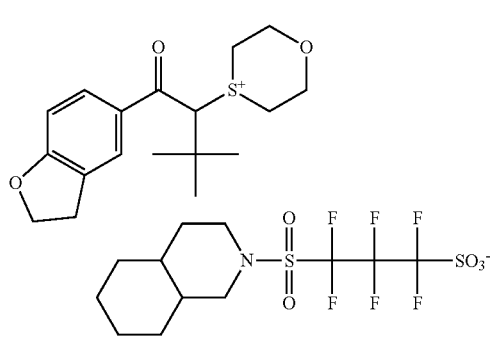

-continued
A-94
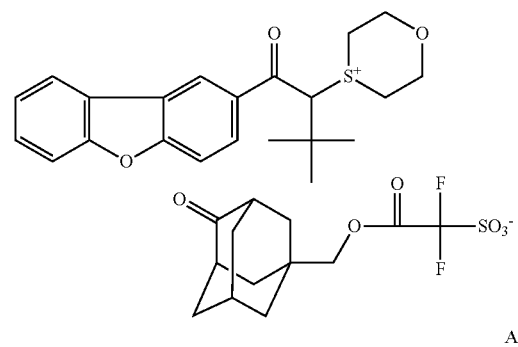
A-95
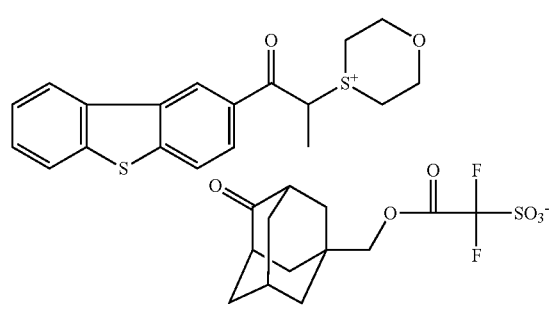
A-96
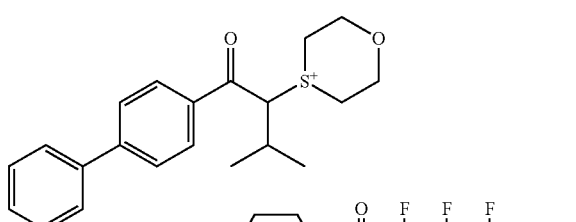
A-97
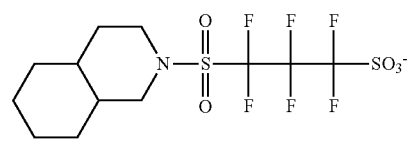
A-98
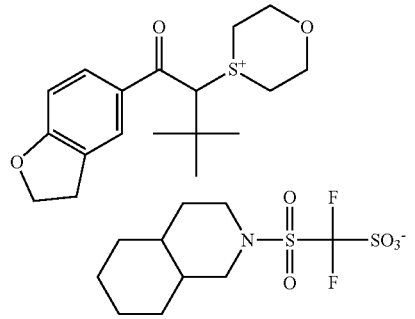
-continued
A-99
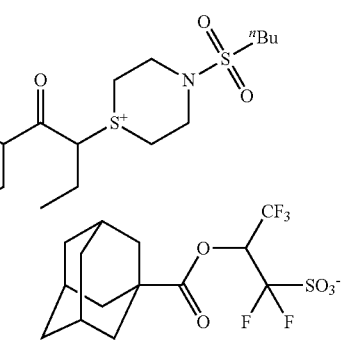
A-100
A-101
A-102
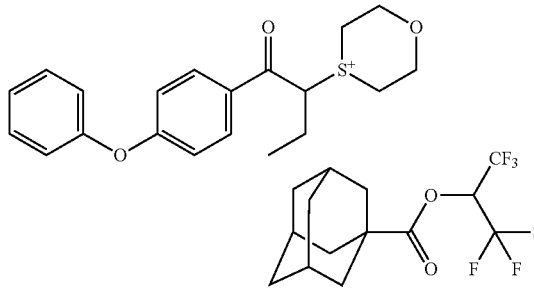

A-103
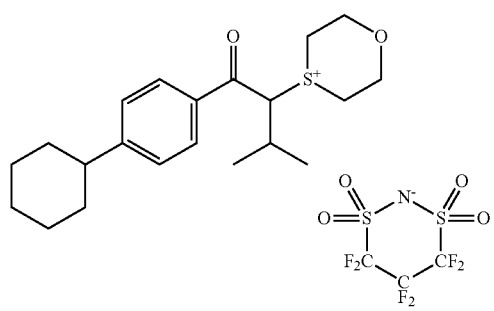
A-104
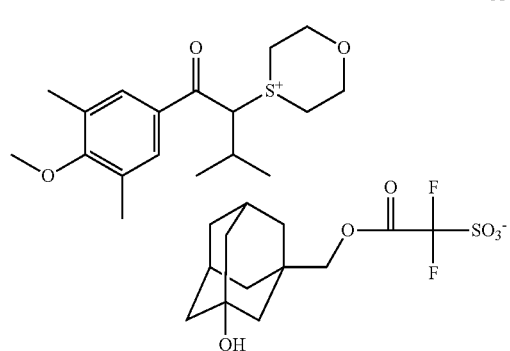
A-105
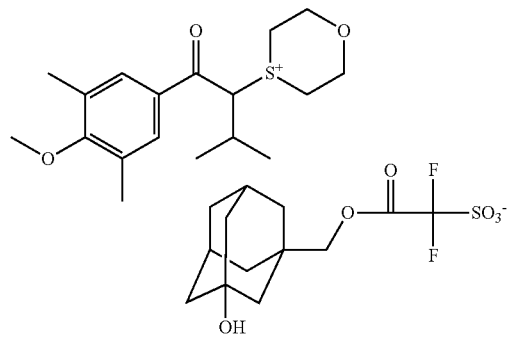
A-106
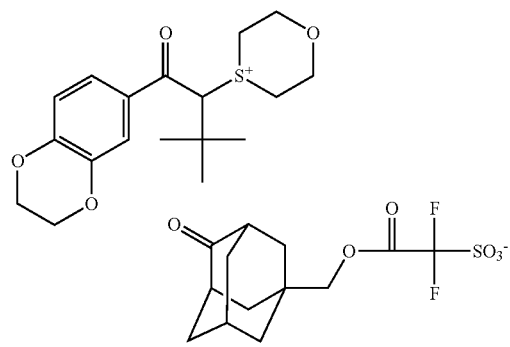
A-107
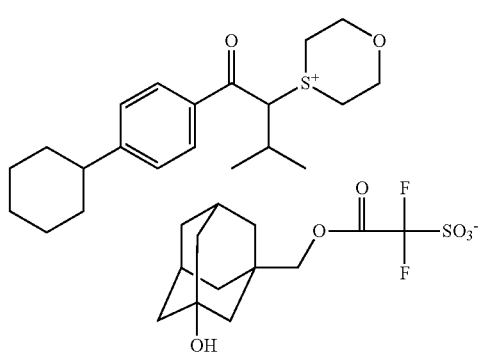
A-108
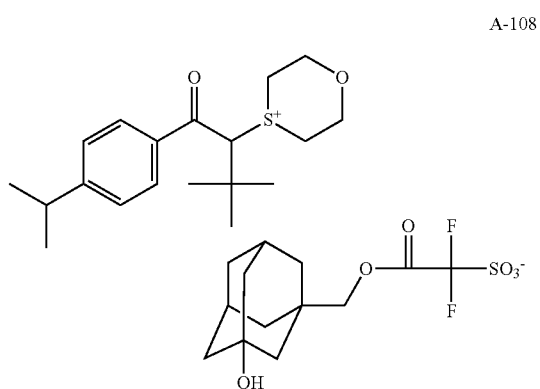
A-109
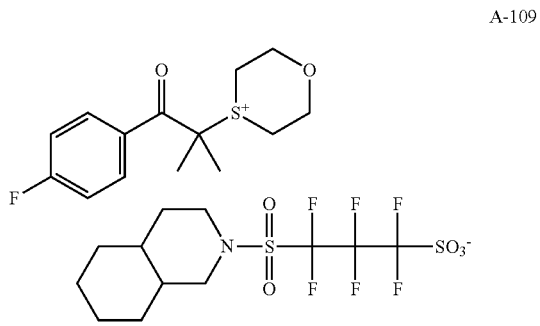
A-110
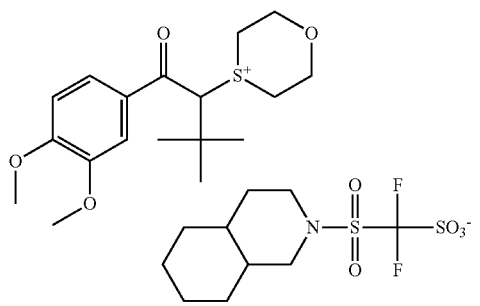

-continued
A-111
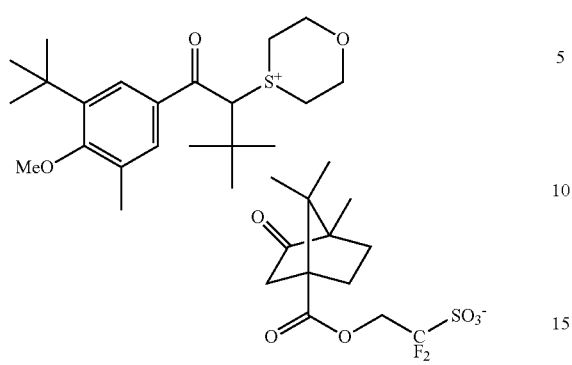
A-112
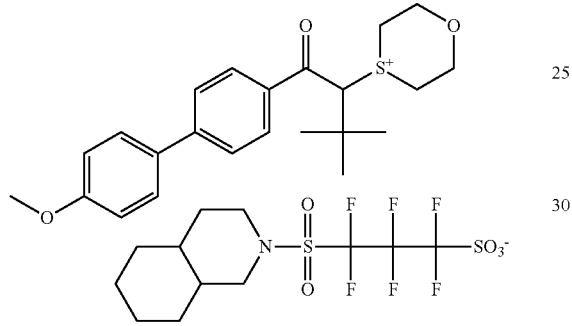
A-113
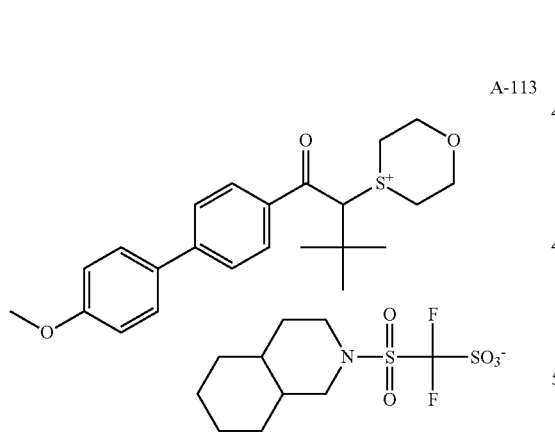
A-114
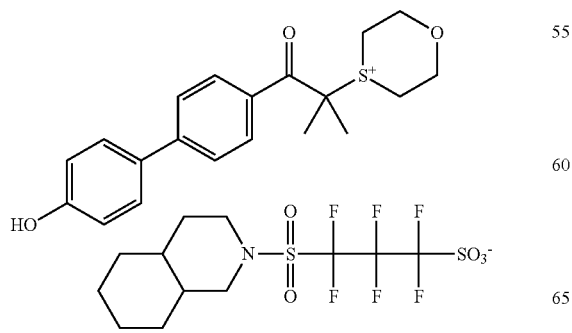
-continued
A-115
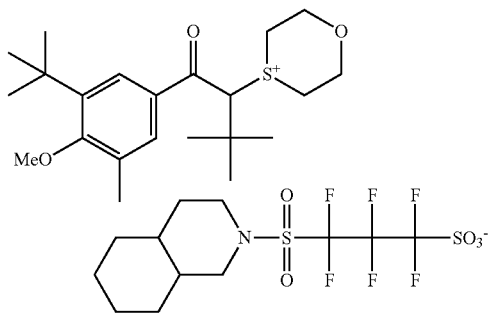
A-116
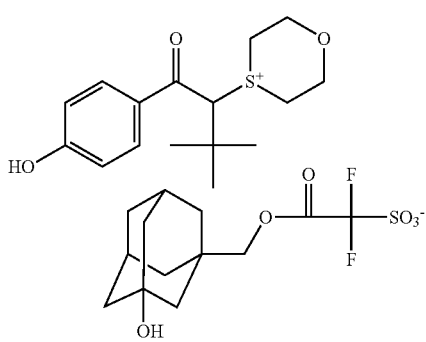
A-117
A-118
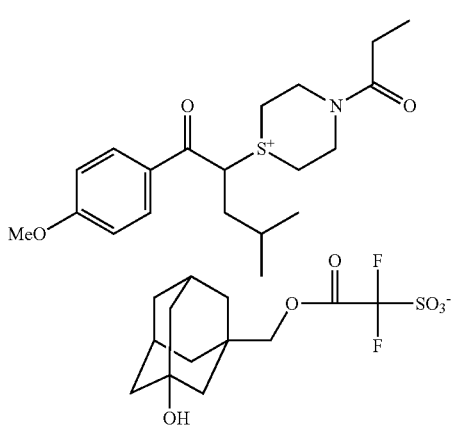

A-119
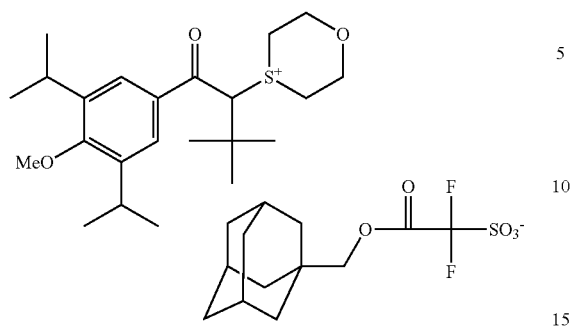
A-123
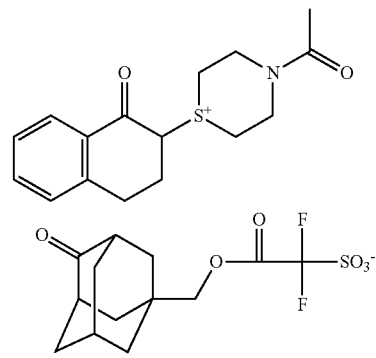
A-120
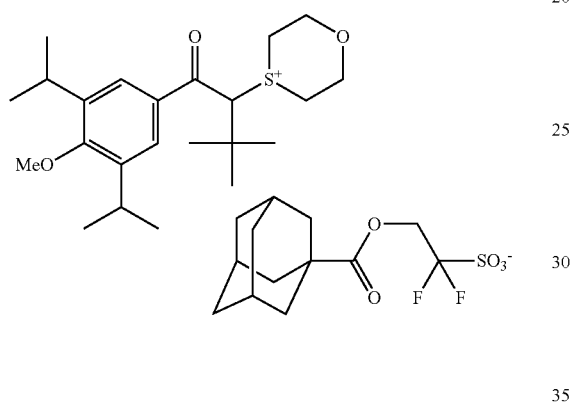
A-124
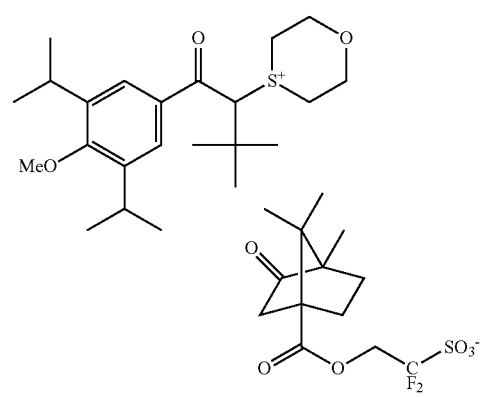
A-121
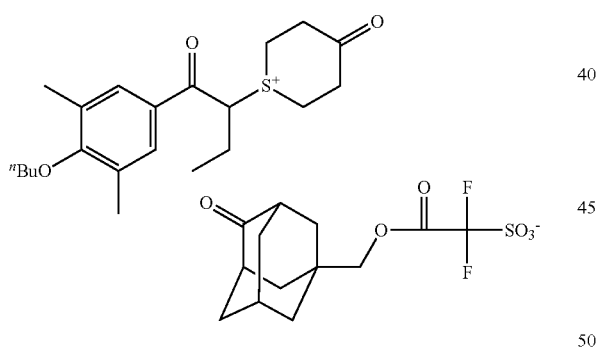
A-125
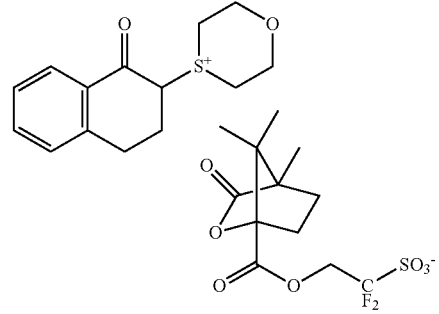
A-122
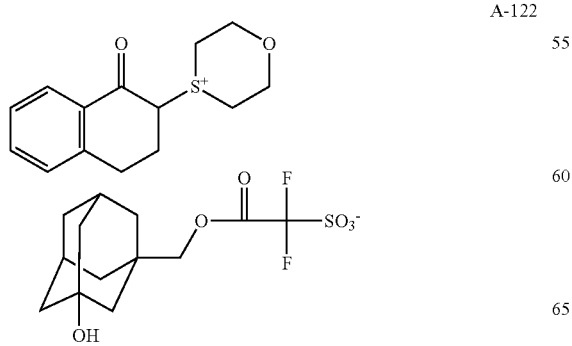
A-126
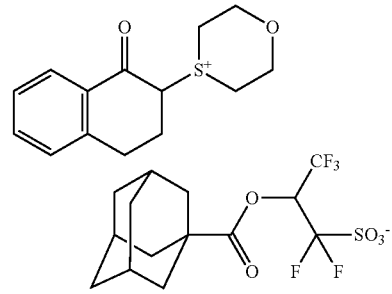

A-127
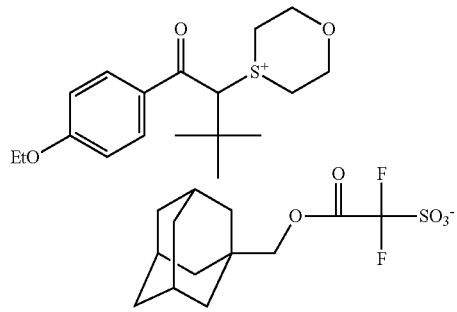
A-128
A-129
A-130
A-131
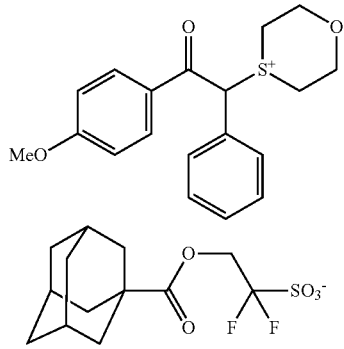
A-132
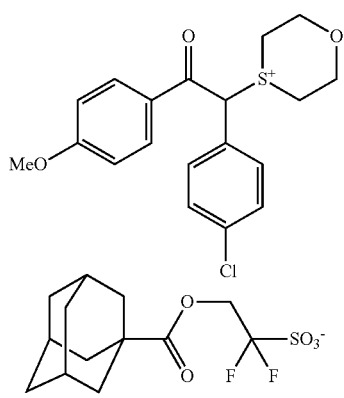
A-133
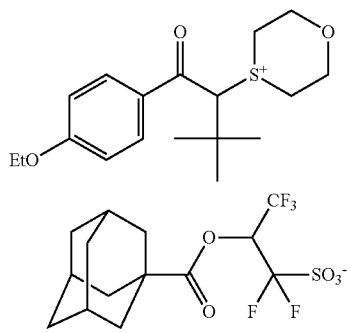
A-134
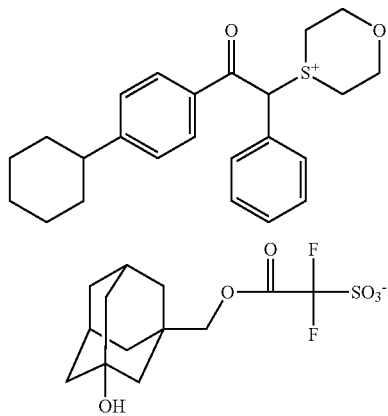

A-135
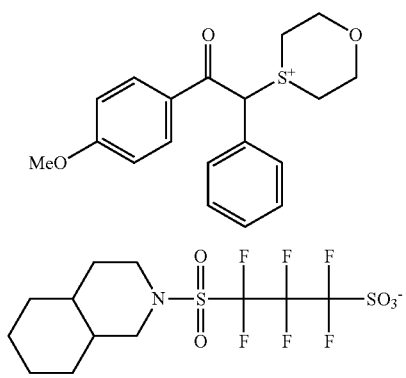
A-136
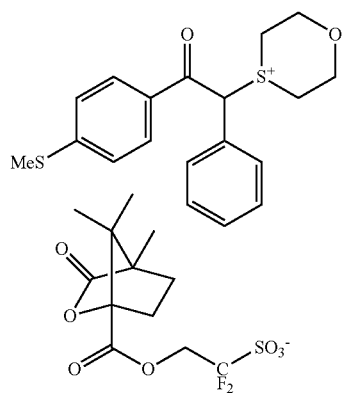
A-137
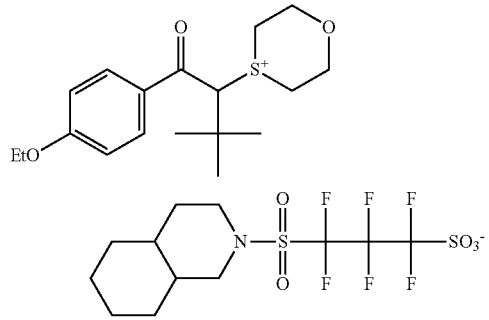
A-138
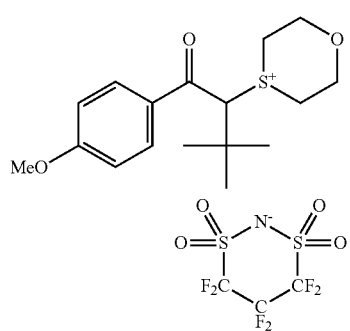
A-139
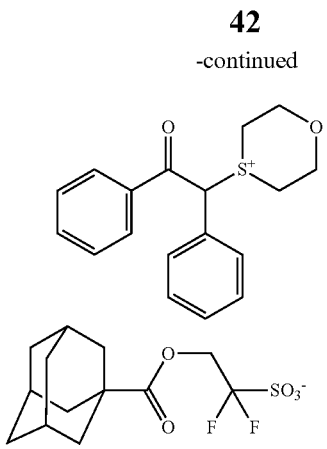
A-140
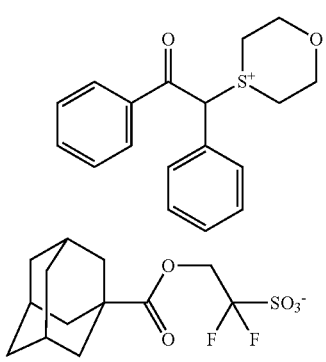
A-141
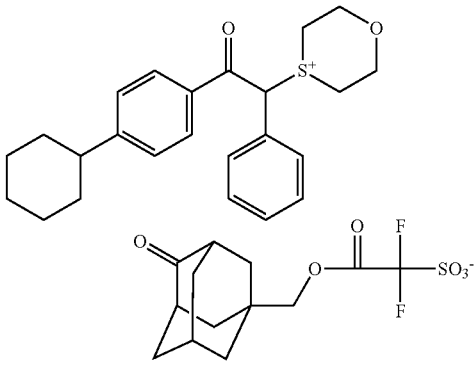
A-142
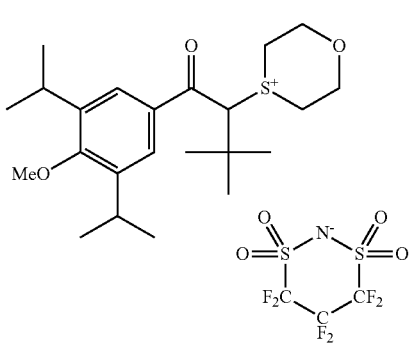

A-143
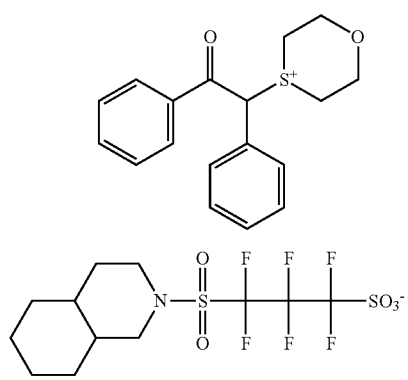
A-147
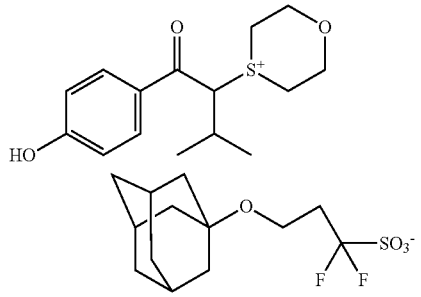
A-144
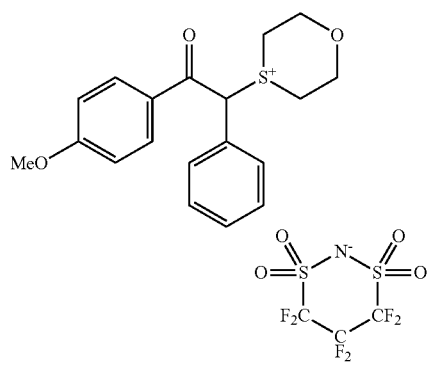
A-148
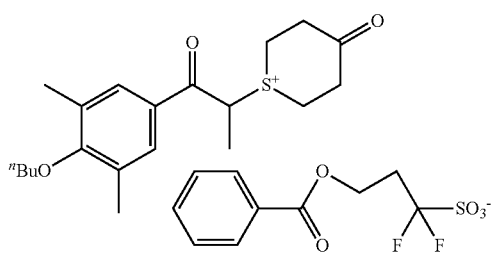
A-145
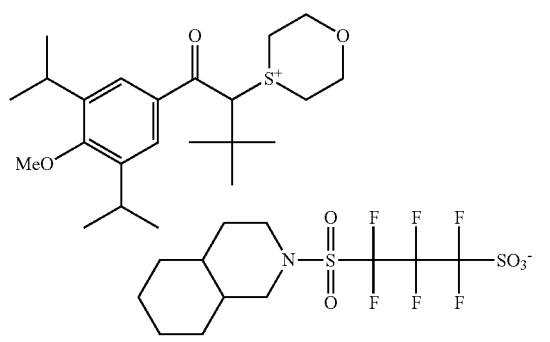
A-149
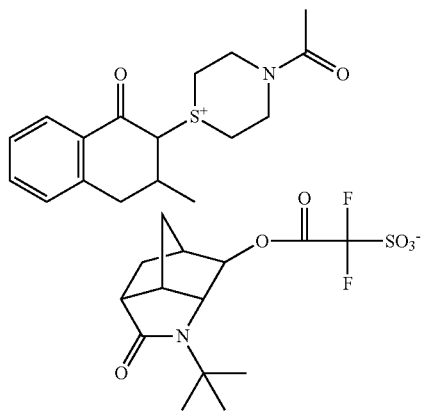
A-146
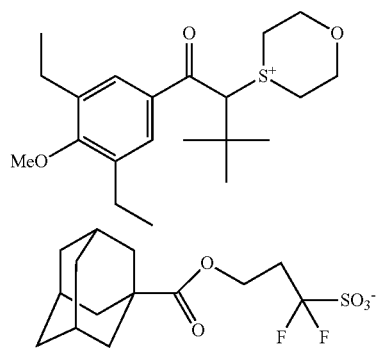
A-150
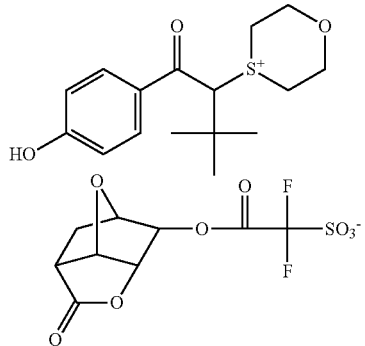

-continued

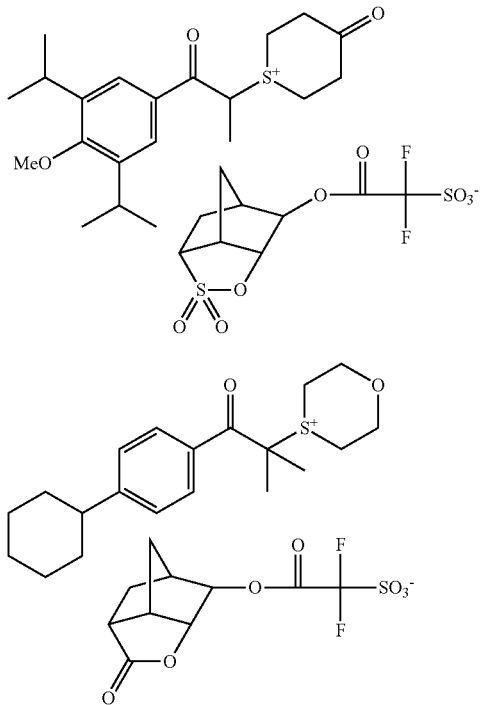

A-151

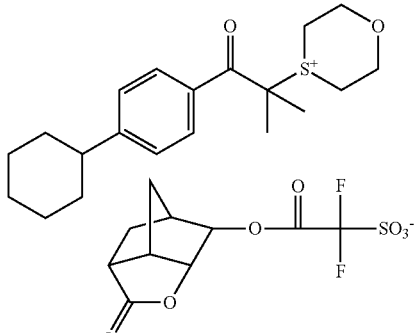

A-152

The sulfonate anion represented by the general formula (2) or a salt thereof (for example, an onium salt or a metal salt) can be synthesized by common sulfonic acid esterization reaction or sulfonamidation reaction. For example, the compound can be synthesized by selectively reacting one sulfonyl halide moiety of bissulfonyl halide with amine, alcohol or amide compound to form a sulfonamide bond, a sulfonic acid ester bond or a sulfonimide bond followed by hydrolysis of another sulfonyl halide moiety thereof. Alternatively, the compound can be synthesized by reacting cyclic sulfonic acid anhydride with amine, alcohol or amide compound to thereby cause a ring-opening.

As the salt containing the sulfonate anion represented by the general formula (2), a sulfonic acid metal salt, a sulfonic acid oniumu salt and the like are exemplified. As the metal in the sulfonic acid metal salt, $Na^+$, $Li^+$, $K^+$ and the like are exemplified. As an onium cation in the sulfonic acid oniumu salt, an ammoniumu cation, a sulfonium cation, a iodonium cation, a phosphonium cation, a diazonium cation and the like are exemplified.

The sulfonate anion represented by the general formula (2) and the sult thereof can be used for synthesis of the compound (A) that generates a sulfonic acid corresponding to the general formula (2) when exposed to actinic rays or radiation.

The compounds (A) can be synthesized by a method comprising a salt exchange between sulfonate anions of general formula (2) above and photoactive onium salts, such as a sulfonium salt corresponding to a sulfonium cation in general formula (1) above.

The content of compound (A) in the composition of the present invention, based on the total solids of the composition, is preferably in the range of 0.1 to 30 mass %, more preferably 0.5 to 25 mass % and further more preferably 5 to 20 mass %.

The composition of the present invention may comprise two or more types of compounds (A) and may comprise a photoacid generator (hereinafter also referred to as a compound (A')) other than the compounds (A) in addition to the compound (A). When two or more types of photoacid generators are contained in the composition of the present invention, it is preferred for the total content of photoacid generators to fall within the above-mentioned range.

The compound (A') is not especially limited, but preferably, those represented by the following general formulae (ZI'), (ZII') and (ZIII") can be exemplified.

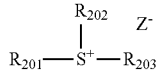 (ZI')

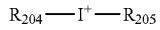 (ZII')

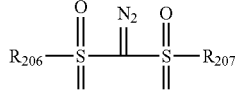 (ZIII')

In the above general formula (ZI'), each of $R_{201}$, $R_{202}$ and $R_{203}$ independently represents an organic group.

The number of carbon atoms in the organic group represented by $R_{201}$, $R_{202}$ and $R_{203}$ is generally in the range of 1 to 30, preferably 1 to 20.

Two of $R_{201}$ to $R_{203}$ may be bonded to each other to thereby form a ring structure. The ring structure may contain therein an oxygen atom, a sulfur atom, an ester group, an amido group or a carbonyl group. As the group formed by the mutual bonding of two of $R_{201}$ to $R_{203}$, there can be mentioned, for example, an alkylene group, such as a butylene group or a pentylene group.

As the organic group represented by $R_{201}$, $R_{202}$ and $R_{203}$, for example, a corresponding group in a compound (ZI'-1) to be described below can be exemplified.

Compounds having two or more of the structures of the general formula (ZI') may be used as the acid generator. For example, use may be made of a compound having a structure in which at least one of the $R_{201}$ to $R_{203}$ of one of the compounds of the general formula (ZI') is bonded to at least one of the $R_{201}$ to $R_{203}$ of another of the compounds of the general formula (ZI') via a single bond or connecting group.

$Z^-$ represents a nonnucleophilic anion (i.e. an anion whose capability of inducing a nucleophilic reaction is extremely low). As the nonnucleophilic anion represented by $Z^-$, a sulfonate anion (an aliphatic sulfonate anion, an aromatic sulfonate anion, a camphor sulfonate anion and the like), a carboxylate anion (an aliphatic carboxylate anion, an aromatic carboxylate anion, an aralkyl carboxylate anion and the like), a sulfonylimide anion, a bis(alkylsulfonyl) imide anion, and a tris(alkylsulfonyl)methide anion can be exemplified.

The aliphatic moiety of the aliphatic sulfonate anion and the aliphatic carboxylate anion may be an alkyl group or a cycloalkyl group, being preferably an alkyl group having 1 to 30 carbon atoms or a cycloalkyl group having 3 to 30 carbon atoms.

As a preferred aromatic group of the aromatic sulfonate anion and aromatic carboxylate anion, an aryl group having 6 to 14 carbon atoms, such as a phenyl group, a tolyl group and a naphthyl group can be exemplified.

The alkyl group, cycloalkyl group and aryl group exemplified abobe may have one or more substituents. As the specific example of the substituent, a nitro group, a halogen atom such as a fluorine atom, a carboxyl group, a hydroxy group, an amino group, a cyano group, an alkoxy group (preferably having 1 to 15 carbon atoms), a cycloalkyl group (preferably having 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), an alkoxycarbonyloxy group (preferably having 2 to 7 carbon atoms), an alkylthio group (preferably having 1 to 15 carbon atoms), an alkylsulfonyl group (preferably having 1 to 15 carbon atoms), an alkyliminosulfonyl group (preferably having 2 to 15 carbon atoms), an aryloxysulfonyl group (preferably having 6 to 20 carbon atoms), an alkylaryloxysulfonyl group (preferably having 7 to 20 carbon atoms), a cycloalkylaryloxysulfonyl group (preferably having 10 to 20 carbon atoms), an alkyloxyalkyloxy group (preferably having 5 to 20 carbon atoms), and a cycloalkylalkyloxyalkyloxy group (preferably having 8 to 20 carbon atoms) can be exemplified. The aryl group or ring structure of these groups may further have an alkyl group (preferably having 1 to 15 carbon atoms) as its substituent.

As a preferred aralkyl group of the aralkyl carboxylate anion, an aralkyl group having 7 to 12 carbon atoms, such as a benzyl group, a phenethyl group, a naphthylmethyl group, a naphthylethyl group, and a naphthylbutyl group can be exemplified.

As the sulfonylimide anion, a saccharin anion can be exemplified.

The alkyl group in the bis(alkylsulfonyl)imide anion and tris(alkylsulfonyl)methide anion is preferably an alkyl group having 1 to 5 carbon atoms.

In the bis(alkylsulfonyl)imide anion, two alkyl groups may be connected to each other to thereby form an alkylene group (preferably 2 to 4 carbon atoms), which may form a ring in cooperation with the imide group and two sulfonyl groups.

As substituents that can be introduced in the above alkyl groups and alkylene group formed by the mutual connection of two alkyl groups in the bis(alkylsulfonyl)imide anion, there can be mentioned a halogen atom, an alkyl group substituted with a halogen atom, an alkoxy group, an alkylthio group, an alkyloxysulfonyl group, an aryloxysulfonyl group, a cycloalkylaryloxysulfonyl group and the like. A fluorine atom and an alkyl group substituted with a fluorine atom are preferred.

As the other nonnucleophilic anions $Z^-$, phosphorus fluoride (for example, $PF_6^-$), boron fluoride (for example, $BF_4^-$) and antimony fluoride (for example, $SbF_6^-$) can be exemplified.

The nonnucleophilic anion represented by $Z^-$ is preferably selected from among an aliphatic sulfonate anion substituted at least at its α-position of sulfonic acid with a fluorine atom, an aromatic sulfonate anion substituted with a fluorine atom or a group having a fluorine atom, a bis(alkylsulfonyl)imide anion whose alkyl group is substituted with a fluorine atom and a tris(alkylsulfonyl)methide anion whose alkyl group is substituted with a fluorine atom. More preferably, the nonnucleophilic anion is a perfluorinated aliphatic sulfonate anion having 4 to 8 carbon atoms or a benzene sulfonate anion having a fluorine atom. Still more preferably, the nonnucleophilic anion is a nonafluorobutane sulfonate anion, a perfluorooctane sulfonate anion, a pentafluorobenzene sulfonate anion or a 3,5-bis(trifluoromethyl)benzene sulfonate anion.

From the viewpoint of acid strength, it is preferred for the pKa value of generated acid to be −1 or below. This would contribute to an enhancement of sensitivity.

As more preferred (ZI') components, the following compound (ZI'-1) can be exemplified.

The compound (ZI'-1) is arylsulfonium compound of the general formula (ZI') wherein at least one of $R_{201}$ to $R_{203}$ is an aryl group, namely, compounds containing an arylsulfonium as a cation.

In the arylsulfonium compounds, all of the $R_{201}$ to $R_{203}$ may be aryl groups. It is also appropriate that the $R_{201}$ to $R_{203}$ are partially an aryl group and the remainder is an alkyl group or a cycloalkyl group. It is preferred that all of the $R_{201}$ to $R_{203}$ may be aryl groups.

As the arylsulfonyl compound, there can be mentioned, for example, a triarylsulfonium compound, a diarylalkylsulfonium compound, an aryldialkylsulfonium compound, a diarylcycloalkylsulfonium compound and an aryldicycloalkylsulfonium compound. Among these, a triarylsulfonium compound is preferred.

The aryl group of the arylsulfonium compounds is preferably a phenyl group or a naphthyl group, more preferably a phenyl group. The aryl group may be one having a heterocyclic structure containing an oxygen atom, nitrogen atom, sulfur atom or the like. As the aryl group having a heterocyclic structure, a pyrrole residue, a furan residue, a thiophene residue, an indole residue, a benzofuran residue, and a benzothiophene residue can be exemplified. When the arylsulfonium compound has two or more aryl groups, the two or more aryl groups may be identical to or different from each other.

The alkyl group or cycloalkyl group contained in the arylsulfonium compound according to necessity is preferably a linear or branched alkyl group having 1 to 15 carbon atoms or a cycloalkyl group having 3 to 15 carbon atoms. As such, a methyl group, an ethyl group, a propyl group, an n-butyl group, a sec-butyl group, a t-butyl group, a cyclopropyl group, a cyclobutyl group, and a cyclohexyl group can be exemplified.

The aryl group, alkyl group or cycloalkyl group represented by $R_{201}$ to $R_{203}$ may have one or more substituents. As the substituent, an alkyl group (for example, 1 to 15 carbon atoms), a cycloalkyl group (for example, 3 to 15 carbon atoms), an aryl group (for example, 6 to 14 carbon atoms), an alkoxy group (for example, 1 to 15 carbon atoms), a halogen atom, a hydroxy group, and a phenylthio group can be exemplified. Preferred substituents are a linear or branched alkyl group having 1 to 12 carbon atoms, a cycloalkyl group having 3 to 12 carbon atoms and a linear, branched or cyclic alkoxy group having 1 to 12 carbon atoms. More preferred substituents are an alkyl group having 1 to 6 carbon atoms and an alkoxy group having 1 to 6 carbon atoms. The substituents may be contained in any one of the three $R_{201}$ to $R_{203}$, or alternatively may be contained in all three of $R_{201}$ to $R_{203}$. When $R_{201}$ to $R_{203}$ represent an aryl group, the substituent preferably lies at the p-position of the aryl group.

Now, the general formulae (ZII') and (ZIII') will be described.

In the general formulae (ZII') and (ZIII'), each of $R_{204}$ to $R_{207}$ independently represents an aryl group, an alkyl group or a cycloalkyl group.

The aryl groups, alkyl groups and cycloalkyl groups represented by $R_{204}$ to $R_{207}$ are the same as set forth above in connection with $R_{201}$ to $R_{203}$ in the compounds (ZI'-1).

Substituents may be introduced in the aryl groups, alkyl groups and cycloalkyl groups represented by $R_{204}$ to $R_{207}$. As the substituents, also, there can be mentioned those set forth above as being introducible in the aryl groups, alkyl groups and cycloalkyl groups represented by $R_{201}$ to $R_{203}$ in the compounds (ZI'-1).

$Z^-$ represents a nonnucleophilic anion. As such, the same nonnucleophilic anions as mentioned with respect to the $Z^-$ in the general formula (ZI') can be exemplified.

As the photoacid generator (A') which can be used in combination with the photoacid generator in the present invention, the compounds represented by the following general formulae (ZIV'), (ZV') and (ZVI') can further be exemplified.

$$Ar_3-SO_2-SO_2-Ar_4 \quad (ZIV')$$

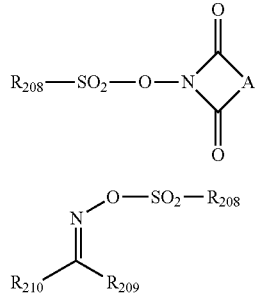

(ZV')

(ZVI')

In the general formulae (ZIV') to (ZVI'), each of $Ar_3$ and $Ar_4$ independently represents an aryl group.

Each of $R_{208}$, $R_{209}$ and $R_{210}$ independently represents an alkyl group, a cycloalkyl group or an aryl group.

A represents an alkylene group, an alkenylene group or an arylene group.

As specific examples of the aryl group represented by $Ar_3$, $Ar_4$, $R_{208}$, $R_{209}$ and $R_{210}$, for example, the same aryl group as explained with respect to $R_{201}$, $R_{202}$ and $R_{203}$ in the general formula (ZI'-1) can be exemplified.

As specific examples of the alkyl group and the cycloalkyl group, for example, the same alkyl group and the cycloalkyl group as explained with respect to $R_{201}$, $R_{202}$ and $R_{203}$ in the general formula (ZI'-1) can be exemplified.

As the alkylene group represented by A, for example, the one having 1 to 12 carbon atoms such as a methylene group, an ethylene group, a propylene group, an isopropylene group, a butylene group, an isobutylene group, or the like can be exemplified. As the alkenylene group represented by A, for example, the one having 2 to 12 carbon atoms such as an ethenylene group, a propenylene group, a butenylene group, or the like can be exemplified. As the arylene group represented by A, for example, the one having 6 to 10 carbon atoms such as a phenylene group, a tolylene group, a naphthylene group, or the like can be exemplified.

Especially preferred examples of the acid generators which can be used in combination with the acid generator according to the present invention will be shown below.

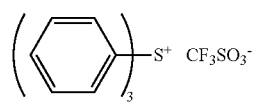

(z1)

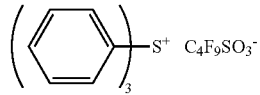

(z2)

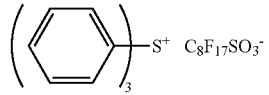

(z3)

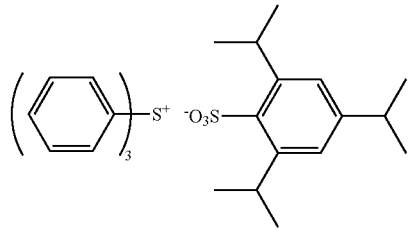

(z4)

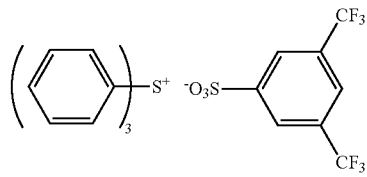

(z5)

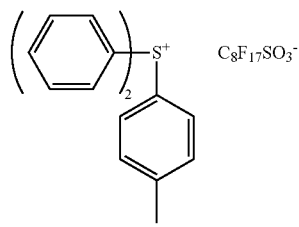

(z6)

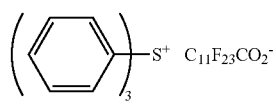

(z7)

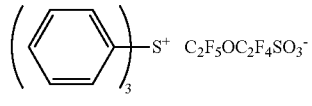

(z8)

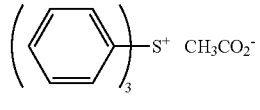

(z9)

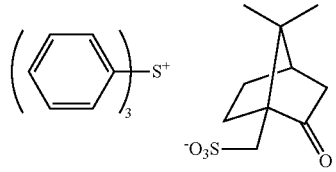

(z10)

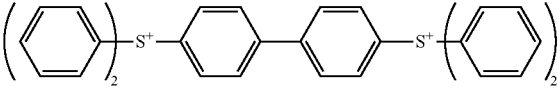

(z11)

-continued (z31) 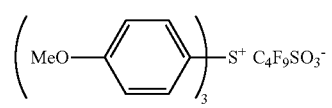
(z32) 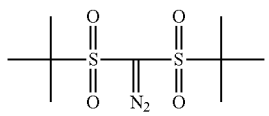
(z33) 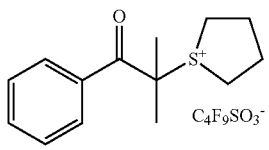
(z34) 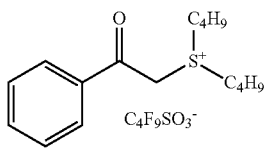
(z35) 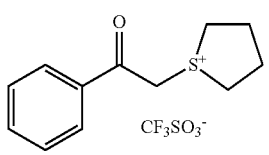
(z36) 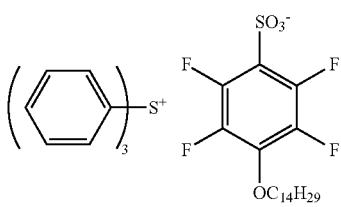
(z37) 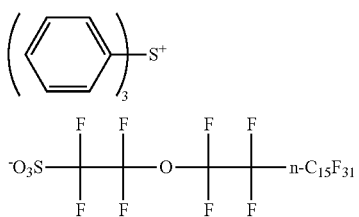
(z38) 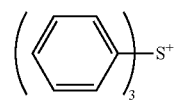
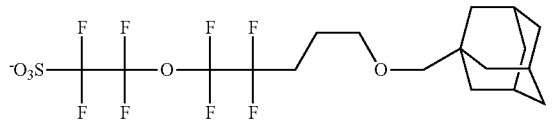
(z39) 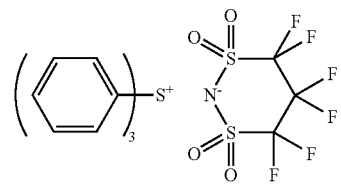
(z40) 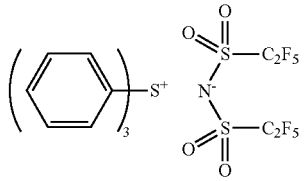
(z41) 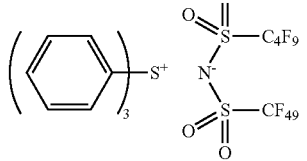
(z42) 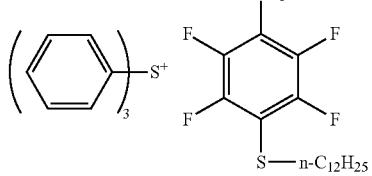
(z43) 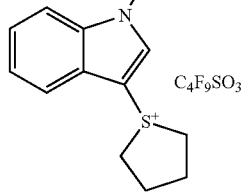
(z44) 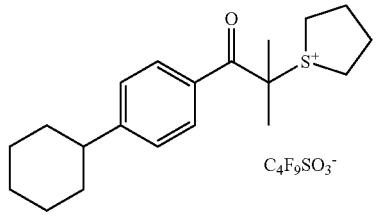
(z45) 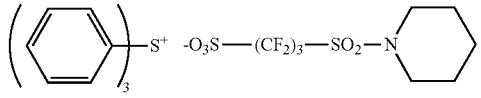
(z46) 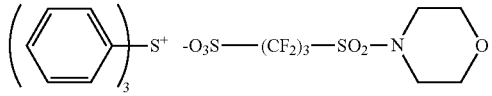
(z47) 
(z48) 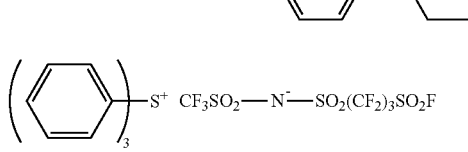

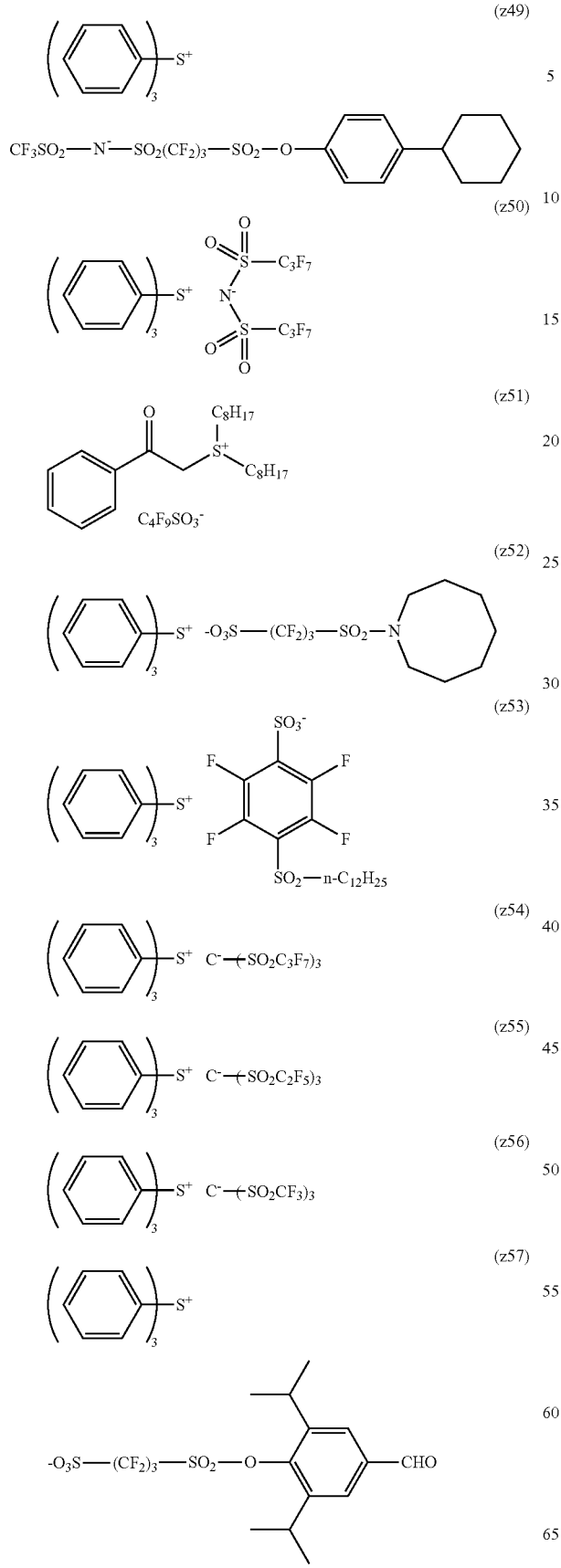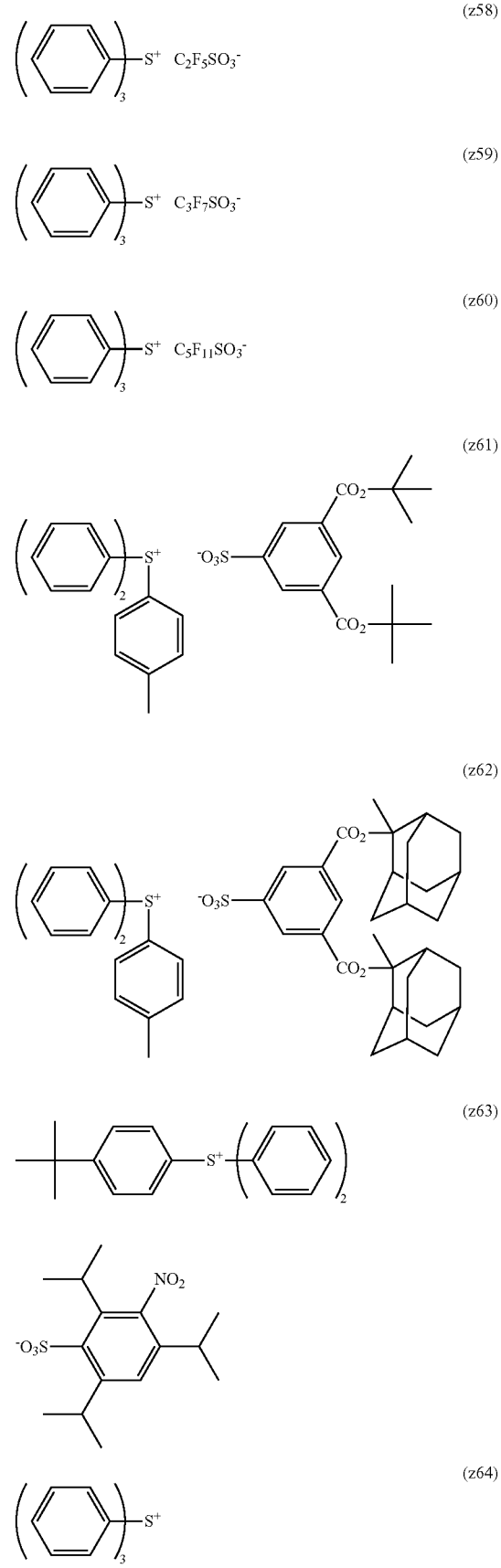

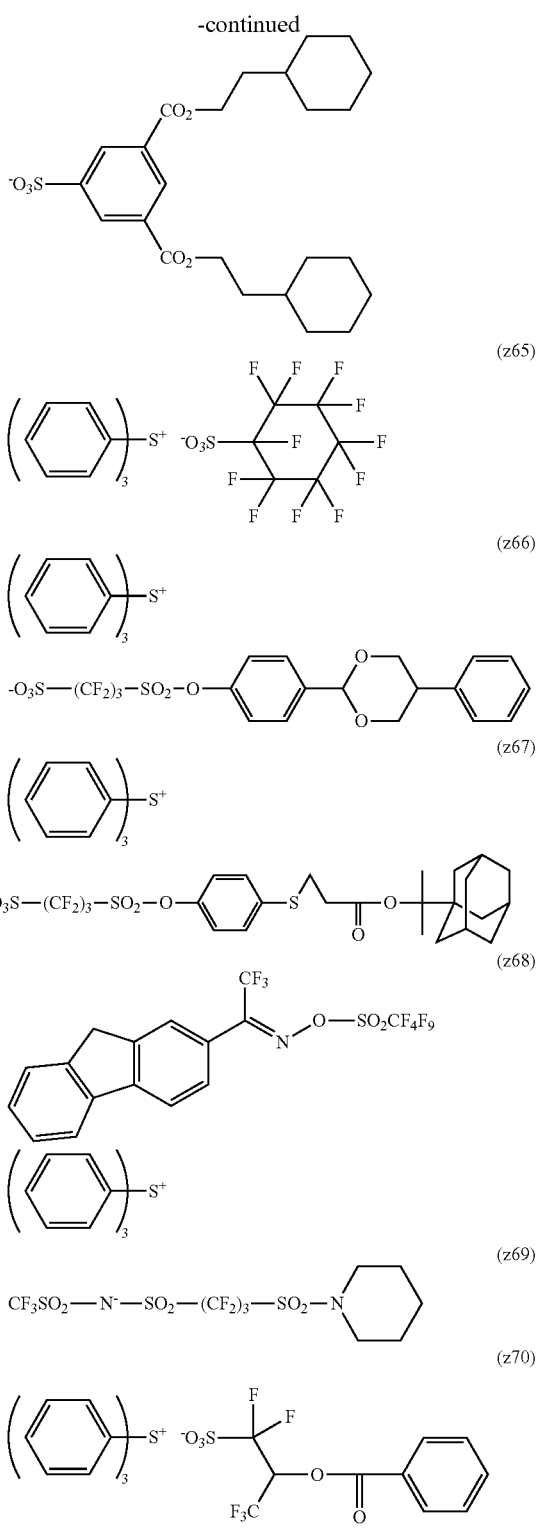

negative actinic ray- or radiation-sensitive resin composition. It is preferred for the resin (B) contained in the composition to be a resin (hereinafter also referred to as an "acid-decomposable resin") that is decomposed by the action of an acid to thereby increase its solubility in an alkali developer. This resin (B) contains a group (hereinafter also referred to as "acid-decomposable group") that is decomposed by the action of an acid to thereby generate an alkali-soluble group, which group is introduced in the principal chain or a side chain, or both the principal chain and the side chain, of the resin. Namely, the resin (B) comprises a repeating unit containing an acid-decomposable group.

(1) Repeating unit containing acid-decomposable group

The acid-decomposable group preferably has a structure in which an alkali-soluble group is protected by a group that is decomposed by the action of an acid to be thereby eliminated.

As the alkali soluble group, there can be mentioned a phenolic hydroxyl group, a carboxyl group, a fluoroalcohol group, a sulfonate group, a sulfonamido group, a sulfonylimide group, an (alkylsulfonyl)(alkylcarbonyl)methylene group, an (alkylsulfonyl)(alkylcarbonyl)imide group, a bis(alkylcarbonyl)methylene group, a bis(alkylcarbonyl)imide group, a bis(alkylsulfonyl)methylene group, a bis(alkylsulfonyl)imide group, a tris(alkylcarbonyl)methylene group, a tris(alkylsulfonyl)methylene group or the like.

As preferred alkali soluble groups, there can be mentioned a carboxyl group, a fluoroalcohol group (preferably hexafluoroisopropanol group) and a sulfonate group.

The acid-decomposable group is preferably a group as obtained by substituting the hydrogen atom of any of these alkali soluble groups with an acid eliminable group.

As the acid eliminable group, there can be mentioned, for example, —C($R_{36}$)($R_{37}$)($R_{38}$), —C($R_{36}$)($R_{37}$)(OR$_{39}$), —C($R_{01}$)($R_{02}$)(OR$_{39}$) or the like.

In the formulae, each of $R_{36}$ to $R_{39}$ independently represents an alkyl group, a cycloalkyl group, an aryl group, an aralkyl group or an alkenyl group. $R_{36}$ and $R_{37}$ may be bonded with each other to thereby form a ring structure.

Each of $R_{01}$ and $R_{02}$ independently represents a hydrogen atom, an alkyl group, a cycloalkyl group, an aryl group, an aralkyl group or an alkenyl group.

Preferably, the acid-decomposable group is a cumyl ester group, an enol ester group, an acetal ester group, a tertiary alkyl ester group or the like. A tertiary alkyl ester group is more preferred.

The repeating unit with an acid-decomposable group which can be contained in the resin (B) is preferably any of those represented by general formula (AI) below.

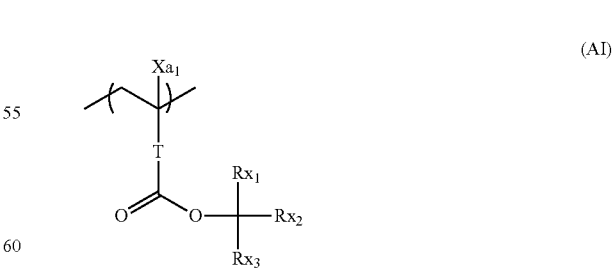

In general formula (AI), $Xa_1$ represents a hydrogen atom, an optionally substituted methyl group or any of the groups of formula —CH$_2$—R$_{11}$. $R_{11}$ represents a hydroxyl group or a monovalent organic group. The monovalent organic group is, for example, an When the compound (A) is used in combination with the compound (A'), the mass ratio of used photoacid generators (compound (A)/compound (A')) is preferably in the range of 99/1 to 20/80, more preferably 99/1 to 40/60 and further more preferably 99/1 to 50/50.

[2] Resin (B)

The actinic ray- or radiation-sensitive resin composition of the present invention may be in the form of a positive or alkyl group having 5 or less carbon atoms or an acyl group having 5 or less carbon atoms. Preferably, the monovalent organic group is an alkyl group having 3 or less carbon atoms, more preferably a methyl group. $Xa_1$ preferably represents a hydrogen atom, a methyl group, a trifluoromethyl group or a hydroxymethyl group.

T represents a single bond or a bivalent connecting group.

Each of $Rx_1$ to $Rx_3$ independently represents an alkyl group (linear or branched) or a cycloalkyl group (monocyclic or polycyclic). At least two of $Rx_1$ to $Rx_3$ may be bonded with each other to thereby form a cycloalkyl group (monocyclic or polycyclic).

As the bivalent connecting group represented by T, there can be mentioned an alkylene group, a group of the formula —COO-Rt-, a group of the formula —O-Rt- or the like. In the formulae, Rt represents an alkylene group or a cycloalkylene group.

T is preferably a single bond or a group of the formula —COO-Rt-. Rt is preferably an alkylene group having 1 to 5 carbon atoms, more preferably a —$CH_2$— group, —$(CH_2)_2$— group or —$(CH_2)_3$— group.

The alkyl group represented by each of $Rx_1$ to $Rx_3$ is preferably one having 1 to 4 carbon atoms, such as a methyl group, an ethyl group, an n-propyl group, an isopropyl group, an n-butyl group, an isobutyl group or a t-butyl group.

The cycloalkyl group represented by each of $Rx_1$ to $Rx_3$ is preferably a cycloalkyl group of one ring, such as a cyclopentyl group or a cyclohexyl group, or a cycloalkyl group of multiple rings, such as a norbornyl group, a tetracyclodecanyl group, a tetracyclododecanyl group or an adamantyl group.

The cycloalkyl group formed by bonding of at least two of $Rx_1$ to $Rx_3$ is preferably a cycloalkyl group of one ring, such as a cyclopentyl group or a cyclohexyl group, or a cycloalkyl group of multiple rings, such as a norbornyl group, a tetracyclodecanyl group, a tetracyclododecanyl group or an adamantyl group. It is particularly preferable to be a cycloalkyl group of one ring having 5 or 6 carbon atoms.

One of the methylene groups constructing the ring of the above cycloalkyl group formed by the mutual bonding of two of $Rx_1$ to $Rx_3$ may be replaced by an oxygen atom.

A form in which $Rx_1$ is a methyl group or an ethyl group while $Rx_2$ and $Rx_3$ are bonded to each other to thereby construct the above cycloalkyl group is preferred.

Each of these groups may have a substituent. As the substituent, there can be mentioned, for example, an alkyl group (1 to 4 carbon atoms), a halogen atom, a hydroxyl group, an alkoxy group (1 to 4 carbon atoms), a carboxyl group, an alkoxycarbonyl group (2 to 6 carbon atoms) or the like. The number of carbon atoms of the substituent is preferably 8 or less.

The total content of the repeating units with acid-decomposable groups is preferably in the range of 20 to 70 mol %, more preferably 30 to 60 mol %, based on all the repeating units of the resin (B).

Specific examples of the preferred repeating units with acid-decomposable groups will be shown below, which however in no way limit the scope of the present invention.

In the following formulae, each of Rx and $Xa_1$ represents a hydrogen atom, $CH_3$, $CF_3$ or $CH_2OH$. Each of Rxa and Rxb represents an alkyl group having 1 to 4 carbon atoms. Z represents a substituent containing a polar group. When a plurality of Zs exist, they may be identical to or different from each other. p represents 0 or a positive integer. Particular examples and preferred example of Z are same as particular examples and preferred example of $R_{10}$ in general formula (II-1) to be described below.

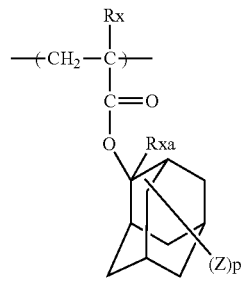

1

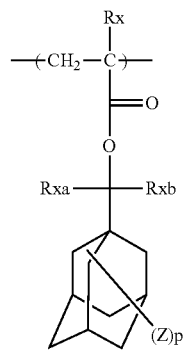

2

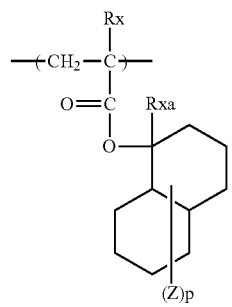

3

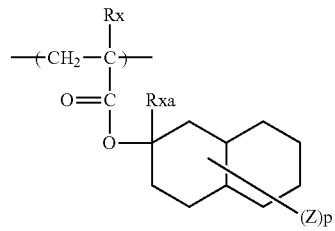

4

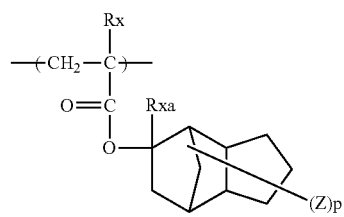

5

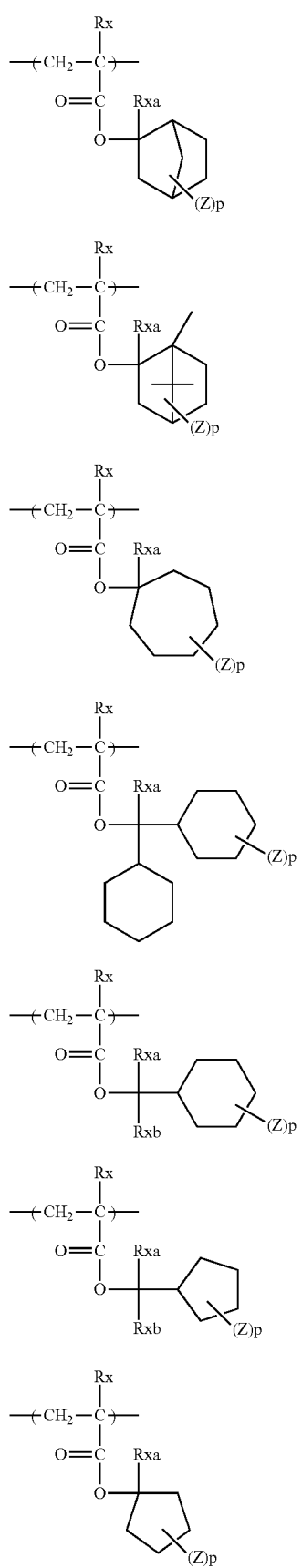
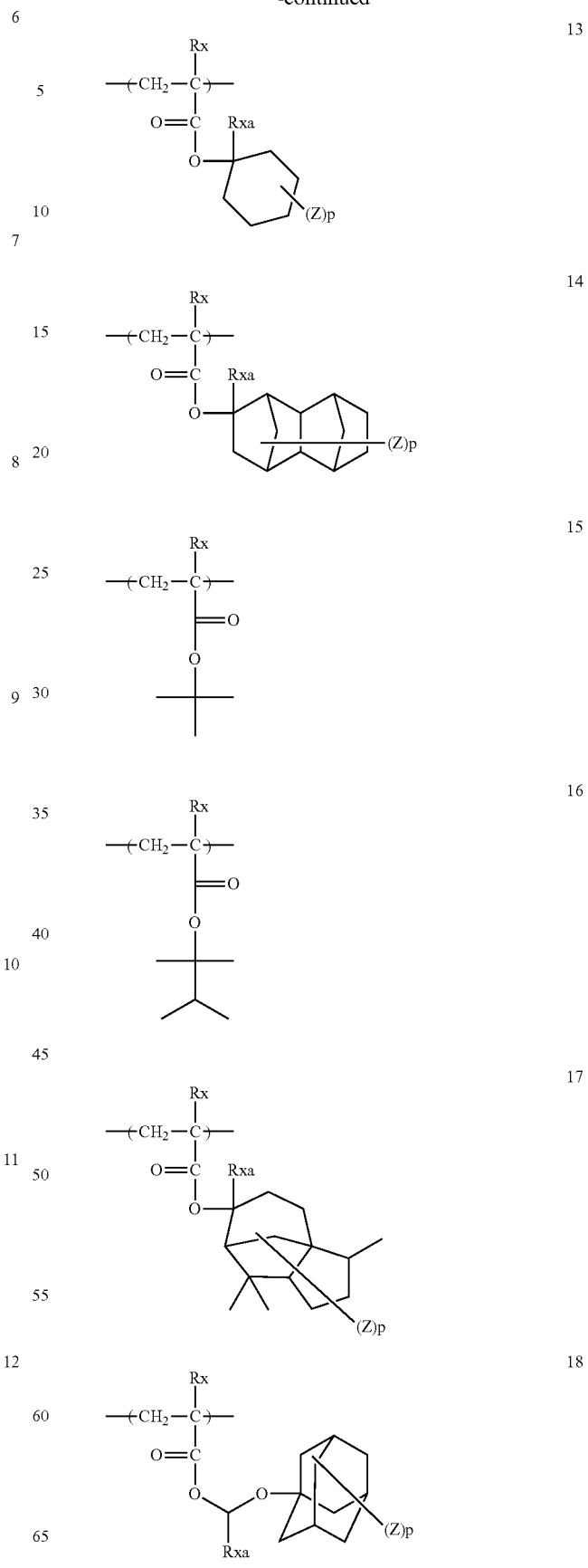

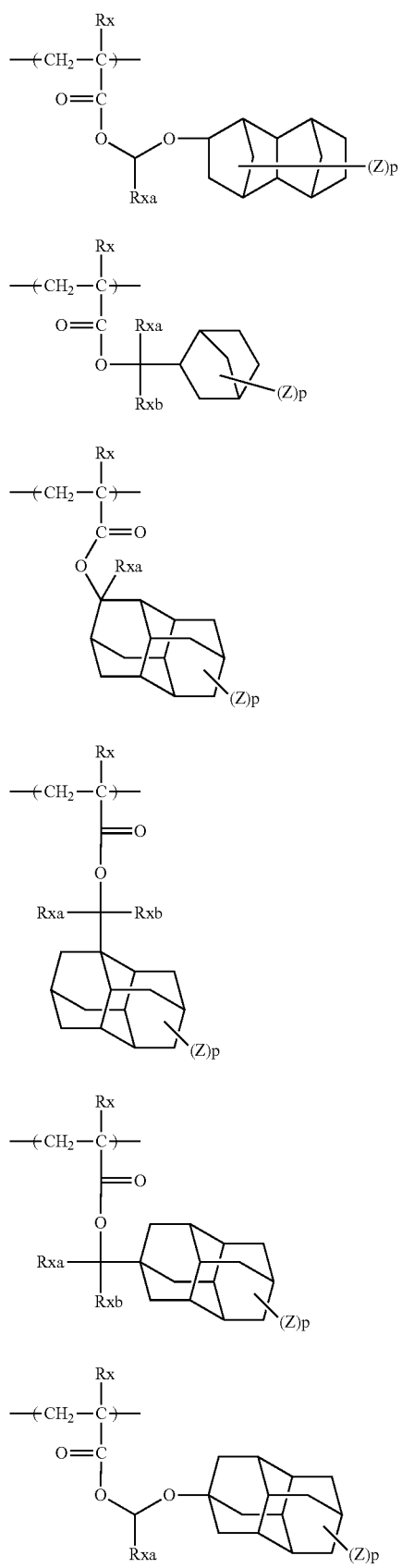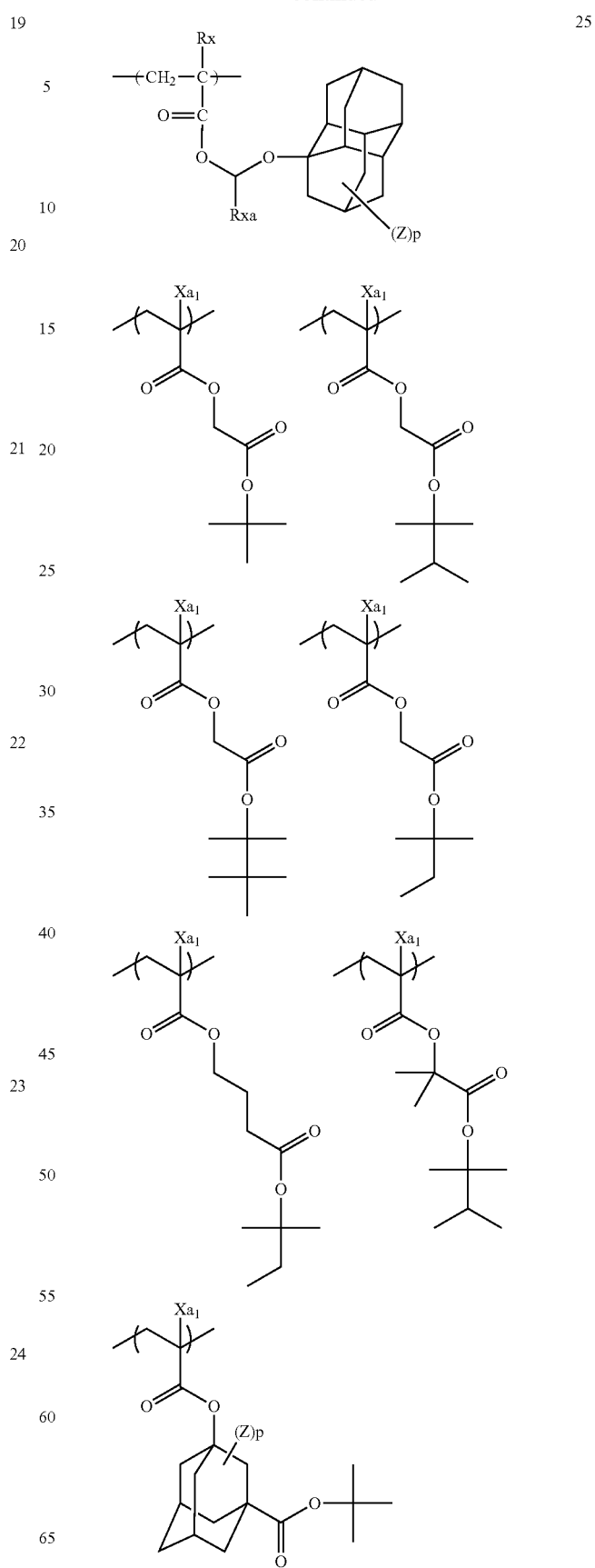

65
-continued
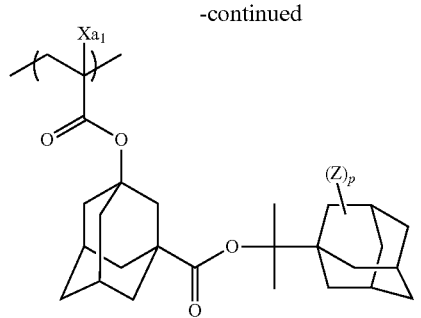
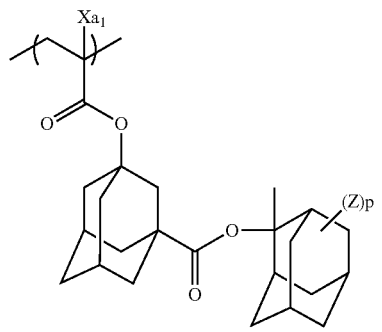
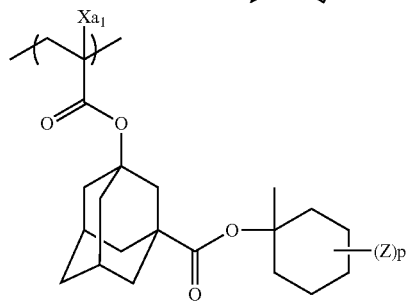
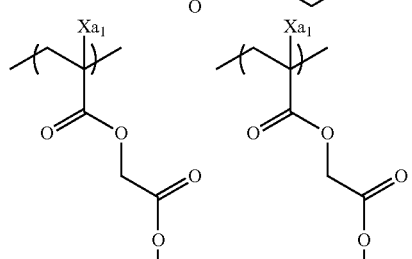
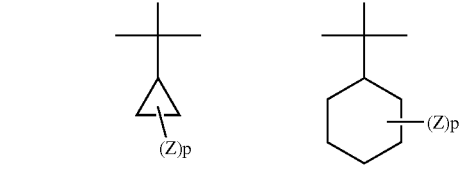
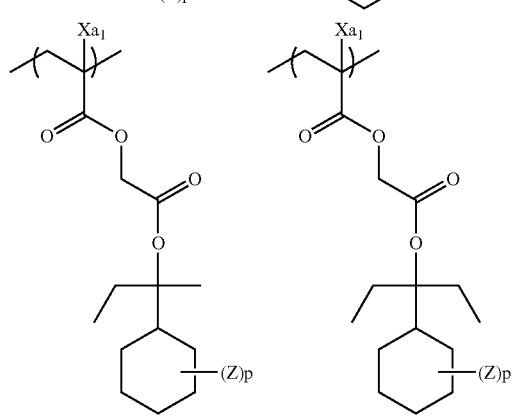
66
-continued
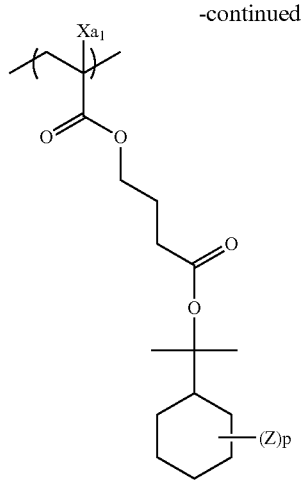
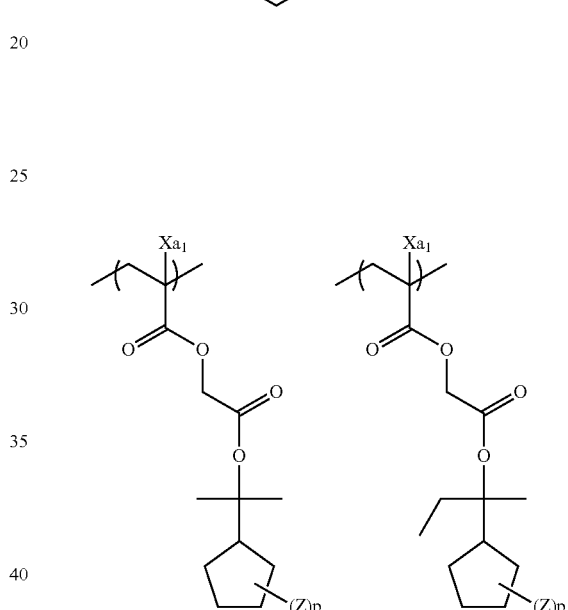
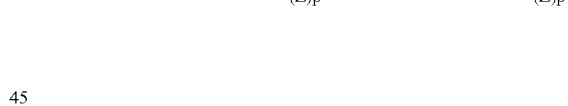
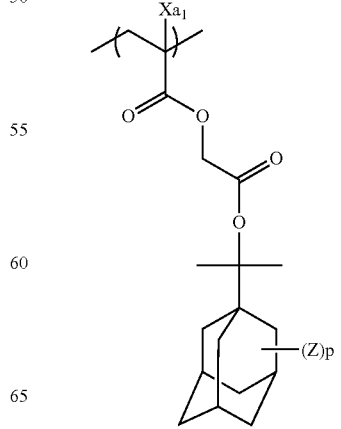

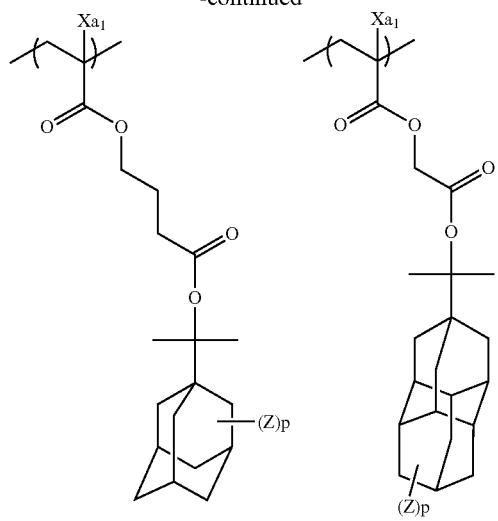
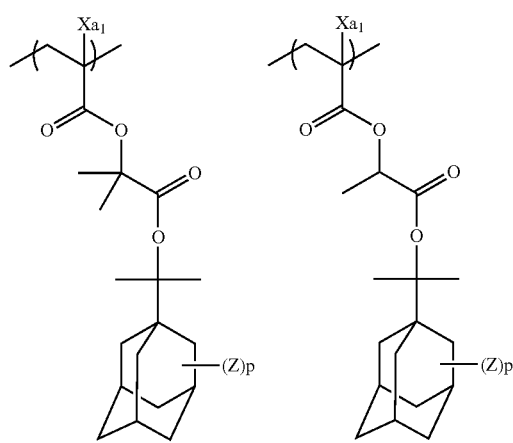
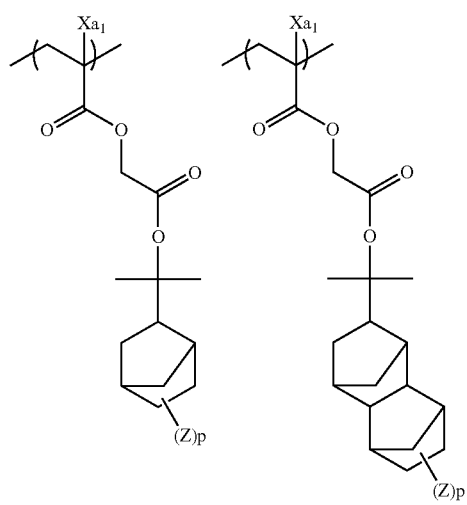
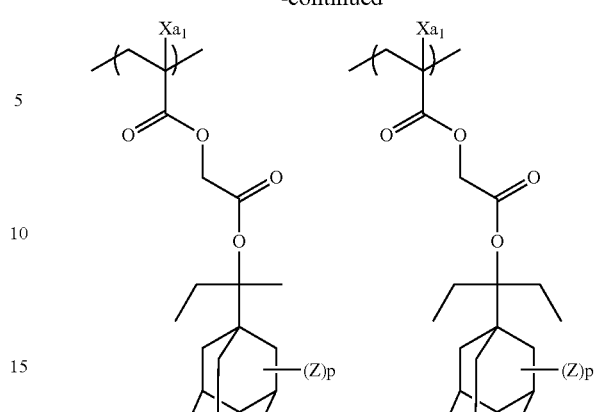
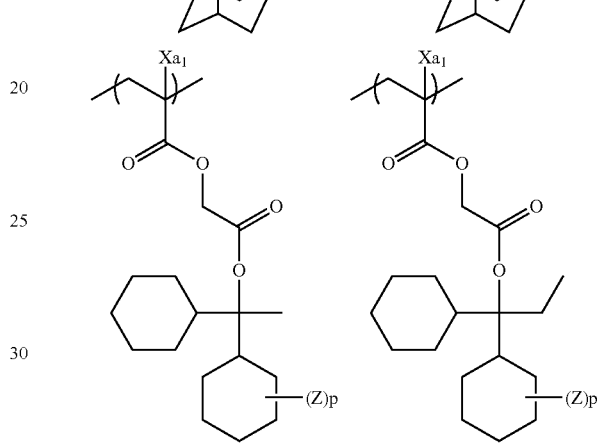
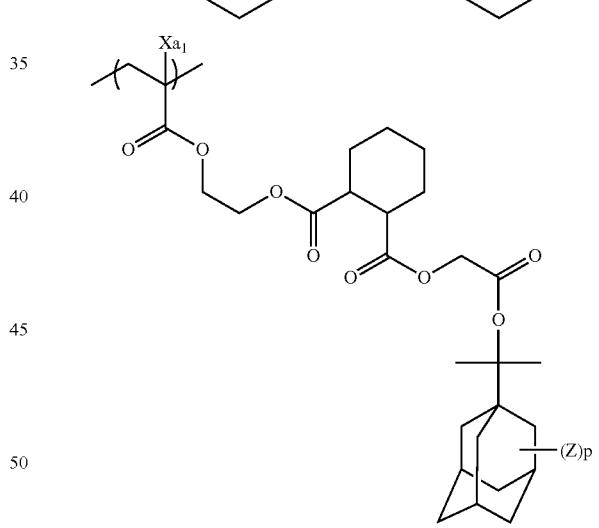
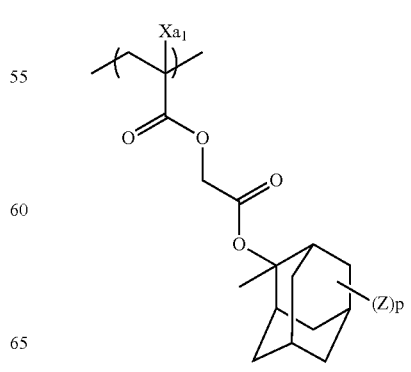

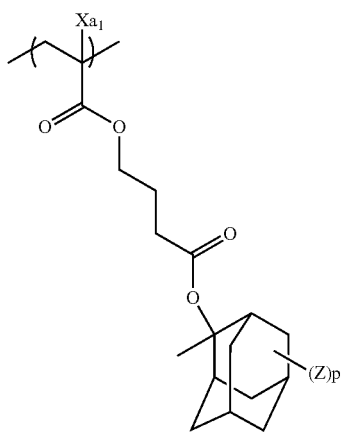
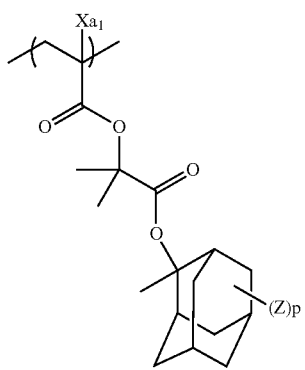
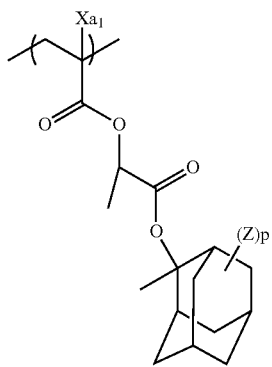
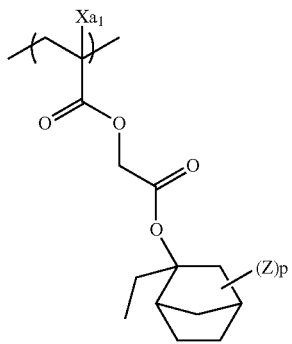
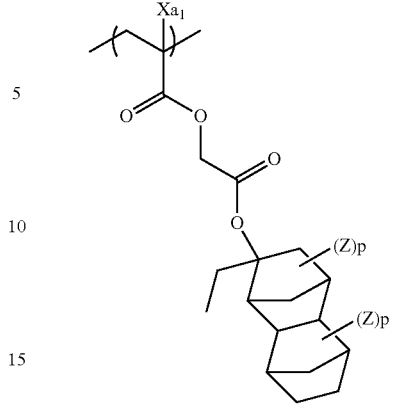
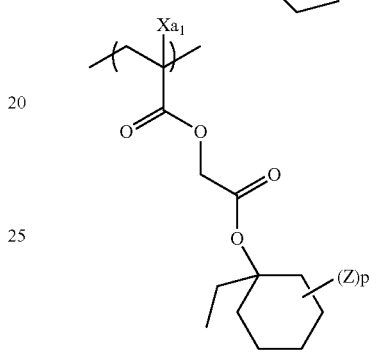
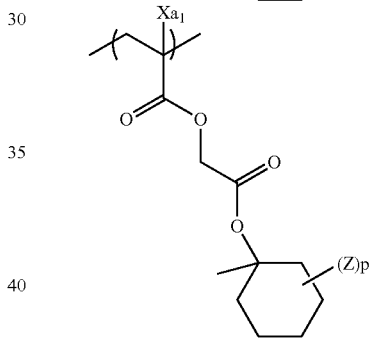
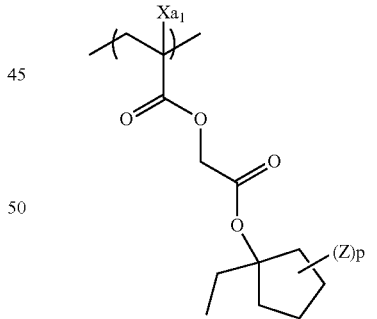
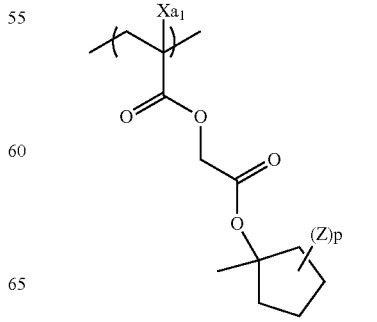

-continued

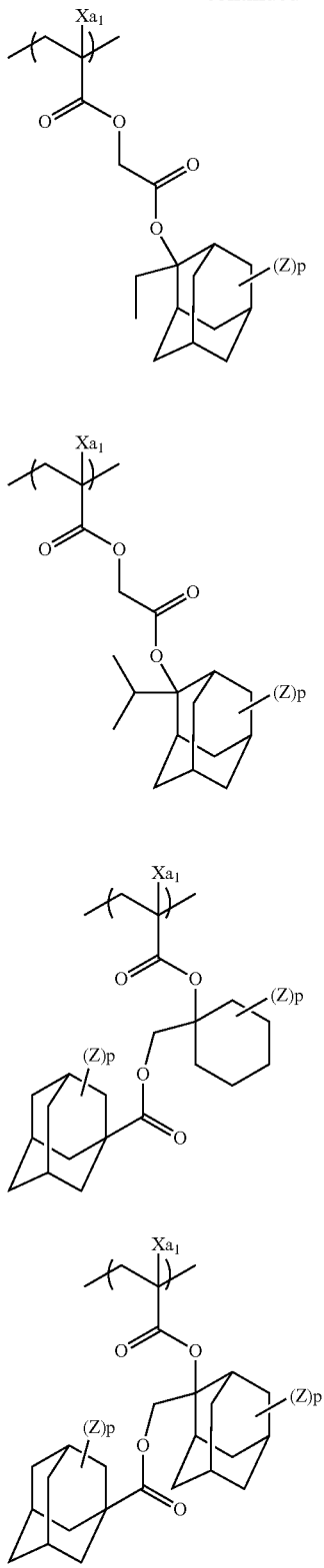

It is more preferred that the resin (B) contains at least either any of repeating units represented by general formula (I) below or any of repeating units represented by general formula (II) below as the repeating unit represented by general formula (AI).

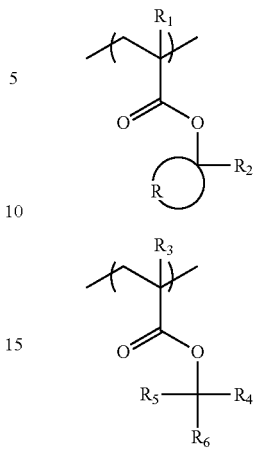

In general formulae (I) and (II), each of $R_1$ and $R_3$ independently represents a hydrogen atom, an optionally substituted methyl group or any of the groups of formula —$CH_2$—$R_{11}$. $R_{11}$ represents a monovalent organic group.

Each of $R_2$, $R_4$, $R_5$ and $R_6$ independently represents an alkyl group or a cycloalkyl group.

R represents an atomic group required for forming an alicyclic structure in cooperation with a carbon atom.

$R_1$ and $R_3$ preferably represents a hydrogen atom, a methyl group, a trifluoromethyl group or a hydroxymethyl group. $R_1$ is more preferably a methyl group. $R_3$ is more preferably a hydrogen atom or a methyl group, especially preferably a methyl group. Particular examples and preferred examples of the monovalent organic group represented by $R_{11}$ are the same as those of $R_{11}$ in the general formula (AI).

The alkyl group represented by $R_2$ may be linear or branched, and may have a substituent.

The cycloalkyl group represented by $R_2$ may be monocyclic or polycyclic, and may have a substituent.

$R_2$ preferably represents an alkyl group, more preferably an alkyl group having 1 to 10 carbon atoms, especially 1 to 5 carbon atoms. As examples thereof, there can be mentioned a methyl group and an ethyl group.

R represents an atomic group required for forming an alicyclic structure together with a carbon atom. The alicyclic structure formed by R together with the carbon atom is preferably an alicyclic structure of a single ring, and preferably has 3 to 7 carbon atoms, more preferably 5 or 6 carbon atoms.

Each of the alkyl groups represented by $R_4$, $R_5$ and $R_6$ may be linear or branched, and may have a substituent. The alkyl groups preferably are those each having 1 to 4 carbon atoms, such as a methyl group, an ethyl group, an n-propyl group, an isopropyl group, an n-butyl group, an isobutyl group and a t-butyl group.

Each of the cycloalkyl groups represented by $R_4$, $R_5$ and $R_6$ may be monocyclic or polycyclic, and may have a substituent. The cycloalkyl groups are preferably a cycloalkyl group of a single ring, such as a cyclopentyl group or a cyclohexyl group, and a cycloalkyl group of multiple rings, such as a norbornyl group, a tetracyclodecanyl group, a tetracyclododecanyl group or an adamantyl group.

As the repeating unit represented by the general formula (I), a repeating unit represented by general formula (3) below is preferred.

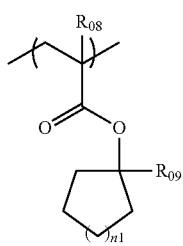

(3)

In general formula (3), $R_{08}$ represents a hydrogen atom or an alkyl group. $R_9$ represents an alkyl group and n1 is an integer of 1 to 6. As the alkyl group, an alkyl group having 1 to 10 carbon atoms is preferable. The alkyl group may have one or more substituents.

n1 is preferably a integer of 1 to 3, more preferably 1 or 2.

One of methylene groups constructing the ring of the cycloalkyl group in the general formula (3) above may be replaced by an oxygen atom.

Each groups described above may have a substituent. As such a substituent, there can be mentioned the group same as a substituent containing each groups in the general formula (AI) above.

The repeating units represented by general formula (II) are preferably those of general formula (II-1) below.

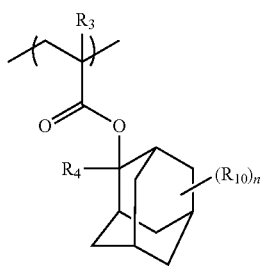

(II-1)

In general formula (II-1),

Each of $R_3$ and $R_4$ has the same meaning as in general formula (II).

$R_{10}$ represents a substituent containing a polar group. When a plurality of $R_{10}$s exist, they may be identical to or different from each other. As the substituent containing a polar group, there can be mentioned, for example, a hydroxyl group, a cyano group, an amino group, an alkylamido group or a sulfonamido group; or a linear or branched alkyl group, or cycloalkyl group having at least one of these groups. An alkyl group having a hydroxyl group is preferred. A branched alkyl group having a hydroxyl group is more preferred. An isopropyl group is especially preferred as the branched alkyl group.

In the formula, n is an integer of 0 to 15, preferably in the range of 0 to 2, and more preferably 0 or 1.

The resin (B) is preferably a resin containing at least one of any of repeating units represented by general formula (I) above and any of repeating units represented by general formula (II) above as the repeating unit represented by the general formula (AI). Also, in the another embodiment, the resin (B) is more preferably a resin containing at least two of repeating units represented by general formula (I) above as the repeating unit represented by the general formula (AI).

The repeating unit containing acid-decomposable group contained in the resins (B) may be used either individually or in combination. When a plurality of the repeating unit containing the acid-decomposable group are simultaneously used in resin (B), preferred combinations thereof are shown below. In the following formulae, each of R independently represents a hydrogen atom or methyl group.

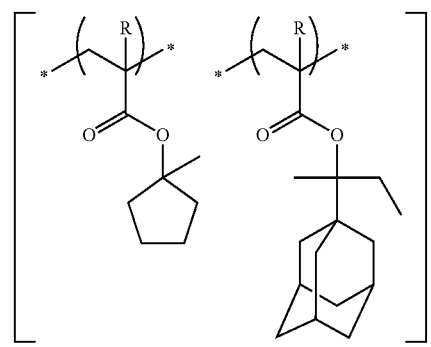

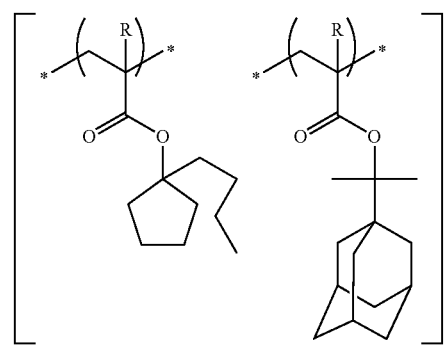

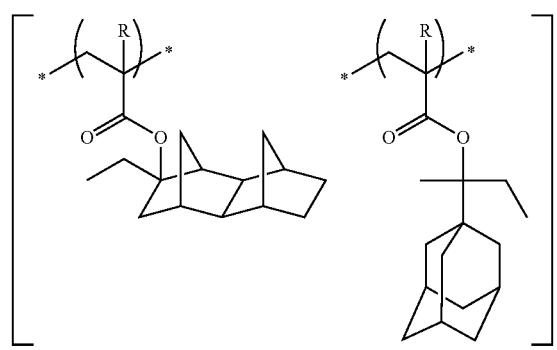

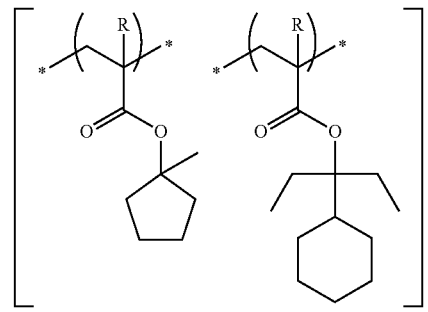

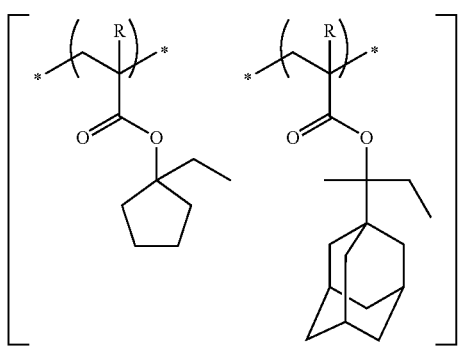
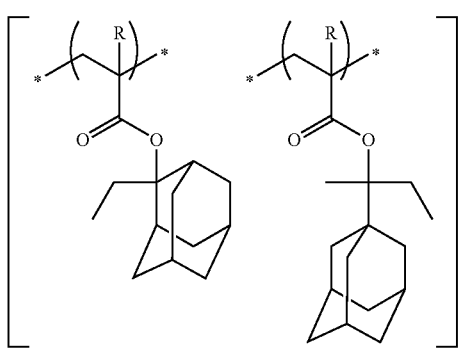
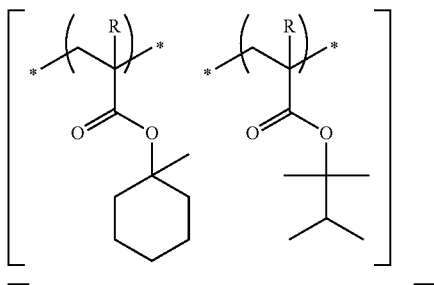
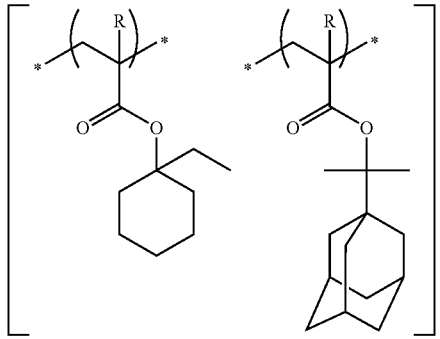
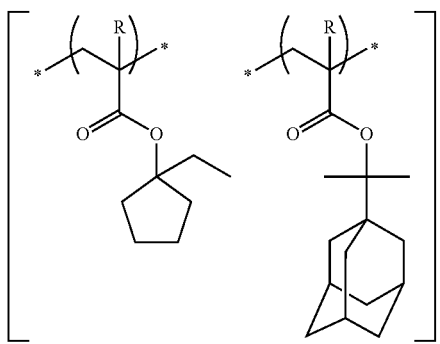
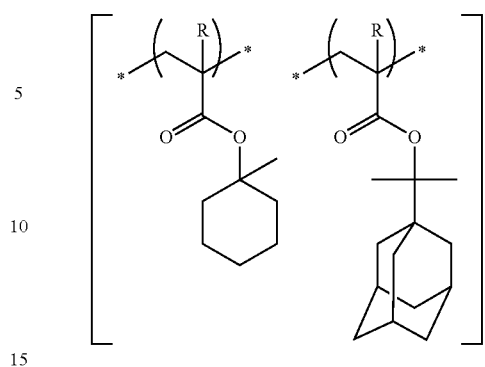
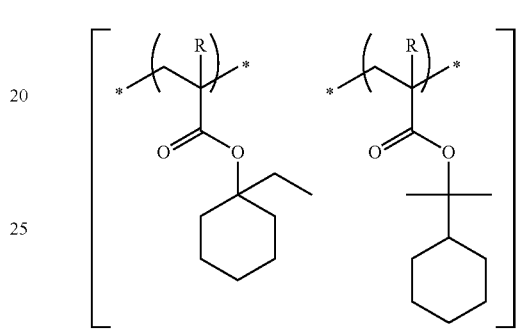
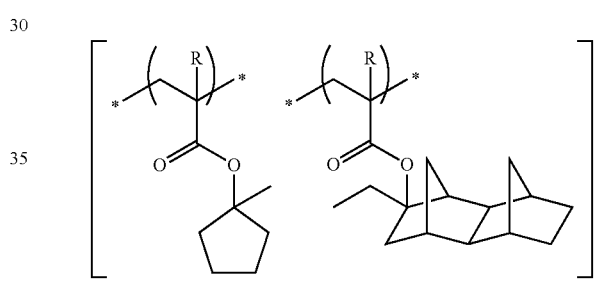
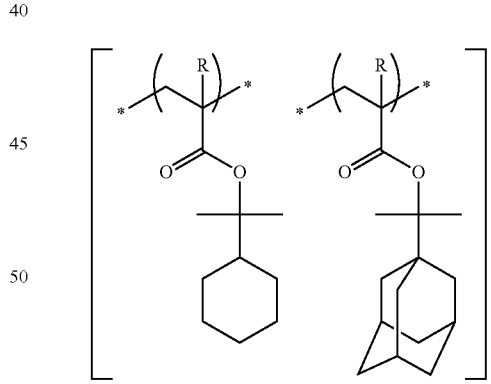
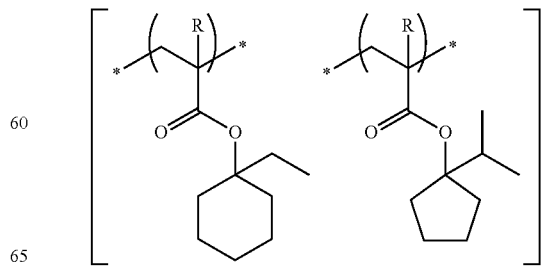

-continued

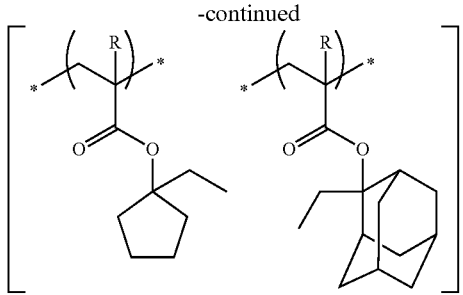

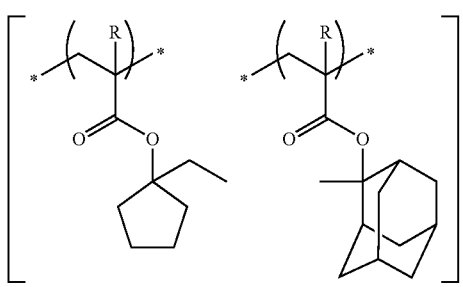

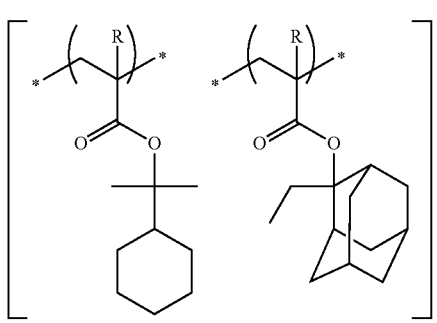

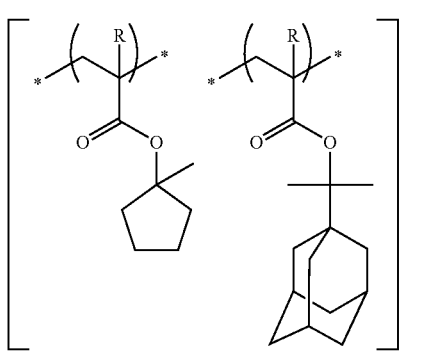

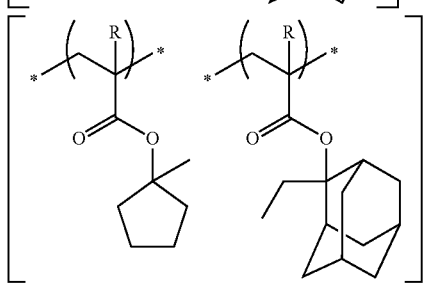

-continued

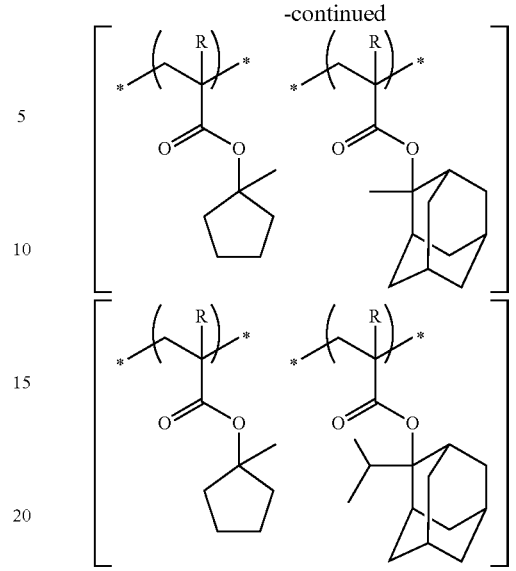

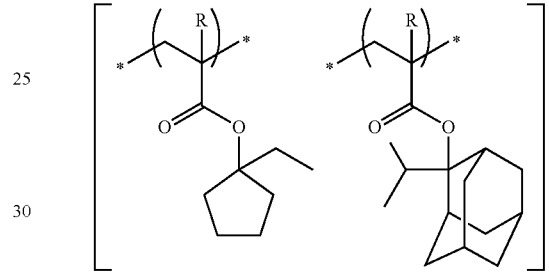

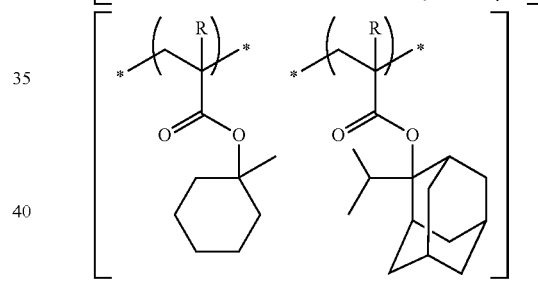

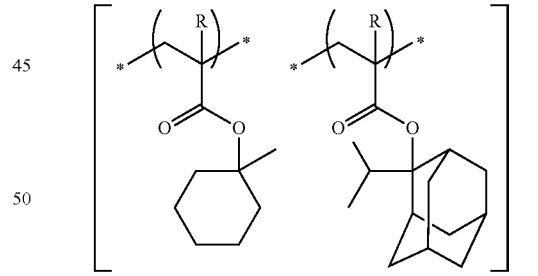

(2) Repeating unit containing a lactone structure or a sultone structure

The resin (B) preferably contains any of the repeating units containing a lactone structure or a sultone structure.

A lactone group and a sultone group are not limited as long as they have the lactone structure or the sultone structure. Lactone structures or sultone structures of a 5 to 7-membered ring are preferred, and in particular, those resulting from condensation of lactone structures or sultone structures of a 5 to 7-membered ring with other cyclic structures effected in a fashion to form a bicyclo structure or spiro structure are preferred. The possession of repeating units having a lactone structure or sultone structure represented by any of the following general formulae (LC1-1) to (LC1-17), (SL1-1) and (SL1-2) is more preferred. The lactone structures or sultone structures may be directly bonded to the principal chain of the resin. Preferred lactone structures or sultone structures are those of formulae (LC1-1), (LC1-4), (LC1-5) or (LC1-8). (LC1-4) is more preferable. The use of these specified lactone structures or sultone structures would ensure improvement in LWR and the reduction of development defects.

LC1-1
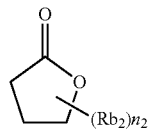

LC1-2
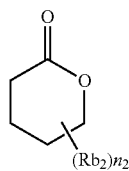

LC1-3
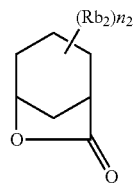

LC1-4
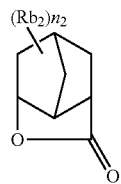

LC1-5
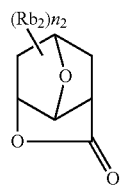

LC1-6
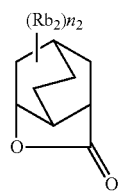

LC1-7
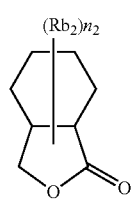

LC1-8
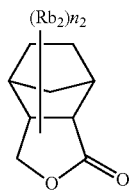

LC1-9
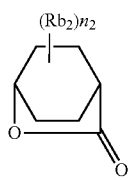

LC1-10
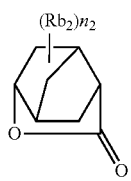

LC1-11
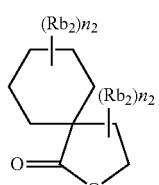

LC1-12
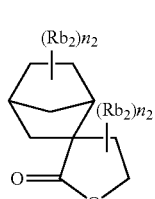

LC1-13
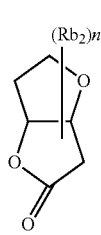

LC1-14
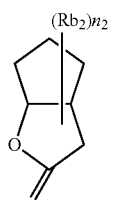

LC1-15
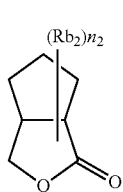

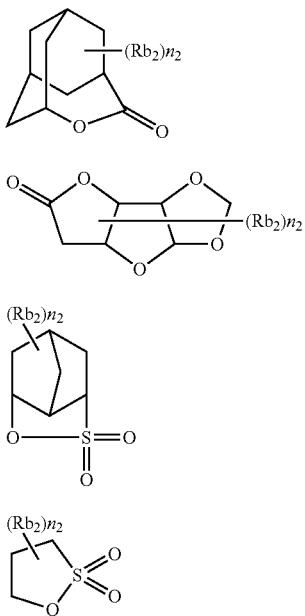

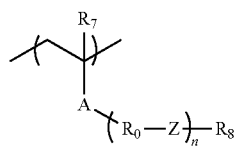

The presence of a substituent (Rb$_2$) on the portion of the lactone structure or the sultone structure is optional. As a preferred substituent (Rb$_2$), there can be mentioned an alkyl group having 1 to 8 carbon atoms, a cycloalkyl group having 4 to 7 carbon atoms, an alkoxy group having 1 to 8 carbon atoms, an alkoxycarbonyl group having 1 to 8 carbon atoms, a carboxyl group, a halogen atom, a hydroxyl group, a cyano group, an acid-decomposable group or the like. Of these, an alkyl group having 1 to 4 carbon atoms, a cyano group and an acid-decomposable group are more preferred. In the formulae, n$_2$ is an integer of 0 to 4. When n$_2$ is 2 or greater, the plurality of present substituents (Rb$_2$) may be identical to or different from each other. Further, the plurality of present substituents (Rb$_2$) may be bonded to each other to thereby form a ring.

It is preferred that the resin (B) contains a repeating unit represented by the following general formula (III) as the repeating unit containing a lactone structure or sultone structure.

(III)

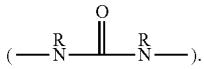

In the formula (III),

A represents an ester bond (—COO—) or an amido bond (—CONH—).

R$_0$, each independently in the presence of two or more groups, represents an alkylene group, a cycloalkylene group or a combination thereof.

Z, each independently in the presence of two or more groups, represents an single bond, an ether bond, an ester bond, an amido bond, a urethane bond represented by (LC1-16)

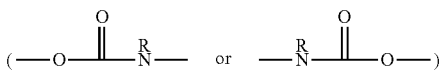

or a urea bond (LC1-17)

$$(-\underset{R}{N}-\overset{O}{\underset{\|}{C}}-\underset{R}{N}-).$$

In the formulae, each R independently represents a hydrogen atom, an alkyl group, a cycloalkyl group or an aryl group.

R$_8$ represents a monovalent organic group with a lactone structure or a sultone structure.

n represents the number of repetitions of the structure of the formula —R$_0$—Z— and is an integer of 0 to 2.

R$_7$ represents a hydrogen atom, a halogen atom or an alkyl group.

Each of the alkylene group and cycloalkylene group represented by R$_0$ may have a substituent.

Z preferably represents an ether bond or an ester bond, most preferably an ester bond.

The alkyl group represented by R$_7$ is preferably an alkyl group having 1 to 4 carbon atoms, more preferably a methyl group or an ethyl group and most preferably a methyl group. Each of the alkylene group and cycloalkylene group represented by R$_0$ and the alkyl group represented by R$_7$ may be substituted. As substituents, there can be mentioned, for example, a halogen atom such as a fluorine atom, a chlorine atom or a bromine atom, a mercapto group, a hydroxyl group, an alkoxy group such as a methoxy group, an ethoxy group, an isopropoxy group, a t-butoxy group or a benzyloxy group, an acetoxy group such as an acetyloxy group or a propionyloxy group and the like. R$_7$ preferably represents a hydrogen atom, a methyl group, a trifluoromethyl group or a hydroxymethyl group.

The chain alkylene group represented by R$_0$ is preferably a chain alkylene having 1 to 10 carbon atoms, more preferably 1 to 5 carbon atoms, for example, a methylene group, an ethylene group, a propylene group or the like. The cycloalkylene group is preferably a cycloalkylene group having 3 to 20 carbon atoms. As such, there can be mentioned, for example, a cyclohexylene group, a cyclopentylene group, a norbornylene group, an adamantylene group or the like. The chain alkylene groups are preferred from the viewpoint of the exertion of the effect of the present invention. A methylene group is especially preferred.

The substituent with a lactone structure or sultone structure represented by R$_8$ is not limited as long as the lactone structure or the sultone structure is contained. As particular examples thereof, there can be mentioned the lactone structures or the sultone structures of general formulae (LC1-1) to (LC1-17), (SL1-1) and (SL1-2) to be shown hereinafter. Of these, the structures of general formula (LC1-4) are most preferred. In general formulae (LC1-1) to (LC1-17), (SL1-1) and (SL1-2), n$_2$ is more preferably 2 or less.

R$_8$ preferably represents a monovalent organic group with an unsubstituted lactone structure or sultone structure or a monovalent organic group with a lactone structure or sultone structure substituted with a methyl group, a cyano group or an alkoxycarbonyl group. More preferably, R$_8$ represents a monovalent organic group with a lactone structure or sultone structure substituted with a cyano group (cyanolactone or cyanosultone).

Specific examples of the repeating units having the groups with a lactone structure or sultone structure of general formula (III) will be shown below, which however in no way limit the scope of the present invention. In the following specific examples, R represents a hydrogen atom, an optionally substituted alkyl group or a halogen atom. Preferably, R represents a hydrogen atom, a methyl group, a hydroxymethyl group or an acetoxymethyl group.

In the following specific examples, Me represents a methyl group.

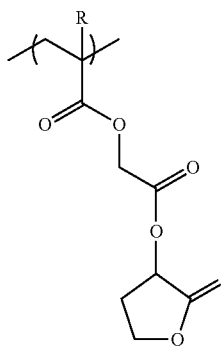
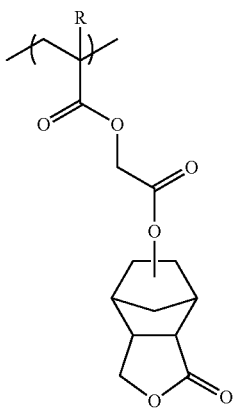
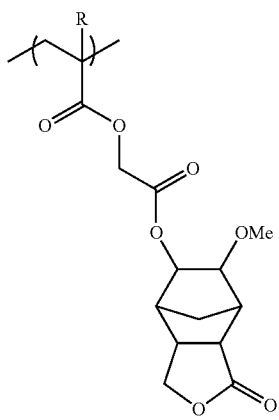
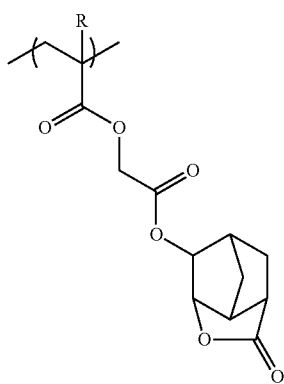

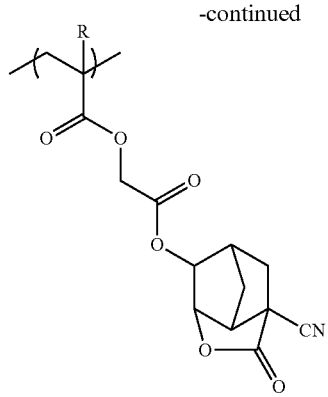

As the repeating units having the lactone structure or sultone structure, a repeating unit represented by following general formula (III-1) or (III-1') is more preferred.

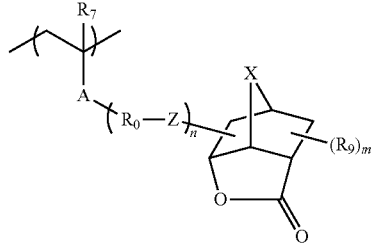

(III-1)

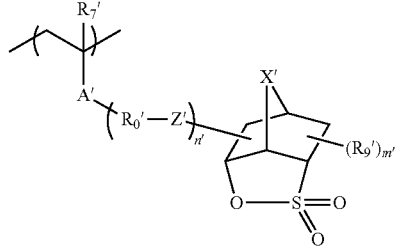

(III-1')

In general formulae (III-1) and (III-1'), $R_7$, A, $R_0$, Z and n are as defined above in connection with general formula (III).

$R_7'$, A', $R_0'$, Z' and n' are respectively the same as $R_7$, A, $R_0$, Z and n in general formula (III).

$R_9$, or each of $R_9$s independently, represents an alkyl group, a cycloalkyl group, an alkoxycarbonyl group, a cyano group, a hydroxyl group or an alkoxy group, provided that any two of two or more $R_9$s may be bonded to each other to thereby form a ring.

$R_9'$, or each of $R_9$'s independently, represents an alkyl group, a cycloalkyl group, an alkoxycarbonyl group, a cyano group, a hydroxyl group or an alkoxy group, provided that any two of two or more $R_9$'s may be bonded to each other to thereby form a ring.

Each of X and X' independently represents an alkylene group, an oxygen atom or a sulfur atom.

Each of m and m' means the number of substituents, being independently an integer of 0 to 5, preferably 0 or 1.

The alkyl group represented by $R_9$ or $R_9'$ is preferably an alkyl group having 1 to 4 carbon atoms, more preferably a methyl group or an ethyl group. A methyl group is most preferable. As the cycloalkyl group, there can be mentioned a cyclopropyl group, a cyclobutyl group, a cyclopentyl group or a cyclohexyl group. As the alkoxycarbonyl group, there can be mentioned, for example, a methoxycarbonyl group, an ethoxycarbonyl group, an n-butoxycarbonyl group and a t-butoxycarbonyl group. As the alkoxy group, there can be mentioned, for example, a methoxy group, an ethoxy group, a propoxy group, an isopropoxy group and a butoxy group. Substituents may be introduced in these groups. As such substituents, there can be mentioned a hydroxyl group; an alkoxy group such as a methoxy group or an ethoxy group; a cyano group; and a halogen atom such as a fluorine atom.

More preferably, each of $R_9$ and $R_9'$ is a methyl group, a cyano group or an alkoxycarbonyl group, further more preferably a cyano group.

As the alkylene group represented by X or X', a methylene group, an ethylene group and the lile are exemplified. It is preferred that each of X and X' is an oxygen atom or a methylene group, more preferably a methylene group.

When m, or m' is 1 or greater, it is preferred for the substitution with at least one $R_9$, or $R_9'$ to take place at the α- or β-position of the carbonyl group of the lactone. The substitution at the α-position is especially preferred.

Specific examples of the repeating units having the groups with a lactone structure or sultone structure of general formulae (III-1) or (III-1') will be shown below, which however in no way limit the scope of the present invention. In the following specific examples, R represents a hydrogen atom, an optionally substituted alkyl group or a halogen atom. Preferably, R represents a hydrogen atom, a methyl group, a hydroxymethyl group or an acetoxymethyl group.

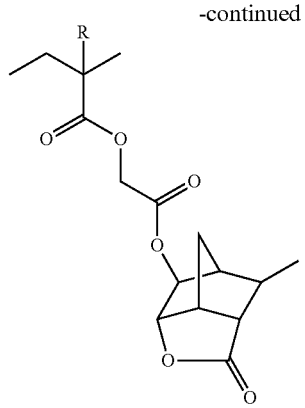

87
-continued
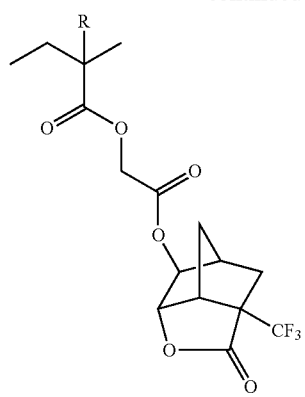
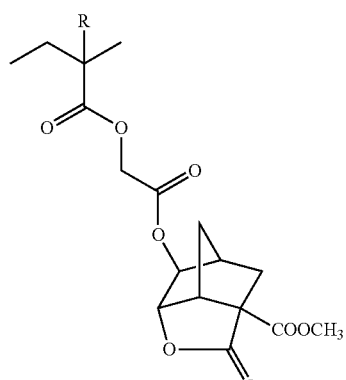
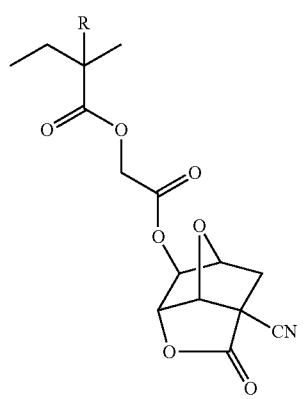
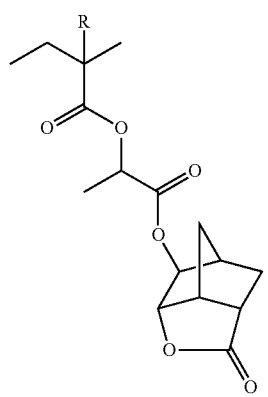
88
-continued
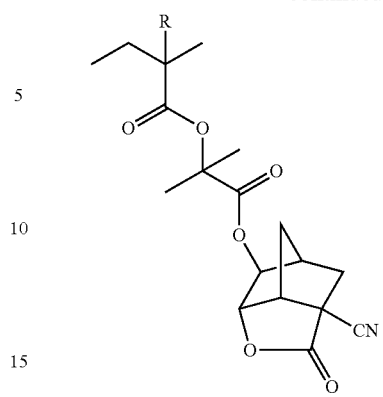
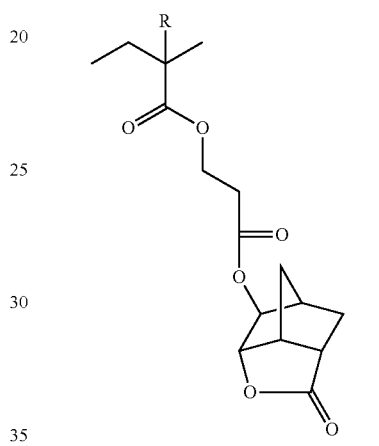
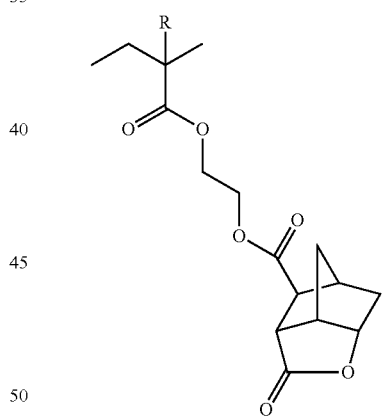
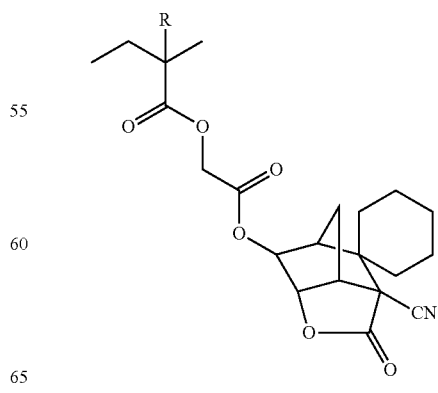

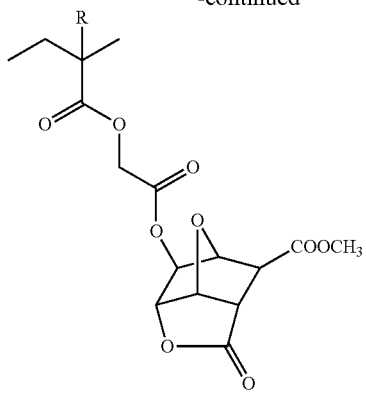

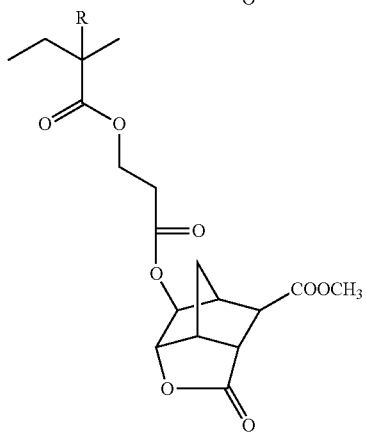

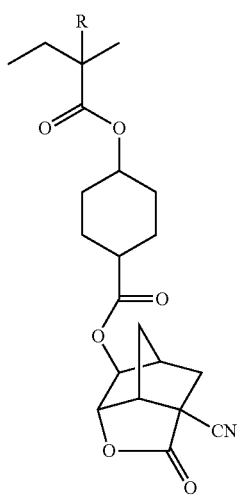

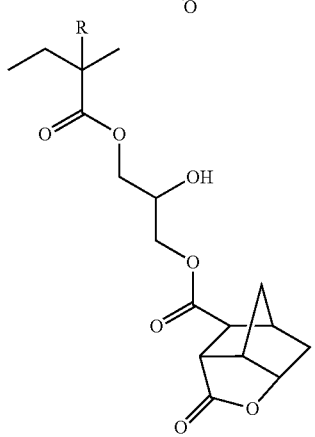

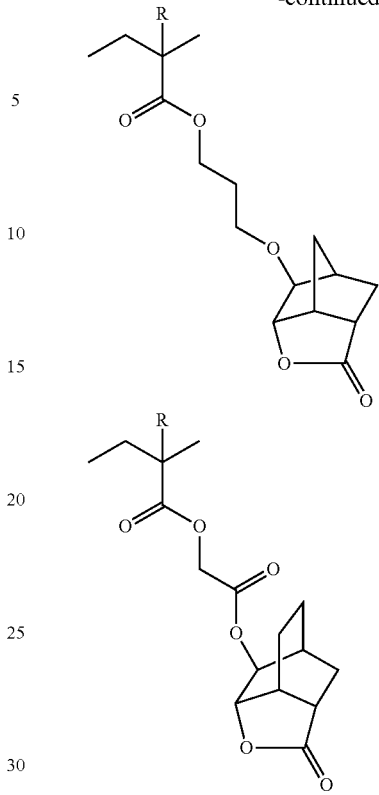

The content of repeating unit represented by the general formula (III) (when two or more types are contained, the sum thereof) based on all the repeating units of the resin is preferably in the range of 15 to 60 mol %, more preferably 20 to 60 mol % and further more preferably 30 to 50 mol %.

In an embodiment, a repeating unit represented by the general formula (III) can be a repeating unit represented by the following general formula (AII').

(AII')

In general formula (AII'), $Rb_0$ represents a hydrogen atom, a halogen atom or an optionally substituted alkyl group having 1 to 4 carbon atoms. As a preferred substituent optionally contained in the alkyl group represented by $Rb_0$, there can be mentioned a hydroxyl group or a halogen atom. As the halogen atom represented by $Rb_0$, there can be mentioned a fluorine atom, a chlorine atom, a bromine atom or an iodine atom. The $Rb_0$ is preferably a hydrogen atom, a methyl group, a hydroxymethyl group or a trifluoromethyl group. A hydrogen atom and a methyl group are especially preferred.

V represents a group having a structure represented by any of general formulae (LC1-1) to (LC1-17), (SL1-1) and (SL1-2) above.

The resin (B) also can contain the repeating unit having a lactone structure or sultone structure described above other than the repeating unit represented by the general formula (III).

Specific examples of the repeating units having a lactone structure or a sultone structure will now be shown in addition to the above examples, which however in no way limit the scope of the present invention. In formulae below, Rx represents H, CH$_3$, CH$_2$OH or CF$_3$.
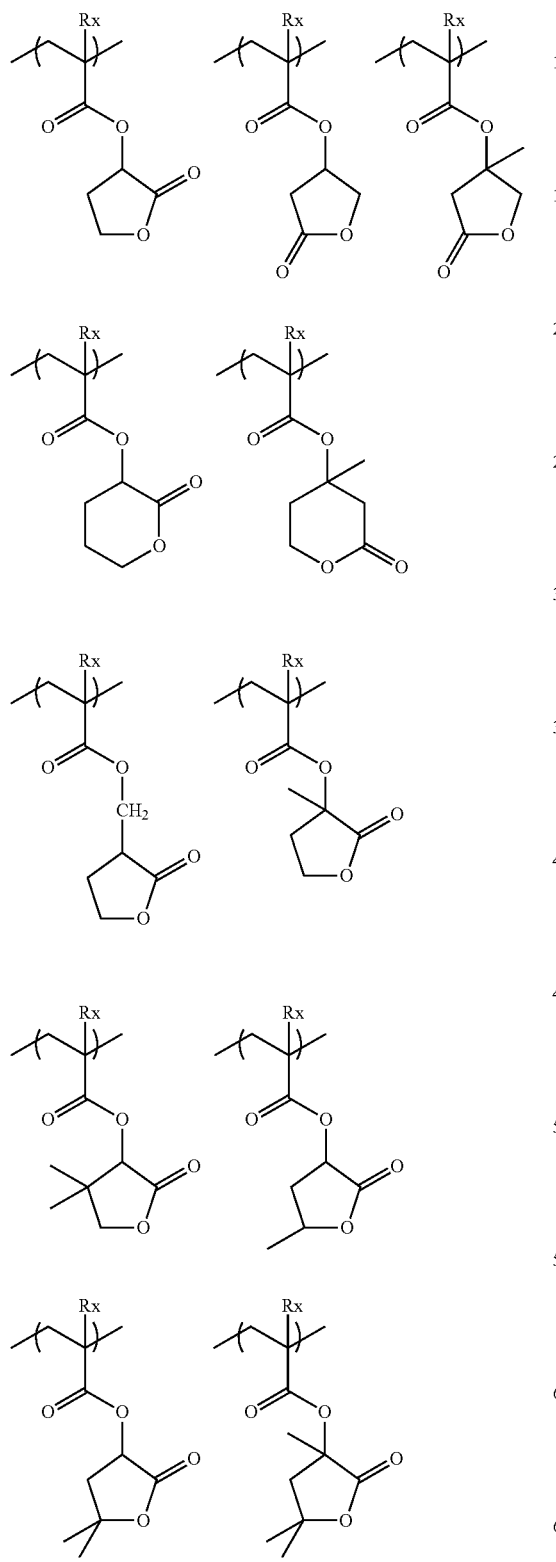
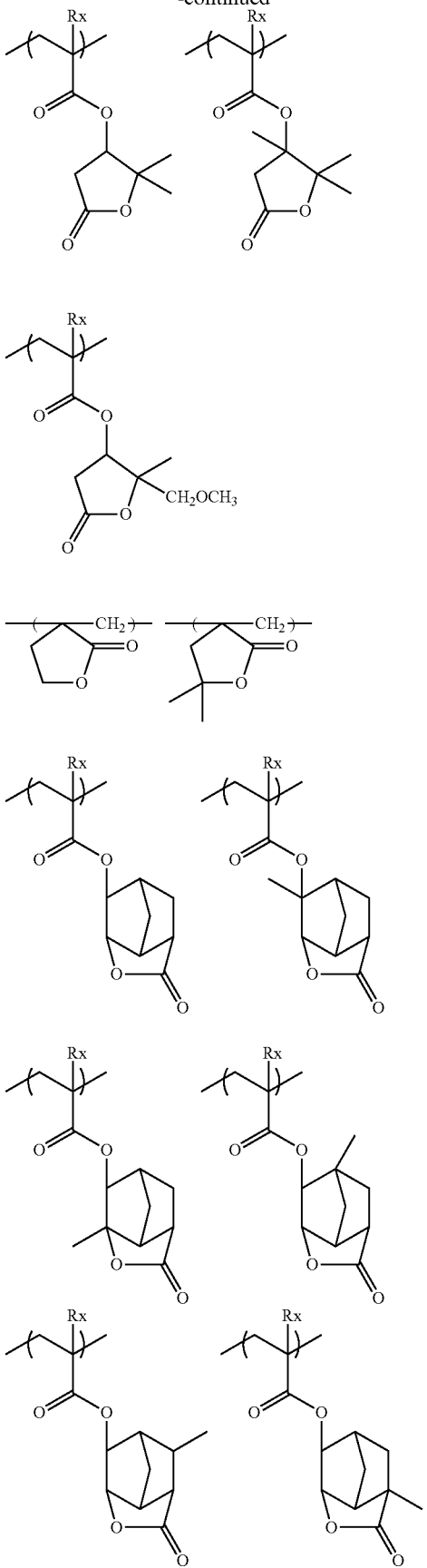

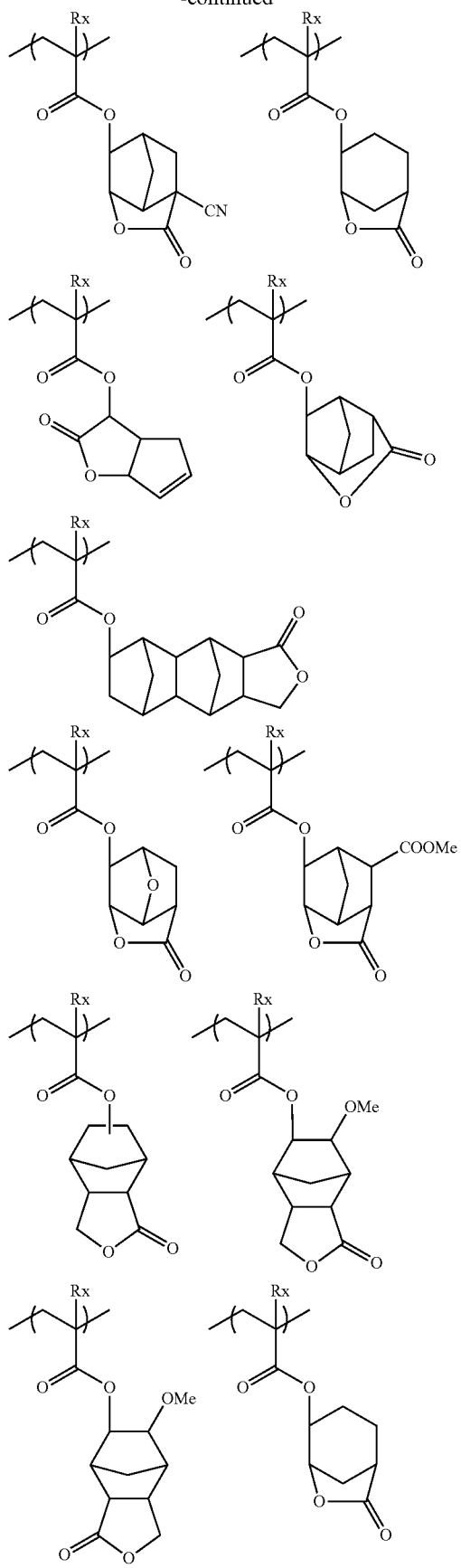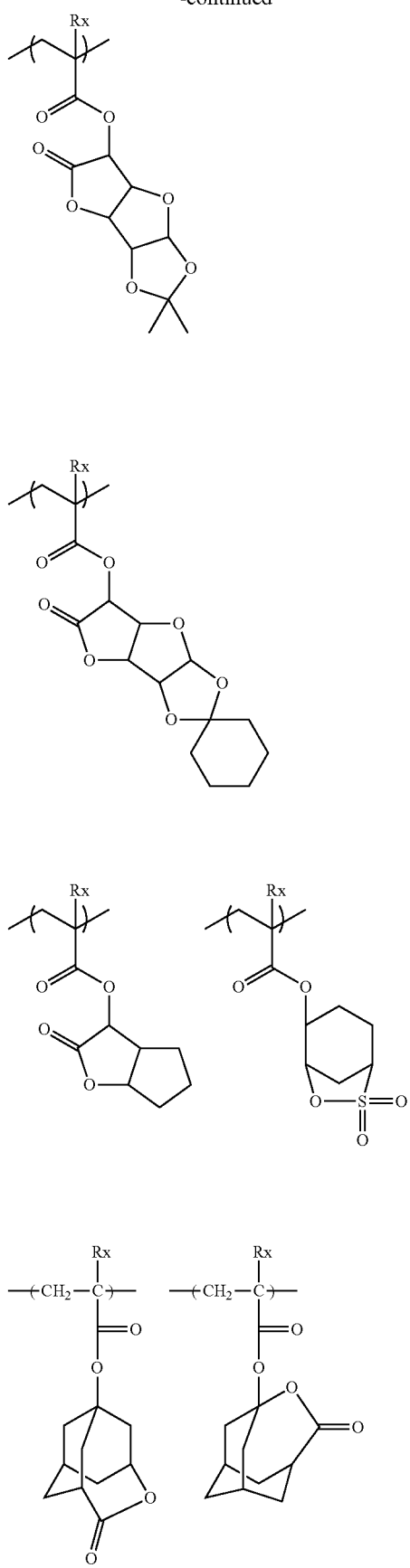

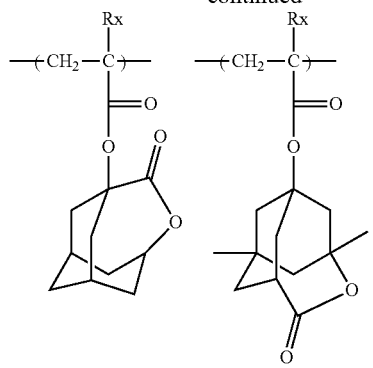
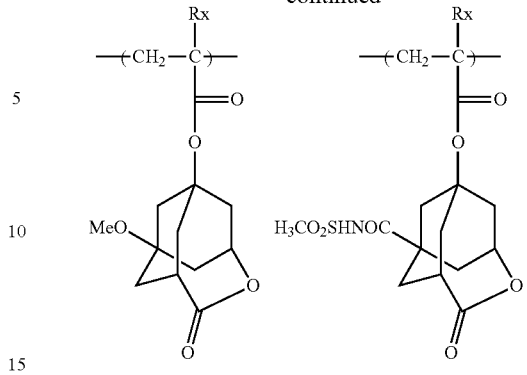
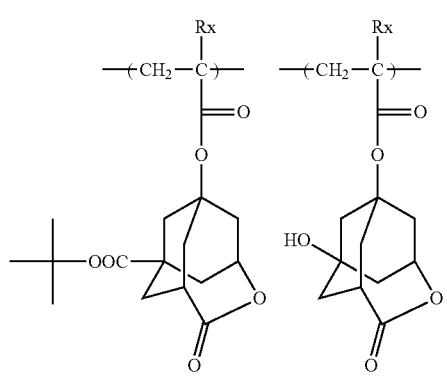
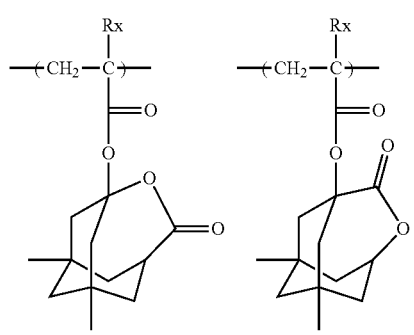
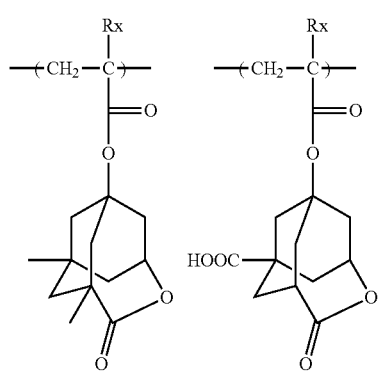
As especially preferred repeating units among the above specific examples, the followings can be exemplified. Selecting the best lactone group or sultone group can improve a pattern profile and iso-dense dependense. In the formulae below, Rx represents H, CH$_3$, CH$_2$OH, or CF$_3$.
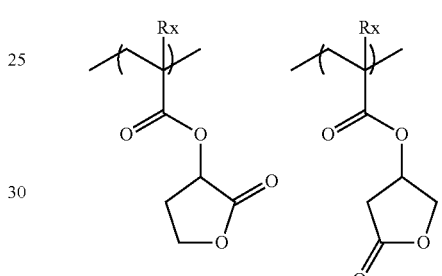
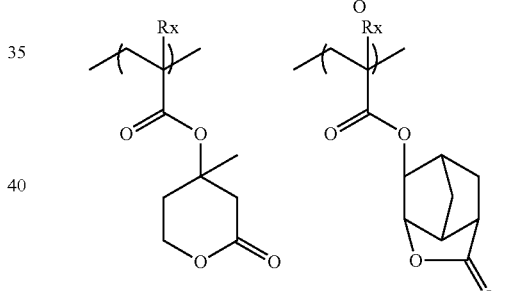
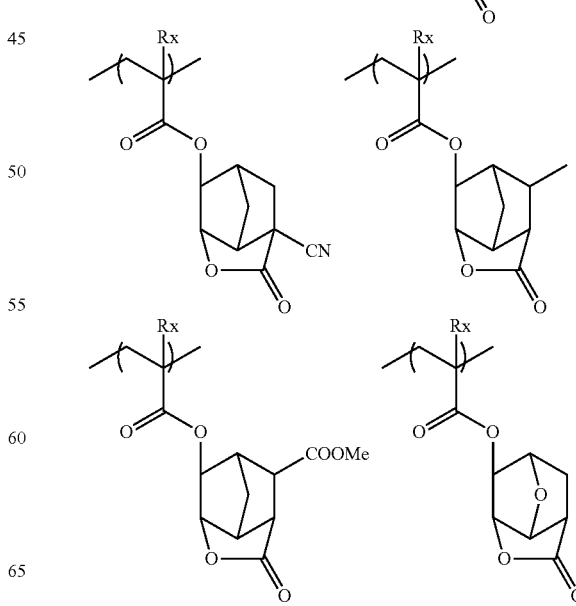

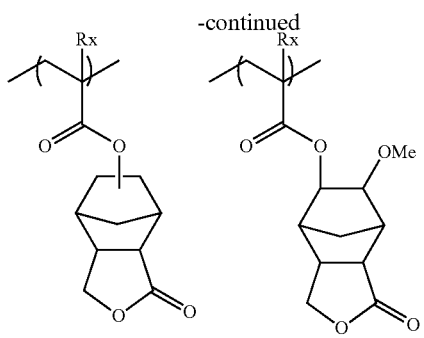

Each of the repeating units having a lactone group or sultone group is generally present in the form of optical isomers. Any of the optical isomers may be used. It is appropriate to use both a single type of optical isomer alone and a plurality of optical isomers in the form of a mixture. When a single type of optical isomer is mainly used, the optical purity (ee) thereof is preferably 90% or higher, more preferably 95% or higher.

The content of repeating unit containing a lactone structure or a sultone structure other than the repeating unit represented by the general formula (III) (when two or more types are contained, the sum thereof) based on all the repeating units of the resin is preferably in the range of 15 to 60 mol %, more preferably 20 to 50 mol % and further more preferably 30 to 50 mol %.

In order to enhance the effect of the present invention, it is practicable to simultaneously employ two or more repeating units having a lactone group or sultone group from among those of general formula (III). Especially, it is preferred to select two or more repeating units having a lactone group or sultone group from among those of general formula (III) in which n is 1 and simultaneously use them.

(3) Repeating unit having a hydroxyl group or a cyano group

The resin (B) preferably contains a repeating unit containing a hydroxyl group or a cyano group other than the repeating unit represented by the general formula (AI) and (III). Introducing this repeating unit enhances the adherence to substrates and the affinity to developer. A repeating unit containing a hydroxyl group or a cyano group is preferably a repeating unit having an alicyclic hydrocarbon structure substituted with a hydroxy group or a cyano group. Further, the repeating unit is preferably free from the acid-decomposable group. In the alicyclic hydrocarbon structure substituted with a hydroxy group or a cyano group, the alicyclic hydrocarbon structure preferably consists of an adamantyl group, a diamantyl group or a norbornane group. As preferred alicyclic hydrocarbon structures substituted with a hydroxy group or a cyano group, the partial structures represented by the following general formulae (VIIa) to (VIId) can be exemplified.

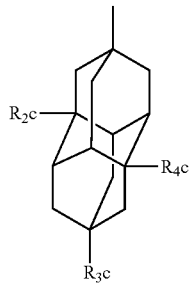
(VIIa)

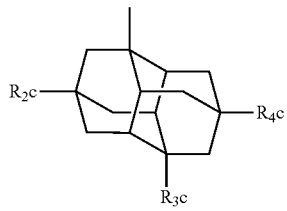
(VIIb)

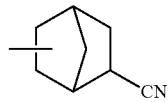
(VIIc)

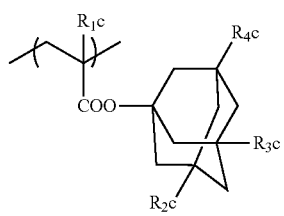
(VIId)

In the general formulae (VIIa) to (VIIc),
each of $R_2c$ to $R_4c$ independently represents a hydrogen atom, a hydroxy group or a cyano group, with the proviso that at least one of the $R_2c$ to $R_4c$ represents a hydroxy group or a cyano group. Preferably, one or two of the $R_2c$ to $R_4c$ are hydroxy groups and the remainder is a hydrogen atom. In the general formula (VIIa), more preferably, two of the $R_2c$ to $R_4c$ are hydroxy groups and the remainder is a hydrogen atom.

As the repeating units having any of the partial structures represented by the general formulae (VIIa) to (VIId), those of the following general formulae (AIIa) to (AIId) can be exemplified.

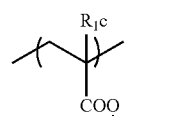
(AIIa)

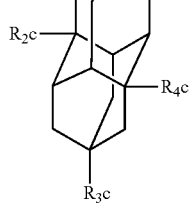
(AIIb)

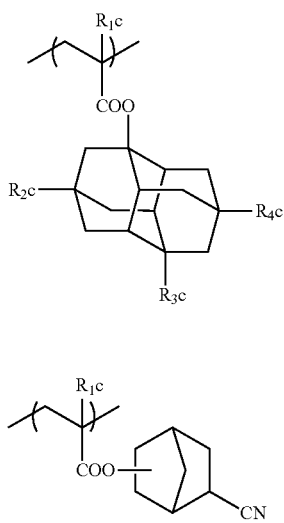

(AIIc)

(AIId)

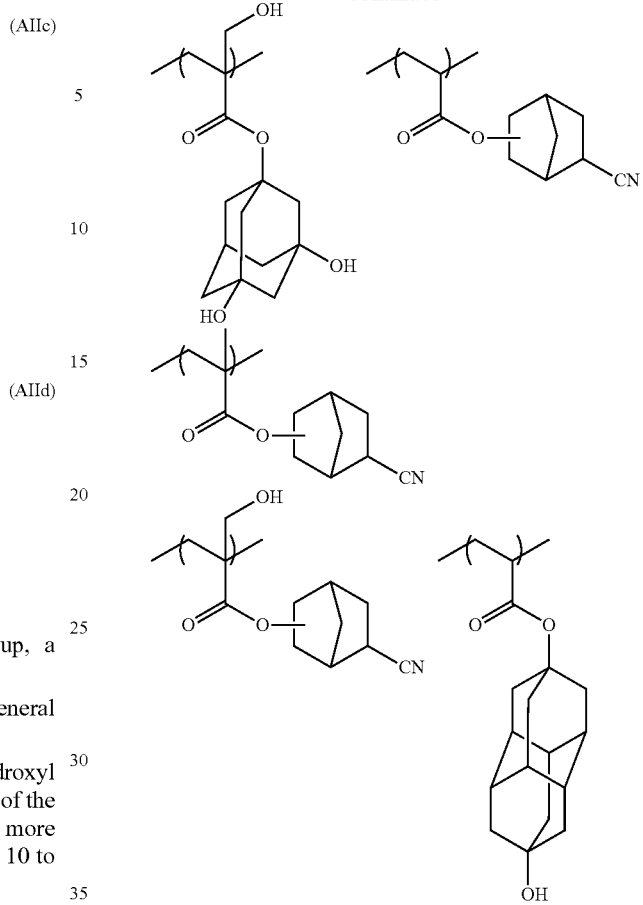

In the general formulae (AIIa) to (AIId), $R_1c$ represents a hydrogen atom, a methyl group, a trifluoromethyl group or a hydroxymethyl group.

$R_2c$ to $R_4c$ have the same meaning as those of the general formulae (VIIa) to (VIIc).

The content of the repeating unit containing a hydroxyl group or a cyano group based on all the repeating units of the resin (B) is preferably in the range of 5 to 40 mol %, more preferably 5 to 30 mol % and further more preferably 10 to 25 mol %.

Specific examples of the repeating units containing a hydroxyl group or a cyano group will be shown below, which however in no way limit the scope of the present invention.

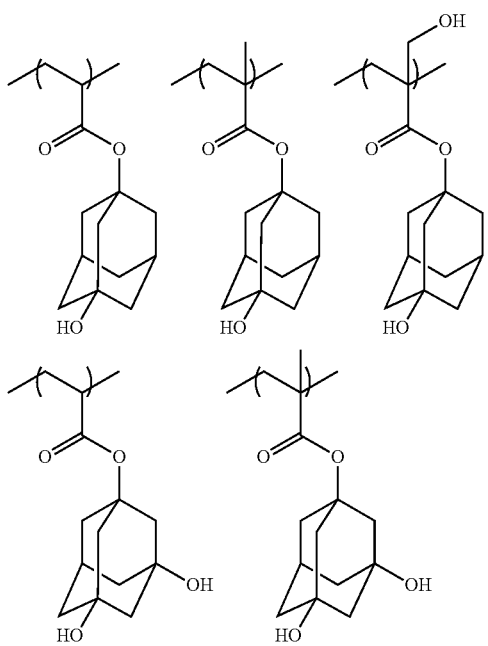

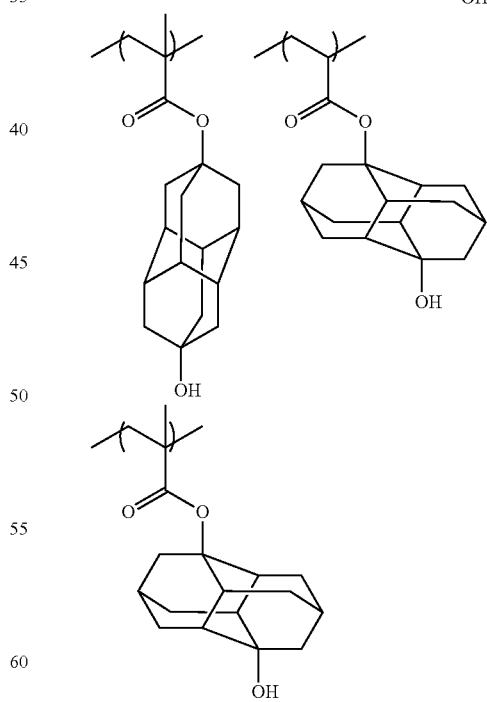

(4) Repeating unit having an alkali-soluble group

The resin contained in the actinic ray- or radiation-sensitive resin composition according to the invention can contain a repeating unit having an alkali-soluble group. As the alkali-soluble group, there can be mentioned a carboxyl group, a sulfonamido group, a sulfonylimide group, a bisulfonylimide group or an aliphatic alcohol substituted at its α-position with an electron-withdrawing group (for example, a hexafluoroisopropanol group). The possession of a repeating unit having a carboxyl group is more preferred. The incorporation of the repeating unit having an alkali-soluble group would increase the resolving power in contact hole usage. The repeating unit having an alkali-soluble group is preferably any of a repeating unit wherein the alkali-soluble group is directly bonded to the principal chain of a resin such as a repeating unit of acrylic acid or methacrylic acid, a repeating unit wherein the alkali-soluble group is bonded via a connecting group to the principal chain of a resin and a repeating unit wherein the alkali-soluble group is introduced in a terminal of a polymer chain by the use of a chain transfer agent or polymerization initiator having the alkali-soluble group in the stage of polymerization. The connecting group may have a monocyclic or polycyclic hydrocarbon structure. The repeating unit of acrylic acid or methacrylic acid is especially preferred.

The content ratio of the repeating unit having an alkali-soluble group based on all the repeating units of resin (B) is preferably in the range of 0 to 20 mol %, more preferably 3 to 15 mol % and still more preferably 5 to 10 mol %.

Specific examples of the repeating units having an alkali-soluble group will be shown below, which however in no way limit the scope of the present invention.

In the formulae, Rx represents H, $CH_3$, $CH_2OH$, or $CF_3$.

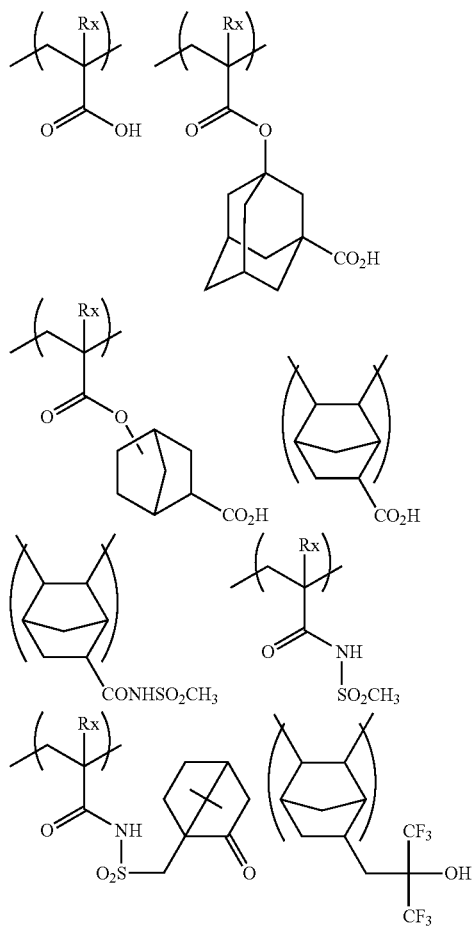

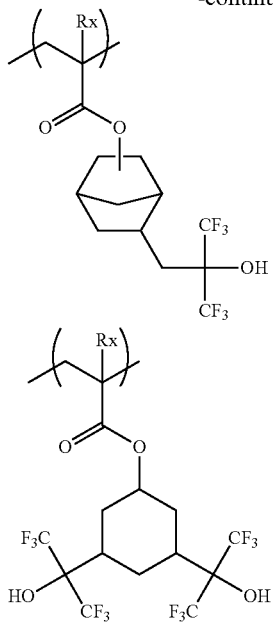

(5) Repeating unit that has a structure of alicyclic hydrocarbon having no polar group Resin (B) can further contain a repeating unit that has a structure of alicyclic hydrocarbon having no polar group (such as an above-mentioned alkali-soluble group, a hydroxyl group, a cyano group, etc.) and that exhibits no acid decomposability. As such a repeating unit, there can be mentioned any of the repeating units of general formula (IV) below.

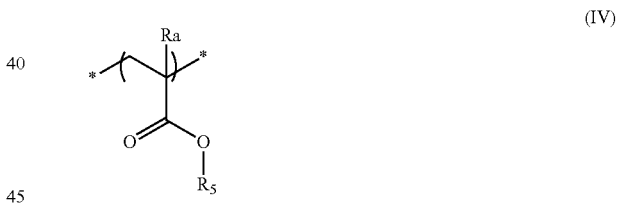

(IV)

In general formula (IV), $R_5$ represents a hydrocarbon group having at least one cyclic structure and having no polar group.

Ra represents a hydrogen atom, an alkyl group or a group of the formula $-CH_2-O-Ra_2$ in which $Ra_2$ represents a hydrogen atom, an alkyl group or an acyl group. Ra preferably represents a hydrogen atom, a methyl group, a trifluoromethyl group, a hydroxymethyl group or the like, more preferably a hydrogen atom and a methyl group.

The cyclic structures contained in $R_5$ include a monocyclic hydrocarbon group and a polycyclic hydrocarbon group. As the monocyclic hydrocarbon group, there can be mentioned, for example, a cycloalkyl group having 3 to 12 carbon atoms, such as a cyclopentyl group, a cyclohexyl group, a cycloheptyl group or a cyclooctyl group, or a cycloalkenyl group having 3 to 12 carbon atoms, such as a cyclohexenyl group. Preferably, the monocyclic hydrocarbon group is a monocyclic hydrocarbon group having 3 to 7 carbon atoms. A cyclopentyl group and a cyclohexyl group are more preferred.

The polycyclic hydrocarbon groups include ring-assembly hydrocarbon groups and crosslinked-ring hydrocarbon groups. Examples of the ring-assembly hydrocarbon groups include a bicyclohexyl group, a perhydronaphthalene group and the like. As the crosslinked-ring hydrocarbon rings, there can be mentioned, for example, bicyclic hydrocarbon rings, such as pinane, bornane, norpinane, norbornane and bicyclooctane rings (e.g., bicyclo[2.2.2]octane ring or bicyclo[3.2.1]octane ring); tricyclic hydrocarbon rings, such as adamantane, tricyclo[5.2.1.0$^{2,6}$]decane and tricyclo[4.3.1.1$^{2,5}$]undecane rings; and tetracyclic hydrocarbon rings, such as tetracyclo[4.4.0.1$^{2,5}$.1$^{7,10}$]dodecane and perhydro-1,4-methano-5,8-methanonaphthalene rings. Further, the crosslinked-ring hydrocarbon rings include condensed-ring hydrocarbon rings, for example, condensed rings resulting from condensation of multiple 5- to 8-membered cycloalkane rings, such as perhydronaphthalene (decalin), perhydroanthracene, perhydrophenanthrene, perhydroacenaphthene, perhydrofluorene, perhydroindene and perhydrophenarene rings.

As preferred crosslinked-ring hydrocarbon rings, there can be mentioned, for example, a norbornyl group, an adamantyl group, a bicyclooctanyl group and a tricyclo[5,2,1,0$^{2,6}$]decanyl group. As more preferred crosslinked-ring hydrocarbon rings, there can be mentioned a norbornyl group and an adamantyl group.

These alicyclic hydrocarbon groups may have substituents. As preferred substituents, there can be mentioned, for example, a halogen atom, an alkyl group, a hydroxyl group in which a hydrogen atom is substituted and an amino group in which a hydrogen atom is substituted. The halogen atom is preferably a bromine, chlorine or fluorine atom, and the alkyl group is preferably a methyl, ethyl, butyl or t-butyl group. The alkyl group may further have a substituent. As the optional further substituent, there can be mentioned a halogen atom, an alkyl group, a hydroxyl group in which a hydrogen atom is substituted or an amino group in which a hydrogen atom is substituted.

As the group in which a hydrogen atom is substituted, there can be mentioned, for example, an alkyl group, a cycloalkyl group, an aralkyl group, a substituted methyl group, a substituted ethyl group, an alkoxycarbonyl group or an aralkyloxycarbonyl group. The alkyl group is preferably an alkyl group having 1 to 4 carbon atoms. The substituted methyl group is preferably a methoxymethyl, methoxythiomethyl, benzyloxymethyl, t-butoxymethyl or 2-methoxyethoxymethyl group. The substituted ethyl group is preferably a 1-ethoxyethyl or 1-methyl-1-methoxyethyl group. The acyl group is preferably an aliphatic acyl group having 1 to 6 carbon atoms, such as a formyl, acetyl, propionyl, butyryl, isobutyryl, valeryl or pivaloyl group. The alkoxycarbonyl group is, for example, an alkoxycarbonyl group having 1 to 4 carbon atoms.

The repeating unit that has a structure of alicyclic hydrocarbon having no polar group, exhibiting no acid decomposability may or may not be contained in the resin (B). When the repeating unit that has a structure of alicyclic hydrocarbon having no polar group, exhibiting no acid decomposability is contained in the resin (B), the content ratio of the repeating unit, based on all repeating units of resin (B), is preferably in the range of 1 to 40 mol %, more preferably 2 to 20 mol %.

Specific examples of the repeating units that have a structure of alicyclic hydrocarbon having no polar group, exhibiting no acid decomposability will be shown below, which however in no way limit the scope of the present invention. In the formulae, Ra represents H, CH$_3$, CH$_2$OH or CF$_3$.

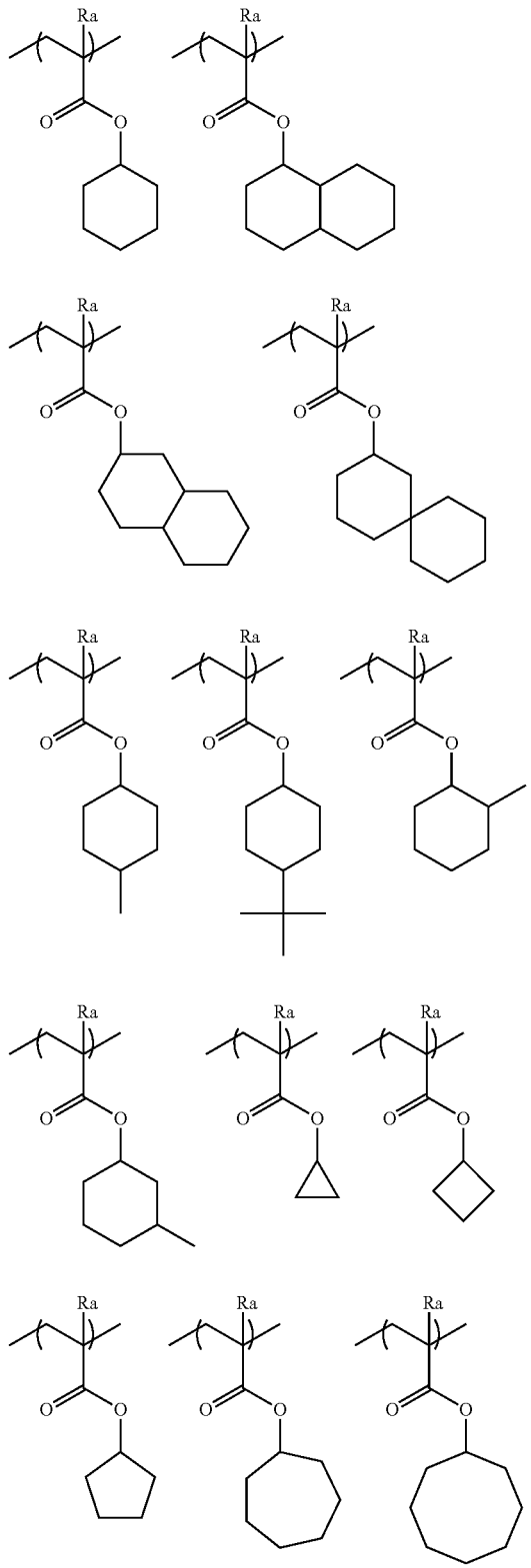

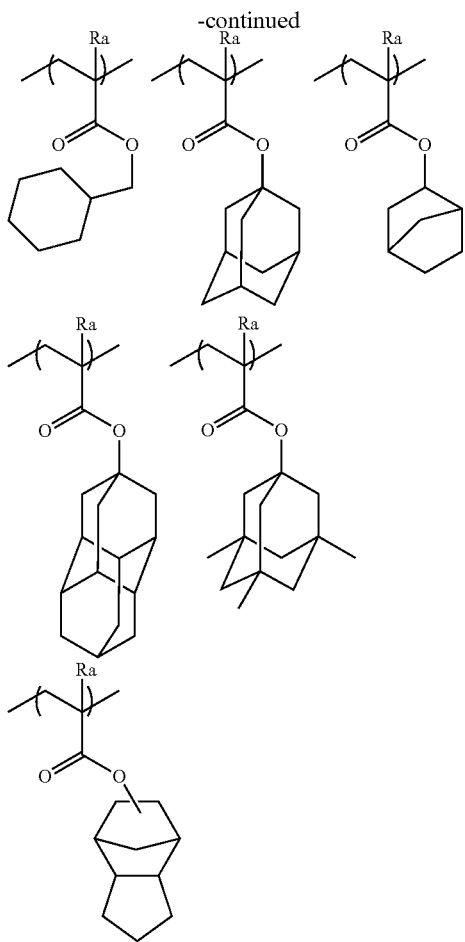

Resin (B) may have, in addition to the foregoing repeating structural units, various repeating structural units for the purpose of regulating the dry etching resistance, standard developer adaptability, substrate adhesion, resist profile and generally required properties of the resist such as resolving power, heat resistance and sensitivity.

As such repeating structural units, there can be mentioned those corresponding to the following monomers, which however are nonlimiting.

The use of such repeating structural units would enable fine regulation of the required properties of a resin contained in the composition of the present invention, especially: (1) solubility in applied solvents, (2) film forming easiness (glass transition point), (3) alkali developability, (4) film thinning (selections of hydrophilicity/hydrophobicity and alkali-soluble group), (5) adhesion of unexposed area to substrate, and (6) dry etching resistance, etc.

As appropriate monomers, there can be mentioned, for example, a compound having an unsaturated bond capable of addition polymerization, selected from among acrylic esters, methacrylic esters, acrylamides, methacrylamides, allyl compounds, vinyl ethers, vinyl esters and the like.

In addition, any unsaturated compound capable of addition polymerization that is copolymerizable with monomers corresponding to the above various repeating structural units may be copolymerized therewith.

The molar ratios of individual repeating structural units contained in resin (B) are appropriately determined from the viewpoint of regulation of not only the dry etching resistance of the resist but also the standard developer adaptability, substrate adhesion, resist profile and generally required properties of the resist such as the resolving power, heat resistance and sensitivity.

When the composition of the present invention is one for ArF exposure, it is preferred for resin (B) to have no aromatic group substantially from the viewpoint of transparency to ArF beams. More specifically, the content ratio of the repeating unit having an aromatic group based on all the repeating units of resin (B) is preferably no more than 5 mol %, more preferably no more than 3 mol % and ideally 0 mol % (i.e. the repeating unit having aromatic group is not contained in resin (B)). It is preferred for resin (B) to contain an alicyclc hydrocarbon structure with single ring or multiple rings.

From the viewpoint of the compatibility with hydrophobic resin as the second resin to be described below, it is preferred for resin (B) to contain neither a fluorine atom nor a silicon atom.

In resin (B), preferably, all the repeating units are (meth)acrylate repeating units. In that instance, use can be made of any of a resin wherein all the repeating units consist of methacrylate repeating units, a resin wherein all the repeating units consist of acrylate repeating units and a resin wherein all the repeating units consist of methacrylate repeating units and acrylate repeating units. However, it is preferred for the acrylate repeating units to account for 50 mol % or less of all the repeating units. It is also preferred that the resin (B) is copolymer containing 20 to 50 mol % of a (meth)acrylate repeating unit having an acid-decomposable group, 20 to 50 mol % of a (meth)acrylate repeating unit having a lactone group, 5 to 30 mol % of a (meth)acrylate repeating unit having an alicyclic hydrocarbon structure substituted with a hydroxy group or a cyano group, and 0 to 20 mol % of additional (meth)acrylate repeating unit.

When the composition of the present invention is exposed to a KrF excimer laser light, electron beams, X-rays or high-energy light rays of wavelength 50 nm or shorter (for example, EUV), it is preferred for the resin (B) to further comprise a hydroxystyrene repeating unit. It is more preferred for the resin (B) to further comprise not only a hydroxystyrene repeating unit but also a hydroxystyrene repeating unit protected by an acid-decomposable group and an acid-decomposable repeating unit of (meth)acrylic acid tertiary alkyl ester or the like.

As hydroxystyrene repeating units containing preferred acid-decomposable groups, there can be mentioned, for example, repeating units of t-butoxycarbonyloxystyrene, 1-alkoxyethoxystyrenes and (meth)acrylic acid tertiary alkyl esters. Repeating units of 2-alkyl-2-adamantyl (meth)acrylates and dialkyl(1-adamantyl)methyl (meth)acrylates are preferred.

Resin (B) can be synthesized by conventional techniques (for example, radical polymerization). As general synthetic methods, there can be mentioned, for example, a batch polymerization method in which a monomer species and an initiator are dissolved in a solvent and heated so as to accomplish polymerization and a dropping polymerization method in which a solution of monomer species and initiator is added by dropping to a heated solvent over a period of 1 to 10 hours. The dropping polymerization method is preferred. As a reaction solvent, there can be mentioned, for example, an ether, such as tetrahydrofuran, 1,4-dioxane or diisopropyl ether; a ketone, such as methyl ethyl ketone or methyl isobutyl ketone; an ester solvent, such as ethyl acetate; an amide solvent, such as dimethylformamide or dimethylacetamide; or the solvent capable of dissolving the composition of the present invention, such as propylene glycol monomethyl ether acetate, propylene glycol monomethyl ether or cyclohexanone, to be described hereinafter. It is preferred to perform the polymerization with the use of the same solvent as employed in the actinic ray- or radiation-sensitive resin composition of the present invention. This would inhibit any particle generation during storage.

The polymerization reaction is preferably carried out in an atmosphere of inert gas, such as nitrogen or argon. The polymerization is initiated by the use of a commercially available radical initiator (azo initiator, peroxide, etc.) as a polymerization initiator. Among the radical initiators, an azo initiator is preferred. An azo initiator having an ester group, a cyano group or a carboxyl group is especially preferred. As preferred initiators, there can be mentioned azobisisobutyronitrile, azobisdimethylvaleronitrile, dimethyl 2,2'-azobis (2-methylpropionate) and the like. According to necessity, a supplementation of initiator or divided addition thereof may be effected. After the completion of the reaction, the reaction mixture is poured into a solvent. The desired polymer is recovered by a method for powder or solid recovery, etc. The concentration during the reaction is in the range of 5 to 50 mass %, preferably 10 to 30 mass %. The reaction temperature is generally in the range of 10° to 150° C., preferably 30° to 120° C. and more preferably 60° to 100° C.

The weight average molecular weight of resin (B) in terms of polystyrene molecular weight as measured by GPC is preferably in the range of 1000 to 200,000, more preferably 2,000 to 20,000, still more preferably 3,000 to 15,000 and further preferably 5,000 to 11,000. The regulation of the weight average molecular weight to 1000 to 200,000 would prevent deteriorations of heat resistance and dry etching resistance and also prevent deterioration of developability and increase of viscosity leading to poor film forming property.

Use is made of the resin whose dispersity (molecular weight distribution) is generally in the range of 1.0 to 3.0, preferably 1.0 to 2.6, more preferably 1.0 to 2.0 and most preferably 1.4 to 2.0. The lower the molecular weight distribution, the more excellent the resolving power and resist profile and the smoother the side wall of the resist pattern to thereby attain an excellence in roughness.

In the actinic ray- or radiation-sensitive resin composition of the present invention, the content ratio of resin (B), based on the total solid content of the whole composition, is preferably in the range of 30 to 99 mass %, more preferably 60 to 95 mass %. Resin (B) may be used either individually or in combination. As long as the effect of the invention is not compromised, the actinic ray- or radiation-sensitive resin composition of the present invention may contain any other resins in addition to resin (B). As any other resins in addition to resin (B), a resin that is decomposed by the action of an acid and may contains the repeating unit included in resin (B) or a resin that is decomposed by the action of an acid and is already-known.

[3] Hydrophobic Resin

The actinic ray- or radiation-sensitive resin composition according to the present invention may further contain a hydrophobic resin (hereinafter, also referred to as "hydrophobic resin (HR)") including a repeating unit containing at least either fluorine atom or silicon atom, especially when the composition is used for a liquid-immersion exposure. When the hydrophobic resin is contained, the hydrophobic resin (HR) is localized in a surface layer of resist film, so that in the use of water as an immersion medium, the static/dynamic contact angle of the film with the immersion liquid can be increased to thereby enhance the immersion liquid tracking property of the film.

Although the hydrophobic resin is unevenly localized on any interface, as different from the surfactant, the hydrophobic resin does not necessarily have to have a hydrophilic group in its molecule and does not need to contribute toward uniform mixing of polar/nonpolar substances.

The hydrophobic resin (HR) is typically a resin containing a fluorine atom and/or a silicon atom. The fluorine atom or the silicon atom in the hydrophobic resin (HR) may present either in the principal chain or in the side chain.

When the hydrophobic resin (HR) contains one or more fluorine atoms, a partial structure containing one or more fluorine atoms is preferably an alkyl group containing one or more fluorine atoms, a cycloalkyl group containing one or more fluorine atoms, or an aryl group containing one or more fluorine atoms.

The alkyl group containing one or more fluorine atoms is a linear or branched alkyl group having at least one hydrogen atom thereof substituted with one or more fluorine atoms. The group preferably has 1 to 10 carbon atoms, more preferably 1 to 4 carbon atoms. Further, other substituents may also be contained.

The cycloalkyl group containing one or more fluorine atoms is a monocyclic or polycyclic alkyl group having at least one hydrogen atom thereof substituted with one or more fluorine atoms. Further, other substituents may also be contained.

The aryl group containing one or more fluorine atoms is an aryl group having at least one hydrogen atom of an aryl group substituted with one or more fluorine atoms. As the aryl group, a phenyl or a naphthyl group can be exemplified. Further, other substituents may also be contained.

As preferred alkyl groups containing one or more fluorine atoms, cycloalkyl groups containing one or more fluorine atoms and aryl groups containing one or more fluorine atoms, groups of the following general formulae (F2) to (F4) can be exemplified, which however in no way limit the scope of the present invention.

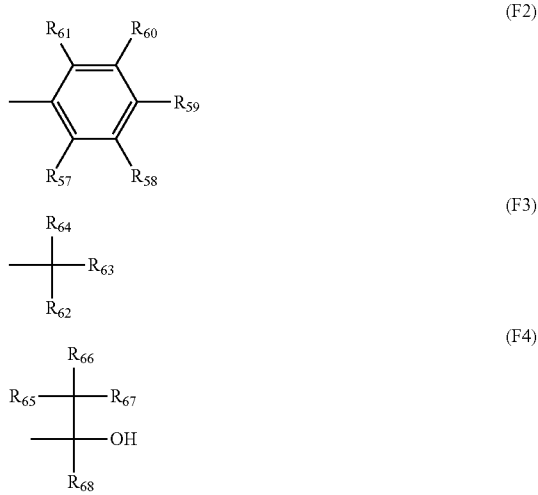

In the general formulae (F2) to (F4), each of $R_{57}$ to $R_{68}$ independently represents a hydrogen atom, a fluorine atom or an alkyl group in condition that: at least one of $R_{57}$-$R_{61}$ represents a fluorine atom or an alkyl group having at least one hydrogen atom thereof substituted with one or more fluorine atoms; at least one of $R_{62}$-$R_{64}$ represents a fluorine atom or an alkyl group having at least one hydrogen atom thereof substituted with one or more fluorine atoms; and at least one of $R_{65}$-$R_{68}$ represents a fluorine atom or an alkyl group having at least one hydrogen atom thereof substituted with one or more fluorine atoms. These alkyl groups preferably are those having 1 to 4 carbon atoms.

It is preferred that all of $R_{57}$-$R_{61}$ and $R_{65}$-$R_{67}$ represent fluorine atoms. Each of $R_{62}$, $R_{63}$ and $R_{68}$ preferably represents a fluoroalkyl group (preferably, having 1 to 4 carbon atoms), and more preferably represents a perfluoroalkyl group having 1 to 4 carbon atoms. When each of $R_{62}$ and $R_{63}$ represents a perfluoroalkyl group, $R_{64}$ preferably represents a hydrogen atom. $R_{62}$ and $R_{63}$ may be bonded to each other to form a ring.

Specific examples of the groups represented by the general formula (F2) include a p-fluorophenyl group, a pentafluorophenyl group, and a 3,5-di(trifluoromethyl)phenyl group.

Specific examples of the groups represented by the general formula (F3) include a trifluoromethyl group, a pentafluoropropyl group, a pentafluoroethyl group, a heptafluorobutyl group, a hexafluoroisopropyl group, a heptafluoroisopropyl group, a hexafluoro(2-methyl)isopropyl group, a nonafluorobutyl group, an octafluoroisobutyl group, a nonafluorohexyl group, a nonafluoro-t-butyl group, a perfluoroisopentyl group, a perfluorooctyl group, a perfluoro(trimethyl)hexyl group, a 2,2,3,3-tetrafluorocyclobutyl group, and a perfluorocyclohexyl group. Of these, a hexafluoroisopropyl group, a heptafluoroisopropyl group, a hexafluoro(2-methyl)isopropyl group, an octafluoroisobutyl group, a nonafluoro-t-butyl group and a perfluoroisopentyl group are preferred. A hexafluoroisopropyl group and a heptafluoroisopropyl group are more preferred.

Specific examples of the groups represented by the general formula (F4) include —C(CF$_3$)$_2$OH, —C(C$_2$F$_5$)$_2$OH, —C(CF$_3$)(CH$_3$)OH, —CH(CF$_3$)OH and the like. Of these, —C(CF$_3$)$_2$OH is particularly preferred.

The partial structure containing a fluorine atom may directly be bonded to the principal chain. Alternatively, the partial structure may be bonded to the principal chain via an alkylene group, a phenylene group, an ether bond, a thioether bond, a carbonyl group, an ester bond, an amido bond, a urethane bond, a ureylene bond, or a combination of at least two of these.

Preferred repeating units containing one or more fluorine atoms are as follows.

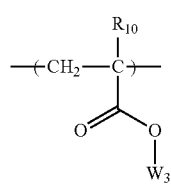

(C-Ia)

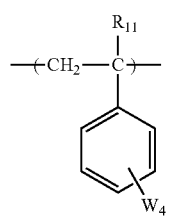

(C-Ib)

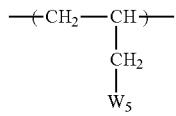

(C-Ic)

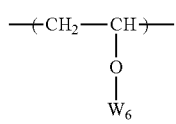

(C-Id)

In the formulae (C-Ia) to (C-Id), $R_{10}$ and $R_{11}$ each independently represents a hydrogen atom, a fluorine atom, and an alkyl group. As the alkyl group, a linear or branched alkyl group having 1 to 4 carbon atoms is preferred and the alkyl group may have one or more substituents. As an alkyl group with one or more substituents, a fluorinated alkyl group can especially be exemplified.

Each of $W_3$ to $W_6$ independently represents an organic group containing one or more fluorine atoms. Specifically, groups represented by the general formulae (F2) to (F4) can be exemplified.

The hydrophobic resin may further contain the following units as the repeating unit containing one or more fluorine atoms other than the repeating unit described above.

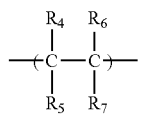

(C-II)

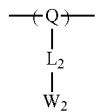

(C-III)

In the formulae (C-II) and (C-III), each of $R_4$ to $R_7$ independently represents a hydrogen atom, a fluorine atom, and an alkyl group. As the alkyl group, a linear or branched alkyl group having 1 to 4 carbon atoms is preferred. As an alkyl group with one or more substituents, a fluorinated alkyl group can especially be exemplified.

With the proviso that at least one of $R_4$ to $R_7$ represents a fluorine atom and $R_4$ and $R_5$ or $R_6$ and $R_7$ may form a ring.

$W_2$ represents an organic group containing one or more fluorine atoms. Specifically, groups represented by the general formulae (F2) to (F4) can be exemplified.

$L_2$ represents a single bond or divalent connecting group. As the divalent connecting group, a substituted or nonsubstituted arylene group, a substituted or nonsubstituted alkylene group, —O—, —SO$_2$—, —CO—, —N(R)— (R represents a hydrogen atom or an alkyl group), —NHSO$_2$—, or a combination of two or more of these groups.

Q represents an alicyclic structure. The alicyclic structure may contain one or more substituents, and may either be monocyclic or polycyclic. When the alicyclic structure contains a polycyclic structure, it may be a bridged type. As the monocyclic one, a cycloalkyl group having 3 to 8 carbon atoms such as a cyclopenryl group, a cyclohexyl group, a cyclobutyl group, or a cyclobutyl group is preferred. As the polycyclic one, a group containing bicyclo-, tricyclo-, or tetracyclo-structure having 5 or more carbon atoms can be exemplified. The polycyclic one preferably is a cycloalkyl group having 6 to 20 carbon atoms such as an adamantyl group, a norbornyl group, a dicyclopentyl group, a tricyclodecanyl group, or a tetracyclododecyl group. At least one of carbon atoms in the cycloalkyl group may be substituted with one or more heteroatoms such as oxygen atoms. Especially preferred Q include a norbornyl group, a tricyclodecanyl group, a tetracyclodecanyl group, or the like.

The hydrophobic resin may contain one or more silicon atoms. As partial structure containing one ore more silicon atoms, an alkylsilyl structure or a cyclosiloxane structure can be exemplified. Preferred alkylsilyl structure is the one containing one or more trialkylsilyl groups.

As the alkylsilyl structure and cyclosiloxane structure, any of the groups represented by the following general formulae (CS-1) to (CS-3) can be exemplified.

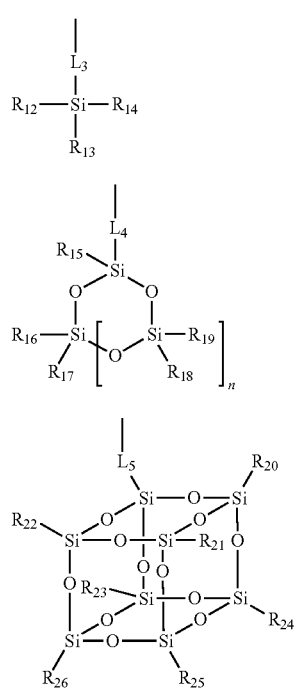

In the general formulae (CS-1) to (CS-3), each of $R_{12}$ to $R_{26}$ independently represents a linear or branched alkyl group or a cycloalkyl group. The alkyl group preferably has 1 to 20 carbon atoms. The cycloalkyl group preferably has 3 to 20 carbon atoms.

Each of $L_3$ to $L_5$ represents a single bond or a bivalent connecting group. As the bivalent connecting group, any one or a combination of two or more groups selected from the group consisting of an alkylene group, a phenylene group, an ether group, a thioether group, a carbonyl group, an ester group, an amido group, a urethane group and a ureylene group can be exemplified.

In the formulae, n is an integer of 1 to 5, and preferably an integer of 2 to 4.

Repeating units having at least either fluorine atom or silicon atom is preferably a (metha)acrylate-type repeating unit.

Specific examples of the repeating units having at least either fluorine atom or silicon atom will be shown below, which however in no way limit the scope of the present invention. In the specific examples, $X_1$ represents a hydrogen atom, $-CH_3$, $-F$ or $-CF_3$, and $X_2$ represents $-F$ or $-CF_3$.

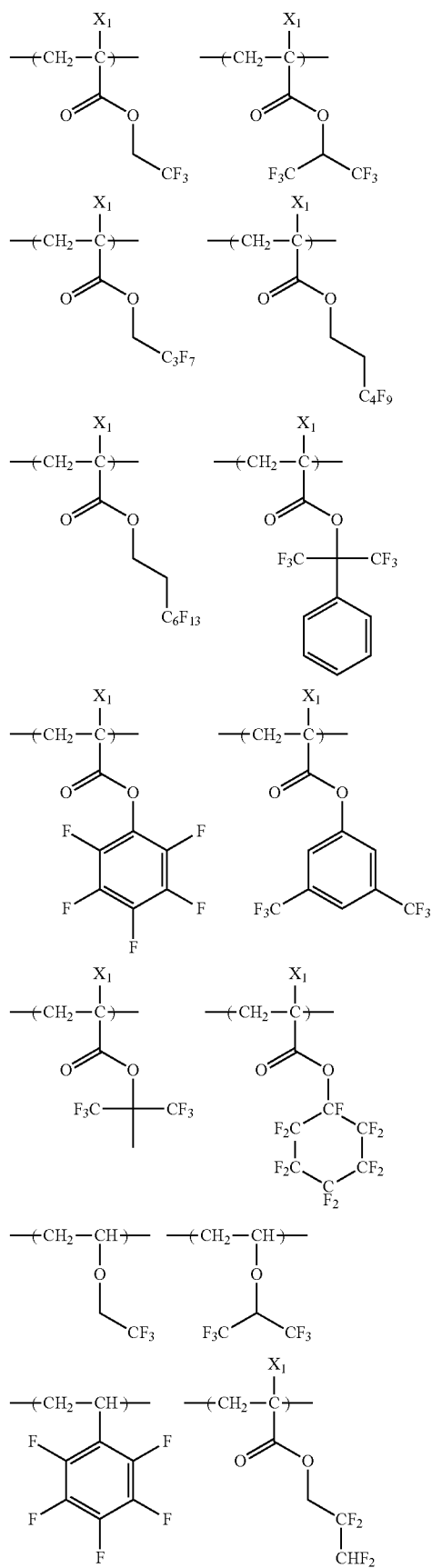

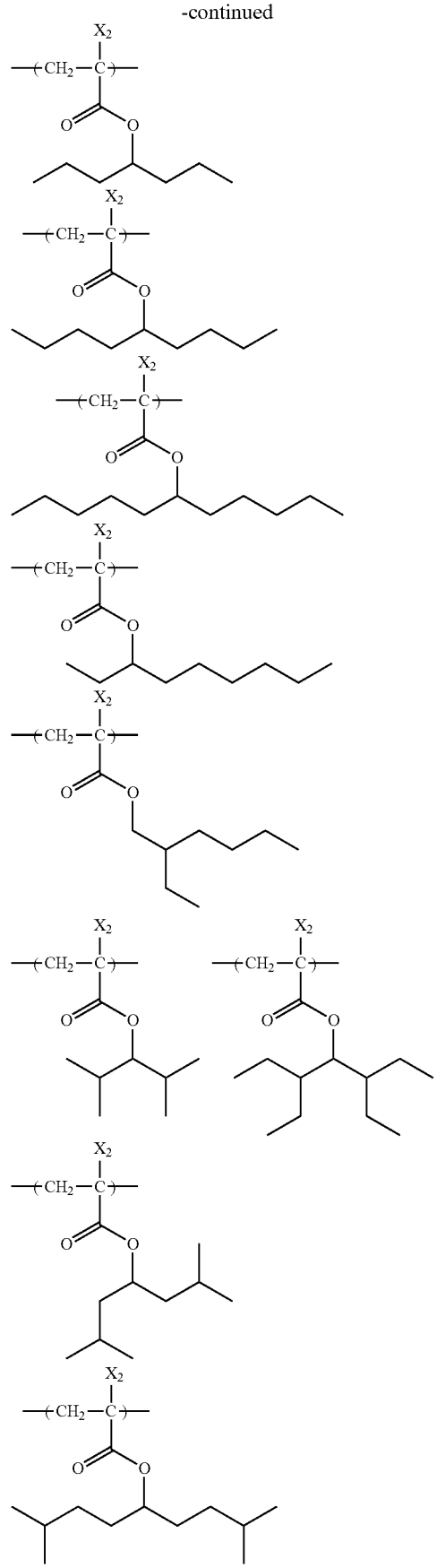
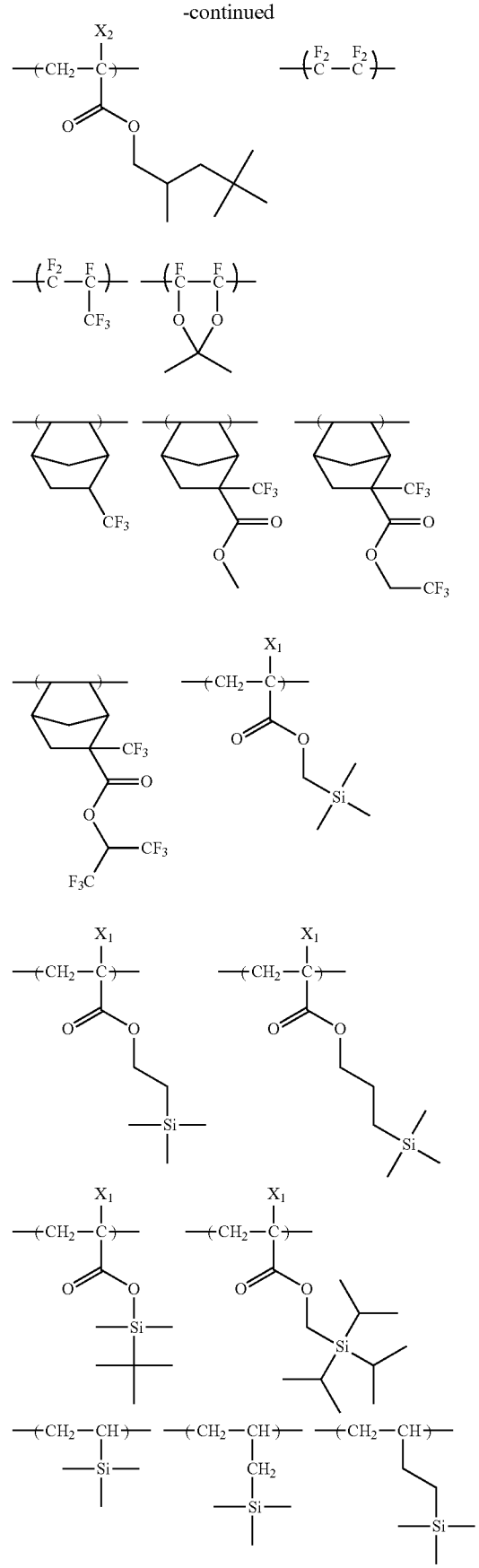

-continued

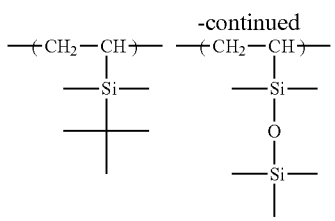

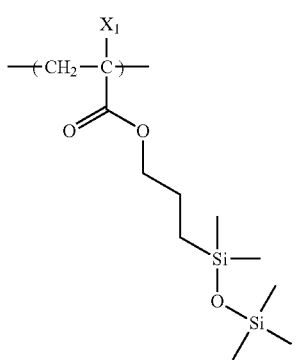

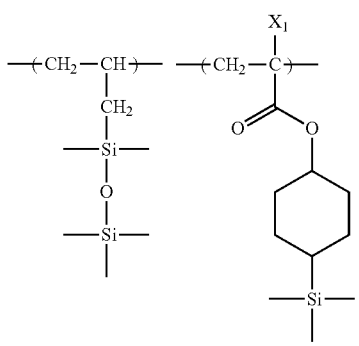

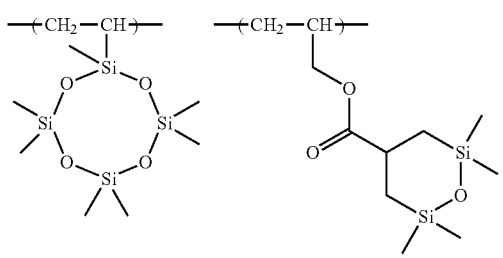

-continued

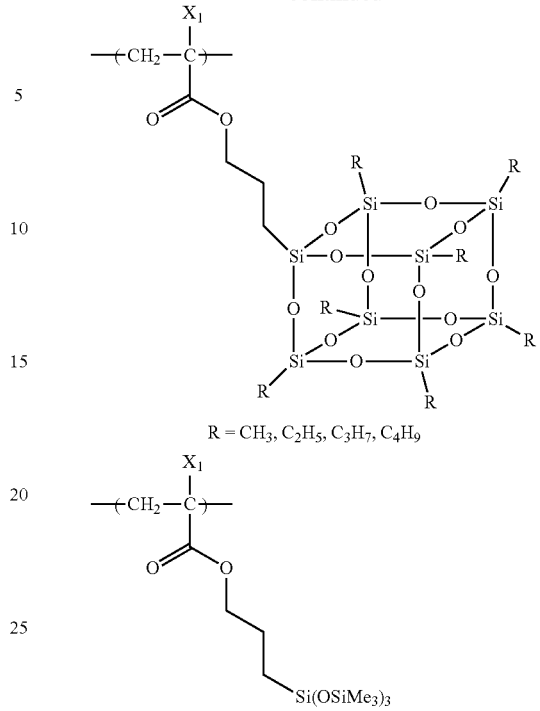

R = $CH_3$, $C_2H_5$, $C_3H_7$, $C_4H_9$

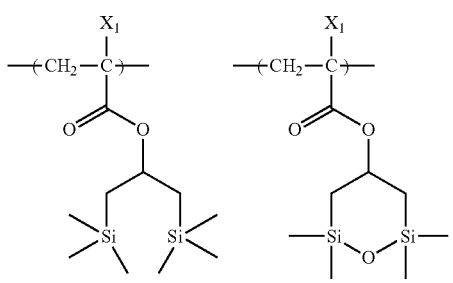

The hydrophobic resin preferably contains a repeating unit (b) having at least one group selected from among the following groups (x) to (z):

(x) an alkali-soluble group;

(y) a group that is decomposed by the action of an alkali developer, resulting in an increase of solubility in the alkali developer; and (z) a group that is decomposed by the action of an acid, resulting in an increase of solubility in the alkali developer.

As the repeating unit (b), the following types are exemplified.

a repeating unit (b') containing at least either a fluorine atom or a silicon atom and at least one group selected from the group consisting of the above groups (x) to (z) simultaneously introduced in one side chain thereof;

a repeating unit (b*) containing at least one group selected from the group consisting of the above groups (x) to (z) but containing neither a fluorine atom nor a silicon atom; or a repeating unit (b") in which at least one group selected from the group consisting of the above groups (x) to (z) is introduced in its one side chain while at least either a fluorine atom or a silicon atom is introduced in a side chain other than the above side chain within the same repeating unit.

It is preferable for the hydrophobic resin to contain the repeating unit (b') as the repeating unit (b). Namely, it is preferable for the repeating unit (b) containing at least one group selected from the group consisting of the above groups (x) to (z) to further contain at least either a fluorine atom or a silicon atom.

When the hydropobic resin contains the repeating unit (b*), it is preferable for the hydrophobic resin to be a copolymer with a repeating unit (repeating unit other than the above-mentioned repeating units [b'] and [b"]) containing at least either a fluorine atom or a silicon atom. In the repeating unit (b"), it is preferable for the side chain containing at least one group selected from the group consisting of the above groups (x) to (z) and the side chain containing at least either a fluorine atom or a silicon atom to be bonded to the same carbon atom of the principal chain, namely to be in a positional relationship shown in formula (K1) below.

In the formula, B1 represents a partial structure containing at least one group selected from the group consisting of the above groups (x) to (z), and B2 represents a partial structure containing at least either a fluorine atom or a silicon atom.

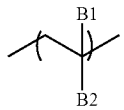

(K1)

The group selected from the group consisting of the above groups (x) to (z) is preferably (x) an alkali-soluble group or (y) a polarity conversion group, more preferably (y) a polarity conversion group.

As the alkali-soluble group (x), a phenolic hydroxy group, a carboxylate group, a fluoroalcohol group, a sulfonate group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, and a tris(alkylsulfonyl)methylene group can be exemplified.

As preferred alkali soluble groups, a fluoroalcohol group (preferably hexafluoroisopropanol group), a sulfonimido group, and a bis(carbonyl)methylene group can be exemplified.

As the repeating unit having an alkali soluble group (x), preferred use is made of any of a repeating unit resulting from direct bonding of an alkali soluble group to the principal chain of a resin like a repeating unit of acrylic acid or methacrylic acid; a repeating unit resulting from bonding, via a connecting group, of an alkali soluble group to the principal chain of a resin; and a repeating unit resulting from polymerization with the use of a chain transfer agent or polymerization initiator having an alkali soluble group to introduce the same in a polymer chain terminal.

When the repeating unit (bx) is a repeating unit containing at least either a fluorine atom or a silicon atom (namely, when corresponding to the above-mentioned repeating unit [b'] or repeating unit [b"]), the partial structure containing a fluorine atom contained in the repeating unit (bx) can be the same as set forth above in connection with the repeating unit containing at least either a fluorine atom or a silicon atom. As such, preferably, there can be mentioned any of the groups of general formulae (F2) to (F4) above. Also in that instance, the partial structure containing a silicon atom contained in the repeating unit (bx) can be the same as set forth above in connection with the repeating unit containing at least either a fluorine atom or a silicon atom. As such, preferably, there can be mentioned any of the groups of general formulae (CS-1) to (CS-3) above.

The content of repeating units (bx) having an alkali soluble group (x) based on all the repeating units in the hydrophobic resin is preferably in the range of 1 to 50 mol %, more preferably 3 to 35 mol %, and still more preferably 5 to 20 mol %.

Specific examples of the repeating units (bx) having an alkali soluble group (x) will be shown below, which however in no way limit the scope of the present invention. In the specific examples, each of $X_1$ represents H, —$CH_3$, —F or —$CF_3$. In the formulae, each of Rx represents H, $CH_3$, $CF_3$ or $CH_2OH$. In the formulae, each of Rx represents H, $CH_3$, $CF_3$ or $CH_2OH$.

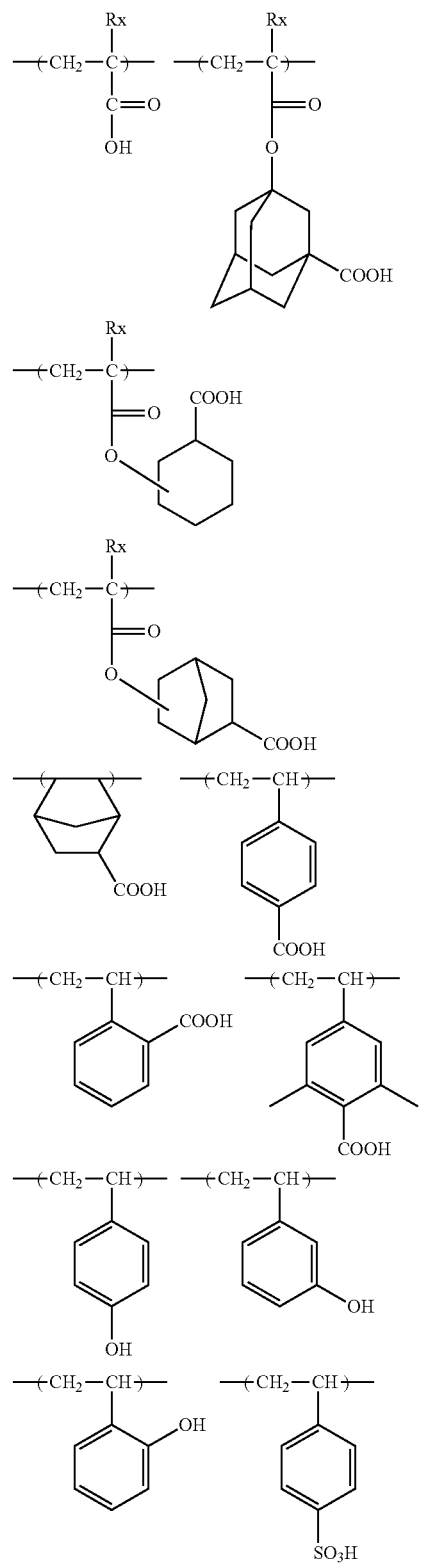

119
-continued
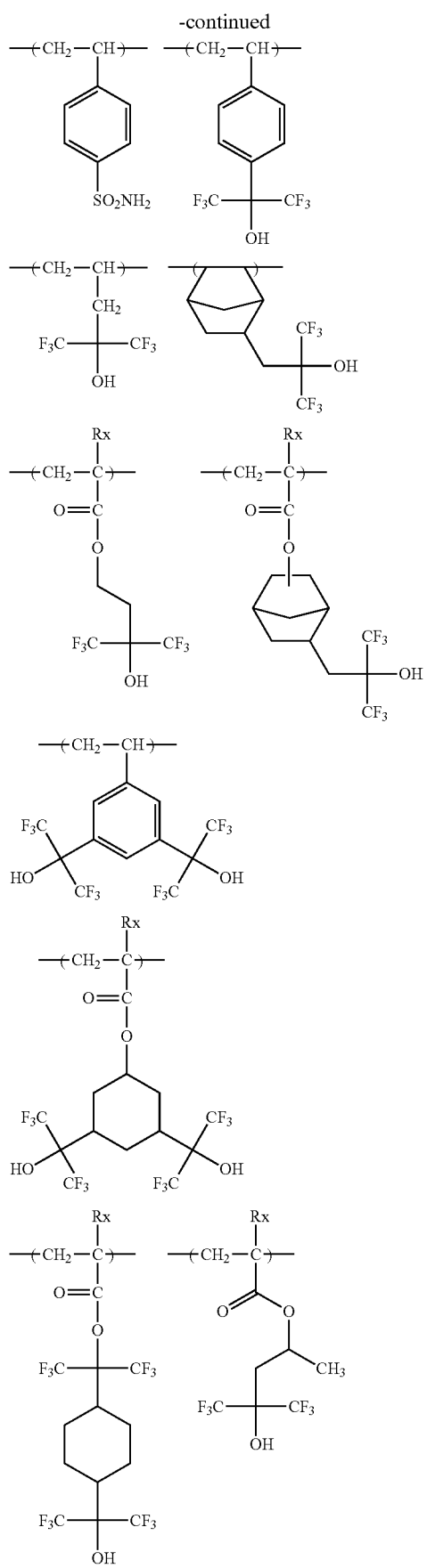
120
-continued
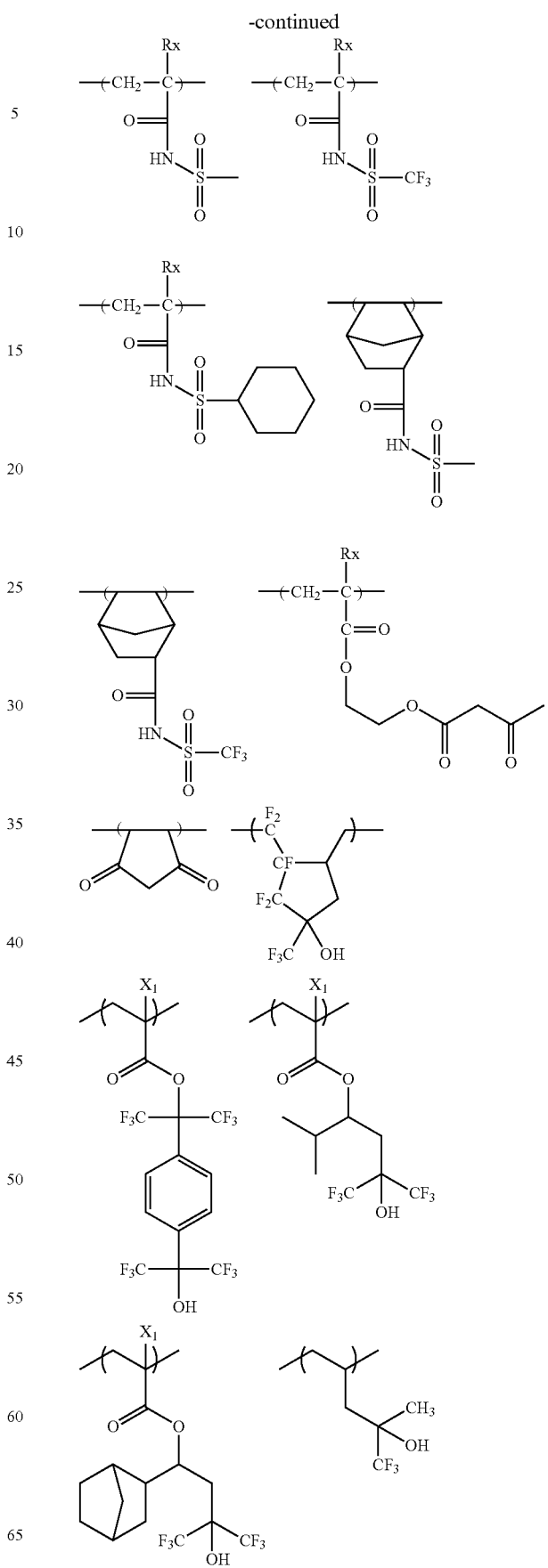

-continued

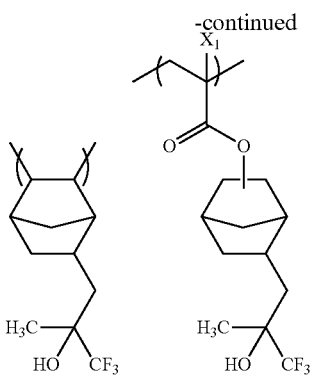

As the polarity conversion group (y), there can be mentioned, for example, a lactone group, a carboxylic ester group (—COO—), an acid anhydride group (—C(O)OC(O)—), an acid imido group (—NHCONH—), a carboxylic thioester group (—COS—), a carbonic ester group (—OC(O)O—), a sulfuric ester group (—OSO$_2$O—), a sulfonic ester group (—SO$_2$O—) or the like. A lactone group is preferred.

The polarity conversion group (y) is contained in, for example, two modes which are both preferred. In one mode, the polarity conversion group is contained in a repeating unit of an acrylic ester or methacrylic ester and introduced in a side chain of a resin. In the other mode, the polarity conversion group is introduced in a terminal of a polymer chain by using a polymerization initiator or chain transfer agent containing the polarity conversion group (y) in the stage of polymerization.

As particular examples of the repeating units (by) each containing a polarity conversion group (y), there can be mentioned the repeating units with lactone structures of formulae (KA-1-1) to (KA-1-17) to be shown hereinafter.

Further, it is preferable for the repeating unit (by) containing a polarity conversion group (y) to be a repeating unit containing at least either a fluorine atom or a silicon atom (namely, corresponding to the above-mentioned repeating unit [b'] or repeating unit [b"]). The resin comprising this repeating unit (by) is hydrophobic, and is especially preferable from the viewpoint of the reduction of development defects.

As the repeating unit (by), there can be mentioned, for example, any of the repeating units of formula (K0) below.

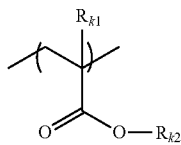

(K0)

In the formula, R$_{k1}$ represents a hydrogen atom, a halogen atom, a hydroxyl group, an alkyl group, a cycloalkyl group, an aryl group or a group containing a polarity conversion group; and R$_{k2}$ represents an alkyl group, a cycloalkyl group, an aryl group or a group containing a polarity conversion group; provided that one of R$_{k1}$ and R$_{k2}$ is a group containing a polarity conversion group.

The polarity conversion group, as mentioned above, refers to a group that is decomposed by the action of an alkali developer to thereby increase its solubility in the alkali developer. It is preferred for the polarity conversion group to be a group represented by X in the partial structures of general formulae (KA-1) and (KB-1) below.

 (KA-1)

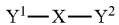 (KB-1)

In general formulae (KA-1) and (KB-1), X represents a carboxylic ester group (—COO—), an acid anhydride group (—C(O)OC(O)—), an acid imido group (—NHCONH—), a carboxylic thioester group (—COS—), a carbonic ester group (—OC(O)O—), a sulfuric ester group (—OSO$_2$O—) or a sulfonic ester group (—SO$_2$O—).

Y$^1$ and Y$^2$ may be identical to or different from each other, and each thereof represents an electron withdrawing group.

The repeating unit (by) contains a preferred group whose solubility in an alkali developer is increased by containing a group with the partial structure of general formula (KA-1) or (KB-1). When the partial structure has no bonding hand as in the case of the partial structure of general formula (KA-1) or the partial structure of general formula (KB-1) in which Y$^1$ and Y$^2$ are monovalent, the above group with the partial structure refers to a group containing a monovalent or higher-valent group resulting from the deletion of at least one arbitrary hydrogen atom from the partial structure.

The partial structure of general formula (KA-1) or (KB-1) is linked at its arbitrary position to the principal chain of the hydrophobic resin via a substituent.

The partial structure of general formula (KA-1) is a structure in which a ring structure is formed in cooperation with a group represented by X.

In general formula (KA-1), X is preferably a carboxylic ester group (namely, in the case of the formation of a lactone ring structure as KA-1), an acid anhydride group or a carbonic ester group. More preferably, X is a carboxylic ester group.

A substituent may be introduced in the ring structure of general formula (KA-1). For example, when Z$_{ka1}$ is a substituent, nka substituents may be introduced.

Z$_{ka1}$, or each of a plurality of Z$_{ka1}$s independently, represents a halogen atom, an alkyl group, a cycloalkyl group, an ether group, a hydroxyl group, an amido group, an aryl group, a lactone ring group or an electron withdrawing group.

Z$_{ka1}$s may be linked to each other to thereby form a ring. As the ring formed by the mutual linkage of Z$_{ka1}$s, there can be mentioned, for example, a cycloalkyl ring or a heterocycle (for example, a cycloether ring or a lactone ring).

The above nka is an integer of 0 to 10, preferably 0 to 8, more preferably 0 to 5, further more preferably 1 to 4 and most preferably 1 to 3.

The electron withdrawing groups represented by Z$_{ka1}$ are the same as those represented by Y$^1$ and Y$^2$ to be described hereinafter. These electron withdrawing groups may be substituted with other electron withdrawing groups.

Z$_{ka1}$ is preferably an alkyl group, a cycloalkyl group, an ether group, a hydroxyl group or an electron withdrawing group. Z$_{ka1}$ is more preferably an alkyl group, a cycloalkyl group or an electron withdrawing group. It is preferred for the ether group to be one substituted with, for example, an alkyl group or a cycloalkyl group, namely, to be an alkyl ether group or the like. The electron withdrawing group is as mentioned above.

As the halogen atom represented by $Z_{ka1}$, there can be mentioned a fluorine atom, a chlorine atom, a bromine atom, an iodine atom or the like. Among these, a fluorine atom is preferred.

The alkyl group represented by $Z_{ka1}$ may contain a substituent, and may be linear or branched. The linear alkyl group preferably has 1 to 30 carbon atoms, more preferably 1 to 20 carbon atoms. As the linear alkyl group, there can be mentioned, for example, a methyl group, an ethyl group, an n-propyl group, an n-butyl group, a sec-butyl group, a t-butyl group, an n-pentyl group, an n-hexyl group, an n-heptyl group, an n-octyl group, an n-nonyl group, an n-decanyl group or the like. The branched alkyl group preferably has 3 to 30 carbon atoms, more preferably 3 to 20 carbon atoms. As the branched alkyl group, there can be mentioned, for example, an i-propyl group, an i-butyl group, a t-butyl group, an i-pentyl group, a t-pentyl group, an i-hexyl group, a t-hexyl group, an i-heptyl group, a t-heptyl group, an i-octyl group, a t-octyl group, an i-nonyl group, a t-decanyl (t-decanoyl) group or the like. It is preferred for the alkyl group represented by $Z_{ka1}$ to be one having 1 to 4 carbon atoms, such as a methyl group, an ethyl group, an n-propyl group, an i-propyl group, an n-butyl group, an i-butyl group or a t-butyl group.

The cycloalkyl group represented by $Z_{ka1}$ may contain a substituent and may be monocyclic or polycyclic. When polycyclic, the cycloalkyl group may be a bridged one. Namely, in that case, the cycloalkyl group may have a bridged structure. The monocycloalkyl group is preferably a cycloalkyl group having 3 to 8 carbon atoms. As such a cycloalkyl group, there can be mentioned, for example, a cyclopropyl group, a cyclopentyl group, a cyclohexyl group, a cyclobutyl group, a cyclooctyl group or the like. As the polycycloalkyl group, there can be mentioned a group with, for example, a bicyclo, tricyclo or tetracyclo structure having 5 or more carbon atoms. This polycycloalkyl group is preferably a cycloalkyl group having 6 to 20 carbon atoms. As such, there can be mentioned, for example, an adamantyl group, a norbornyl group, an isobornyl group, a camphonyl group, a bicyclopentyl group, an α-pinel group, a tricyclodecanyl group, a tetracyclododecyl group, and an androstanyl group. As the cyclooctyl group, any of the following structures are also preffered. At least one carbon atoms in each of the cycloalkyl groups may be replaced with a heteroatom, such as an oxygen atom.

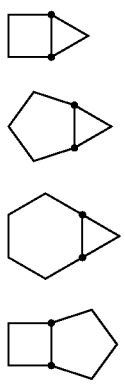

(1)

(2)

(3)

(4)

-continued

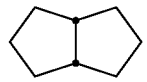

(5)

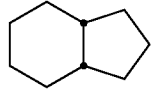

(6)

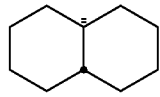

(7)

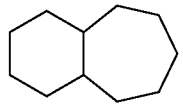

(8)

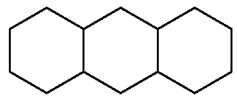

(9)

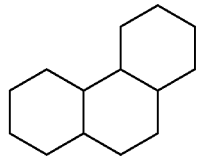

(10)

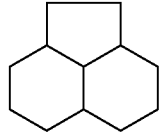

(11)

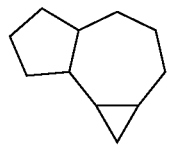

(12)

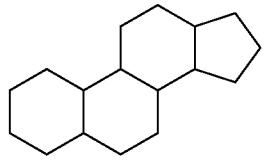

(13)

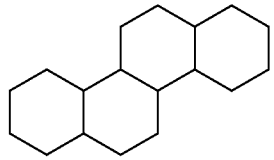

(14)

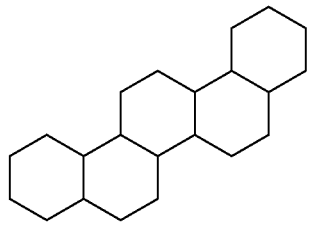

(15)

-continued
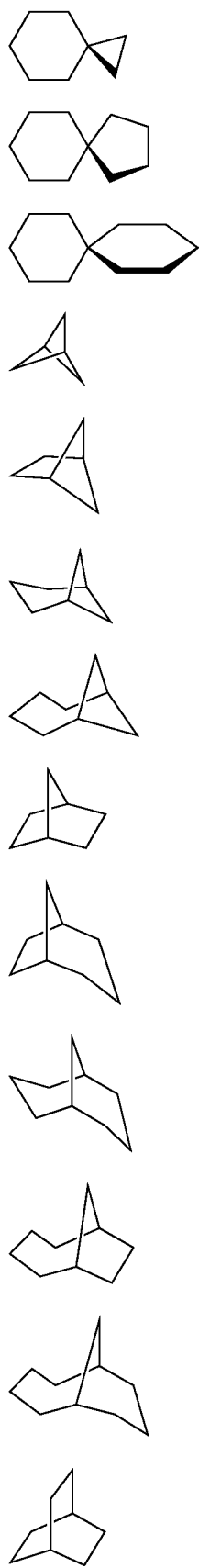
-continued
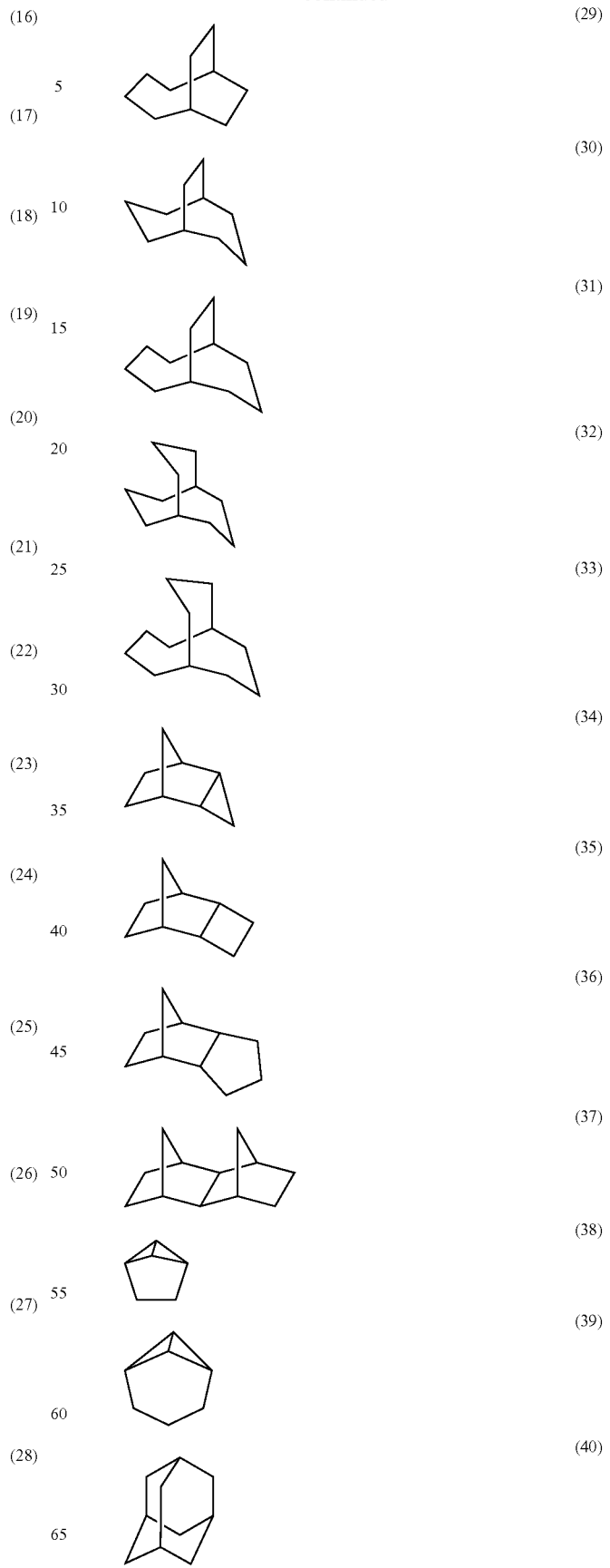

(41) 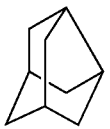

(42) 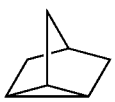

(43) 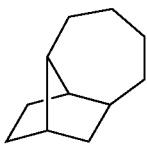

(44) 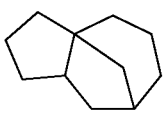

(45) 

(46) 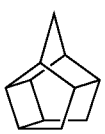

(47) 

(48) 

(49) 

(50) 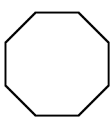

As preferred alicyclic moieties among the above, there can be mentioned an adamantyl group, a noradamantyl group, a decalin group, a tricyclodecanyl group, a tetracyclododecanyl group, a norbornyl group, a cedrol group, a cyclohexyl group, a cycloheptyl group, a cyclooctyl group, a cyclodecanyl group and a cyclododecanyl group. As more preferred alicyclic moieties, there can be mentioned an adamantyl group, a decalin group, a norbornyl group, a cedrol group, a cyclohexyl group, a cycloheptyl group, a cyclooctyl group, a cyclodecanyl group, a cyclododecanyl group and a tricyclodecanyl group.

As a substituent that can be introduced in these alicyclic structures, there can be mentioned an alkyl group, a halogen atom, a hydroxyl group, an alkoxy group, a carboxyl group or an alkoxycarbonyl group. The alkyl group is preferably a lower alkyl group, such as a methyl group, an ethyl group, a propyl group, an isopropyl group or a butyl group. More preferably, the alkyl group is a methyl group, an ethyl group, a propyl group or an isopropyl group. As preferred alkoxy groups, there can be mentioned those each having 1 to 4 carbon atoms, such as a methoxy group, an ethoxy group, a propoxy group and a butoxy group. As a substituent that may be introduced in these alkyl and alkoxy groups, there can be mentioned a hydroxyl group, a halogen atom, an alkoxy group (preferably having 1 to 4 carbon atoms) or the like.

Further substituents may be introduced in these groups. As further substituents, there can be mentioned a hydroxyl group; a halogen atom (fluorine, chlorine, bromine or iodine); a nitro group; a cyano group; the above alkyl groups; an alkoxy group, such as a methoxy group, an ethoxy group, a hydroxyethoxy group, a propoxy group, a hydroxypropoxy group, an n-butoxy group, an isobutoxy group, a sec-butoxy group or a t-butoxy group; an alkoxycarbonyl group, such as a methoxycarbonyl group or an ethoxycarbonyl group; an aralkyl group, such as a benzyl group, a phenethyl group or a cumyl group; an aralkyloxy group; an acyl group, such as a formyl group, an acetyl group, a butyryl group, a benzoyl group, a cyanamyl group or a valeryl group; an acyloxy group, such as a butyryloxy group; an alkenyl group, such as a vinyl group, a propenyl group or an allyl group; an alkenyloxy group, such as a vinyloxy group, a propenyloxy group, an allyloxy group or a butenyloxy group; an aryl group, such as a phenyl group or a naphthyl group; an aryloxy group, such as a phenoxy group; an aryloxycarbonyl group, such as a benzoyloxy group; and the like.

Preferably, X of general formula (KA-1) represents a carboxylic ester group and the partial structure of general formula (KA-1) is a lactone ring. A 5- to 7-membered lactone ring is preferred.

Further, as shown in formulae (KA-1-1) to (KA-1-17) below, the 5- to 7-membered lactone ring as the partial structure of general formula (KA-1) is preferably condensed with another ring structure in such a fashion that a bicyclo structure or a spiro structure is formed.

The peripheral ring structures to which the ring structure of general formula (KA-1) may be bonded can be, for example, those shown in formulae (KA-1-1) to (KA-1-17) below, or those similar to the same.

It is preferred for the structure containing the lactone ring structure of general formula (KA-1) to be the structure of any of formulae (KA-1-1) to (KA-1-17) below. The lactone structure may be directly bonded to the principal chain. As preferred structures, there can be mentioned those of formulae (KA-1-1), (KA-1-4), (KA-1-5), (KA-1-6), (KA-1-13), (KA-1-14) and (KA-1-17).

KA-1-1

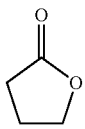

KA-1-2

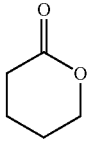

-continued

KA-1-3 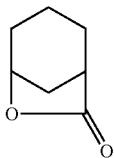

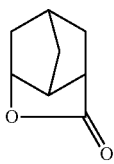 KA-1-4

KA-1-5 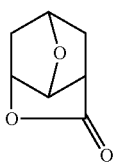

KA-1-6 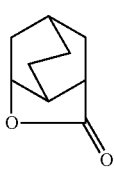

KA-1-7 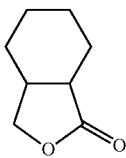

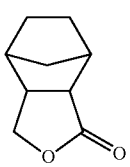 KA-1-8

KA-1-9 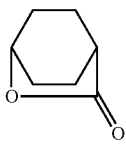

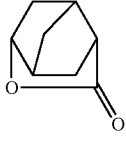 KA-1-10

KA-1-11 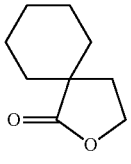

-continued

KA-1-12 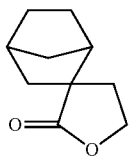

KA-1-13 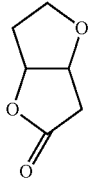

KA-1-14 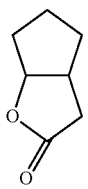

KA-1-15 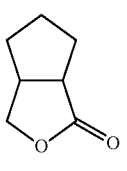

KA-1-16 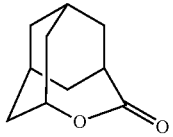

KA-1-17 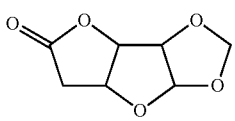

A substituent may optionally be introduced in the above structures containing the lactone ring structure. As preferred substituents, there can be mentioned the same as the substituents $Z_{ka1}$ that may be introduced in the ring structure of general formula (KA-1) above.

In general formula (KB-1), X is preferably a carboxylic ester group (—COO—).

In general formula (KB-1), each of $Y^1$ and $Y^2$ independently represents an electron withdrawing group.

The electron withdrawing group has the partial structure of formula (EW) below. In formula (EW), * represents either a bonding hand directly bonded to the structure of general formula (KA-1) or a bonding hand directly bonded to X of general formula (KB-1).

(EW)

In formula (EW),

Each of $R_{ew1}$ and $R_{ew2}$ independentry represents an arbitrary substituent, for example, a hydrogen atom, an alkyl group, a cycloalkyl group or an aryl group.

$n_{ew}$ is the number of repetitions of each of the connecting groups of the formula —C($R_{ew1}$)($R_{ew2}$)—, being an integer of 0 or 1. When $n_{ew}$ is 0, a single bond is represented, indicating the direct bonding of $Y_{ew1}$.

$Y_{ew1}$ can be any of a halogen atom, a cyano group, a nitrile group, a nitro group, any of the halo(cyclo)alkyl groups or haloaryl groups of the formula —C($R_{f1}$)($R_{f2}$)—$R_{f3}$ to be described hereinafter, an oxy group, a carbonyl group, a sulfonyl group, a sulfinyl group and a combination thereof. The electron withdrawing groups may have, for example, the following structures. Herein, the "halo(cyclo)alkyl group" refers to an at least partially halogenated alkyl group or cycloalkyl group. The "haloaryl group" refers to an at least partially halogenated aryl group. In the following structural formulae, each of $R_{ew3}$ and $R_{ew4}$ independently represents an arbitrary structure. Regardless of the types of the structures of $R_{ew3}$ and $R_{ew4}$, the partial structures of formula (EW) exhibit electron withdrawing properties, and may be linked to, for example, the principal chain of the resin. Preferably, each of $R_{ew3}$ and $R_{ew4}$ is an alkyl group, a cycloalkyl group or a fluoroalkyl group.

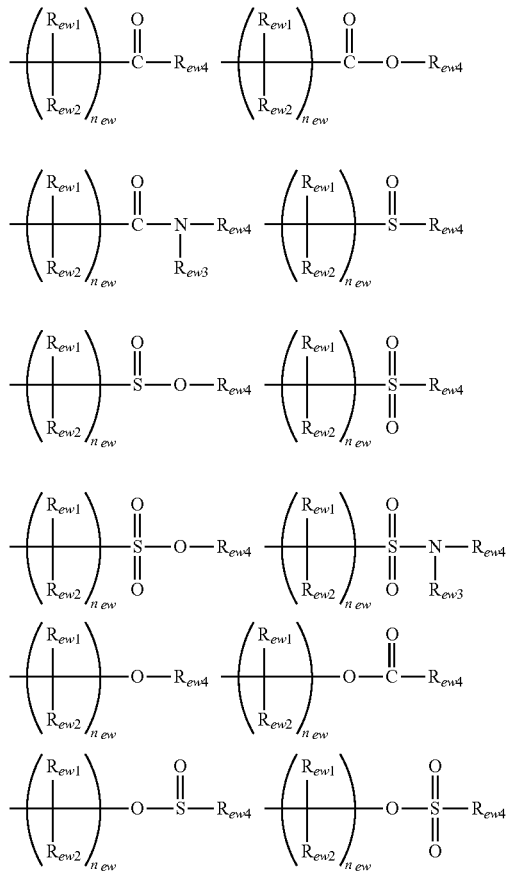

When $Y_{ew1}$ is a bivalent or higher-valent group, the remaining bonding hand or hands form a bond with an arbitrary atom or substituent. At least any of the groups represented by $Y_{ew1}$, $R_{ew1}$ and $R_{ew2}$ may be linked via a further substituent to the principal chain of the hydrophobic resin.

$Y_{ew1}$ is preferably a halogen atom or any of the halo(cyclo)alkyl groups or haloaryl groups of the formula —C($R_{f1}$)($R_{f2}$)—$R_{f3}$.

At least two of $R_{ew1}$, $R_{ew2}$ and $Y_{ew1}$ may be linked to each other to thereby form a ring.

In the above formula, $R_{f1}$ represents a halogen atom, a perhaloalkyl group, a perhalocycloalkyl group or a perhaloaryl group. $R_{f1}$ is preferably a fluorine atom, a perfluoroalkyl group or a perfluorocycloalkyl group, more preferably a fluorine atom or a trifluoromethyl group.

Each of $R_{f2}$ and $R_{f3}$ independently represents a hydrogen atom, a halogen atom or an organic group. $R_{f2}$ and $R_{f3}$ may be linked to each other to thereby form a ring. As the organic group, there can be mentioned, for example, an alkyl group, a cycloalkyl group, an alkoxy group or the like. It is preferred for $R_{f2}$ to represent the same groups as $R_{f1}$ or to be linked to $R_{f3}$ to thereby form a ring.

$R_{f1}$ to $R_{f3}$ may be linked to each other to thereby form a ring. As the formed ring, there can be mentioned a (halo)cycloalkyl ring, a (halo)aryl ring or the like.

As the (halo)alkyl groups represented by $R_{f1}$ to $R_{f3}$, there can be mentioned, for example, the alkyl groups mentioned above as being represented by $Z_{ka1}$ and structures resulting from halogenation thereof.

As the (per)halocycloalkyl groups and (per)haloaryl groups represented by $R_{f1}$ to $R_{f3}$ or contained in the ring formed by the mutual linkage of $R_{f2}$ and $R_{f3}$, there can be mentioned, for example, structures resulting from halogenation of the cycloalkyl groups mentioned above as being represented by $Z_{ka1}$, preferably fluorocycloalkyl groups of the formula —$C_{(n)}F_{(2n-2)}H$ and perfluoroaryl groups of the formula —$C_{(n)}F_{(n-1)}$. The number of carbon atoms, n, is not particularly limited. Preferably, however, it is in the range of 5 to 13, more preferably 6.

As preferred rings that may be formed by the mutual linkage of at least two of $R_{ew1}$, $R_{ew2}$ and $Y_{ew1}$, there can be mentioned cycloalkyl groups and heterocyclic groups. Preferred heterocyclic groups are lactone ring groups. As the lactone rings, there can be mentioned, for example, the structures of formulae (KA-1-1) to (KA-1-17) above.

The repeating unit (by) may contain two or more of the partial structures of general formula (KA-1), or two or more of the partial structures of general formula (KB-1), or both any one of the partial structures of general formula (KA-1) and any one of the partial structures of general formula (KB-1).

A part or the whole of any of the partial structures of general formula (KA-1) may double as the electron withdrawing group represented by $Y^1$ or $Y^2$ of general formula (KB-1). For example, when X of general formula (KA-1) is a carboxylic ester group, the carboxylic ester group can function as the electron withdrawing group represented by $Y^1$ or $Y^2$ of general formula (KB-1).

When the repeating unit (by) corresponds to the above-mentioned repeating unit (b*) or repeating unit (b") and contains any of the partial structures of general formula (KA-1), it is preferable for the partial structures of general formula (KA-1) to be a partial structure in which the polarity conversion group is expressed by —COO— appearing in the structures of general formula (KA-1).

The repeating unit (by) can be a repeating unit with the partial structure of general formula (KY-0) below.

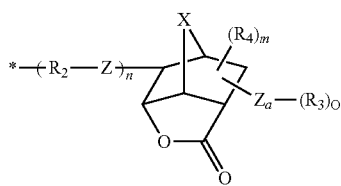

(KY-0)

In general formula (KY-0), $R_2$ represents a chain or cyclic alkylene group, provided that when there are a plurality of $R_2$s, they may be identical to or different from each other.

$R_3$ represents a linear, branched or cyclic hydrocarbon group whose hydrogen atoms on constituent carbons are partially or entirely substituted with fluorine atoms.

$R_4$ represents a halogen atom, a cyano group, a hydroxyl group, an amido group, an alkyl group, a cycloalkyl group, an alkoxy group, a phenyl group, an acyl group, an alkoxycarbonyl group or any of the groups of the formula R—C(=O)— or R—C(=O)O— in which R is an alkyl group or a cycloalkyl group. When there are a plurality of $R_4$s, they may be identical to or different from each other. Two or more $R_4$s may be bonded to each other to thereby form a ring.

X represents an alkylene group, a cycloalkylene group, an oxygen atom or a sulfur atom.

Each of Z and Za represents a single bond, an ether bond, an ester bond, an amido bond, a urethane bond or a urea bond. When there are a plurality thereof, they may be identical to or different from each other.

In the formula, * represents a bonding hand to the principal chain or a side chain of the resin; o is the number of substituents, being an integer of 1 to 7; m is the number of substituents, being an integer of 0 to 7; and n is the number of repetitions, being an integer of 0 to 5.

The structure —$R_2$—Z— is preferably the structure of formula —$(CH_2)$p-COO— in which p is an integer of 1 to 5, preferably 1.

With respect to the chain or cyclic alkylene group represented by $R_2$, the preferred number of carbon atoms and particular examples are as mentioned above in connection with the chain or cyclic alkylene group represented by $Z_2$ of general formula (bb).

The number of carbon atoms of the linear, branched or cyclic hydrocarbon group represented by $R_3$ is preferably in the range of 1 to 30, more preferably 1 to 20 when the hydrocarbon group is linear; is preferably in the range of 3 to 30, more preferably 3 to 20 when the hydrocarbon group is branched; and is in the range of 6 to 20 when the hydrocarbon group is cyclic. As particular examples of the $R_3$ groups, there can be mentioned the above particular examples of the alkyl and cycloalkyl groups represented by $Z_{ka1}$.

With respect to the alkyl groups and cycloalkyl groups represented by $R_4$ and R, the preferred number of carbon atoms and particular examples are as mentioned above in connection with the alkyl groups and cycloalkyl groups represented by $Z_{ka1}$.

The acyl group represented by $R_4$ preferably has 1 to 6 carbon atoms. As such, there can be mentioned, for example, a formyl group, an acetyl group, a propionyl group, a butyryl group, an isobutyryl group, a valeryl group, a pivaloyl group or the like.

As the alkyl moiety of the alkoxy group and alkoxycarbonyl group represented by $R_4$, there can be mentioned a linear, branched or cyclic alkyl moiety. With respect to the alkyl moiety, the preferred number of carbon atoms and particular examples are as mentioned above in connection with the alkyl groups and cycloalkyl groups represented by $Z_{ka1}$.

With respect to the alkylene group represented by X, a chain or cyclic alkylene group can be exemplified. The preferred number of carbon atoms and particular examples are as mentioned above in connection with the chain or cyclic alkylene group represented by $R_2$.

Moreover, as particular structures of the repeating units (by), there can be mentioned the repeating units with the following partial structures.

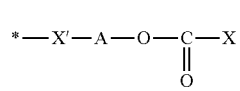

(rf-1)

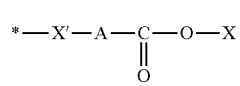

(rf-2)

In general formulae (rf-1) and (rf-2),

X' represents an electron withdrawing substituent, preferably a carbonyloxy group, an oxycarbonyl group, an alkylene group substituted with a fluorine atom or a cycloalkylene group substituted with a fluorine atom.

A represents a single bond or a bivalent connecting group of the formula —C(Rx)(Ry)-. In the formula, each of Rx and Ry independently represents a hydrogen atom, a fluorine atom, an alkyl group (preferably having 1 to 6 carbon atoms, optionally substituted with a fluorine atom) or a cycloalkyl group (preferably having 5 to 12 carbon atoms, optionally substituted with a fluorine atom). Each of Rx and Ry is preferably a hydrogen atom, an alkyl group or an alkyl group substituted with a fluorine atom.

X represents an electron withdrawing group. As particular examples thereof, there can be mentioned the electron withdrawing groups set forth above as being represented by $Y^1$ and $Y^2$. X is preferably a fluoroalkyl group, a fluorocycloalkyl group, an aryl group substituted with fluorine or a fluoroalkyl group, an aralkyl group substituted with fluorine or a fluoroalkyl group, a cyano group or a nitro group.

* represents a bonding hand to the principal chain or a side chain of the resin, namely, a bonding hand bonded to the principal chain of the resin through a single bond or a connecting group.

When X' is a carbonyloxy group or an oxycarbonyl group, A is not a single bond.

The receding contact angle with water of the resist film after alkali development can be decreased by the polarity conversion effected by the decomposition of the polarity conversion group by the action of an alkali developer. The decrease of the receding contact angle between water and the film after alkali development is preferred from the viewpoint of the inhibition of development defects.

The receding contact angle with water of the resist film after alkali development is preferably 50° or less, more preferably 40° or less, further more preferably 35° or less and most preferably 30° or less at 23±3° C. in a humidity of 45±5%.

The receding contact angle refers to a contact angle determined when the contact line at a droplet-substrate interface draws back. It is generally known that the receding contact angle is useful in the simulation of droplet mobility in a dynamic condition. In brief, the receding contact angle can be defined as the contact angle exhibited at the recession of the droplet interface at the time of, after application of a droplet discharged from a needle tip onto a substrate, re-indrawing the droplet into the needle. Generally, the receding contact angle can be measured according to a method of contact angle measurement known as the dilation/contraction method.

The rate of hydrolysis of the hydrophobic resin in an alkali developer is preferably 0.001 nm/sec or greater, more preferably 0.01 nm/sec or greater, further more preferably 0.1 nm/sec or greater and most preferably 1 nm/sec or greater.

Herein, the rate of hydrolysis of the hydrophobic resin in an alkali developer refers to the rate of decrease of the thickness of a resin film formed from only the hydrophobic resin in 23° C. TMAH (aqueous solution of tetramethylammonium hydroxide) (2.38 mass %)

It is preferred for the repeating unit (by) to be a repeating unit containing at least two polarity conversion groups.

When the repeating unit (by) contains at least two polarity conversion groups, it is preferred for the repeating unit to contain a group with any of the partial structures having two polarity conversion groups of general formula (KY-1) below. When the structure of general formula (KY-1) has no bonding hand, a group with a mono- or higher-valent group resulting from the removal of at least any arbitrary one of the hydrogen atoms contained in the structure is referred to.

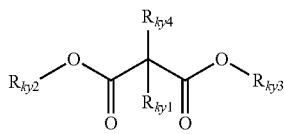
(KY-1)

In general formula (KY-1), each of $R_{ky1}$ and $R_{ky4}$ independently represents a hydrogen atom, a halogen atom, an alkyl group, a cycloalkyl group, a carbonyl group, a carbonyloxy group, an oxycarbonyl group, an ether group, a hydroxyl group, a cyano group, an amido group or an aryl group. Alternatively, both $R_{ky1}$ and $R_{ky4}$ may be bonded to the same atom to thereby form a double bond. For example, both $R_{ky1}$ and $R_{ky4}$ may be bonded to the same oxygen atom to thereby form a part (=O) of a carbonyl group.

Each of $R_{ky2}$ and $R_{ky3}$ independently represents an electron withdrawing group. Alternatively, $R_{ky1}$ and $R_{ky2}$ are linked to each other to thereby form a lactone structure, while $R_{ky3}$ is an electron withdrawing group. The formed lactone structure is preferably any of the above-mentioned structures (KA-1-1) to (KA-1-17). As the electron withdrawing group, there can be mentioned any of the same groups as mentioned above with respect to $Y^1$ and $Y^2$ of general formula (KB-1). This electron withdrawing group is preferably a halogen atom, or any of the halo(cyclo)alkyl groups or haloaryl groups of the formula —C($R_{f1}$)($R_{f2}$)—$R_{f3}$ above. Preferably, $R_{ky3}$ is a halogen atom, or any of the halo(cyclo)alkyl groups or haloaryl groups of the formula —C($R_{f1}$)($R_{f2}$)—$R_{f3}$ above, while $R_{ky2}$ is either linked to $R_{ky1}$ to thereby form a lactone ring, or an electron withdrawing group containing no halogen atom.

$R_{ky1}$, $R_{ky2}$ and $R_{ky4}$ may be linked to each other to thereby form a monocyclic or polycyclic structure.

As $R_{ky1}$ and $R_{ky4}$, there can be mentioned, for example, the same groups as set forth above with respect to $Z_{ka1}$ of general formula (KA-1).

The lactone rings formed by the mutual linkage of $R_{ky1}$ and $R_{ky2}$ preferably have the structures of formulae (KA-1-1) to (KA-1-17) above. As the electron withdrawing groups, there can be mentioned those mentioned above as being represented by $Y^1$ and $Y^2$ of general formula (KB-1) above.

It is more preferred for the structure of general formula (KY-1) to be the structure of general formula (KY-2) below. The structure of general formula (KY-2) refers to a group with a mono- or higher-valent group resulting from the removal of at least any arbitrary one of the hydrogen atoms contained in the structure.

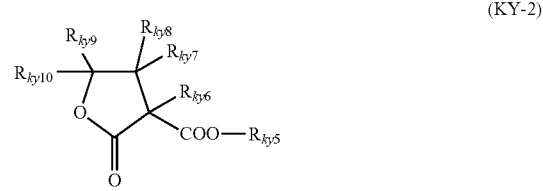
(KY-2)

In formula (KY-2), each of $R_{ky6}$ to $R_{ky10}$ independently represents a hydrogen atom, a halogen atom, an alkyl group, a cycloalkyl group, a carbonyl group, a carbonyloxy group, an oxycarbonyl group, an ether group, a hydroxyl group, a cyano group, an amido group or an aryl group.

At least two of $R_{ky6}$ to $R_{ky10}$ may be linked to each other to thereby form a monocyclic or polycyclic structure.

$R_{ky5}$ represents an electron withdrawing group. As the electron withdrawing group, there can be mentioned any of the same groups as set forth above with respect to $Y^1$ and $Y^2$. This electron withdrawing group is preferably a halogen atom, or any of the halo(cyclo)alkyl groups or haloaryl groups of the formula —C($R_{f1}$)($R_{f2}$)—$R_{f3}$ above.

As $R_{ky5}$ to $R_{ky10}$, there can be mentioned, for example, the same groups as set forth above with respect to $Z_{ka1}$ of formula (KA-1).

It is more preferred for the structure of formula (KY-2) to be the partial structure of general formula (KY-3) below.

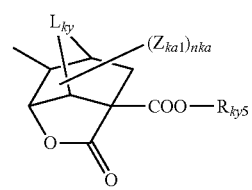
(KY-3)

In formula (KY-3), $Z_{ka1}$ and nka are as defined above in connection with general formula (KA-1). $R_{ky5}$ is as defined above in connection with formula (KY-2).

$L_{ky}$ represents an alkylene group, an oxygen atom or a sulfur atom. As the alkylene group represented by $L_{ky}$, there can be mentioned a methylene group, an ethylene group or the like. $L_{ky}$ is preferably an oxygen atom or a methylene group, more preferably a methylene group.

The repeating units (b) are not limited as long as they are derived by polymerization, such as addition polymerization, condensation polymerization or addition condensation. Preferred repeating units are those obtained by the addition polymerization of a carbon to carbon double bond. As such repeating units, there can be mentioned, for example, acrylate repeating units (including the family having a substituent at the α- and/or β-position), styrene repeating units (including the family having a substituent at the α- and/or β-position), vinyl ether repeating units, norbornene repeating units, repeating units of maleic acid derivatives (maleic anhydride, its derivatives, maleimide, etc.) and the like. Of these, acrylate repeating units, styrene repeating units, vinyl ether repeating units and norbornene repeating units are preferred. Acrylate repeating units, vinyl ether repeating units and norbornene repeating units are more preferred. Acrylate repeating units are most preferred.

When the repeating unit (by) is a repeating unit containing at least either a fluorine atom or a silicon atom (namely, corresponding to the above repeating unit (b') or (b")), as the partial structure containing a fluorine atom within the repeating unit (by), there can be mentioned any of those set forth in connection with the repeating unit containing at least either a fluorine atom or a silicon atom above, preferably the groups of general formulae (F2) to (F4) above. As the partial structure containing a silicon atom within the repeating unit (by), there can be mentioned any of those set forth in connection with the repeating unit containing at least either a fluorine atom or a silicon atom above, preferably the groups of general formulae (CS-1) to (CS-3) above.

The content of repeating unit (by) in the hydrophobic resin, based on all the repeating units of the hydrophobic resin, is preferably in the range of 10 to 100 mol %, more preferably 20 to 99 mol %, further more preferably 30 to 97 mol % and most preferably 40 to 95 mol %.

Particular examples of the repeating units (by) containing a group whose solubility in an alkali developer is increased are shown below, which however in no way limit the scope of the repeating units.

In particular examples below, Ra represents a hydrogen atom, a fluorine atom, a methyl group or a trifluoromethyl group.

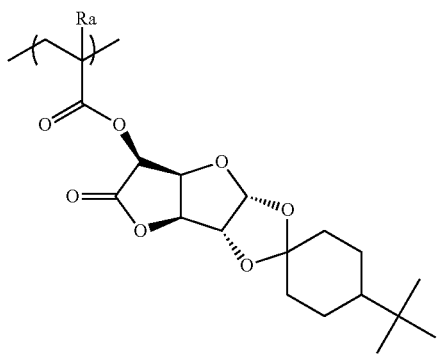

-continued

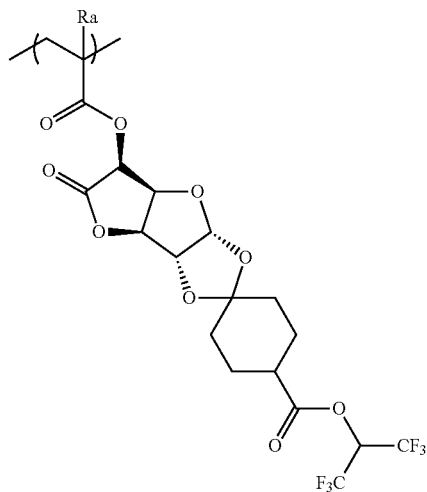

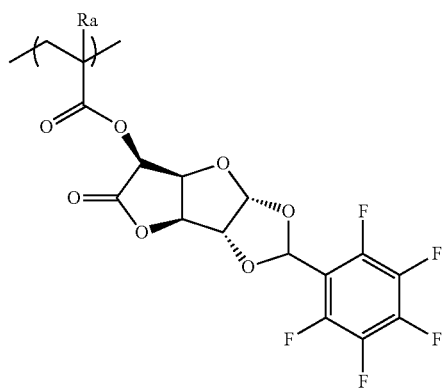

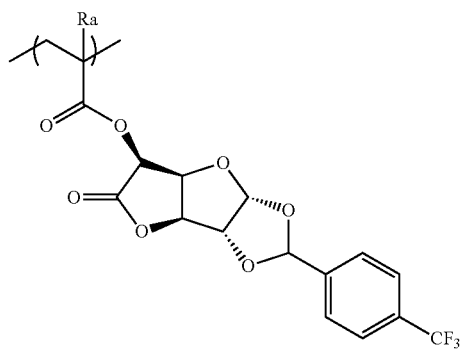

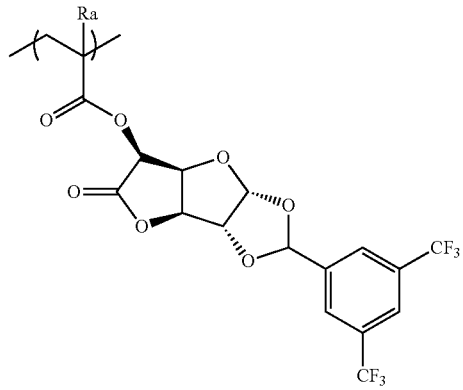

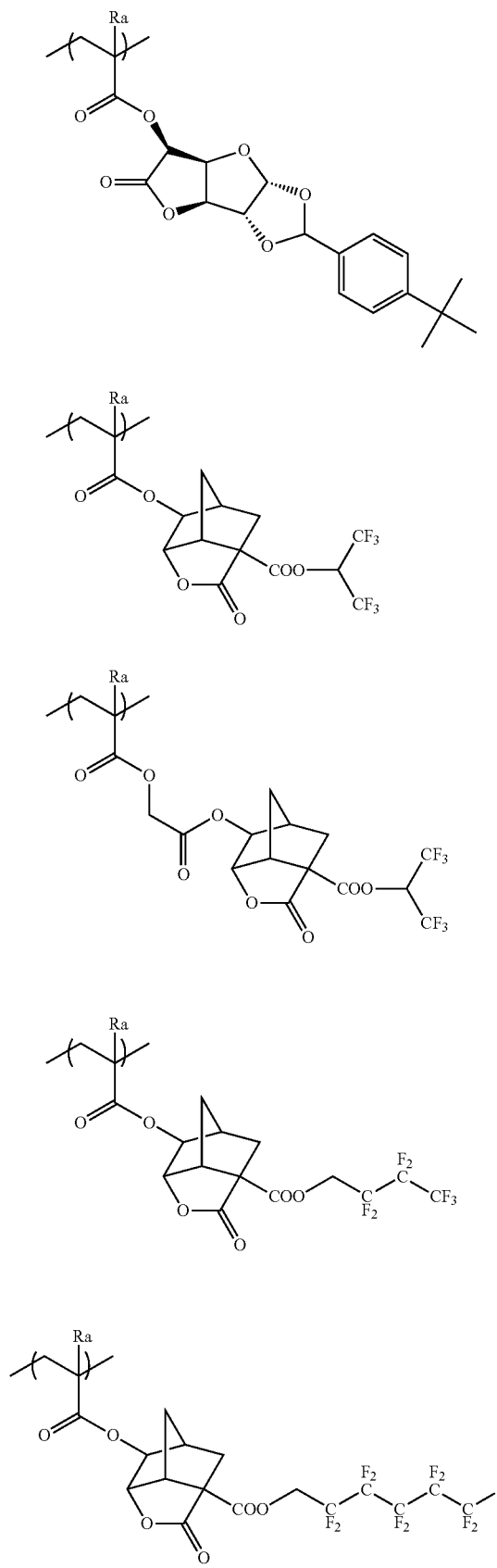
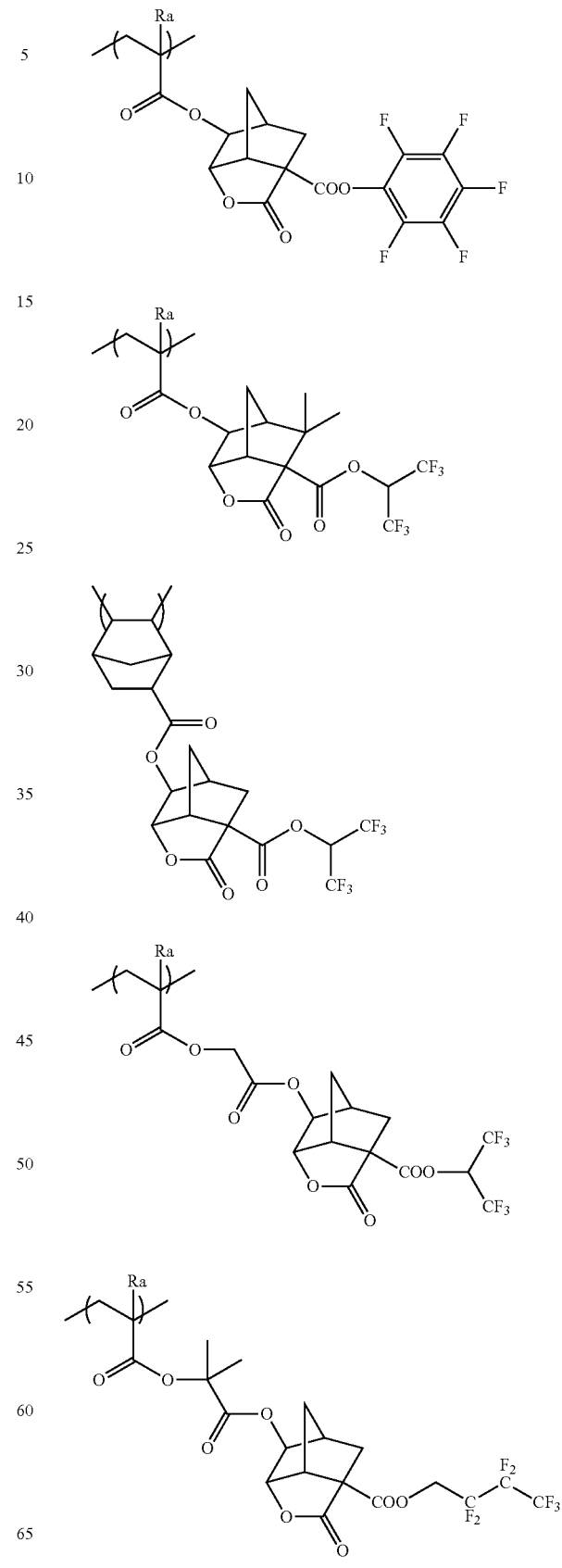

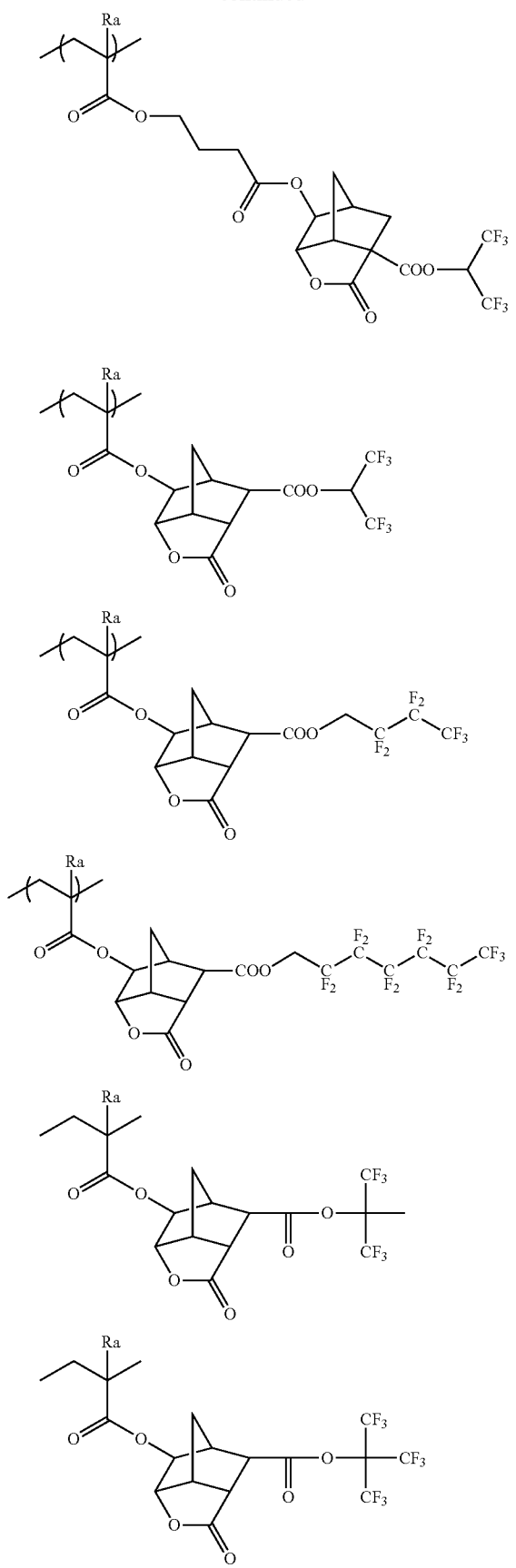
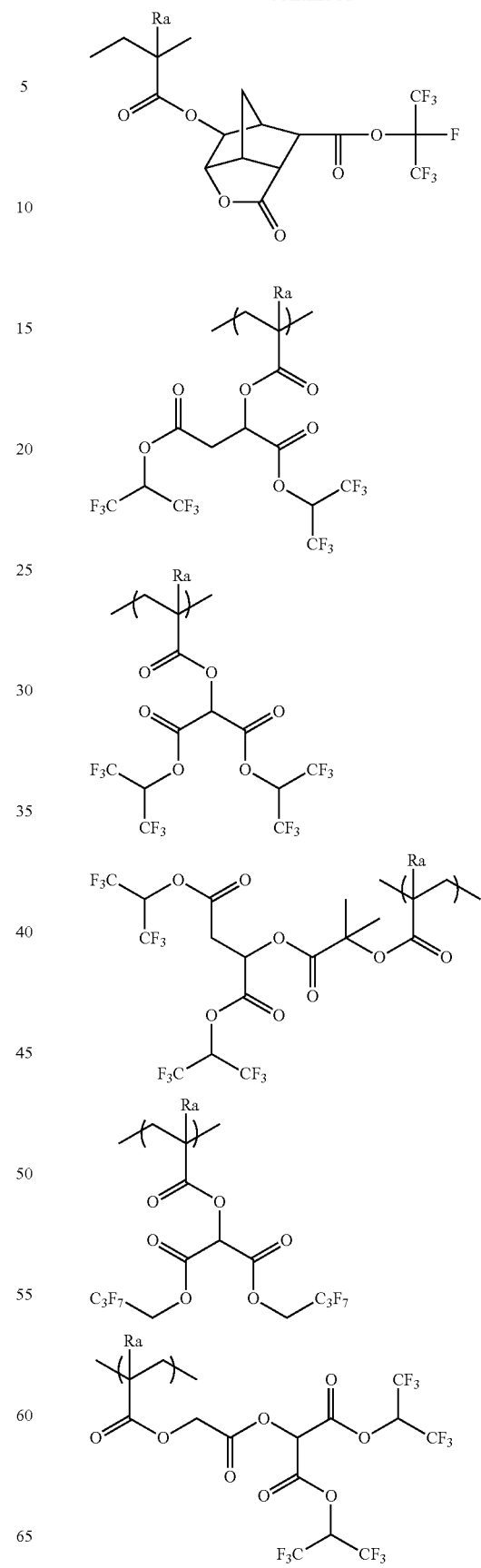

-continued

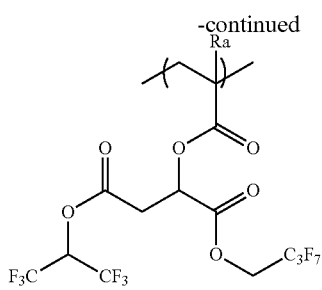

A monomer corresponding to the repeating unit (by) containing a polarity conversion group can be synthesized by referring to, for example, the method described in the pamphlet of International Publication No. 2010/067905.

The repeating unit (bz) containing a group that is decomposed by the action of an acid (z), contained in the hydrophobic resin can be the same as any of the repeating units each containing an acid-decomposable group set forth above in connection with the resin (B).

When the repeating unit (bz) is a repeating unit containing at least either a fluorine atom or a silicon atom (namely, when corresponding to the above-mentioned repeating unit [b'] or repeating unit [b"]), the partial structure containing a fluorine atom contained in the repeating unit (bz) can be the same as set forth above in connection with the repeating unit containing at least either a fluorine atom or a silicon atom. As such, preferably, there can be mentioned any of the groups of general formulae (F2) to (F4) above. Also in that instance, the partial structure containing a silicon atom contained in the repeating unit (bz) can be the same as set forth above in connection with the repeating unit containing at least either a fluorine atom or a silicon atom. As such, preferably, there can be mentioned any of the groups of general formulae (CS-1) to (CS-3) above.

The content of repeating unit (bz) containing a group that is decomposed by the action of an acid (z) in the hydrophobic resin, based on all the repeating units of the hydrophobic resin, is preferably in the range of 1 to 80 mol %, more preferably 10 to 80 mol % and further more preferably 20 to 60 mol %.

The repeating unit (b) containing at least one group selected from the group consisting of the above groups (x) to (z) has been described. The content of repeating unit (b) in the hydrophobic resin is preferably in the range of 1 to 98 mol %, more preferably 3 to 98 mol %, further more preferably 5 to 97 mol % and most preferably 10 to 95 mol %, based on all the repeating units of the hydrophobic resin.

The content of repeating unit (b') in the hydrophobic resin is preferably in the range of 1 to 100 mol %, more preferably 3 to 99 mol %, further more preferably 5 to 97 mol % and most preferably 10 to 95 mol %, based on all the repeating units of the hydrophobic resin.

The content of repeating unit (b*) in the hydrophobic resin is preferably in the range of 1 to 90 mol %, more preferably 3 to 80 mol %, further more preferably 5 to 70 mol % and most preferably 10 to 60 mol %, based on all the repeating units of the hydrophobic resin. The content of repeating unit containing at least either a fluorine atom or a silicon atom used in combination with the repeating unit (b*) is preferably in the range of 10 to 99 mol %, more preferably 20 to 97 mol %, further more preferably 30 to 95 mol % and most preferably 40 to 90 mol %, based on all the repeating units of the hydrophobic resin.

The content of repeating unit (b") in the hydrophobic resin is preferably in the range of 1 to 100 mol %, more preferably 3 to 99 mol %, further more preferably 5 to 97 mol % and most preferably 10 to 95 mol %, based on all the repeating units of the hydrophobic resin.

The hydrophobic resin may further contain any of the repeating units represented by the following general formula (CIII).

In the formula (CIII), $R_{c31}$ represents a hydrogen atom, an alkyl group, an alkyl group optionally substituted with one or more fluorine atoms, a cyano group or a group of the formula —$CH_2$—O—$R_{ac2}$ in which $R_{ac2}$ represents a hydrogen atom, an alkyl group or an acyl group. $R_{c31}$ is preferably a hydrogen atom, a methyl group, a hydroxymethyl group, or a trifluoromethyl group, more preferably a hydrogen atom or a methyl group.

$R_{c32}$ represents a group containing an alkyl group, a cycloalkyl group, an alkenyl group, a cycloalkenyl group, or an aryl group. These groups may be substituted with fluorine atom and/or silicon atom.

$L_{c3}$ represents a single bond or a bivalent connecting group.

In the formula (CIII), the alkyl group represented by $R_{c32}$ is preferably a linear or branched alkyl group having 3 to 20 carbon atoms.

The cycloalkyl group is preferably a cycloalkyl group having 3 to 20 carbon atoms.

The alkenyl group is preferably an alkenyl group having 3 to 20 carbon atoms.

The cycloalkenyl group is preferably a cycloalkenyl group having 3 to 20 carbon atoms.

The aryl group is preferably an aryl group having 6 to 20 carbon atoms such as a phenyl group or a naphthyl group.

These groups may have one or more substituents.

Preferably, $R_{c32}$ represents an unsubstituted alkyl group or an alkyl group substituted with one or more fluorine atoms.

$L_{c3}$ represents a single bond or a bivalent connecting group. As the bivalent connecting group represented by $L_{c3}$, an alkylene group (preferably having 1 to 5 carbon atoms), an oxy group, a phenylene group, or an ester bond (a group represented by —COO—) can be exemplified.

The hydrophobic resin may further contain any of the repeating units represented by general formula (BII-AB) below.

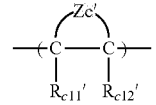

In the formula (BII-AB), each of $R_{c11}'$ and $R_{c12}'$ independently represents a hydrogen atom, a cyano group, a halogen atom or an alkyl group.

Zc' represents an atomic group containing bonded two carbon atoms (C—C) and required for forming an alicyclic structure.

When any of the groups contained in the repeating unit represented by general formulae (CIII) or (BII-AB) is substituted with a fluorine atom or a silicone atom, the repeating unit is also corresponding to the aforementioned repeating unit containing at least either a fluorine atom or a silicon atom.

Specific examples of the repeating unit represented by general formulae (CIII) or (BII-AB) will be shown below, which however in no way limit the scope of the present invention. In the formulae, Ra represents H, $CH_3$, $CH_2OH$, $CF_3$ or CN. Note that the repeating unit in which Ra represents $CF_3$ also corresponds to the repeating unit containing at least either a fluorine atom or a silicon atom.

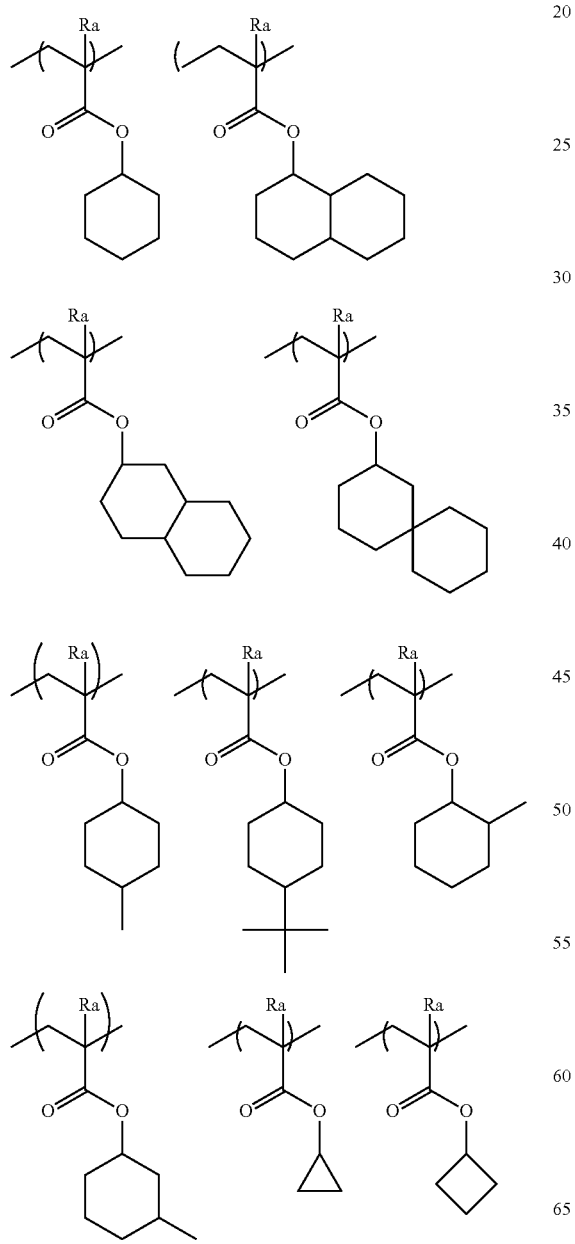

-continued

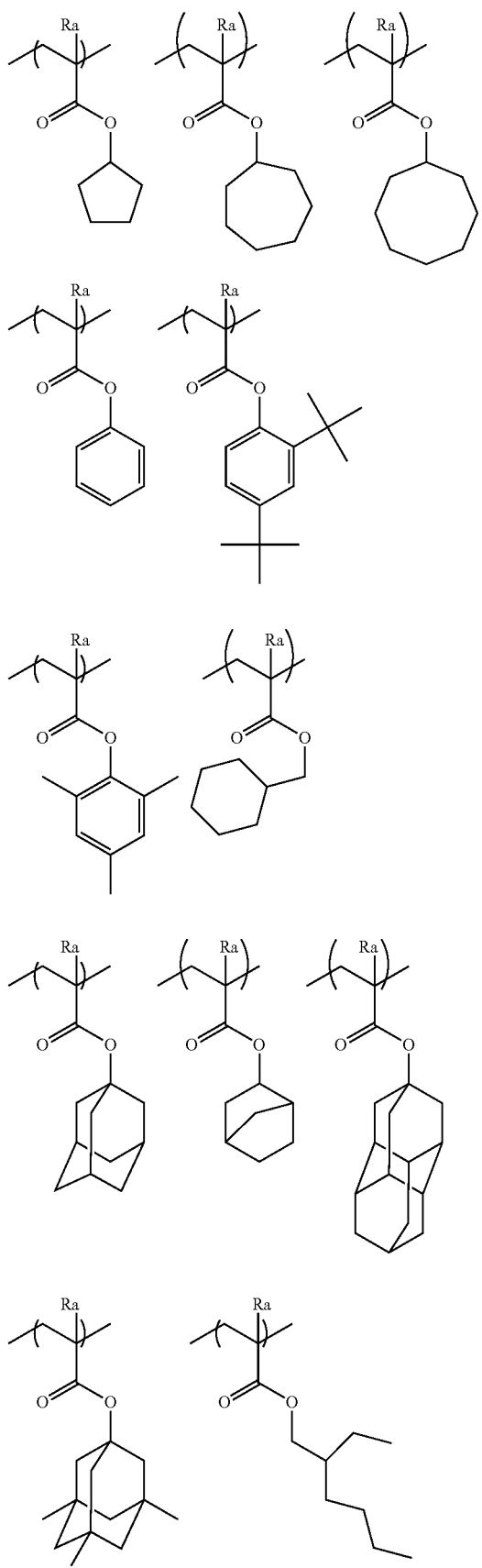

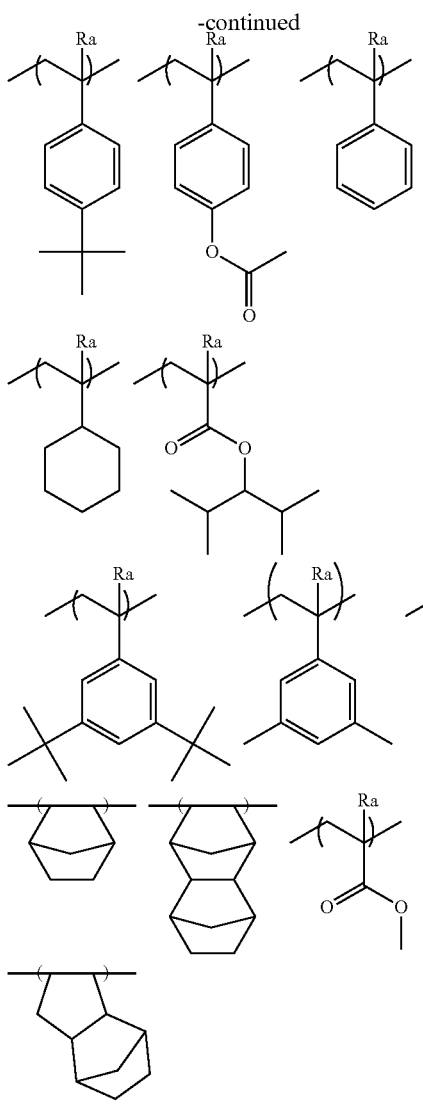

Impurities such as metals in the hydrophobic resin should naturally be of low quantity as in the resin (B) described above. The content of residual monomers and oligomer components is preferably in the range of 0 to 10 mass %, more preferably 0 to 5 mass %, and still more preferably 0 to 1 mass %. Accordingly, there can be obtained a composition being free from in-liquid foreign matters and a change in sensitivity, etc. over time. From the viewpoint of resolving power, resist profile, side wall of resist pattern, roughness, etc., the molecular weight distribution (Mw/Mn, also referred to as the degree of dispersal) thereof is preferably in the range of 1 to 3, more preferably 1 to 2, still more preferably 1 to 1.8 and most preferably 1 to 1.5.

A variety of commercially available products can be used as the hydrophobic resin, and also the resin can be synthesized in accordance with conventional methods (for example, by radical polymerization). As general synthesizing methods, a batch polymerization method in which a monomer species and an initiator are dissolved in a solvent and heated to carry out polymerization and a dropping polymerization method in which a solution of monomer species and initiator is dropped into a hot solvent over a period of 1 to 10 hours can be exemplified. Of these, the dropping polymerization method is preferred.

A reaction solvent, a polymerization initiator, a condition of a reaction (temperature, concentration or the like) and a purification method after a reaction are the same as the case of the resin (B) described above.

Specific examples of the hydrophobic resin (HR) will be shown below. The following Table 1 shows the molar ratio of individual repeating units (the positional relationship of numerics indicating component ratios of Table 1 corresponds to that of the individual repeating units of each resin shown in the specific examples below), weight average molecular weight, and degree of dispersal with respect to each of the resins.

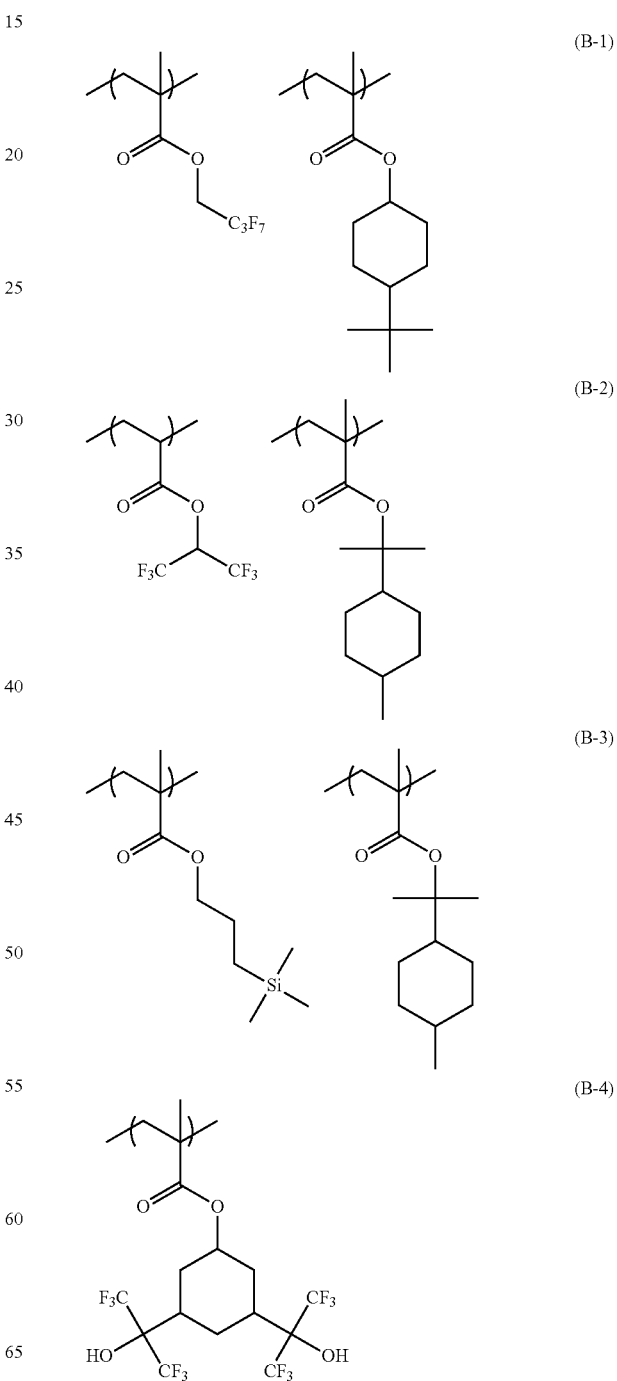

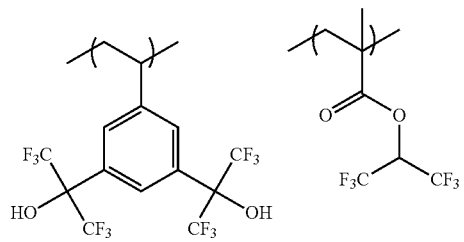
(B-5)
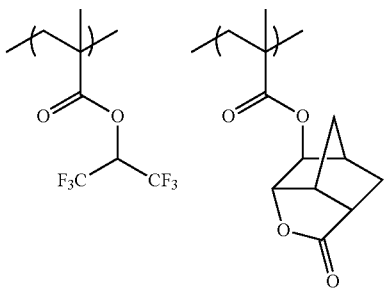
(B-10)
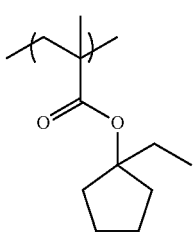
(B-6)
(B-11)
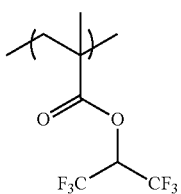
(B-7)
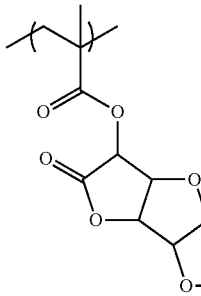
(B-8)
(B-12)
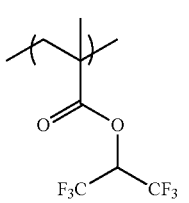
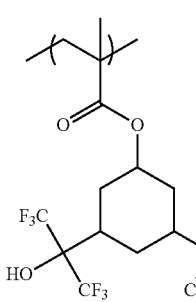
(B-9)

(B-13)
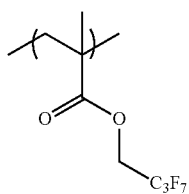
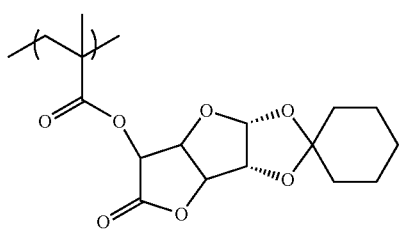
(B-14)
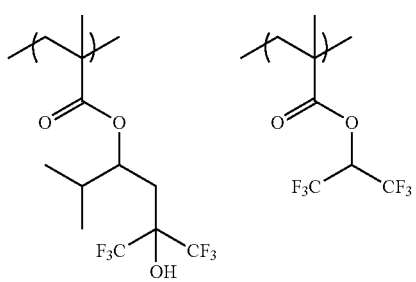
(B-15)
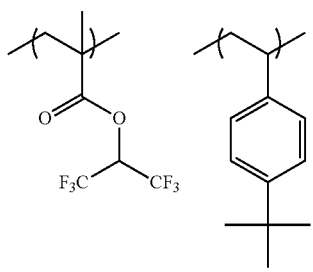
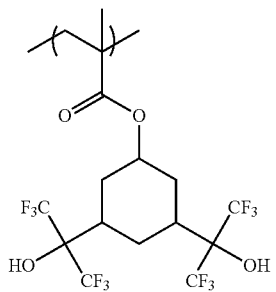
(B-16)
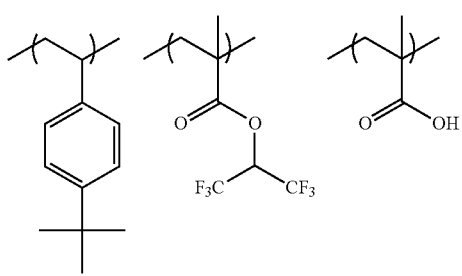
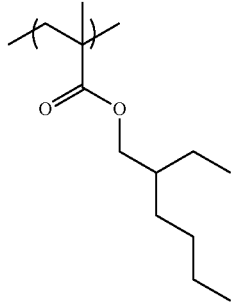
(B-17)
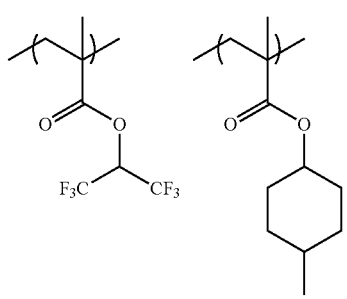
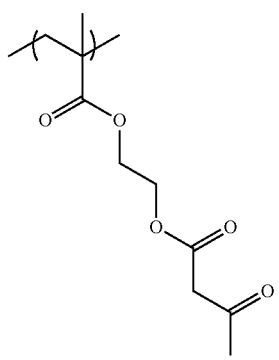
(B-18)
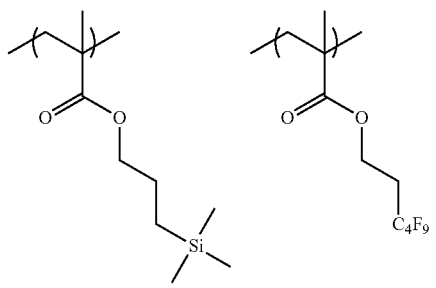
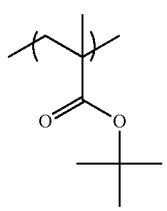

(B-19)
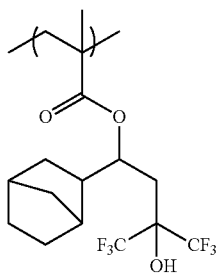
(B-20)
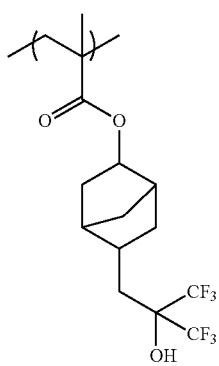
(B-21)
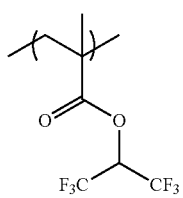 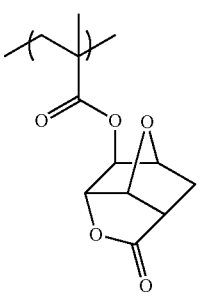
(B-22)
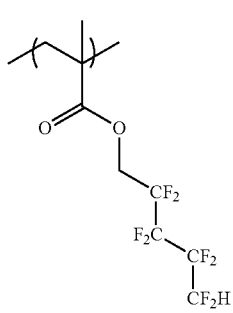
(B-23)
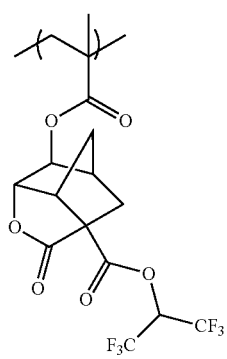
(B-24)
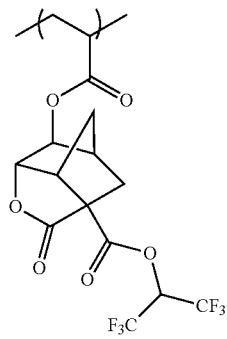
(B-25)
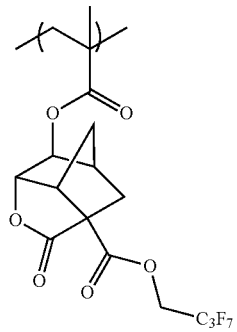
(B-26)
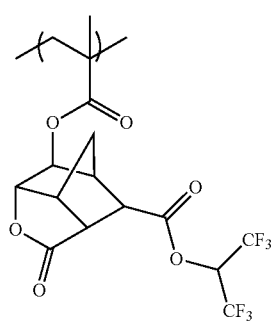
(B-27)
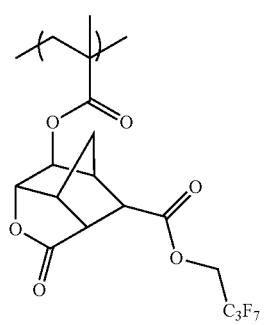

(B-28)
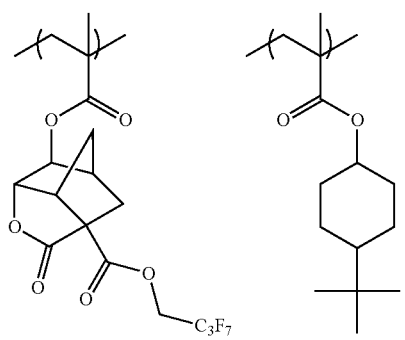
(B-29)
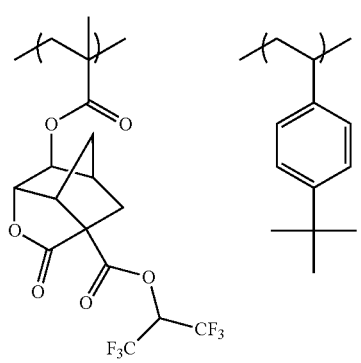
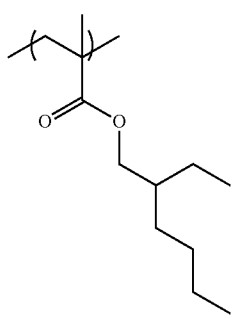
(B-30)
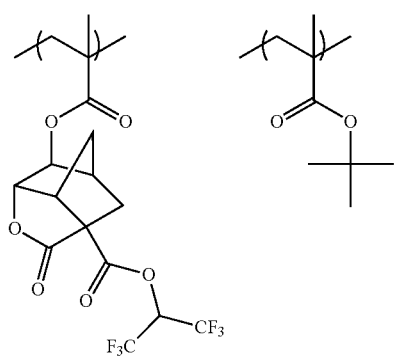
(B-31)
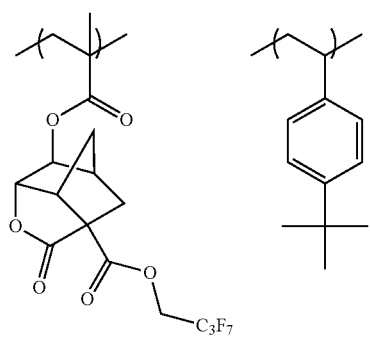
(B-32)
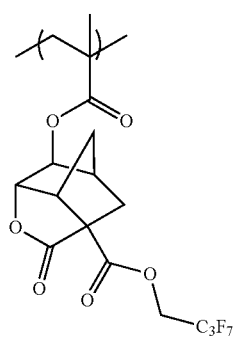
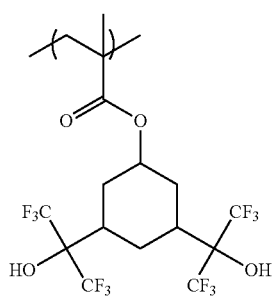
(B-33)
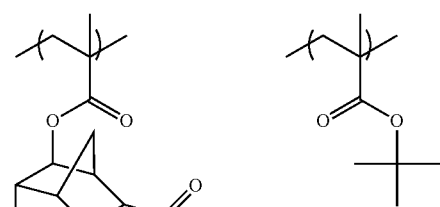
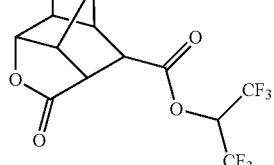
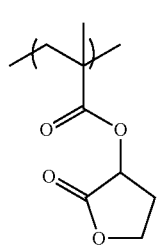

(B-34)
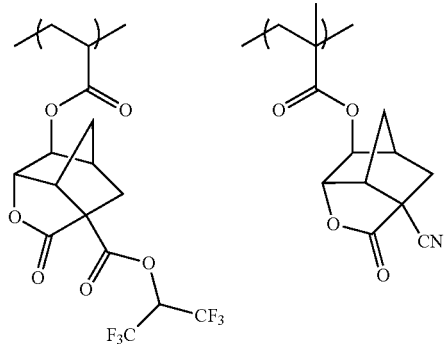
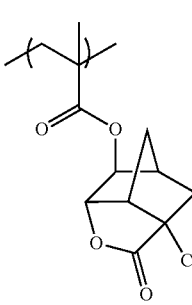
(B-35)
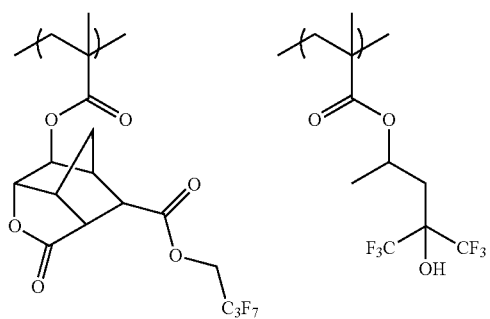
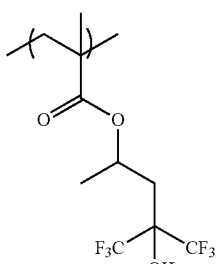
(B-36)
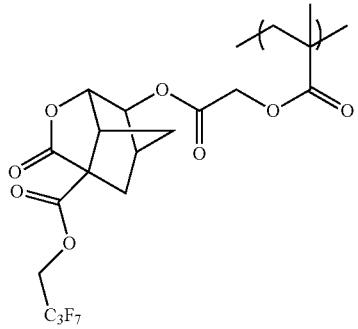
(B-37)
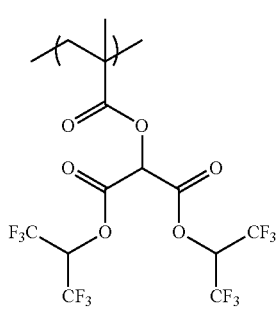
(B-38)
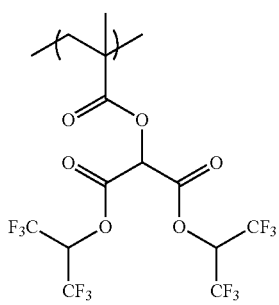
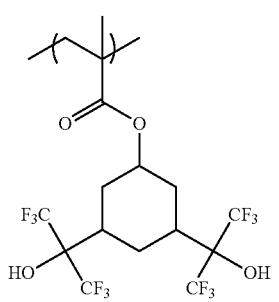
(B-39)
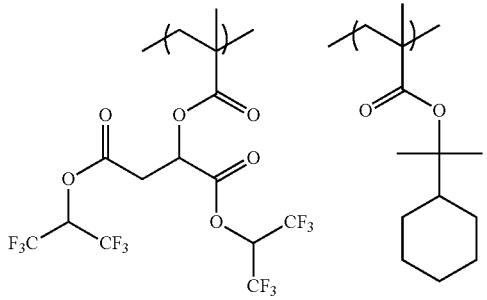
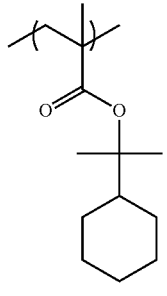
(B-40)
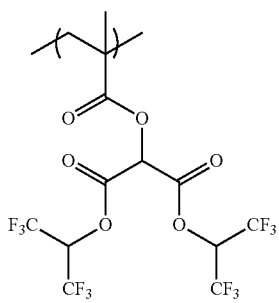

(B-41)
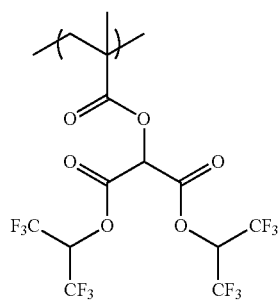
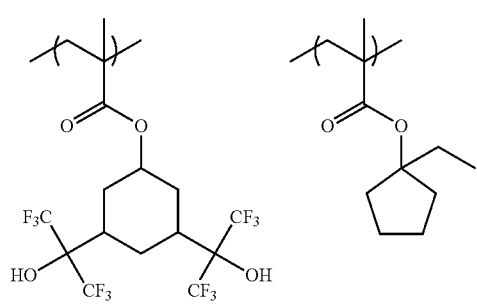
(B-42)
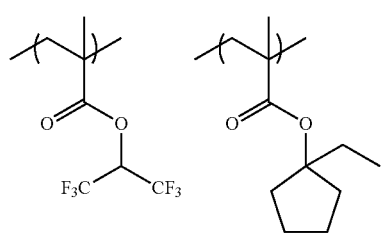
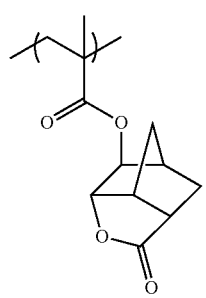
(B-43)
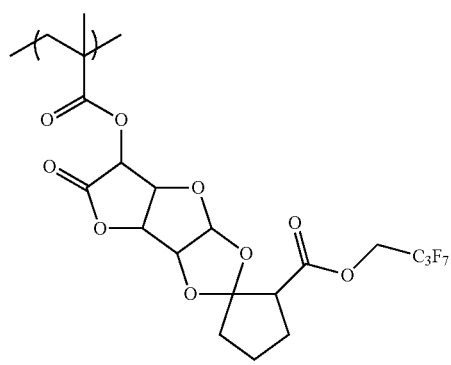
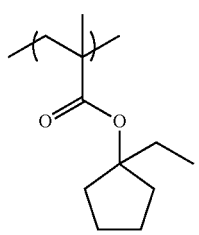 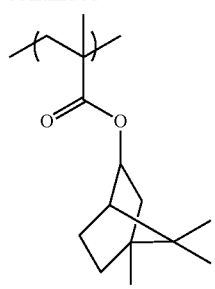
(B-44)
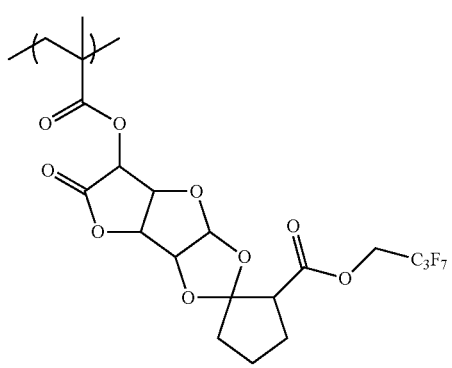
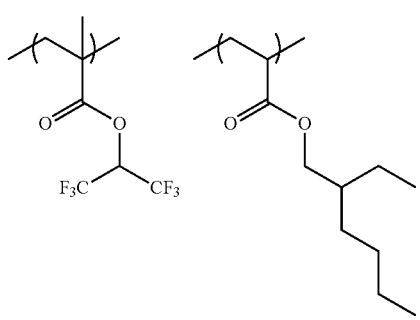
(B-45)
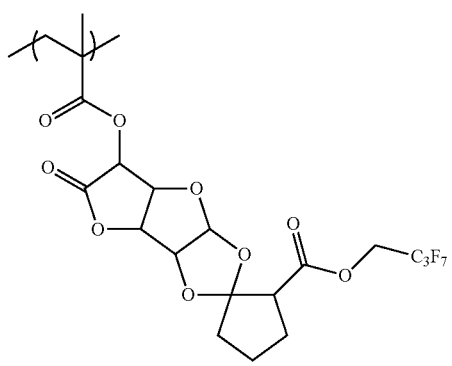
(B-46)
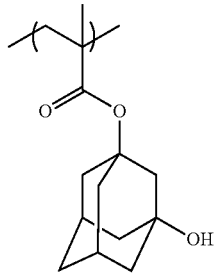

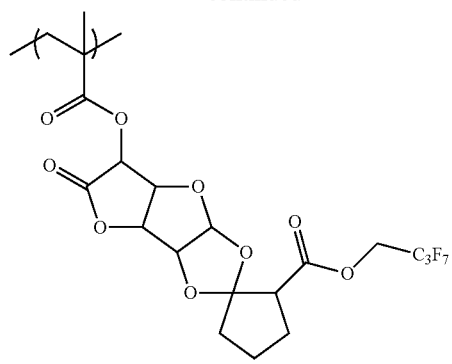
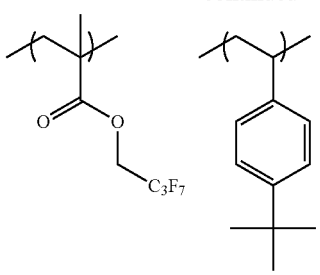
(B-47)
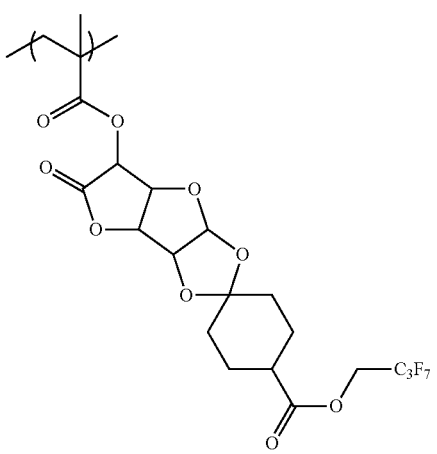
(B-49)
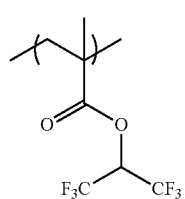
(B-48)
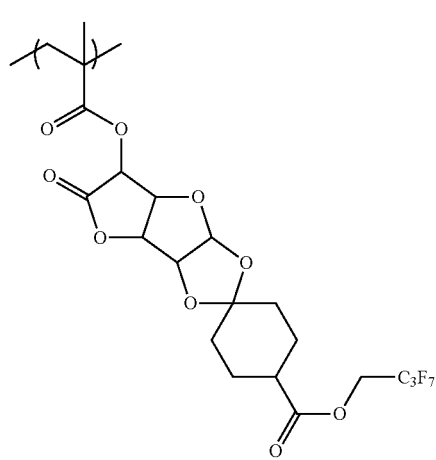
(B-50)
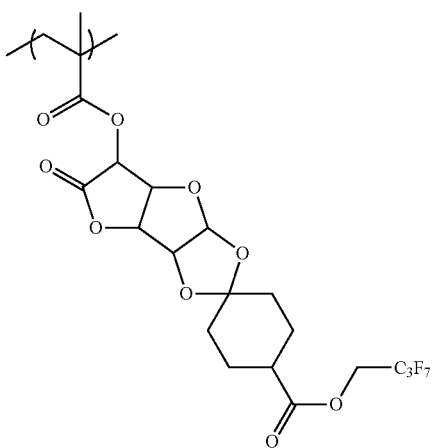
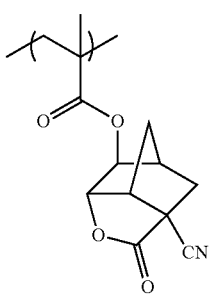

(B-51)
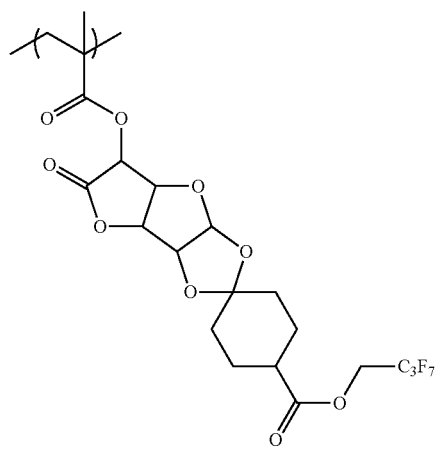
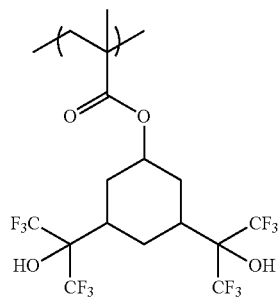
(B-52)
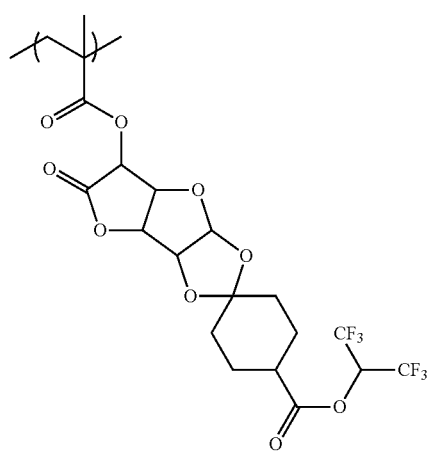
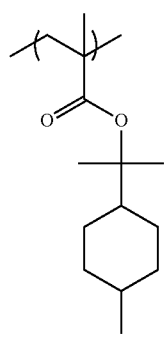
(B-53)
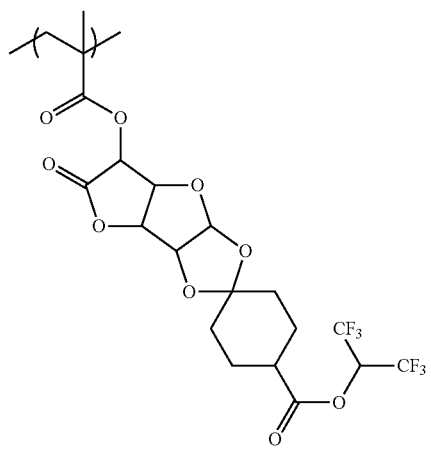
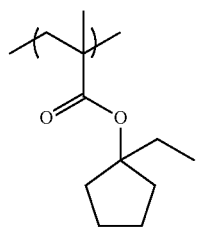
(B-54)
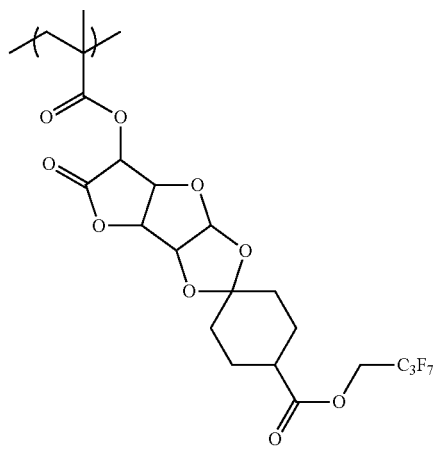
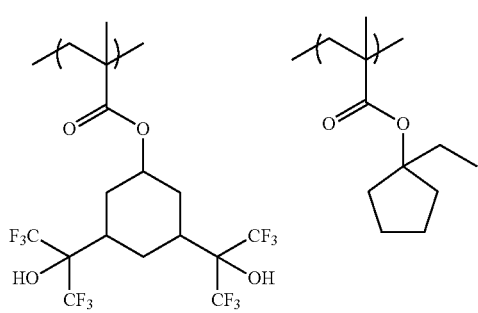

(B-55)

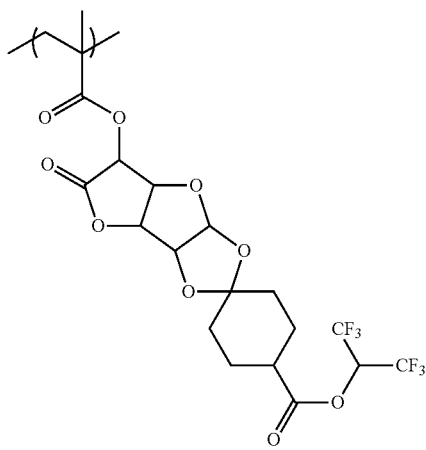

TABLE 1

| Polymer | Component ratio (mol %) | Mw | Mw/Mn |
|---|---|---|---|
| B-1 | 50/50 | 6000 | 1.5 |
| B-2 | 30/70 | 6500 | 1.4 |
| B-3 | 45/55 | 8000 | 1.4 |
| B-4 | 100 | 15000 | 1.7 |
| B-5 | 60/40 | 6000 | 1.4 |
| B-6 | 40/60 | 8000 | 1.4 |
| B-7 | 30/40/30 | 8000 | 1.4 |
| B-8 | 60/40 | 8000 | 1.3 |
| B-9 | 50/50 | 6000 | 1.4 |
| B-10 | 40/40/20 | 7000 | 1.4 |
| B-11 | 40/30/30 | 9000 | 1.6 |
| B-12 | 30/30/40 | 6000 | 1.4 |
| B-13 | 60/40 | 9500 | 1.4 |
| B-14 | 60/40 | 8000 | 1.4 |
| B-15 | 35/35/30 | 7000 | 1.4 |
| B-16 | 50/40/5/5 | 6800 | 1.3 |
| B-17 | 20/30/50 | 8000 | 1.4 |
| B-18 | 25/25/50 | 6000 | 1.4 |
| B-19 | 100 | 9500 | 1.5 |
| B-20 | 100 | 7000 | 1.5 |
| B-21 | 50/50 | 6000 | 1.6 |
| B-22 | 40/60 | 9600 | 1.3 |
| B-23 | 100 | 20000 | 1.7 |
| B-24 | 100 | 25000 | 1.4 |
| B-25 | 100 | 15000 | 1.7 |
| B-26 | 100 | 12000 | 1.8 |
| B-27 | 100 | 18000 | 1.3 |
| B-28 | 70/30 | 15000 | 2.0 |
| B-29 | 80/15/5 | 18000 | 1.8 |
| B-30 | 60/40 | 25000 | 1.8 |
| B-31 | 90/10 | 19000 | 1.6 |
| B-32 | 60/40 | 20000 | 1.8 |
| B-33 | 50/30/20 | 11000 | 1.6 |
| B-34 | 60/40 | 12000 | 1.8 |
| B-35 | 60/40 | 15000 | 1.6 |
| B-36 | 100 | 22000 | 1.8 |
| B-37 | 20/80 | 35000 | 1.6 |
| B-38 | 30/70 | 12000 | 1.7 |
| B-39 | 30/70 | 9000 | 1.5 |
| B-40 | 100 | 9000 | 1.5 |
| B-41 | 40/15/45 | 12000 | 1.9 |
| B-42 | 30/30/40 | 13000 | 2.0 |
| B-43 | 40/40/20 | 23000 | 2.1 |
| B-44 | 65/30/5 | 25000 | 1.6 |
| B-45 | 100 | 15000 | 1.7 |
| B-46 | 20/80 | 9000 | 1.7 |
| B-47 | 70/30 | 18000 | 1.5 |
| B-48 | 60/20/20 | 18000 | 1.8 |
| B-49 | 100 | 12000 | 1.4 |
| B-50 | 60/40 | 20000 | 1.6 |
| B-51 | 70/30 | 33000 | 2.0 |
| B-52 | 60/40 | 19000 | 1.8 |
| B-53 | 50/50 | 15000 | 1.5 |
| B-54 | 40/20/40 | 35000 | 1.9 |
| B-55 | 100 | 16000 | 1.4 |

When the hydrophobic resin containing at least either a fluorine atom or a silicon atom is contained in the actinic ray- or radiation-sensitive resin composition according to the present invention, the hydrophobic resin is unevenly distributed in the surface layer of the film formed from the composition. When the immersion medium is water, the receding contact angle of the surface of the film with respect to water is increased after bake and before exposure, so that the immersion-water tracking properties can be enhanced.

The receding contact angle of a film after baking and before exposing the film cinsisting of the actinic ray- or radiation-sensitive resin composition according to the present invention is preferably in the range of 60° to 90°, more preferably 65° or higher, further more preferably 70° or higher, and particularly preferably 75° or higher as measured under the conditions of temperature 23±3° C. and humidity 45±5%.

Although the hydrophobic resin is unevenly localized on any interface, as different from the surfactant, the hydrophobic resin does not necessarily have to have a hydrophilic group in its molecule and does not need to contribute toward uniform mixing of polar/nonpolar substances.

In the operation of liquid immersion exposure, it is needed for the liquid for liquid immersion to move on a wafer while tracking the movement of an exposure head involving high-speed scanning on the wafer and thus forming an exposure pattern. Therefore, the contact angle of the liquid for liquid immersion with respect to the film in dynamic condition is important, and it is required for the actinic ray-sensitive or radiation-sensitive resin composition to be capable of tracking the high-speed scanning of the exposure head without leaving droplets.

Because of its hydrophobicity, the hydrophobic resin is likely to cause impairment of development residue (scum) and blob defects after alkali development. Containing three or more polymer chains via at least one branch portion increases the rate of dissolution in alkali as compared with that of a linear-chain resin, so that the development residue (scum) and blob defect performances can be improved thereby.

When the hydrophobic resin contains fluorine atoms, the content of the fluorine atoms based on the molecular weight of the hydrophobic resin is preferably in the range of 5 to 80 mass %, and more preferably 10 to 80 mass %. The repeating unit containing fluorine atoms preferably exists in the hydrophobic resin in an amount of 10 to 100 mol %, more preferably 30 to 100 mol %.

When the hydrophobic resin contains silicon atoms, the content of the silicon atoms based on the molecular weight of the hydrophobic resin is preferably in the range of 2 to 50 mass %, more preferably 2 to 30 mass %. The repeating unit containing silicon atoms preferably exists in the hydrophobic resin in an amount of 10 to 90 mol %, more preferably 20 to 80 mol %.

The weight average molecular weight of the hydrophobic resin is preferably in the range of 1,000 to 100,000, more preferably 2,000 to 50,000, and still more preferably 3,000 to 35,000. Here, the weight average molecular weight of the resin is in terms of standard polystyrene molecular weight and is measured by GPC (carrier: tetrahydrofurane(THF)).

The content of hydrophobic resin in the actinic ray- or radiation-sensitive resin composition can be controlled so that the receding contact angle of a film of the actinic ray- or radiation-sensitive resin composition is in the range above. The content of the hydrophobic resin in the actinic ray- or radiation-sensitive resin composition, based on the total solids of the actinic ray- or radiation-sensitive resin composition, is preferably in the range of 0.01 to 20 mass %, more preferably 0.1 to 15 mass %, further more preferably 0.1 to 10 mass % and especially preferably 0.2 to 8 mass %.

The hydrophobic resin either may be used individually or in combination.

[4] Basic Compound

The actinic ray- or radiation-sensitive resin composition of the present invention preferably contains a basic compound in order to reduce any performance change over time from exposure to bake.

As preferred basic compounds, the compounds having the structures represented by the following formulae (A) to (E) can be exemplified.

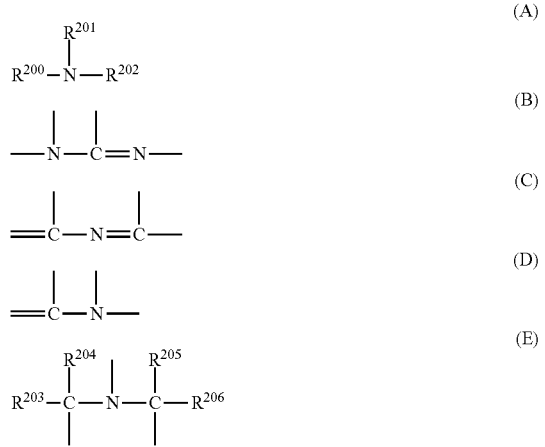

In the general formulae (A) and (E), $R_{200}$, $R_{201}$ and $R_{202}$ each independently represents a hydrogen atom, an alkyl group (preferably having 1 to 20 carbon atoms), a cycloalkyl group (preferably having 3 to 20 carbon atoms) or an aryl group (having 6 to 20 carbon atoms). $R_{201}$ and $R_{202}$ may be bonded to each other to form a ring.

$R_{203}$, $R_{204}$, $R_{205}$ and $R_{206}$ each independently represents an alkyl group having 1 to 20 carbon atoms.

With respect to the above alkyl group, as a preferred substituted alkyl group, an aminoalkyl group having 1 to 20 carbon atoms, a hydroxyalkyl group having 1 to 20 carbon atoms, and a cyanoalkyl group having 1 to 20 carbon atoms can be exemplified. More preferably, the alkyl groups in the general formulae (A) and (E) are unsubstituted.

As preferred basic compounds, guanidine, aminopyrrolidine, pyrazole, pyrazoline, piperazine, aminomorpholine, aminoalkylmorpholine and piperidine can be exemplified. As more preferred compounds, those with an imidazole structure, a diazabicyclo structure, an onium hydroxide structure, an onium carboxylate structure, a trialkylamine structure, an aniline structure or a pyridine structure, alkylamine derivatives having a hydroxy group and/or an ether bond, and aniline derivatives having a hydroxy group and/or an ether bond can be exemplified.

As the compounds with an imidazole structure, imidazole, 2,4,5-triphenylimidazole, benzimidazole and 2-phenylbenzimidazole can be exemplified. As the compounds with a diazabicyclo structure, 1,4-diazabicyclo[2,2,2]octane, 1,5-diazabicyclo[4,3,0]non-5-ene, and 1,8-diazabicyclo[5,4,0]undec-7-ene can be exemplified. As the compounds with an onium hydroxide structure, tetrabutylammonium hydroxide, triarylsulfonium hydroxide, phenacylsulfonium hydroxide, sulfonium hydroxides having a 2-oxoalkyl group, such as triphenylsulfonium hydroxide, tris(t-butylphenyl)sulfonium hydroxide, bis(t-butylphenyl)iodonium hydroxide, phenacylthiophenium hydroxide, and 2-oxopropylthiophenium hydroxide can be exemplified. As the compounds with an onium carboxylate structure, those having a carboxylate at the anion moiety of the compounds with an onium hydroxide structure, such as acetate, adamantane-1-carboxylate, and perfluoroalkyl carboxylate can be exemplified. As the compounds with a trialkylamine structure, tri(n-butyl)amine and tri(n-octyl)amine can be exemplified. As the aniline compounds, 2,6-diisopropylaniline, N,N-dimethylaniline, N,N-dibutylaniline, and N,N-dihexylaniline can be exemplified. As the alkylamine derivatives having a hydroxy group and/or an ether bond, ethanolamine, diethanolamine, triethanolamine, N-phenyldiethanolamine and tris(methoxyethoxyethyl)amine can be exemplified. As the aniline derivatives having a hydroxy group and/or an ether bond, N,N-bis(hydroxyethyl)aniline can be exemplified.

As preferred basic compounds, an amine compound having a phenoxy group, an ammonium salt compound having a phenoxy group, an amine compound having a sulfonic ester group, and an ammonium salt compound having a sulfonic ester group can further be exemplified.

As the amine compound, use can be made of primary, secondary and tertiary amine compounds. An amine compound having at least one alkyl group bonded to the nitrogen atom thereof is preferred. Among the amine compounds, a tertiary amine compound is more preferred. In the amine compounds, as long as at least one alkyl group (preferably having 1 to 20 carbon atoms) is bonded to the nitrogen atom, a cycloalkyl group (preferably having 3 to 20 carbon atoms) or an aryl group (preferably having 6 to 12 carbon atoms) besides the alkyl group may be bonded to the nitrogen atom. In the amine compounds, it is preferred for the alkyl chain thereof to contain an oxygen atom, thereby forming an oxyalkylene group. The number of oxyalkylene groups in each molecule is one or more, preferably 3 to 9, and more preferably 4 to 6. The oxyalkylene group is preferably an oxyethylene group (—CH$_2$CH$_2$O—) or an oxypropylene group (—CH(CH$_3$)CH$_2$O— or —CH$_2$CH$_2$CH$_2$O—), more preferably an oxyethylene group.

As the ammonium salt compound, use can be made of primary, secondary and tertiary ammonium salt compounds. An ammonium salt compound having at least one alkyl group bonded to the nitrogen atom thereof is preferred. In the ammonium salt compounds, as long as at least one alkyl group (preferably having 1 to 20 carbon atoms) is bonded to the nitrogen atom, a cycloalkyl group (preferably having 3 to 20 carbon atoms) or an aryl group (preferably having 6 to 12 carbon atoms) besides the alkyl group may be bonded to the nitrogen atom. In the ammonium salt compounds, it is preferred for the alkyl chain thereof to contain an oxygen atom, thereby forming an oxyalkylene group. The number of oxyalkylene groups in each molecule is one or more, preferably 3 to 9, and more preferably 4 to 6. The oxyalkylene group is preferably an oxyethylene group (—CH$_2$CH$_2$O—)

or an oxypropylene group (—CH(CH₃)CH₂O— or —CH₂CH₂CH₂O—), more preferably an oxyethylene group.

As the anion in each of the ammonium salt compounds, there can be mentioned a halogen atom, a sulfonate, a borate, a phosphate or the like. Of these, a halogen atom and a sulfonate are preferred. Among halogen atoms, chloride, bromide and iodide are especially preferred. Among sulfonates, an organic sulfonate having 1 to 20 carbon atoms is especially preferred. As the organic sulfonate, there can be mentioned an aryl sulfonate or an alkyl sulfonate having 1 to 20 carbon atoms. A substituent may be introduced in the alkyl group in the alkyl sulfonate. As the substituent, there can be mentioned, for example, fluorine, chlorine, bromine, an alkoxy group, an acyl group, an aryl group or the like. As specific examples of the alkyl sulfonates, there can be mentioned methane sulfonate, ethane sulfonate, butane sulfonate, hexane sulfonate, octane sulfonate, benzyl sulfonate, trifluoromethane sulfonate, pentafluoroethane sulfonate, nonafluorobutane sulfonate and the like. As the aryl group in the aryl sulfonate, there can be mentioned a benzene ring, a naphthalene ring or an anthracene ring. A substituent may be introduced in the benzene ring, naphthalene ring or anthracene ring. As preferred substituents, there can be mentioned a linear or branched alkyl group having 1 to 6 carbon atoms and a cycloalkyl group having 3 to 6 carbon atoms. As specific examples of the linear or branched alkyl groups and cycloalkyl groups, there can be mentioned methyl, ethyl, n-propyl, isopropyl, n-butyl, i-butyl, t-butyl, n-hexyl, cyclohexyl and the like. As other substituents, there can be mentioned an alkoxy group having 1 to 6 carbon atoms, a halogen atom, cyano, nitro, an acyl group, an acyloxy group and the like.

The amine compounds with a phenoxy group and the ammonium salt compounds with a phenoxy group are those having a phenoxy group at the end of the alkyl group of each of the amine compound and the ammonium salt compound opposite to the nitrogen atom. The phenoxy group may have a substituent, such as an alkyl group, an alkoxy group, a halogen atom, a cyano group, a nitro group, a carboxyl group, a carboxylic ester group, a sulfonic ester group, an aryl group, an aralkyl group, an acyloxy group, an aryloxy group or the like. The position of the substituent may be any of 2- to 6-position. The number of the substituents may be any of 1 to 5.

Compounds having at least one oxyalkylene chain between the phenoxy group and the nitrogen atom are preferred. The number of oxyalkylene groups in each molecule is one or more, preferably 3 to 9, and more preferably 4 to 6. The oxyalkylene group is preferably an oxyethylene group (—CH₂CH₂O—) or an oxypropylene group (—CH(CH₃)CH₂O— or —CH₂CH₂CH₂O—), more preferably an oxyethylene group.

The sulfonic ester group in the amine compound having a sulfonic ester group or ammonium salt compound having a sulfonic ester group may be any of an alkylsulfonic ester, a cycloalkylsulfonic ester and an arylsulfonic ester. In the alkylsulfonic ester, the alkyl group preferably has 1 to 20 carbon atoms. In the cycloalkylsulfonic ester, the cycloalkyl group preferably has 3 to 20 carbon atoms. In the arylsulfonic ester, the aryl group preferably has 6 to 12 carbon atoms. Substituents may be introduced in the alkylsulfonic ester, cycloalkylsulfonic ester and arylsulfonic ester. As preferred substituents, there can be mentioned a halogen atom, a cyano group, a nitro group, a carboxyl group, a carboxylic ester group and a sulfonic ester group.

It is preferred for at least one oxyalkylene group to exist between the sulfonic ester group and the nitrogen atom. The number of oxyalkylene groups in each molecule is one or more, preferably 3 to 9 and more preferably 4 to 6. The oxyalkylene group is preferably an oxyethylene group (—CH₂CH₂O—) or an oxypropylene group (—CH(CH₃)CH₂O— or —CH₂CH₂CH₂O—), more preferably an oxyethylene group.

Also, the following compounds are preferred basic compounds.

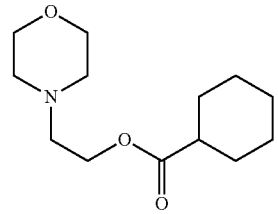

(MO-1)

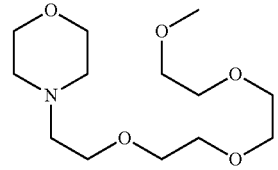

(MO-2)

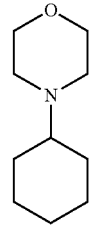

(MO-3)

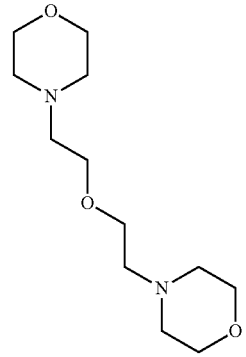

(MO-4)

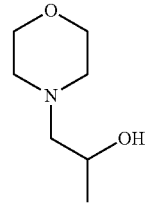

(MO-5)

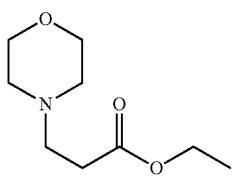

(MO-6)

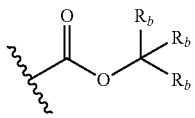

(d-1)

In the formula (d-1),

Each of Rbs independently represents a hydrogen atom, an alkyl group, a cycloalkyl group, an aryl group, an aralkyl group, or an alkoxyalkyl group. At least two of Rbs may be connected to each other to form a ring.

The alkyl group, the cycloalkyl group, the aryl group and the aralkyl group represented by Rb may be substituted with a functional group (a hydroxyl group, a cyano group, an amino group, a pyrrolidino group, a piperidino group, a morpholino group, an oxo group or the like), an alkoxy group or a halogen atom. The same applies to the alkoxyalkyl group represented by Rb.

As the alkyl group, the cycloalkyl group, the aryl group, and the aralkyl group (these groups may be substituted with the above functional group, an alkoxy group, or a halogen atom) represented by Rb, the following groups can be exemplified:

a group derived from a linear or branched alkane such as methane, ethane, propane, butane, pentane, hexane, heptane, octane, nonane, decane, undecane, or dodecane; and the group derived from the alkane and substituted with one or more cycloalkyl groups such as a cyclobutyl group, a cyclopentyl group, or a cyclohexyl group;

a group derived from cycloalkane such as cyclobutane, cyclopentane, cyclohexane, cycloheptane, cyclooctane, norbornane, adamantane, or noradamantane; and the group derived from the cycloalkane and substituted with one or more linear or branched alkyl group such as a methyl group, an ethyl group, a n-propyl group, an i-propyl group, a n-butyl group, a 2-methylpropyl group, a 1-methylpropyl group, or a t-butyl group;

a group derived from aromatic compound such as benzene, naphthalene, or anthracene; and the group derived from the atomatic compound and substituted with one or more linear or branched alkyl group such as a methyl group, an ethyl group, a n-propyl group, an i-propyl group, a n-butyl group, a 2-methylpropyl group, a 1-methylpropyl group, or a t-butyl group;

a group derived from heterocyclic compound such as pyrrolidine, piperidine, morpholine, tetrahydrofuran, tetrahydropyrane, indole, indoline, quinoline, perhydroquinoline, indazole, or benzimidazole; the group derived from heterocyclic compound and substituted with one or more linear or branched alkyl group or a group derived from the aromatic compound;

a group derived from linear or branched alkane and substituted with a group derived from aromatic compound such as a phenyl group, a naphthyl group, or an anthracenyl group;

a group derived from cycloalkane and substituted with a group derived from aromatic compound such as a phenyl group, a naphthyl group, or an anthracenyl group; or each of these groups substituted with a functional group such as a hydroxyl group, a cyano group, an amino group, a pyrrolidino group, a piperidino group, a morpholino group, or an oxo group.

Rb represents prelerably a linear or branched alkyl group, a cycloalkyl group or aryl group, more preferably a linear or branched alkyl group or a cycloalkyl group.

Among these basic compounds, one type thereof may be used alone, or two or more types thereof may be used in combination.

It is optional for the composition of the present invention to contain a basic compound. When a basic compound is contained, the content of basic compound is generally in the range of 0.001 to 10 mass %, preferably 0.01 to 5 mass %, based on the total solids of the actinic ray- or radiation-sensitive resin composition.

The molar ratio of acid generator (including acid generator (A')) to basic compound (acid generator/basic compound) used in the composition is preferably in the range of 2.5 to 300. Namely, a molar ratio of 2.5 or higher is preferred from the viewpoint of the enhancement of sensitivity and resolution. A molar ratio of 300 or below is preferred from the viewpoint of the inhibition of any resolution deterioration due to resist pattern thickening over time until baking treatment after exposure. The molar ratio of acid generator/basic compound is more preferably in the range of 5.0 to 200, further more preferably 7.0 to 150.

These basic compounds are preferably used in a molar ratio relative to the low-molecular compound (D) to be described in section [5] below [low-molecular compound (D)/basic compound] of 100/0 to 10/90, more preferably 100/0 to 30/70 and most preferably 100/0 to 50/50.

Herein, the basic compounds do not include any low-molecular compound (D) containing a nitrogen atom and a group eliminated under the action of an acid, which compound functions as a basic compound.

[5] Low-molecular compound having a nitrogen atom and a group that is eliminated by the action of an acid The composition according to the present invention may further contain a low-molecular compound having a nitrogen atom and a group that is eliminated by the action of an acid [hereinafter also referred to as "low-molecular compound (D)" or "compound (D)"].

The group that is cleaved when acted on by an acid is not particularly limited. However, an acetal group, a carbonate group, a carbamate group, a tertiary ester group, a tertiary hydroxyl group and a hemiaminal ether group are preferably used. A carbamate group and a hemiaminal ether group are especially preferred.

The molecular weight of the low-molecular compound (D) having a group that is cleaved when acted on by an acid is preferably in the range of 100 to 1000, more preferably 100 to 700 and most preferably 100 to 500.

As the compound (D), an amine derivative having a group that is cleaved when acted on by an acid being connected to a nitrogen atom is preferred.

The compound (D) may contain a carbamate group with a protective group, the carbamate group being connected to a nitrogen atom. The protective group contained in the carbamate group can be represented, for example, by the following formula (d-1).

As the ring formed by connecting two of Rb's each other, an alicyclic hydrocarbon group, an aromatic hydrocarbon group, a heterocyclic hydrocarbon group, or their derivatives are exemplified.
Concrete structures of groups represented by the general formula (d-1) will be shown below.
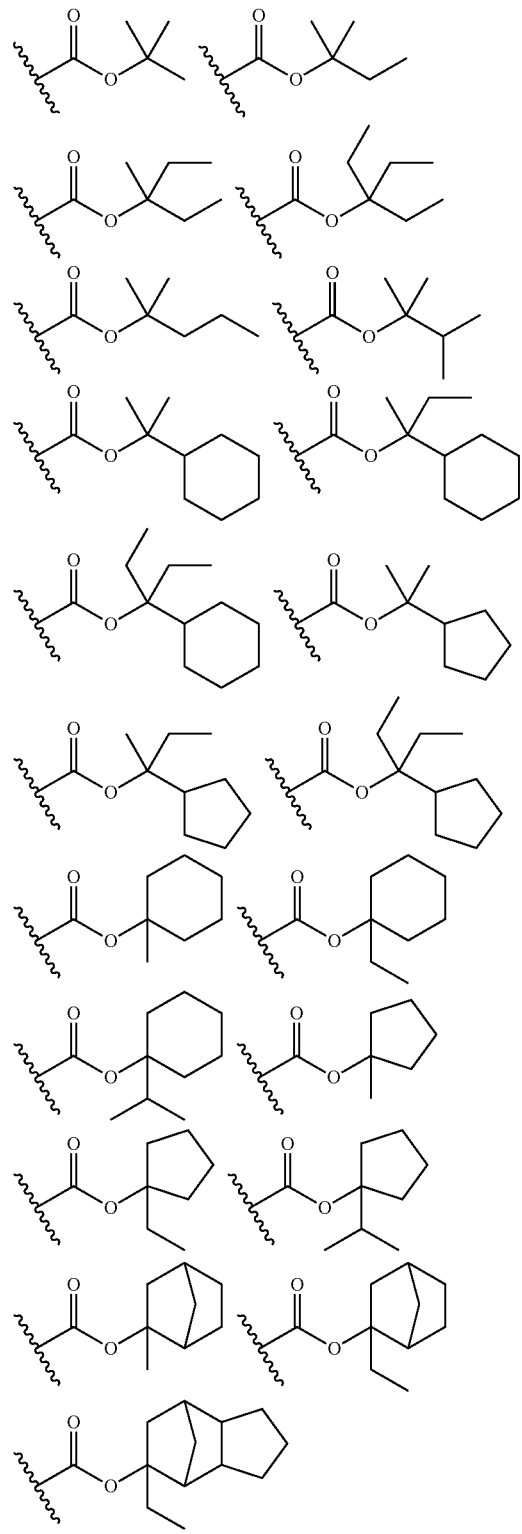
-continued
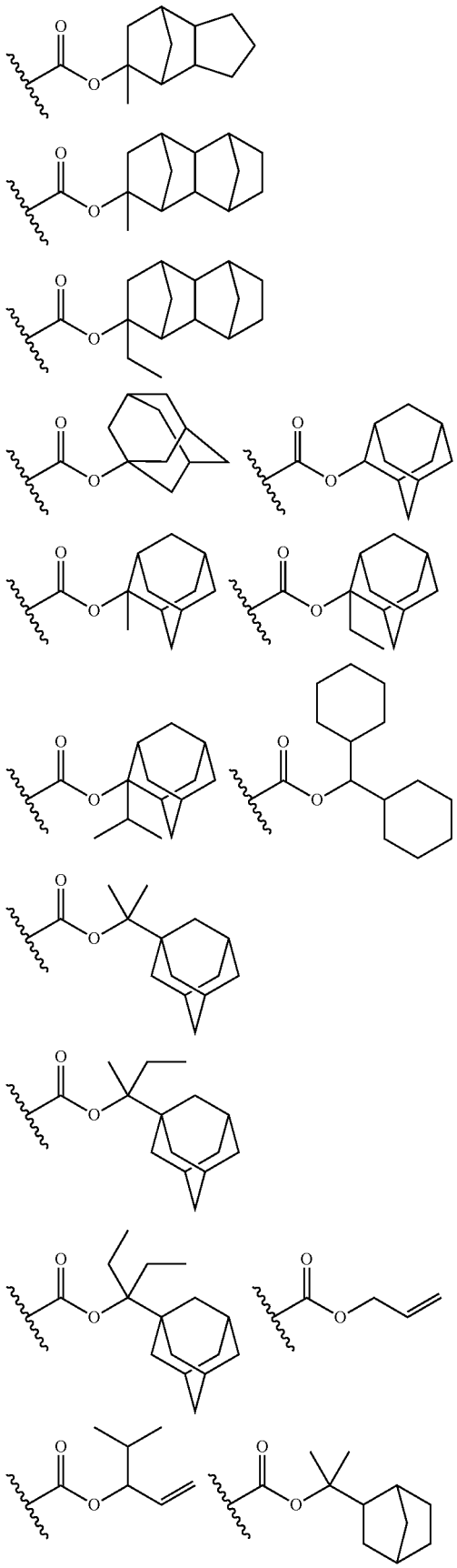

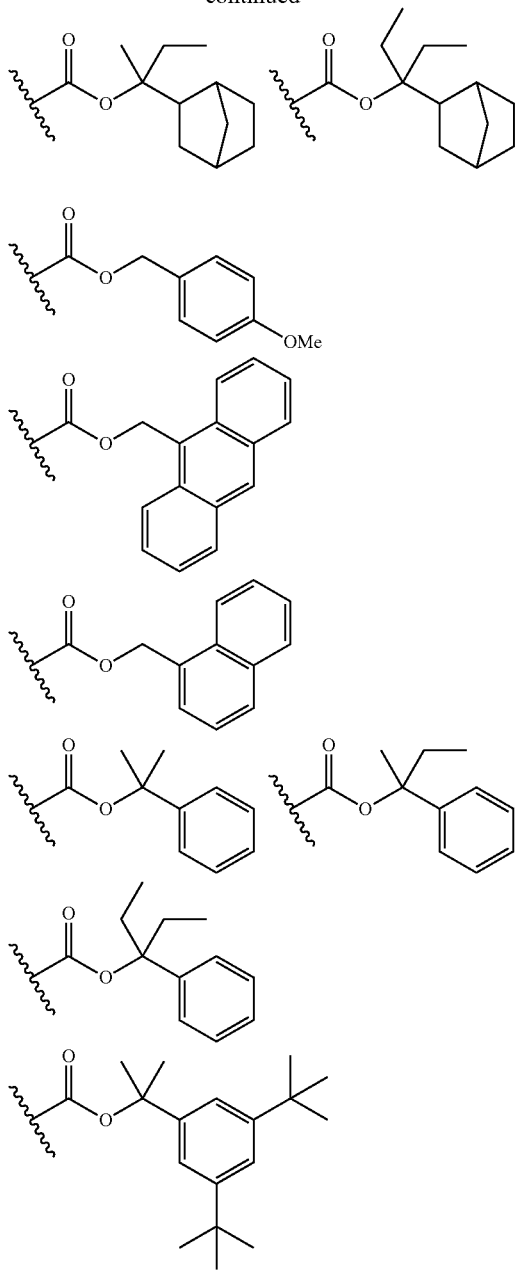

The compound (D) may have a structure in which any of the above-mentioned basic compounds are combined with the structure represented by general formula (d-1).

The compound (D) is especially preferred to be the one represented by general formula (a) below.

Note that, the compound (D) may be any of the basic compounds described above as long as it is a low-molecular compound containing a group that is eliminated by the action of an acid.

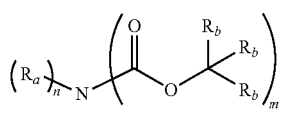

(a)

In the general formula (a), Ra represents a hydrogen atom, an alkyl group, a cycloalkyl group, an aryl group, or an aralkyl group. When n=2, two Ra's may be the same or different from each other, and may be connected to each other to form a bivalent heterocyclic hydrocarbon group (preferably having 20 or less carbon atoms) or its derivatives.

Rb has the same definition as Rb in the general formula (d-1) above, and ditto for preferable examples. When at least one of Rb's are hydrogen atoms in —C(Rb)(Rb)(Rb), at least one of the remainder represents a cyclopropyl group, 1-alkoxyalkyl group, or an aryl group.

n represents an integer of 0 to 2, m represents an integer of 1 to 3, and n+m=3.

In the formula (a), the alkyl group, the cycloalkyl group, the aryl group, and the aralkyl group represented by Ra may be substituted with a functional group same as the functional group above which substitutes the alkyl group, the cycloalkyl group, the aryl group, and the aralkyl group represented by Rb.

As specific examples of the alkyl group, the cycloalkyl group, the aryl group, and the aralkyl group represented by Ra (the alkyl group, the cycloalkyl group, the aryl group, and the aralkyl group may be substituted with the functional group above), the same group as the specific examples of Rb are exemplified.

Further, as the bivalent heterocyclic hydrocarbon group (preferably having 1 to 20 carbon atoms) or its derivative, formed by mutual binding of Ra's, for example, the followings can be exemplified:

a group derived from heterocyclic compound such as pyrrolidine, piperidine, morpholine, 1,4,5,6-tetrahydropyrimidine, 1,2,3,4-tetrahydroquinoline, 1,2,3,6-tetrahydroquinoline, homopiperadine, 4-azabenzimidazole, benztriazole, 5-azabenztriazole, 1H-1,2,3-triazole, 1,4,7-triazacyclononane, tetrazole, 7-azaindole, indazole, benzimidazole, imidazo[1,2-a]pyridine, (1S,4S)-(+)2,5-azabicyclo[2.2.1]heptane, 1,5,7-triazabicyclo[4.4.0]dec-5-en, indole, indoline, 1,2,3,4-tetrahydroquinoxaline, perhydroquinoline, or 1,5,9-triazacyclododecane; or the group derived from heterocyclic compound and substituted with at least one of a group derived from linear or branched alkane, a group derived from cycloalkane, a group derived from aromatic compound, a group derived from heterocyclic compound, or a functional group such as a hydroxyl group, a cyano group, an amino group, a pyrrolidino group, a piperidino group, a morpholino group, or an oxo group.

Particularly preferred examples of the compound (D) will be shown below, which however in no way limit the scope of the present invention.

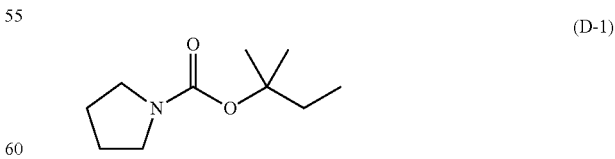

(D-1)

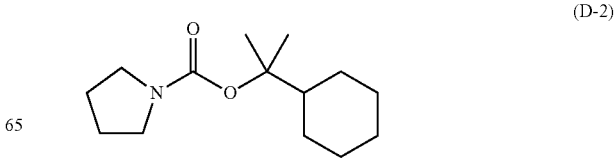

(D-2)

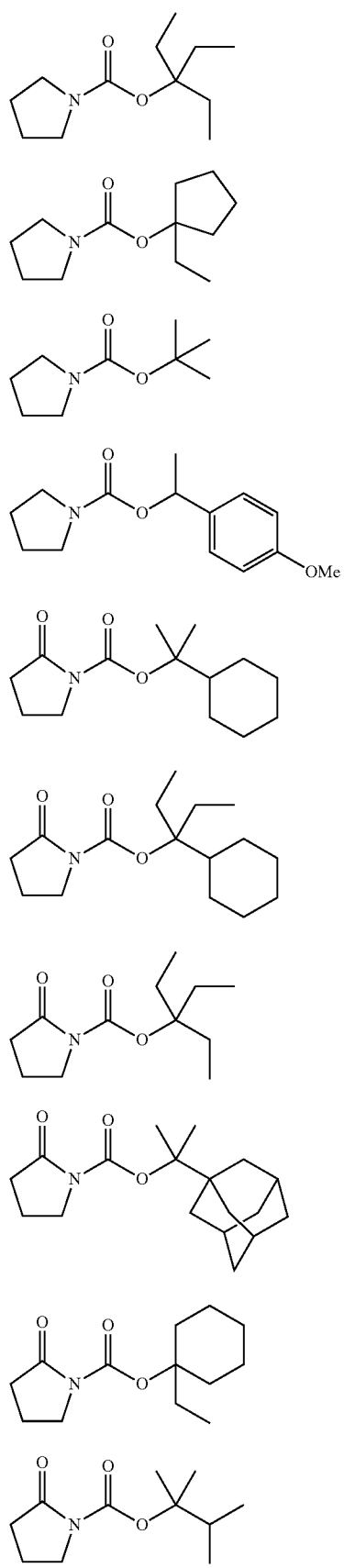
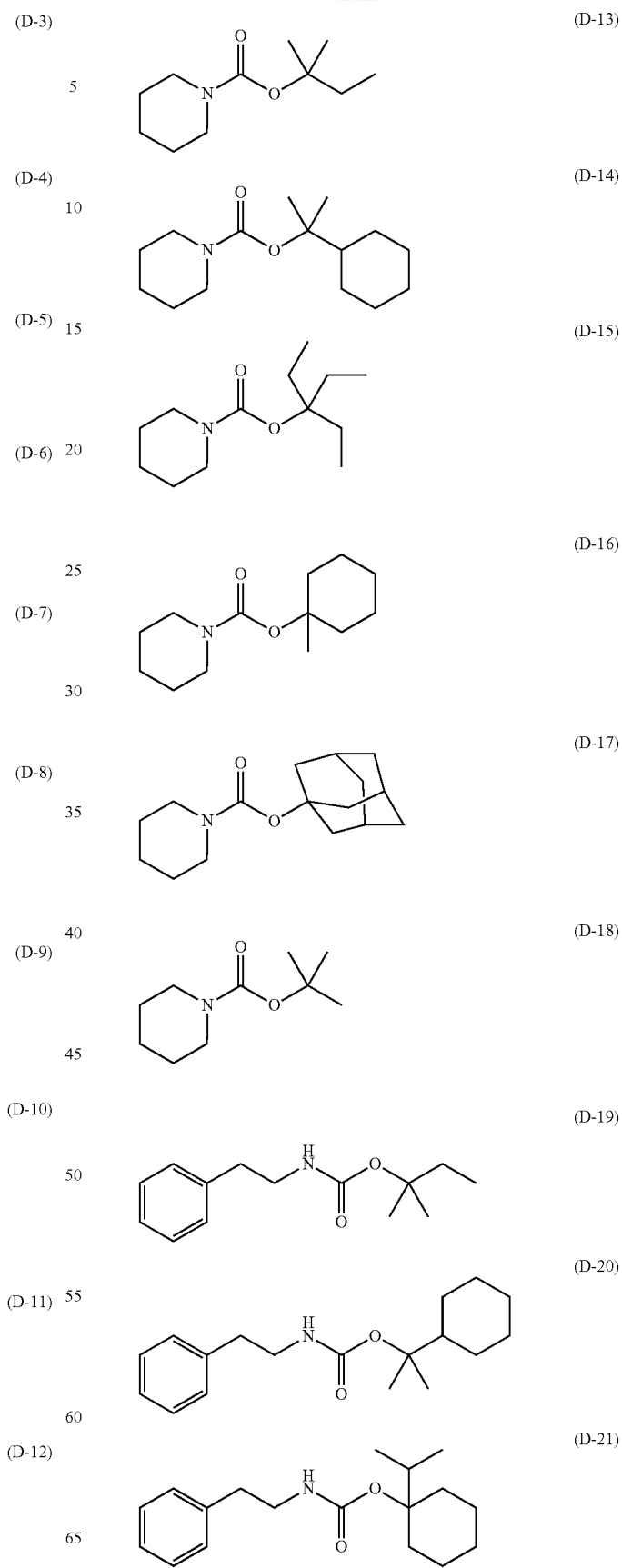

(D-22) 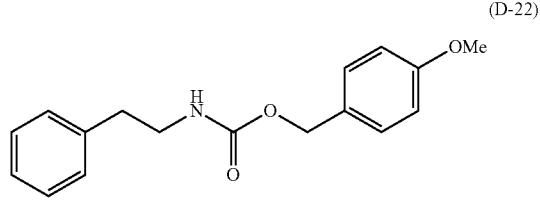
(D-23) 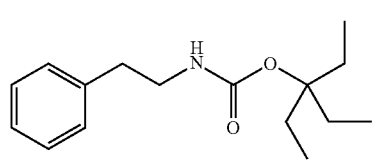
(D-24) 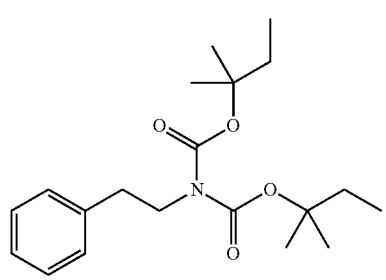
(D-25) 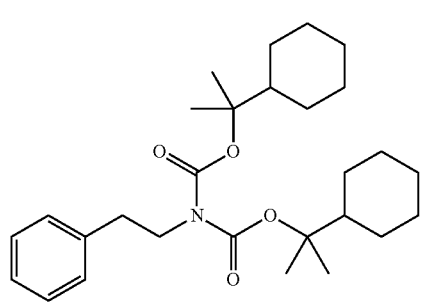
(D-26) 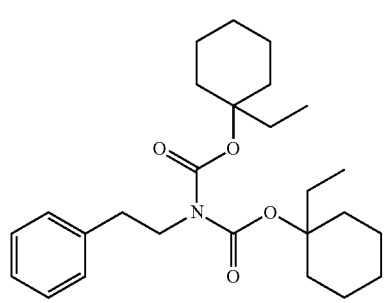
(D-27) 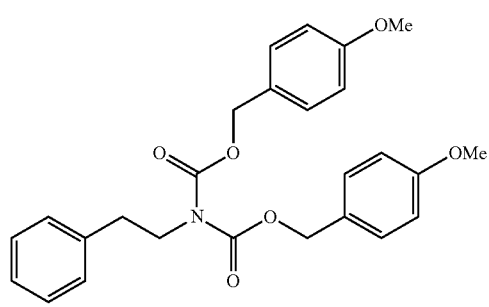
(D-28) 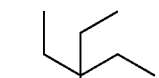 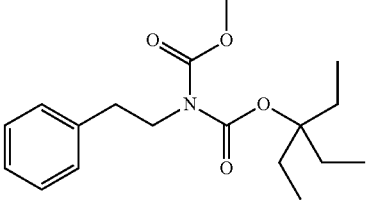
(D-29) 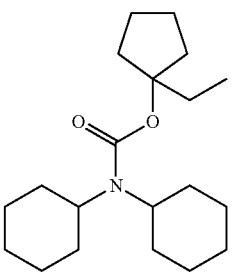
(D-30) 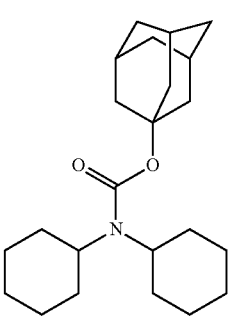
(D-31) 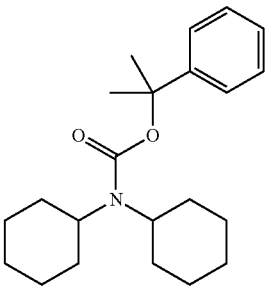
(D-32) 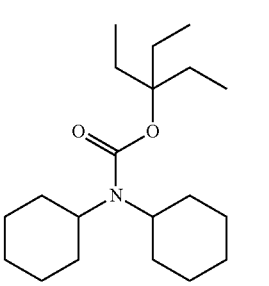

-continued
(D-33)
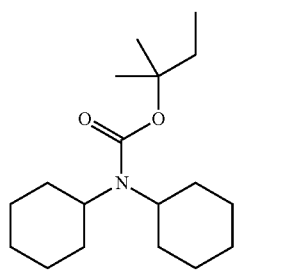
(D-34)
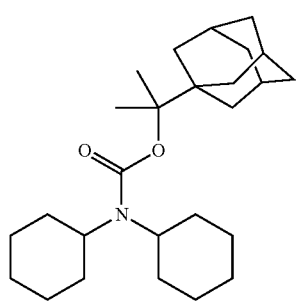
(D-35)
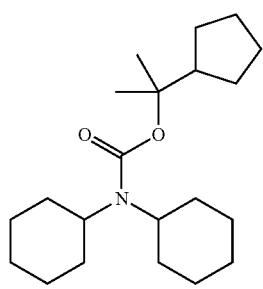
(D-36)
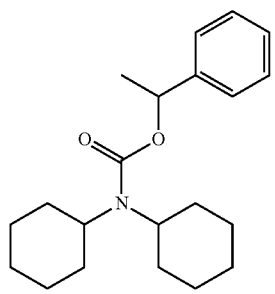
(D-37)
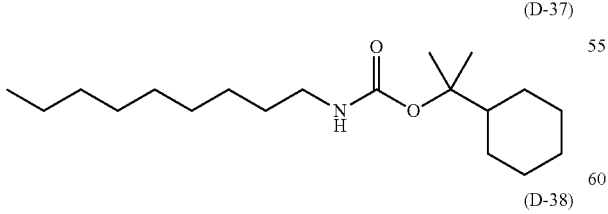
(D-38)
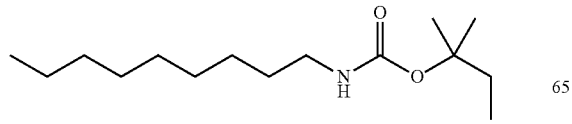
-continued
(D-39)
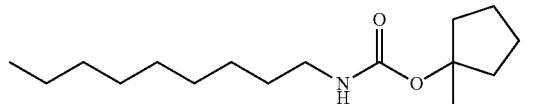
(D-40)
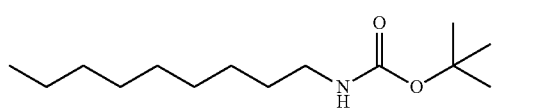
(D-41)
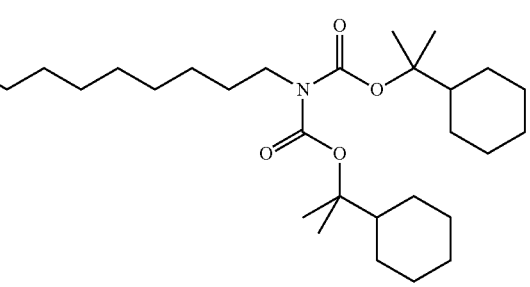
(D-42)
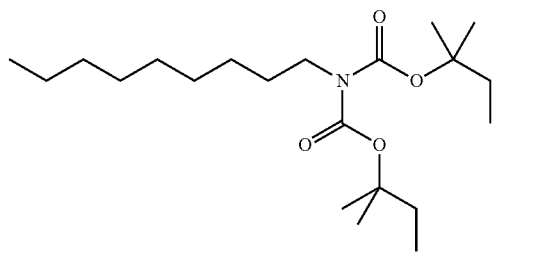
(D-43)
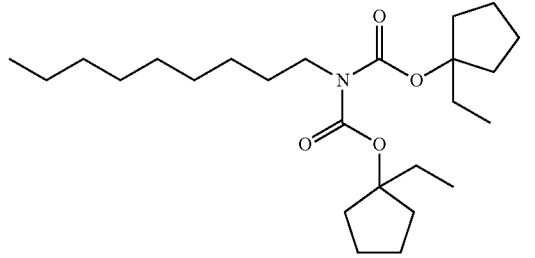
(D-44)
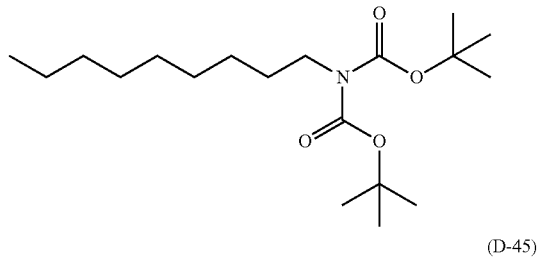
(D-45)
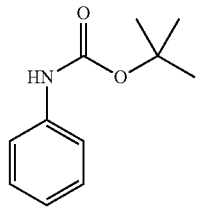

(D-46) 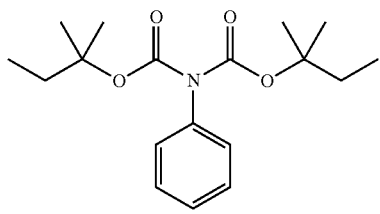

(D-47) 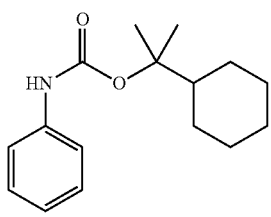

(D-48) 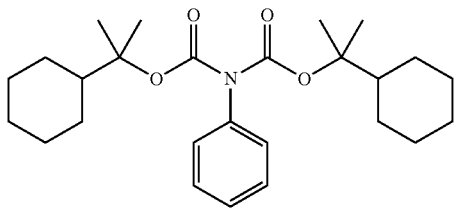

(D-49) 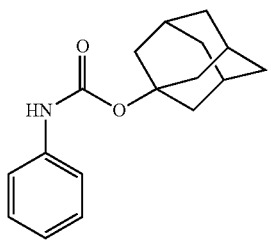

(D-50) 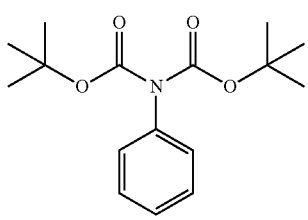

(D-51) 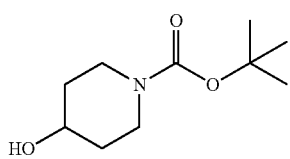

(D-52) 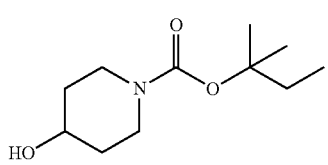

(D-53) 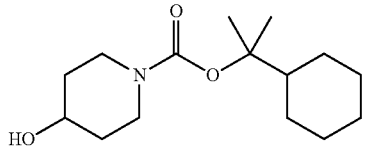

(D-54) 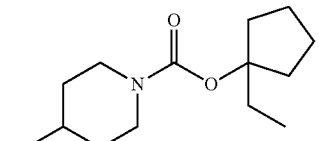

(D-55) 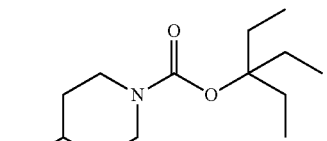

The compounds of general formula (a) can be synthesized based on JP-A-2007-298569, JP-A-2009-199021, and the like.

In the present invention, each of the low-molecular compounds (D) containing a nitrogen atom and a group that is eliminated by the action of an acid may be used alone, or two or more thereof may be used in a mixture.

The actinic ray- or radiation-sensitive resin composition according to the present invention may or may not contain the low-molecular compounds (D) having a nitrogen atom and a group that is eliminated by the action of an acid. When the actinic ray- or radiation-sensitive resin composition according to the present invention contains the low-molecular compounds (D) having a nitrogen atom and a group that is eliminated by the action of an acid, the content of the compound (D), based on the total solids of the actinic ray- or radiation-sensitive resin composition (containing above-mentioned basic compound), is generally in the range of 0.001 to 20 mass %, preferably 0.001 to 10 mass % and more preferably 0.01 to 5 mass %.

[6] Basic compound whose basicity is decreased or disappeared by irradiation with actinic rays or radiation The compositon according to the present invention may contain a basic compound whose basicity is decreased or disappeared by irradiation with actinic rays or radiation. As examples of the basic compound whose basicity is decreased or disappeared by irradiation with actinic rays or radiation, compounds described in WO 2011/083872 A1, page 171-188 can be exemplified. Furthermore, as examples of the basic compound whose basicity is decreased or disappeared by irradiation with actinic rays or radiation, sulfonium salt compounds shown by the following formula (a1) and iodonium salt compounds shown by the following formula (a2) can be exemplified.

(a1)

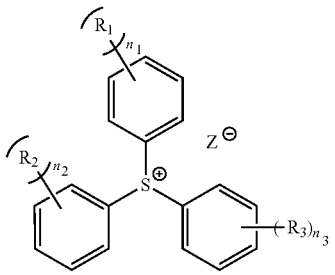

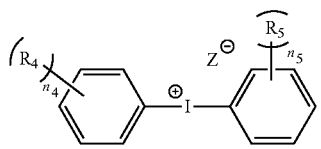
(a2)

In the above formulae (a1) and (a2), each of $R_1$ to $R_5$ independently represents a hydrogen atom, an alkyl group, a cycloalkyl group, an alkoxy group, a hydroxyl group or a halogen atom. $Z^-$ is a counter anion, for example, $OH^-$, $R-COO^-$, $R-SO_3^-$ or an anion represented by the following formula (a3) (wherein R represents an alkyl group or an aryl group, and R may be substituted).

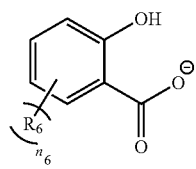
(a3)

In the above formula (a3), $R_6$ represents a substituent and $n_6$ is integer of 0 to 4.

As examples of the compounds represented by the formulae (a1) and (a2), compounds represented by the structural formulae below are exemplified.

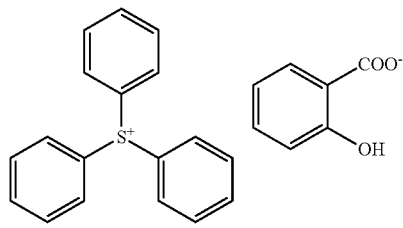

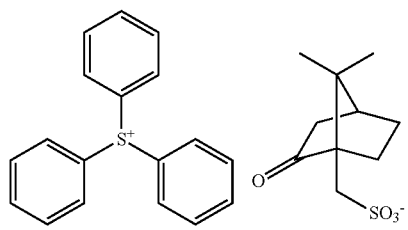

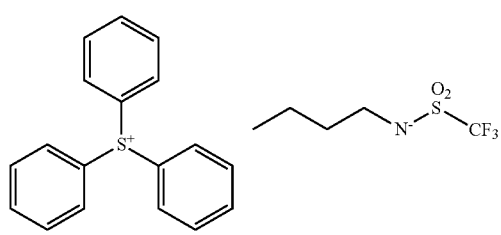

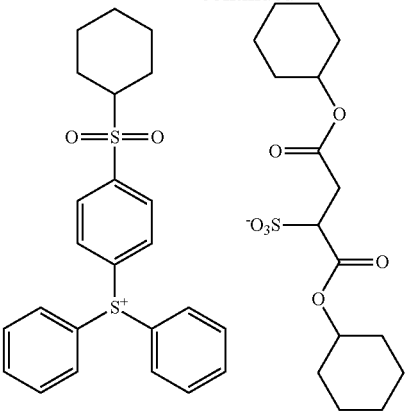

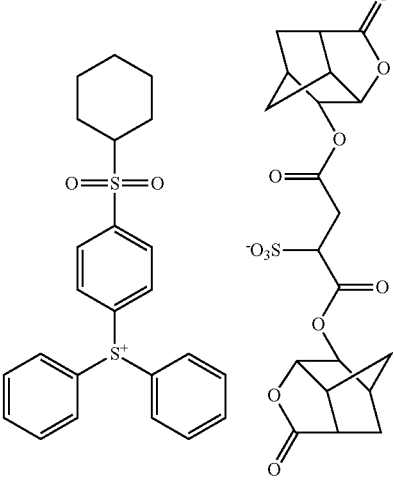

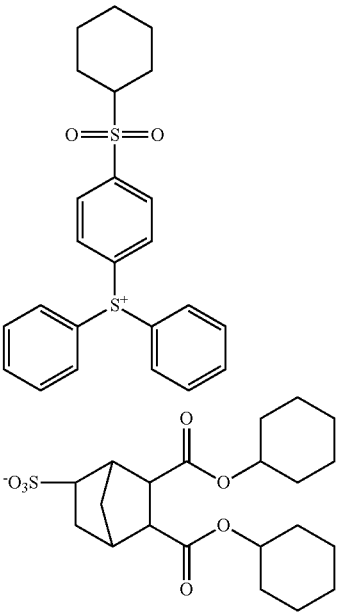

[7] Surfactant

The composition according to the present invention may further contain one or more surfactants. When the composition contains surfactants, it is especially preferred to use a fluorinated and/or siliconized surfactant as the surfactant.

As such surfactants, for example, Megafac F176 and (produced by DIC Corporation); PF656 and PF6320 (produced by OMNOVA); Troy Sol 5-366 (produced by Troy Chemical Co., Ltd.); Florad FC 430 (produced by Sumitomo 3M Ltd.); and polysiloxane polymer KP-341 (produced by Shin-Etsu Chemical Co., Ltd.) can be exemplified.

Further, use may be made of surfactants other than the fluorinated and/or siliconized surfactants. More specifically, for example, a polyoxyethylenealkylether and a polyoxyethylenealkylarylether can be exemplified.

Further, other known surfactants can also be used. As employable surfactants, those described in section [0273] et seq. of US Patent Application Publication No. 2008/0248425 can be exemplified.

These surfactants may be used either individually or in combination.

It is optional for the actinic ray- or radiation-sensitive resin composition of the present invention to contain the surfactant. When the composition according to the present invention contains the surfactant, the total amount thereof used based on the total solids of the composition is preferably in the range of 0 to 2 mass %, more preferably 0.0001 to 2 mass %, and especially preferably 0.0005 to 1 mass %.

On the other hand, it is preferable to control the amount of surfactant added at 10 ppm or less, or nil. If so, the uneven distribution of the hydrophobic resin in the surface portion is promoted, so that the surface of the resist film can be rendered highly hydrophobic, thereby enhancing the water tracking property in the stage of liquid-immersion exposure.

[8] Solvent

A solvent which can be used for preparing the actinic ray- or radiation-sensitive resin composition of the present invention is not particularly limited as long as each component in the composition can be dissolved. For example, use can be made of an alkylene glycol monoalkyl ether carboxylate (propylene glycol monomethyl ether acetate or the like), an alkylene glycol monoalkyl ether (propylene glycol monomethyl ether or the like), an alkyl lactate (ethyl lactate, methyl lactate or the like), a cyclolactone (γ-butyrolactone or the like, preferably having 4 to 10 carbon atoms), a chain or cyclic ketone (2-heptanone, cyclohexanone or the like, preferably having 4 to 10 carbon atoms), an alkylene carbonate (ethylene carbonate, propylene carbonate or the like), an alkyl carboxylate (preferably an alkyl acetate such as butyl acetate), an alkyl alkoxycarboxylate (ethyl ethoxypropionate or the like) or the like.

As other useful solvents, there can be mentioned, for example, those described in section [0244] et seq. of US 2008/0248425 A1 and the like.

Among the above solvents, an alkylene glycol monoalkyl ether carboxylate and an alkylene glycol monoalkyl ether are preferred.

Any of these solvents may be used alone, and also two or more of these solvents may be used in combination. When two or more of these solvents are mixed together, it is preferred to mix a hydroxylated solvent with a non-hydroxylated solvent. The mass ratio of hydroxylated solvent to non-hydroxylated solvent is in the range of 1/99 to 99/1, preferably 10/90 to 90/10 and more preferably 20/80 to 60/40.

The hydroxylated solvent is preferably an alkylene glycol monoalkyl ether. The non-hydroxylated solvent is preferably an alkylene glycol monoalkyl ether carboxylate.

[9] Other Component

The composition of the present invention can be appropriately loaded with, in addition to the above components, an onium salt of carboxylic acid, any of the dissolution inhibiting compounds of 3000 or less molecular weight described in, for example, Proceeding of SPIE, 2724,355 (1996), an acid-increasing agent, a dye, a plasticizer, a photosensitizer, a light absorber, etc.

[10] Method of forming pattern

The method of forming a pattern according to the present invention comprises forming the actinic ray- or radiation-sensitive film (hereinafter also referred to as "a resist film") containing the actinic ray- or radiation-sensitive resin composition; exposing the film to the actinic rays or radiation; and developing the exposed film.

The resist film is one formed from the above actinic ray- or radiation-sensitive resin composition of the present invention. In particular, the resist film is preferably formed on a substrate. In the patterning method of the present invention, the operation of forming a film of the resist composition on a substrate, the operation of exposing the film to light and the operation of developing the exposed film can be carried out by generally known methods.

From the viewpoint of enhancement of resolving power, it is preferred that the actinic ray- or radiation-sensitive resin composition of the present invention be used with a coating thickness of 30 to 250 nm. More preferably, it is used with a coating thickness of 30 to 200 nm. This coating thickness can be attained by setting the solid content of the actinic ray- or radiation-sensitive resin composition within an appropriate range so as to cause the composition to have an appropriate viscosity, thereby improving the applicability and film forming property.

The total solid content of the actinic ray- or radiation-sensitive resin composition according to the present invention is generally in the range of 1 to 10 mass %, preferably 1 to 8.0 mass % and still preferably 1.0 to 6.0 mass %.

In the use of the actinic ray- or radiation-sensitive resin composition of the present invention, the above-described components are dissolved in a solvent, filtered and applied to a support. The filter medium is preferably one made of a polytetrafluoroethylene, polyethylene or nylon having a pore size of 0.1 µm or less, more preferably 0.05 µm or less and further more preferably 0.03 µm or less. In the filtration, two or more types of filters may be connected in series or parallel. Moreover, the composition may be filtered two or more times. Further, the composition may be deaerated prior to and/or after the filtration.

The composition of the present invention can be applied to a substrate, such as one for use in the production of integrated circuit elements (e.g., silicon/silicon dioxide coating), by appropriate application means, such as a spinner. Thereafter, the applied composition is dried, thereby forming a photosensitive resist film.

This resist film is exposed through a given mask to actinic rays or radiation, preferably baked (heated), developed and rinsed. Thus, a favorable pattern can be obtained. When the film is irradiated with electron beams, lithography through no mask (direct lithography) is generally carried out.

The method preferably comprises a prebake (PB) operation performed after the film formation but before the exposure operation.

The method also preferably comprises a post-exposure bake (PEB) operation performed after the exposure operation but before the development operation.

In both the PB operation and the PEB operation, the baking is preferably performed at 70 to 120° C. and more preferably 80 to 110° C.

The baking time is preferably in the range of 30 to 300 seconds, more preferably 30 to 180 seconds, and further more preferably 30 to 90 seconds.

The baking can be carried out by means provided in common exposure/development equipment. The baking may also be carried out with the use of a hot plate or the like.

The baking accelerates the reaction in exposed areas, thereby enhancing the sensitivity and pattern profile.

The actinic rays or radiation is not particularly limited, and, for example, a KrF excimer laser, an ArF excimer laser, EUV light, electron beams and the like are used. An ArF excimer laser, EUV light and electron beams are preferred.

A developer which is used in the process of developing the resist film containing the actinic ray- or radiation-sensitive resin composition is not especially limited. For example, an alkali developer or a developer containing organic solvent (hereinafter also referred to as "an organic developer") can be used.

As the alkali developer, use can be made of any of alkaline aqueous solutions containing, for example, an inorganic alkali compound such as sodium hydroxide, potassium hydroxide, sodium carbonate, sodium silicate, sodium metasilicate or aqueous ammonia; a primary amine such as ethylamine or n-propylamine; a secondary amine such as diethylamine or di-n-butylamine; a tertiary amine such as triethylamine or methyldiethylamine; an alcoholamine such as dimethylethanolamine or triethanolamine; a quaternary ammonium salt such as tetramethylammonium hydroxide or tetraethylammonium hydroxide; or a cycloamine such as pyrrole or piperidine. Appropriate amounts of an alcohol and/or a surfactant may be added to the alkali developer. The concentration of alkali developer is generally in the range of 0.1 to 20 mass %. The pH value of the alkali developer is generally in the range of 10.0 to 15.0.

As the organic developer, a polar solvent such as a ketone solvent, an ester solvent, an alcohol solvent, an amide solvent and an ether solvent, and a hydrocarbon solvent.

As the ketone solvent, there can be mentioned, for example, 1-octanone, 2-octanone, 1-nonanone, 2-nonanone, acetone, 2-heptanone (methyl amyl ketone), 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetylcarbinol, acetophenone, methyl naphthyl ketone, isophorone, propylene carbonate or the like.

As the ester solvent, there can be mentioned, for example, methyl acetate, butyl acetate, ethyl acetate, isopropyl acetate, pentyl acetate, isopentyl acetate, amyl acetate, propylene glycol monoethyl ether acetate, ethylene glycol monoethyl ether acetate, diethylene glycol monobutyl ether acetate, diethylene glycol monoethyl ether acetate, ethyl 3-ethoxypropionate, 3-methoxybutyl acetate, 3-methyl-3-methoxybutyl acetate, methyl formate, ethyl formate, butyl formate, propyl formate, ethyl lactate, butyl lactate, propyl lactate or the like.

As the alcohol solvent, there can be mentioned, for example, an alcohol, such as methyl alcohol, ethyl alcohol, n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol or n-decanol; a glycol solvent, such as ethylene glycol, diethylene glycol or triethylene glycol; or a glycol ether solvent, such as ethylene glycol monomethyl ether, propylene glycol monomethyl ether, ethylene glycol monoethyl ether, propylene glycol monoethyl ether, diethylene glycol monomethyl ether, triethylene glycol monoethyl ether or methoxymethylbutanol.

As the ether solvent, there can be mentioned, for example, not only any of the above-mentioned glycol ether solvents but also dioxane, tetrahydrofuran or the like.

As the amide solvent, there can be mentioned, for example, N-methyl-2-pyrrolidone, N,N-dimethylacetamide, N,N-dimethylformamide, hexamethylphosphoric triamide, 1,3-dimethyl-2-imidazolidinone or the like.

As the hydrocarbon solvent, there can be mentioned, for example, an aromatic hydrocarbon solvent, such as toluene or xylene, or an aliphatic hydrocarbon solvent, such as pentane, hexane, octane or decane.

Two or more of these solvents may be mixed together before use. Alternatively, each of the solvents may be used in a mixture with water or a solvent other than those mentioned above. It is preferred for the water content of the whole developer to be less than 10 mass %. More preferably, the developer substantially does not contain any water.

Namely, the content of organic solvent in the organic developer is preferably in the range of 90 to 100 mass %, more preferably 95 to 100 mass %, based on the total amount of the developer.

Especially, it is preferred that the organic developer contains at least one of the organic solvent selected from the group consisting of a ketone solvent, an ester solvent, an alcohol solvent, an amide solvent and an ether solvent.

According to necessity, an appropriate amount of surfactant can be added to the organic developer.

The surfactant is not particularly limited. For example, use can be made of any of ionic and nonionic fluorinated and/or siliconized surfactants and the like. As such fluorinated and/or siliconized surfactants, there can be mentioned, for example, those described in JP-A's S62-36663, S61-226746, S61-226745, S62-170950, S63-34540, H7-230165, H8-62834, H9-54432 and H9-5988 and U.S. Pat. Nos. 5,405,720, 5,360,692, 5,529,881, 5,296,330, 5,436,098, 5,576,143, 5,294,511 and 5,824,451. Nonionic surfactants are preferred. Although nonionic surfactants are not particularly limited, using a nonionic fluorinated surfactant or siliconized surfactant is more preferred. The amount of surfactant added is generally in the range of 0.001 to 5 mass %, preferably 0.005 to 2 mass % and further more preferably 0.01 to 0.5 mass % based on the whole amount of the developer.

Pure water is preferably used as a rinse liquid, and before the use, an appropriate amount of surfactant can be added thereto.

As the development method, use can be made of, for example, a method in which the substrate is dipped in a tank filled with a developer for a given period of time (dip method), a method in which a developer is puddled on the surface of the substrate by its surface tension and allowed to stand still for a given period of time to thereby effect development (puddle method), a method in which a developer is sprayed onto the surface of the substrate (spray method), or a method in which a developer is continuously discharged onto the substrate being rotated at a given speed while scanning a developer discharge nozzle at a given speed (dynamic dispense method).

Further, the development operation or rinse operation may be followed by the operation of removing any portion of developer or rinse liquid adhering onto the pattern by use of a supercritical fluid.

For example, an antireflection film may be provided as an underlayer of the resist.

As the antireflection film, use can be made of both an inorganic film of titanium, titanium oxide, titanium nitride, chromium oxide, carbon, amorphous silicon or the like and an organic film composed of a light absorber and a polymer material. Also, as the organic antireflection film, use can be made of commercially available organic antireflection films, such as DUV30 Series and DUV40 Series produced by Brewer Science Inc. and AR-2, AR-3 and AR-5 produced by Shipley Co., Ltd.

Exposure to a resist film including the actinic ray- or radiation-sensitive resin composition of the present invention may be carried out after filling the interstice between the film and a lens with a liquid (immersion medium) of refractive index higher than that of air at the time of exposure to actinic rays or radiation. That is, liquid immersion exposure may also be carried out. The resolution can be enhanced by the exposure through the immersion medium. Any liquid can be used as long as the liquid has refractive index higher than that of air. Especially, pure water is preferable. Water is appropriate from the viewpoints of coefficient of refractive index being low, easy procurement and easy handling.

Further, from the viewpoint of refractive index increase, use can be made of a medium of 1.5 or higher refractive index. Such a medium may be an aqueous solution or an organic solvent.

In the use of water as a liquid for liquid immersion, a slight proportion of additive may be added in order to increase refractive index. Examples of the additive are described in detail in Chapter 12 of "Process and Material of Liquid Immersion Lithography" published by CMC Publishing Co., Ltd. On the other hand, when a substance being opaque in 193 nm rays or an impurity whose refractive index is greatly different from that of water is mixed in, the mixing would invite a strain of optical image projected on the resist film. Accordingly, it is preferred to use distilled water as the liquid immersion water. Furthermore, use may be made of pure water having been purified through an ion exchange filter or the like. Desirably, the electrical resistance of the pure water is 18.3 MΩcm or higher, and the TOC (organic matter concentration) thereof is 20 ppb or below. Prior deaeration of the water is desired.

For the prevention of direct contact of the resist film with a liquid for liquid immersion, a film that is highly insoluble in the liquid for liquid immersion (hereinafter also referred to as a "top coat") may be provided between the resist film and the liquid for liquid immersion. The functions to be fulfilled by the top coat are suitability for applying on the resist film, transparency in radiation of especially 193 nm and being highly insoluble in the liquid for liquid immersion. Preferably, the top coat does not mix with the resist film and is uniformly applicable on the resist film.

From the viewpoint of 193 nm transparency, the top coat preferably consists of a polymer not abundantly containing an aromatic moiety. As such, there can be mentioned, for example, a hydrocarbon polymer, an acrylic ester polymer, polymethacrylic acid, polyacrylic acid, polyvinyl ether, a siliconized polymer, a fluoropolymer or the like. The aforementioned hydrophobic resins also find appropriate application in the top coat. From the viewpoint of contamination of an optical lens by elution of impurities from the top coat into the liquid for liquid immersion, it is preferred to reduce the amount of residual monomer components of the polymer contained in the top coat.

At the detachment of the top coat, use may be made of a developer, or a separate peeling agent may be used. The peeling agent preferably consists of a solvent having a lower permeation into the resist film. Detachability by an alkali developer is preferred from the viewpoint of simultaneous attainment of the detachment step with the development processing step for the resist film. The top coat is preferred to be acidic from the viewpoint of detachment with the use of an alkali developer. However, from the viewpoint of non-intermixability with the resist film, the top coat may be neutral or alkaline.

It is preferred that the difference in refractive index between the top coat and the liquid for liquid immersion is none or less from the viewpoint of increasing the resolving power. When an ArF excimer laser (wavelength: 193 nm) is used as an exposure source, water is preferably used as the liquid for liquid immersion. In this case, the top coat for ArF liquid immersion exposure preferably has a refractive index close to that of water (1.44).

From the viewpoint of transparency and refractive index, it is preferred to reduce the thickness of the film.

Preferably, the top coat does not mix with the film and also does not mix with the liquid for liquid immersion. From this viewpoint, when the liquid for liquid immersion is water, it is preferred for the solvent used in the top coat to be highly insoluble in the solvent used in the positive resist composition and be a non-water-soluble medium. When the liquid for liquid immersion is an organic solvent, the top coat may be soluble or insoluble in water.

Furthermore, the present invention relates to a process for manufacturing an electronic device in which the above-described patterning method of the present invention is included, and relates to an electronic device manufactured by the process.

The electronic device of the present invention can be appropriately mounted in electrical and electronic equipments (household electronic appliance, OA/media-related equipment, optical apparatus, telecommunication equipment and the like).

EXAMPLES

The present invention will be described in greater detail below with reference to the following Examples, which however in no way limit the scope of the present invention.

Synthetic Example 1

Synthesis of Compound A-1

In a 3-necked flask, 15 g (49.6 mmol) of starting compound A shown below and 17.9 g (148.7 mmol) of 1,4-thioxane-4-oxide were dissolved in 75 g of dichloromethane, and cooled in an acetonitrile bath with the use of liquid nitrogen until the inside temperature became −41° C. Subsequently, 20.8 ml (148.7 mmol) of trifluoroacetic anhydride (TFAA) was dropped into the cooled reaction liquid at a rate of 0.5 ml per minute by means of a syringe pump. During the dropping, the temperature was controlled so that the inside temperature was maintained at −30° C. or below. The reaction liquid was further agitated for an hour while maintaining the inside temperature at −25 to −30° C., and 75 g of water was added thereto. Thereafter, 22.6 g (49.6 mmol) of sodium 1,1,2,2,3,3-hexafluoro-3-(decahydroisoquinoline-2-sulfonyl)propane-1-sulfonate was added to the mixture, and agitated at room temperature for an hour. An organic phase was separated, washed with 75 g of water, concentrated and crystallized. Thus, 28.4 g (37.1 mmol) of desired compound A-1 shown below was obtained.

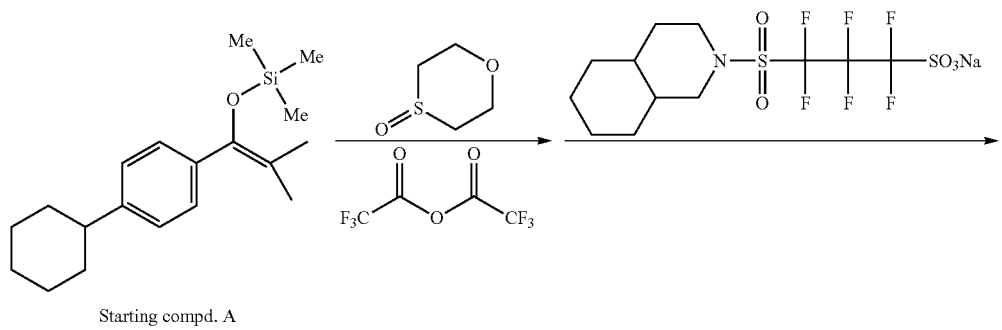

Starting compd. A

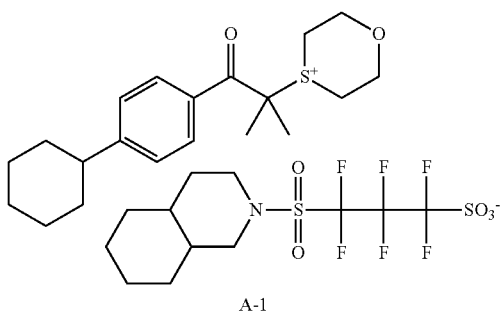

A-1

¹H-NMR (300 MHz, CDCl₃):
δ8.0 (d. 2H), δ7.45 (d. 2H), δ4.4 (d. 2H), δ4.0-3.9 (m. 2H), δ3.85 (d. 1H), δ3.65 (d. 1H), δ3.45 (m. 4H), δ3.2-3.05 (m. 1H), δ2.8-2.6 (m. 2H), δ2.05 (s. 6H), δ1.8-0.8 (m. 22H).

Other photoacid generators indicated in Table 2 to be given hereinafter were synthesized in the same manner as in Synthetic Example 1.

Synthetic Example 2

Synthesis of Resin C

In a nitrogen gas stream, 11.5 g of cyclohexanone was placed in a three-necked flask and heated at 85° C. A solution obtained by dissolving the following compounds (monomers) amounting in order from the left side to 1.98 g, 3.05 g, 0.95 g, 2.19 g and 2.76 g and further 0.562 g of polymerization initiator V601 (produced by Wako Pure Chemical Industries, Ltd.) in 21.0 g of cyclohexanone was dropped thereinto over a period of 6 hours. After the completion of the dropping, reaction was continued at 85° C. for 2 hours. The thus obtained reaction liquid was allowed to stand still to cool and was dropped into a mixed liquid comprised of 420 g of hexane and 180 g of ethyl acetate over a period of 20 minutes. The thus precipitated powder was collected by filtration and dried, thereby obtaining 9.1 g of resin C. The polymer component ratio determined by NMR was 20/25/10/30/15. The standard-polystyrene-equivalent weight average molecular weight of the obtained resin C was 9200, and the polydispersity index (Mw/Mn) thereof was 1.55.

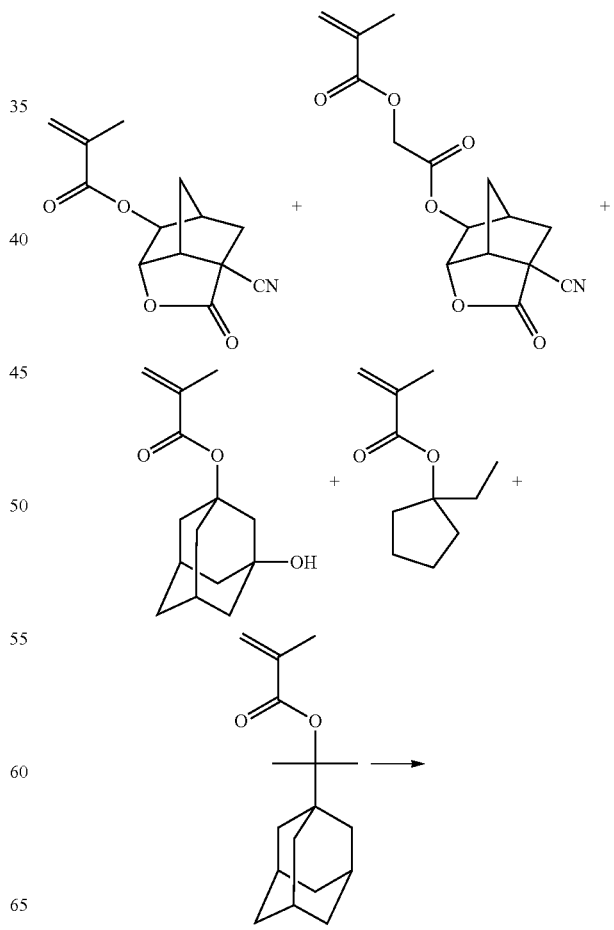

-continued

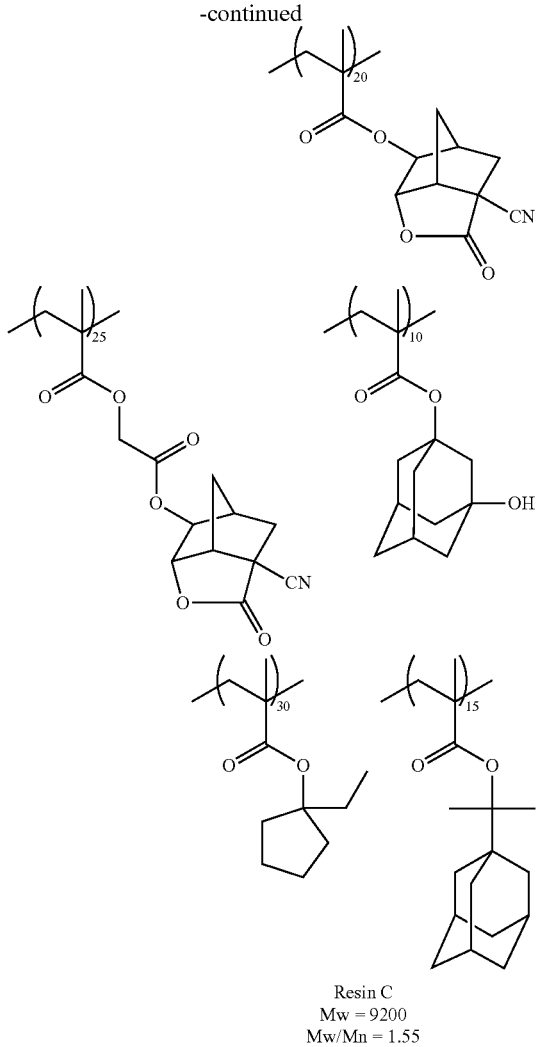

Resin C
Mw = 9200
Mw/Mn = 1.55

Resins A, B and D to G were synthesized through the same procedure as in Synthetic Example 2.

[Evaluation of Resist when Alkali Developer is Used]
<Preparation of Resist>

Dissolution of individual components in solvents as indicated in Table 2 to be shown hereinafter was carried out, thereby obtaining solutions each of 4 mass % solid content. The solutions were each passed through a polyethylene filter of 0.05 μm pore size, thereby obtaining actinic ray- or radiation-sensitive resin compositions (hereinafter also referred to as resist compositions). The thus obtained actinic ray- or radiation-sensitive resin compositions were evaluated by the following methods, and the results are given in Table 2.

With respect to the solvents in Table 2, the numerals in the table indicate mass ratios.

In Table 2, when the actinic ray- or radiation-sensitive resin composition contained a hydrophobic resin (HR), "added" is noted as the type of usage of the hydrophobic resin. In contrast, when the actinic ray- or radiation-sensitive resin composition did not contain any hydrophobic resin (HR) and when after the formation of a film, a top coat protective film containing a hydrophobic resin (HR) was formed on an upper layer of the film, "TC" is noted as the type of usage of the hydrophobic resin.

<Evaluation of Resist>
(ArF Liquid Immersion Exposure)

An organic antireflection film ARC29SR (produced by Nissan Chemical Industries, Ltd.) was applied onto a 12-inch silicon wafer and baked at 205° C. for 60 seconds, thereby forming a 98-nm-thick antireflection film. Each of the above prepared actinic ray- or radiation-sensitive resin compositions was applied thereonto and baked at 95° C. for 60 seconds, thereby forming a 120-nm-thick resist film. When use was made of a top coat, a 3 mass % solution obtained by dissolving a top coat resin in decane/octanol (mass ratio 9/1) was applied onto the above resist film and baked at 85° C. for 60 seconds, thereby forming a 50-nm-thick top coat layer. The resultant wafer was exposed through a 6% half-tone mask of 48 nm line width 1:1 line and space pattern to light by means of an ArF excimer laser liquid immersion scanner (manufactured by ASML, XT1700i, NA1.20, C-Quad, outer sigma 0.981, inner sigma 0.895, XY deflection). Ultrapure water was used as the immersion liquid. Thereafter, the exposed wafer was baked at 90° C. for 60 seconds, developed by puddling with an aqueous solution of tetramethylammonium hydroxide (2.38 mass %) for 30 seconds, rinsed by puddling with pure water and spin dried, thereby obtaining a pattern.

(Evaluation of Exposure Latitude)

The optimum exposure amount was defined as the exposure amount in which a 48 nm line width 1:1 line and space mask pattern was reproduced. The exposure amount range in which when the exposure amount was varied, the pattern size fell within the range of 48 nm±10% was measured. The exposure latitude is the quotient of the value of the exposure amount range divided by the optimum exposure amount, the quotient expressed by a percentage. The greater the value of the exposure latitude, the less the change of performance by exposure amount changes and the better the exposure latitude.

(Evaluation of LWR)

The obtained line pattern of line/space=1/1 (ArF liquid-immersion exposure: 48 nm line width) was observed by means of a scanning electron microscope (model 59380 manufactured by Hitachi, Ltd.). In an edge 2 μm region along the longitudinal direction of the line pattern, the line width was measured at 50 points. With respect to the dispersion of measurements, the standard deviation was determined, and 3σ was computed therefrom. The smaller the value thereof, the more favorable the performance exhibited.

(Elution Test)

Each of the prepared resist compositions was applied onto an 8-inch silicon wafer, and baked at 120° C. for 60 seconds, thereby forming a 150 nm resist film. The resist film on its whole surface was exposed to light by means of a 193-nm-wavelength exposure apparatus (ArF excimer laser scanner manufactured by ASML, PAS5500/1100) at an intensity of 20 mJ/cm². Thereafter, 5 ml of pure water having been deionized by means of an ultrapure water production apparatus (manufactured by Japan Millipore Co., Ltd., Milli-Q Jr.) was dropped on the exposed resist film. The water was held on the resist film for 50 seconds, and collected. The concentration of acid eluted in the water was determined by an LC-MS system.

LC apparatus: model 2695 manufactured by Waters Corporation

MS apparatus: Esquire 3000plus manufactured by Bruker Daltonics, Inc.

Using the LC-MS system, the detection intensity with respect to ion species of molecular weights corresponding to anions was measured, and the amount of eluted acid was computed.

(Evaluation of Particle)

With respect to each of the prepared resist solutions, the number of particles (particle initial value) contained in the solution immediately after the preparation and the number of particles (number of particles after aging) contained in the solution having been allowed to stand still at 4° C. for one week were counted by means of a particle counter manufactured by Rion Co., Ltd., and the particle increment [(number of particles after aging)−(particle initial value)] was calculated. In the counting, the number of particles whose diameter is 0.25 μm or greater contained in 1 ml of solution was counted. The evaluation marks A, B, C and D were given when the particle increment in the solution was 0.2 particle/ml or less, from over 0.2 to 1 particle/ml, from over 1 to 5 particles/ml and greater than 5 particles/ml, respectively.

TABLE 2

| | Photoacid generator (g) | Resin (B) (10 g) | Basic compound/Low-molecular compound (D) (g) | Hydrophobic resin (35 mg) | Solvent | Surfactant (10 mg) | Exposure latitude (%) | LWR (nm) | Elution of acid into immersion liquid ($\times 10^{-12}$ mol/cm$^2$) | Particle |
|---|---|---|---|---|---|---|---|---|---|---|
| Example | | | | | | | | | | |
| 1 | A-1 (2.1) | A | DIA (0.3) | added B-2 | A1 = 100 | W-1 | 18.9 | 4.6 | 29 | A |
| 2 | A-2 (2.1) | C | D-52 (0.33) | added B-10 | A1/B1 = 60/40 | W-2 | 18.8 | 4.8 | 33 | A |
| 3 | A-3 (2.0) | C | DBA (0.35) | added B-12 | A1/A2 = 90/10 | W-1 | 17.7 | 5.5 | 35 | B |
| 4 | A-4 (1.9) | A | D-13 (0.28) | TC B-41 | A1/A3 = 95/5 | W-3 | 19.1 | 4.5 | 33 | A |
| 5 | A-5 (1.9) | D | PBI (0.38) | added B-28 | A1/B2 = 90/10 | — | 17.9 | 5.4 | 28 | B |
| 6 | A-6 (1.6) | B | TEA (0.36) | TC B-41 | A1 = 100 | W-4 | 18.1 | 5.2 | 30 | A |
| 7 | A-7 (1.8) | E | D-13 (0.33) | added B-52 | A1/A3 = 97/3 | W-1 | 18.5 | 4.9 | 31 | A |
| 8 | A-8 (1.9) | D | PBI (0.38) | added B-30 | A1 = 100 | — | 18.3 | 5.0 | 37 | A |
| 9 | A-9 (2.0) | B | DTA/D-13 (0.1/0.2) | added B-16 | A1/A2 = 90/10 | W-1 | 18.0 | 5.3 | 35 | B |
| 10 | A-10 (2.1) | D | D-13 (0.33) | TC B-8 | A1/A3 = 97/3 | W-1 | 17.5 | 5.6 | 38 | B |
| 11 | A-1/PAG-X (1.5/0.3) | A | D-13 (0.33) | TC B-8 | A1/A3 = 97/3 | W-1 | 18.5 | 4.8 | 31 | A |
| 12 | A-4/PAG-X (1.8/0.3) | A | DIA (0.3) | added B-2 | A1 = 100 | W-1 | 18.8 | 4.6 | 35 | A |
| 13 | A-1 (2.2) | A/D (5 g/5 g) | D-52 (0.33) | added B-10 | A1/B1 = 60/40 | W-2 | 18.9 | 4.7 | 30 | A |
| 14 | A-1 (2.1) | F | DIA (0.3) | added B-16 | A1 = 100 | W-1 | 18.2 | 4.9 | 35 | A |
| 15 | A-6 (1.6) | G | TEA (0.36) | TC B-41 | A1 = 100 | W-4 | 17.5 | 5.5 | 31 | A |
| 16 | A-15 (2.1) | A | DIA (0.3) | added B-16 | A1 = 100 | W-1 | 18.7 | 4.7 | 34 | A |
| 17 | A-16 (2.1) | A | DIA (0.3) | added B-2 | A1 = 100 | W-2 | 18.5 | 4.9 | 30 | A |
| 18 | A-17 (2.1) | D | D-52 (0.33) | added B-16 | A1/A3 = 97/3 | W-1 | 17.5 | 5.8 | 38 | B |
| 19 | A-18 (2.0) | D | D-13 (0.33) | added B-16 | A1/A2/A3 = 87/10/3 | W-2 | 18.5 | 4.9 | 33 | A |
| 20 | A-19 (1.9) | E | D-52 (0.33) | TC B-8 | A1 = 100 | W-3 | 17.3 | 5.6 | 31 | A |
| 21 | A-21 (1.9) | C | D-52 (0.33) | added B-2 | A1/A3 = 97/3 | W-3 | 18.2 | 5.0 | 32 | A |
| 22 | A-22 (2.0) | B | DIA (0.3) | TC B-8 | A1 = 100 | W-4 | 18.9 | 4.5 | 30 | A |
| 23 | A-27 (1.9) | C | D-13 (0.33) | added B-28 | A1/A3/A2 = 87/3/10 | W-2 | 19.0 | 4.5 | 30 | A |
| 24 | A-40 (2.0) | A | D-52 (0.33) | added B-2 | A1 = 100 | W-1 | 17.5 | 5.5 | 36 | B |
| 25 | A-41 (1.8) | C | DIA (0.3) | added B-14 | A1/A2/A3 = 87/10/3 | W-2 | 18.9 | 4.7 | 32 | A |
| 26 | A-44 (2.1) | C | D-52 (0.33) | added B-28 | A1 = 100 | W-1 | 18.8 | 4.7 | 34 | A |
| 27 | A-45 (2.1) | C | D-52 (0.33) | added B-29 | A1/A3 = 97/3 | W-3 | 18.9 | 4.8 | 33 | A |
| 28 | A-47 (2.1) | C | DBA (0.35) | added B-30 | A1/A3 = 97/3 | — | 19.0 | 4.6 | 31 | A |
| 29 | A-49 (1.9) | C | DIA (0.3) | added B-14 | A1/A2/A3 = 87/10/3 | W-4 | 18.9 | 4.7 | 32 | A |

TABLE 2-continued

| | Photoacid generator (g) | Resin (B) (10 g) | Basic compound/Low-molecular compound (D) (g) | Hydrophobic resin (35 mg) | Solvent | Surfactant (10 mg) | Evaluation | | | |
|---|---|---|---|---|---|---|---|---|---|---|
| | | | | | | | Exposure latitude (%) | LWR (nm) | Elution of acid into immersion liquid ($\times 10^{-12}$ mol/cm$^2$) | Particle |
| 30 | A-50 (2.0) | B | DIA (0.3) | added B-30 | A1/A2/A3 = 87/10/3 | W-1 | 18.6 | 4.9 | 30 | A |
| 31 | A-51 (2.3) | C | D-52 (0.33) | added B-28 | A1 = 100 | W-3 | 18.7 | 4.9 | 30 | A |
| 32 | A-52 (1.9) | D | D-13 (0.28) | added B-29 | A1/A3 = 97/3 | W-2 | 17.4 | 5.6 | 40 | B |
| 33 | A-54 (1.8) | A | DBA (0.35) | added B-14 | A1 = 100 | — | 18.9 | 4.7 | 31 | A |
| 34 | A-60 (1.9) | C | DIA (0.3) | added B-14 | A1/A2/A3 = 87/10/3 | W-3 | 18.9 | 4.7 | 33 | A |
| 35 | A-58 (1.6) | G | TEA (0.36) | added B-29 | A1 = 100 | W-1 | 17.5 | 5.4 | 32 | A |
| 36 | A-61 (2.1) | C | DIA (0.3) | added B-14 | A1/A2/A3 = 87/10/3 | W-3 | 19.0 | 4.7 | 35 | A |
| 37 | A-71 (2.1) | B | PBI (0.3) | added B-2 | A1 = 100 | W-3 | 19.2 | 4.6 | 29 | A |
| 38 | A-82 (2.1) | C | D-13 (0.33) | added B-28 | A1/B1 = 70/30 | W-2 | 19.5 | 4.8 | 31 | A |
| 39 | A-84 (2.0) | A | D-52 (0.3) | added B-2 | A1 = 100 | W-3 | 19.2 | 4.5 | 28 | A |
| 40 | A-94 (2.0) | B | D-13 (0.28) | added B-12 | A1/A3 = 95/5 | W-1 | 19.1 | 4.8 | 33 | A |
| 41 | A-1/A-101 (0.8/1.1) | D | DBA (0.38) | added B-28 | A1/B1 = 92/8 | — | 19.1 | 4.9 | 28 | A |
| 42 | A-106 (2.2) | A | PBI (0.38) | added B-10 | A1/B2 = 90/10 | W-2 | 18.9 | 4.5 | 28 | A |
| 43 | A-131 (1.5) | B | TEA (0.36) | TC B-41 | A1 = 100 | W-4 | 19.1 | 4.8 | 30 | A |
| 44 | A-2/A-140 (0.8/0.9) | C | D-13 (0.31) | added B-52 | A1/A3 = 95/5 | W-1 | 19.2 | 4.9 | 31 | A |
| 45 | A-145 (1.9) | E | D-52 (0.3) | added B-52 | A1/A2 = 90/10 | W-4 | 19.3 | 4.6 | 29 | A |
| Comparative example | | | | | | | | | | |
| 1 | RA-1 (2.0) | A | PEA (0.42) | added B-12 | A1 = 100 | W-1 | 15.3 | 7.5 | 111 | C |
| 2 | RA-2 (2.0) | A | D-13 (0.42) | added B-10 | A1 = 100 | W-1 | 15.0 | 7.7 | 120 | D |
| 3 | RA-3 (2.0) | A | D-13 (0.42) | added B-10 | A1 = 100 | W-1 | 17.2 | 6.0 | 74 | C |

The designations in Table 2 represent substances described in the specific examples above and substances to be described below.

[Photoacid Generator]

Appropriate compounds A for use were selected from among the above-mentioned compounds (A-1) to (A-145). As photoacid generators other than the compounds A, use was made of the following compounds (RA-1) to (RA-3) and (PAG-X).

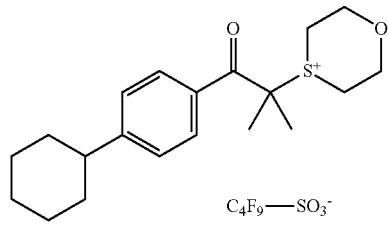

RA-1

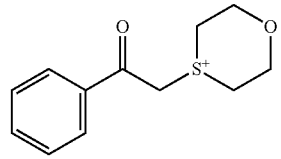

RA-2

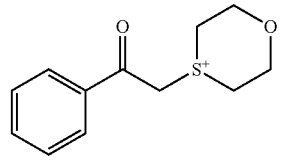

RA-3

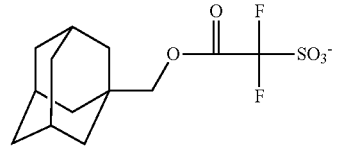

PAG-X
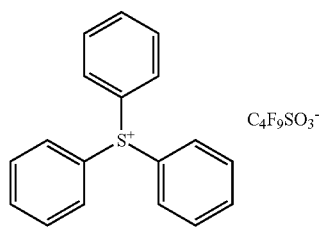
[Resin (B)]
With respect to each of the following resins, the repeating unit component ratio is a molar ratio.
Resin A
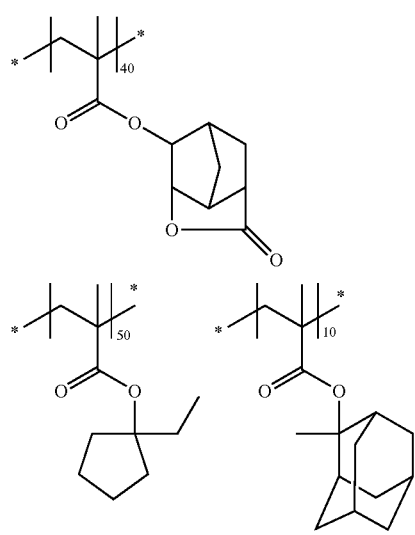
Mw = 9800
Mw/Mn = 1.53
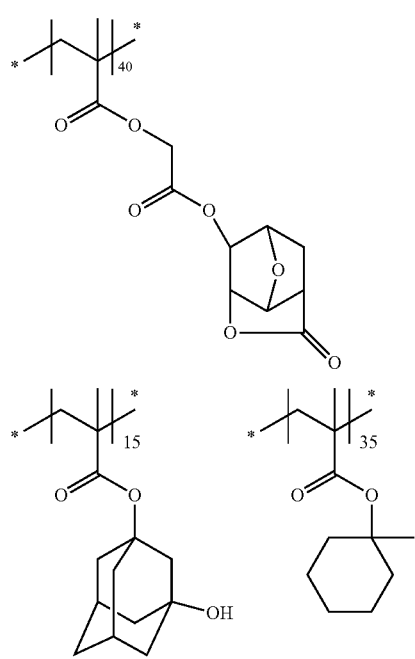
Resin C
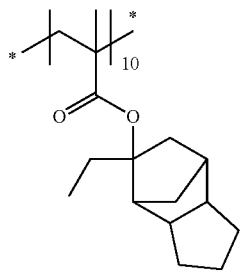
Mw = 9500
Mw/Mn = 1.55
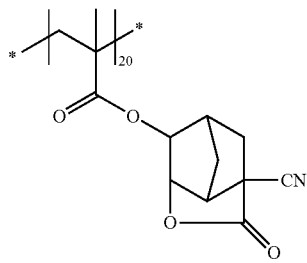
Resin B
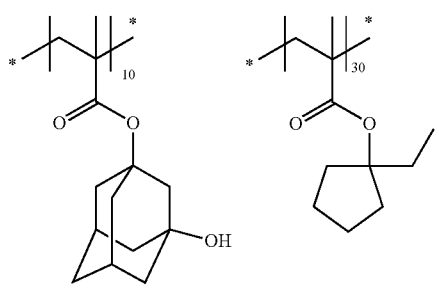
Mw = 9200
Mw/Mn = 1.55

-continued
Resin D
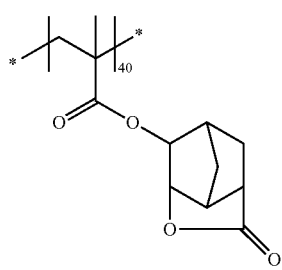
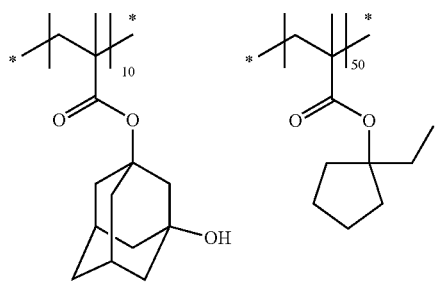
Mw = 6900
Mw/Mn = 1.53
Resin E
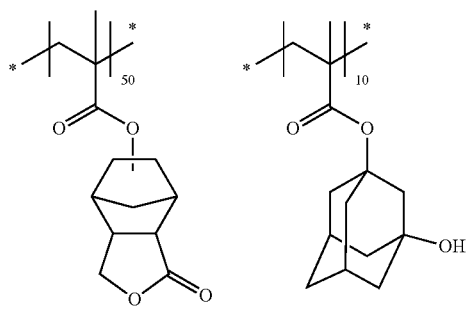
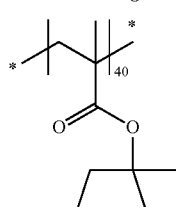
Mw = 6500
Mw/Mn = 1.52
Resin F
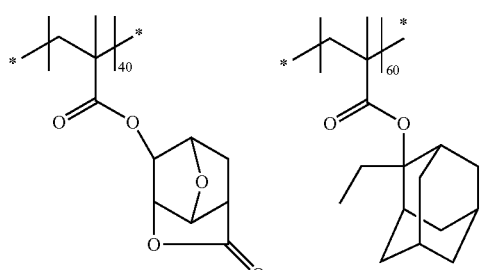
Mw = 11000
Mw/Mn = 1.55
-continued
Resin G
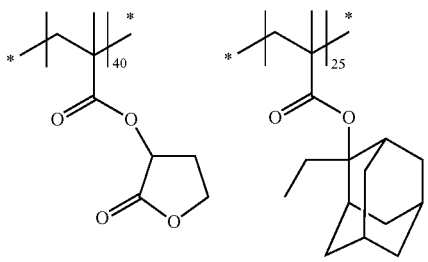
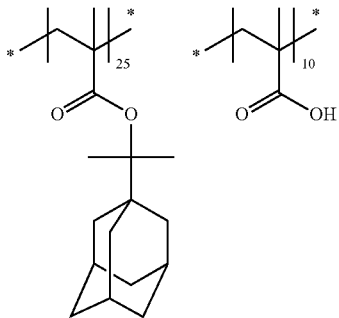
Mw = 9000
Mw/Mn = 1.53
Resin H
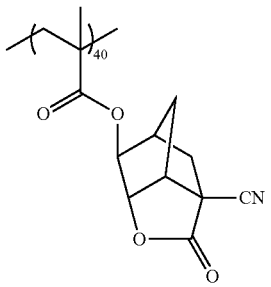
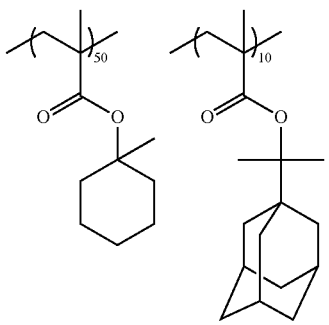
Mw = 19600
Mw/Mn = 1.54
Resin I
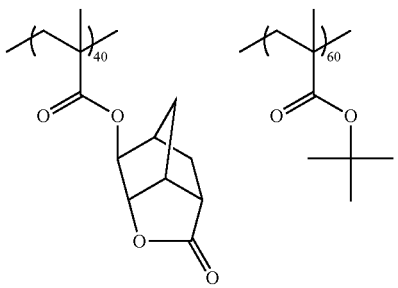
Mw = 10400
Mw/Mn = 1.66

[Basic Compound]
DIA: 2,6-diisopropylaniline,
TEA: triethanolamine,
DBA: N,N-dibutylaniline,
PBI: 2-phenylbenzimidazole, and
PEA: N-phenyldiethanolamine.

[Low-molecular compound containing a group eliminated under the action of an acid (D) (low-molecular compound (D))]

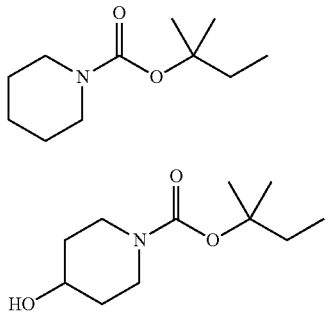

D-13

D-52

[Surfactant]
W-1: Megafac F176 (produced by DIC Corporation, fluorinated),
W-2: Megafac R08 (produced by DIC Corporation, fluorinated and siliconized),
W-3: PF6320 (produced by Omnova Solutions, Inc., fluorinated), and
W-4: Troy Sol S-366 (produced by Troy Chemical Co., Ltd.).

[Solvent]
A1: propylene glycol monomethyl ether acetate (PGMEA),
A2: cyclohexanone,
A3: γ-butyrolactone,
B1: propylene glycol monomethyl ether (PGME), and
B2: ethyl lactate.

It is apparent from Table 2 above that the compositions employed in Working Examples excel in exposure latitude and pattern roughness characteristic, such as LWR, ensure less occurrence of particles over time and further ensure less elution of any generated acid into an immersion liquid. In particular, with respect to the occurrence of particles, favorable results were obtained in Examples 1, 2, 4, 6 to 8, 11 to 17, 19 to 23 and 37 to 45 in which the cyclic structure in general formula (1) contained an oxygen atom or any of groups of the formula $>N-SO_2-R_4$.

[Evaluation of Resist when Organic-Solvent-Based Developer is Used]
(Preparation of Resist)
Dissolution of individual components in solvents as indicated in Table 3 below was carried out, thereby obtaining solutions each of 3.8 mass % solid content. The solutions were each passed through a polyethylene filter of 0.03 μm pore size, thereby obtaining actinic ray- or radiation-sensitive resin compositions (resist compositions). The designations in Table 3 are the same as when use was made of an alkali developer.

(Evaluation of Resist)
An organic antireflection film ARC29SR (produced by Nissan Chemical Industries, Ltd.) was applied onto a silicon wafer and baked at 205° C. for 60 seconds, thereby forming a 95-nm-thick antireflection film. Each of the above prepared actinic ray- or radiation-sensitive resin compositions was applied thereonto and baked (prebaked: PB) at 100° C. for 60 seconds, thereby forming a 100-nm-thick resist film.

The resultant wafer was exposed through a 6% half-tone mask of 48 nm line width 1:1 line and space pattern to light by means of an ArF excimer laser liquid immersion scanner (manufactured by ASML, XT1700i, NA1.20, C-Quad, outer sigma 0.900, inner sigma 0.812, XY deflection). Ultrapure water was used as the immersion liquid. Thereafter, the exposed wafer was baked (post-exposure baked: PEB) at 105° C. for 60 seconds. The wafer after PEB was developed by puddling with a negative developer (butyl acetate) for 30 seconds, and rinsed by puddling with a rinse liquid [methyl isobutyl carbinol (MIBC)] for 30 seconds. Thereafter, the wafer was rotated at a rotating speed of 4000 rpm for 30 seconds, thereby obtaining a 48 nm line width 1:1 line and space pattern.

The evaluation of exposure latitude, evaluation of LWR, elution test and particle evaluation were performed in the same manner as when use was made of an alkali developer. The evaluation results are given in Table 3 below.

TABLE 3

| Example | Photoacid generator (g) | Resin (B) (10 g) | Basic compound/Low-molecurar compound (D) (g) | Hydrophobic resin (35 mg) | Solvent | Surfactant (10 mg) | Exposure latitude (%) | LWR (nm) | Elution of acid into immersion liquid ($\times 10^{-12}$ mol/cm$^2$) | Particle |
|---|---|---|---|---|---|---|---|---|---|---|
| 46 | A-1 (2.0) | A | DIA (0.3) | added B-2 | A1 = 100 | W-2 | 18.9 | 4.9 | 29 | A |
| 47 | A-7 (1.9) | D | PBI (0.3) | added B-12 | A1/B2 = 90/10 | — | 18.1 | 5.4 | 28 | A |
| 48 | A-9 (1.8) | B/H (7 g/3 g) | TEA (0.35) | TC B-41 | A1 = 100 | W-4 | 17.5 | 5.8 | 39 | B |
| 49 | A-41 (1.7) | D | D-13 (0.33) | added B-52 | A1/A3 = 97/3 | W-1 | 18.5 | 4.6 | 31 | A |
| 50 | A-47/A-70 (1.0/1.0) | A | DIA (0.32) | added B-2 | A1 = 100 | W-3 | 18.8 | 4.9 | 29 | A |
| 51 | A-49 (2.1) | C | DBA (0.33) | added B-2 | A1/B1 = 60/40 | W-2 | 18.4 | 4.8 | 33 | A |
| 52 | A-51 (2.0) | D | DBA (0.35) | added B-12 | A1 = 100 | — | 17.9 | 4.6 | 32 | A |
| 53 | A-52 (2.2) | A | D-13 (0.28) | TC B-41 | A1/A3/B1 = 90/5/5 | W-3 | 17.1 | 5.6 | 38 | B |
| 54 | A-61 (2.0) | D/E (5 g/5 g) | PBI (0.31) | added B-12 | A1/B1 = 90/10 | W-1 | 18.2 | 5.4 | 28 | A |

TABLE 3-continued

| Example | Photoacid generator (g) | Resin (B) (10 g) | Basic compound/Low-molecurar compound (D) (g) | Hydrophobic resin (35 mg) | Solvent | Surfactant (10 mg) | Exposure latitude (%) | LWR (nm) | Elution of acid into immersion liquid ($\times 10^{-12}$ mol/cm$^2$) | Particle |
|---|---|---|---|---|---|---|---|---|---|---|
| 55 | A-66 (2.1) | I | PBI (0.3) | added B-10 | A1/A2 = 80/20 | W-1 | 19.0 | 4.6 | 27 | A |
| 56 | A-67 (1.9) | C | PBI (0.33) | TC B-41 | A1/A2 = 70/30 | W-2 | 18.8 | 4.8 | 33 | A |
| 57 | A-68/PAG-X (1.2/0.3) | C | D-52 (0.31) | added B-28 | A1/A2 = 70/30 | W-1 | 17.9 | 5.5 | 33 | A |
| 58 | A-70 (2.0) | H | PBI (0.3) | added B-10 | A1/A2 = 70/30 | W-3 | 18.8 | 4.5 | 30 | A |
| 59 | A-72 (1.9) | D | PBI (0.38) | added B-10 | A1/B2 = 90/10 | — | 17.9 | 5.4 | 28 | A |
| 60 | A-74 (1.9) | F | PBI (0.35) | added B-28 | A1/B2 = 60/40 | — | 19.5 | 4.4 | 28 | A |
| 61 | A-75 (1.6) | H | PBI (0.31) | TC B-41 | A1 = 100 | W-4 | 19.1 | 4.6 | 30 | A |
| 62 | A-77 (1.7) | E | D-52 (0.33) | added B-52 | A1/A2 = 97/3 | W-1 | 18.0 | 4.9 | 31 | A |
| 63 | A-80 (2.1) | A | DIA/PBI (0.15/0.15) | added B-2 | A1 = 100 | W-1 | 18.9 | 4.7 | 33 | A |
| 64 | A-88 (2.0) | C | D-52 (0.33) | added B-10 | A1/B2 = 60/40 | W-2 | 18.8 | 4.8 | 33 | A |
| 65 | A 99 (2.0) | F | DBA (0.31) | added B-28 | A1/A2 = 90/10 | W-1 | 18.7 | 5.1 | 35 | A |
| 66 | A-112 (1.6) | A | D-13 (0.28) | TC B-41 | A1/A2 = 95/5 | W-4 | 18.1 | 4.9 | 33 | A |
| 67 | A-113 (2.4) | D | PBI (0.3) | added B-28 | A1/B2 = 90/10 | — | 18.9 | 5.0 | 29 | A |
| 68 | A-114 (1.9) | H | DIA (0.37) | added B-41 | A1/B2 = 80/20 | — | 18.2 | 5.0 | 34 | A |
| 69 | A-130 (1.6) | B | DIA (0.37) | TC B-41 | A1 = 100 | W-2 | 18.2 | 5.2 | 30 | A |
| 70 | A-145 (2.0) | E | D-13 (0.31) | added B-52 | A1/A3 = 90/10 | W-1 | 18.3 | 4.9 | 35 | A |
| 71 | A-91 (1.3) | A | D-13 (0.27) | added B-1 | A1/A3/B1 = 90/5/5 | W-3 | 19.6 | 4.7 | 28 | A |
| 72 | A-95 (1.4) | D/E (5 g/5 g) | PBI (0.29) | added B-14 | A1/B1 = 90/10 | W-1 | 19.5 | 4.8 | 27 | A |
| 73 | A-96 (1.3) | I | PBI (0.26) | added B-10 | A1/A2 = 80/20 | W-2 | 19.7 | 4.6 | 26 | A |
| 74 | A-91/A-75 (1.0/0.3) | A | DIA (0.31) | added B-16 | A1 = 100 | W-3 | 19.7 | 4.9 | 29 | A |
| 75 | A-98 (1.3) | C | DBA (0.34) | added B-6 | A1/B1 = 60/40 | W-2 | 19.4 | 4.7 | 28 | A |
| 76 | A-101 (1.3) | F | D-13 (0.37) | added B-2 | A1 = 100 | W-1 | 19.3 | 4.7 | 30 | A |
| 77 | A-139 (1.5) | A | PBI (0.3) | added B-28 | A1/A3/B1 = 90/5/5 | W-3 | 19.5 | 5.0 | 28 | A |
| 78 | A-102 (2.0) | G | PBI (0.3) | added B-3 | A1 = 100 | W-1 | 19.1 | 4.9 | 35 | A |
| Comparative Example 4 | RA-1 (2.0) | A | PEA (0.4) | added B-12 | A1 = 100 | W-3 | 14.1 | 8.1 | 131 | C |
| Comparative Example 5 | RA-2 (2.0) | A | D-13 (0.33) | added B-10 | A1 = 100 | W-1 | 12.0 | 8.0 | 122 | D |
| Comparative Example 6 | RA-3 (2.0) | A | D-13 (0.31) | added B-10 | A1 = 100 | W-1 | 15.0 | 6.2 | 65 | C |

It was proved that the resist compositions of the present invention exhibited excellent performance in the exposure latitude, LWR, elution of any generated acid into an immersion liquid and particle occurrence even when an organic developer was used in the development operation.

What is claimed is:

1. An actinic ray- or radiation-sensitive resin composition comprising:
(A) a compound represented by a general formula (1) below that generates an acid when exposed to actinic rays or radiation, and
(B) a resin,

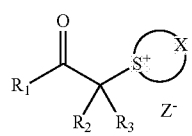

(1)

wherein
X represents a bivalent group containing an oxygen atom, a sulfur atom or a nitrogen atom, which bivalent group is connected to S$^+$ to thereby form a cyclic structure;

R₁ represents an alkyl group, an alkoxy group, a cycloalkyl group, a cycloalkoxy group, an aryl group or an alkenyl group;

each of R₂ and R₃ independently represents a hydrogen atom, an alkyl group, a cycloalkyl group or an aryl group, provided that R₂ and R₃ may be connected to each other to thereby form a ring, and that at least one of R₂ and R₃ is an alkyl group, a cycloalkyl group or an aryl group;

provided that R₁ and R₂ may be connected to each other to thereby form a ring; and Z⁻ represents a sulfonate anion represented by a general formula (2) below or a disulfonylimidate anion represented by a general formula (2') below,

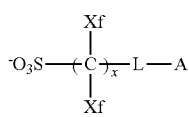  (2)

wherein
each Xfs independently represents a fluorine atom or an alkyl group substituted with at least one fluorine atom;
L represents a single bond or a bivalent connecting group;
A represents an organic group with a cyclic structure; and
x is an integer of 1 to 20,

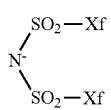  (2')

wherein
Xf is as defined above in the general formula (2), provided that two Xfs may be connected to each other to thereby form a cyclic structure.

2. The actinic ray- or radiation-sensitive resin composition according to claim 1, wherein in the general formula (1), X contains an oxygen atom or a group represented by >N—SO₂—R₄ in which R₄ represents an alkyl group, a cycloalkyl group or an aryl group.

3. The actinic ray- or radiation-sensitive resin composition according to claim 1, wherein the compound represented by the general formula (1) is represented by general formulae (1a) or (1b) below,

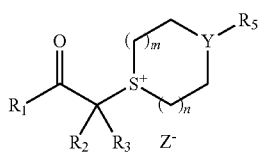  (1a)

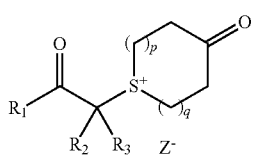  (1b)

wherein
R₁, R₂ and R₃ are as defined above in claim 1;
Y represents an oxygen atom, a sulfur atom or a nitrogen atom;
R₅ represents an electron withdrawing group when Y is a nitrogen atom and is not in existence when Y is an oxygen atom or a sulfur atom; and
each of m, n, p and q is an integer of 0 to 3.

4. The actinic ray- or radiation-sensitive resin composition according to claim 3, wherein in the general formula (1a), Y is an oxygen atom or a nitrogen atom, provided that when Y is a nitrogen atom, R₅ is a group represented by —SO₂—R₄, in which R₄ represents an alkyl group, a cycloalkyl group or an aryl group.

5. The actinic ray- or radiation-sensitive resin composition according to claim 1, wherein the resin (B) is a resin that is decomposed by an action of the acid to thereby increase its solubility in an alkali developer.

6. The actinic ray- or radiation-sensitive resin composition according to claim 1, wherein the resin (B) contains at least one of repeating units represented by a general formula (3) below and a lactone structure,

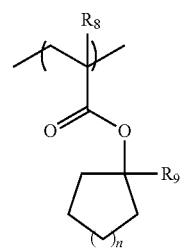  (3)

wherein
R₈ represents a hydrogen atom or a substituted or unsubstituted alkyl group having 1 to 10 carbon atoms;
R₉ represents a substituted or unsubstituted alkyl group having 1 to 10 carbon atoms; and
n is an integer of 1 to 6.

7. An actinic ray- or radiation-sensitive film comprising the actinic ray- or radiation-sensitive resin composition according to claim 1.

8. A method of forming a pattern, comprising:
forming the actinic ray- or radiation-sensitive film containing the actinic ray- or radiation-sensitive resin composition according to claim 1;
exposing the film to the actinic rays or radiation, and developing the exposed film.

9. The method according to claim 8, wherein the exposure is an ArF liquid-immersion exposure.

10. A process for manufacturing an electronic device, comprising the method according to claim 8.

11. The actinic ray- or radiation-sensitive resin composition according to claim 1, wherein the anion Z⁻ in general formula (1) is a sulfonate anion represented by general formula (2) and A general formula (2) is a alicyclic group having a polycyclic structure.

* * * * *